United States Patent
Rancati et al.

(10) Patent No.: US 8,877,774 B2
(45) Date of Patent: Nov. 4, 2014

(54) COMPOUNDS HAVING MUSCARINIC RECEPTOR ANTAGONIST AND BETA2 ADRENERGIC RECEPTOR AGONIST ACTIVITY

(75) Inventors: Fabio Rancati, Parma (IT); Andrea Rizzi, Parma (IT); Gabriele Amari, Parma (IT); Matteo Biagetti, Parma (IT); Ian Linney, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 64 days.

(21) Appl. No.: 13/492,458

(22) Filed: Jun. 8, 2012

(65) Prior Publication Data

US 2013/0045169 A1 Feb. 21, 2013

(30) Foreign Application Priority Data

Jun. 10, 2011 (EP) .................................. 11169537
Apr. 24, 2012 (EP) .................................. 12165283

(51) Int. Cl.
| | | |
|---|---|---|
| A61K 9/00 | (2006.01) | |
| C07D 211/92 | (2006.01) | |
| C07D 215/20 | (2006.01) | |
| A61K 31/4704 | (2006.01) | |
| C07D 211/46 | (2006.01) | |
| A61K 31/4525 | (2006.01) | |
| A61K 31/439 | (2006.01) | |
| C07D 221/22 | (2006.01) | |

(52) U.S. Cl.
CPC .......... *C07D 4543/02* (2013.01); *C07D 211/92* (2013.01); *C07D 215/20* (2013.01); *A61K 31/4704* (2013.01); *C07D 211/46* (2013.01); *A61K 31/4525* (2013.01); *A61K 31/439* (2013.01); *C07D 221/22* (2013.01); *A61K 9/0075* (2013.01); *A61K 9/0078* (2013.01); *A61K 9/008* (2013.01)

USPC ........... 514/305; 514/312; 514/321; 546/134; 546/135; 546/133; 546/157; 546/198

(58) Field of Classification Search
CPC .. C08D 211/92; C08D 211/46; C08D 215/20; C08D 221/22; A61K 31/439; A61K 31/4525; A61K 31/4704
USPC ................. 546/159, 134, 135, 133, 157, 198; 514/305, 312, 321
See application file for complete search history.

(56) References Cited

FOREIGN PATENT DOCUMENTS

WO 2009/090010 7/2009

OTHER PUBLICATIONS

Extended European Search Report issued in EP Application No. 11169537.5 on Nov. 23, 2011.
A.D. Hughes. et al., Bioorganic & Medicinal Chemistry Letters, vol. 21, pp. 1354-1358 (2011).
R. Naito et al., Chem. Pharm. Bull., vol. 46, pp. 1286-1294 (1999).
R. Naito et al., Chem. Pharm. Bull., vol. 46, pp. 1274-1285 (1998).
U.S. Appl. No. 14/098,662, filed Dec. 6, 2013, Rancati, et al.
U.S. Appl. No. 14/098,735, filed Dec. 6, 2013, Rancati, et al.

*Primary Examiner* — D M Seaman
(74) *Attorney, Agent, or Firm* — Oblon, Spivak, McClelland, Maier & Neustadt, L.L.P.

(57) ABSTRACT

Compounds of formula(I) act both as muscarinic receptor antagonists and beta2 adrenergic receptor agonists and are useful for the prevention and/or treatment of broncho-obstructive and inflammatory diseases.

21 Claims, No Drawings

US 8,877,774 B2

COMPOUNDS HAVING MUSCARINIC RECEPTOR ANTAGONIST AND BETA2 ADRENERGIC RECEPTOR AGONIST ACTIVITY

CROSS REFERENCES TO RELATED APPLICATIONS

This application claims priority to European Patent Application No. 11169535.9, filed on Jun. 10, 2011, and European Patent Application No. 12165283.8 filed on Apr. 24, 2012, both of which are incorporated herein by reference in their entireties.

BACKGROUND OF THE INVENTION

1. Field of the Invention

The present invention relates to compounds, which act both as muscarinic receptor antagonists and beta2 adrenergic receptor agonists, to processes for preparing such a compound, to compositions which contain such a compound, to therapeutic uses of such a compound, and combinations of such a compound with other pharmaceutical active ingredients.

2. Discussion of the Background

Pulmonary disorders, such as asthma and chronic obstructive pulmonary disease (COPD), are commonly treated with bronchodilators. A well known class of bronchodilators consists of beta-2 adrenergic receptor agonists, such as salbutamol, fenoterol, formoterol and salmeterol. These compounds are generally administered by inhalation.

Another well known class of bronchodilators consists of muscarinic receptor antagonists (anticholinergic compounds), such as ipratropium and tiotropium. These compounds are also typically administered by inhalation.

Inhaled formulations of both beta-2 agonists and muscarinic receptor antagonists are valuable agents in the treatment of asthma and COPD, with both classes of agents providing symptomatic relief due to their ability to relax constricted airways. Observations that the bronchodilator effects of the two classes of agents were additive, prompted studies with combinations of the two agents. In 1975, it was shown that that beneficial effects could be achieved by combining two ingredients such as fenoterol and ipratropium bromide in a single aerosol. This prompted the development of fixed dose combinations of ipratropium bromide firstly with fenoterol (Berodual, introduced in 1980), and then with salbutamol (Combivent, introduced in 1994).

More recently the availability of both long-acting muscarinic antagonists and long-acting beta-2 agonists prompted the development of combinations of these agents. For example, WO 00/69468, which is incorporated herein by reference in its entirety, discloses medicament compositions containing a muscarinic receptor antagonist, such as tiotropium bromide, and beta-2 adrenergic receptor agonists, such as formoterol fumarate or salmeterol, and WO 2005/115467, which is incorporated herein by reference in its entirety, discloses a combination which comprises a beta-2 agonist and an antagonist of M3 muscarinic receptors which is a salt of 3(R)-(2-hydroxy-2,2-dithien-2-ylacetoxy)-1-(3-phenoxypropyl)-1-azoniabicyclo[2.2.2]octane.

An alternative approach to the development of fixed dose combinations is the identification of molecules that combine both muscarinic antagonism and beta-2 agonism. In fact compounds possessing both beta-2 adrenergic receptor agonist and muscarinic receptor antagonist activity are highly desirable since such bifunctional compounds would provide bronchodilation through two independent mechanisms of action while having a single molecule pharmacokinetics.

Such kind of compounds have been described in some patent applications, such as WO 2004/074246, WO 2004/074812, WO 2005/051946, WO 2006/023457, WO 2006/023460, WO 2010/123766, and WO 2011/048409, all of which are incorporated herein by reference in their entireties.

However, there remains a need for compounds which exhibit both muscarinic antagonism and beta-2 agonism.

SUMMARY OF THE INVENTION

Accordingly, it is one object of the present invention to provide novel compounds, which act both as muscarinic receptor antagonists and beta2 adrenergic receptor agonists, to processes for preparing such a compound, to compositions which contain such a compound, to therapeutic uses of such a compound, and combinations of such a compound with other pharmaceutical active ingredients.

It is another object of the present invention to provide novel processes for preparing such a compound.

It is another object of the present invention to provide novel compositions which contain such a compound.

It is another object of the present invention to provide novel therapeutic uses of such a compound.

It is another object of the present invention to provide novel combinations of such a compound with other pharmaceutical active ingredients.

These and other objects, which will become apparent during the following detailed description, have been achieved by the inventors' discovery that compounds of general formula I, act both as muscarinic receptor antagonists and beta2 adrenergic receptor agonists.

Thus, in a first embodiment, the present invention provides compounds of formula (I) and pharmaceutically acceptable salts thereof.

In a second embodiment, the present invention provides processes for preparing such a compound.

In another embodiment, the present invention provides compositions which contain such a compound.

In another embodiment, the present invention provides therapeutic uses of such a compound.

In another embodiment, the present invention provides combinations of such a compound with another pharmaceutical active ingredients among which are, for instance, those currently used in the treatment of respiratory disorders, e.g. corticosteroids, P38 MAP kinase inhibitors, IKK2, HNE inhibitors, PDE4 inhibitors, leukotriene modulators, NSAIDs and mucus regulators.

It has now been found that some particular carbamate derivatives, besides possessing both beta-2 adrenergic receptor agonist and muscarinic receptor antagonist activity, possess elevated affinity for the M3 muscarinic receptors and long lasting bronchodilating activity.

DETAILED DESCRIPTION OF THE PREFERRED EMBODIMENTS

In particular, the invention is directed to compounds of general formula I

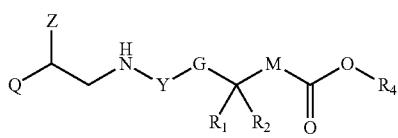
(I)

wherein
Q is a group of formula Q1, Q2, Q3, Q4, Q5 or Q6:

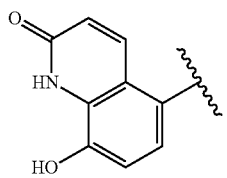
Q1

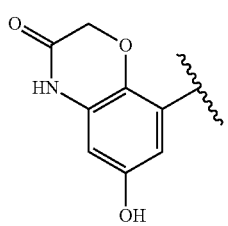
Q2

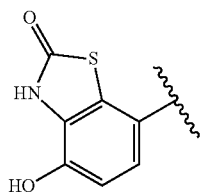
Q3

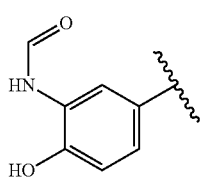
Q4

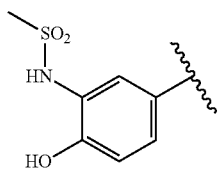
Q5

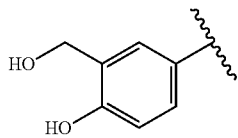
Q6

Z is H or OH;
Y is selected from Y' and Y1 which are divalent groups of formula:

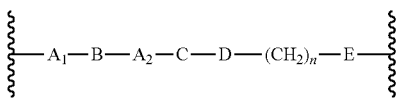
Y'

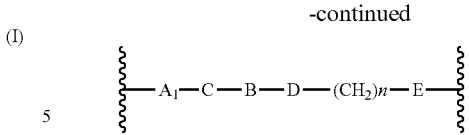
Y1 wherein
A1 and A2 are independently absent or are selected from the group consisting of $(C_1-C_{12})$alkylene, $(C_3-C_8)$cycloalkylene, and $(C_3-C_8)$heterocycloalkylene optionally substituted by one or more substituents selected from the group consisting of $(C_1-C_6)$alkyl, aryl$(C_1-C_6)$alkyl, and heteroaryl$(C_1-C_6)$alkyl;

B is absent or is selected from the group consisting of $(C_3-C_8)$cycloalkylene, $(C_3-C_8)$heterocycloalkylene, arylene, and heteroarylene or is a group of formula B1

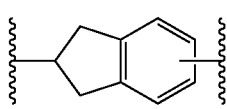
B1 optionally substituted by one or more groups selected from halogens, nitrile, $(C_1-C_6)$alkyl, $(C_1-C_6)$alkoxy, and aryl$(C_1-C_6)$alkyl;

C is absent or is selected from the group consisting of —O—, —CO—, —OC(O)—, —C(O)—, —S—, —S(O)—, —S(O)$_2$—, and —N(R$_7$)—, or is one of the following groups C1-C18:

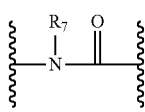
C1

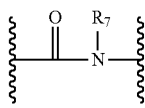
C2

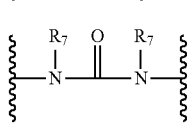
C3

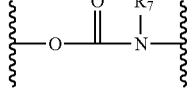
C4

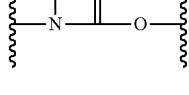
C5

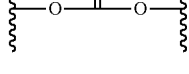
C6

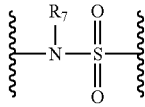
C7

-continued

C8 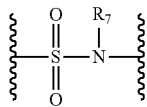

C9 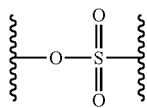

C10 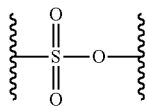

C11 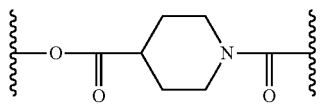

C12 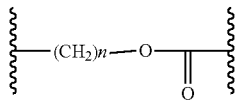

C13 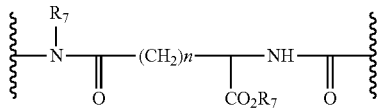

C14 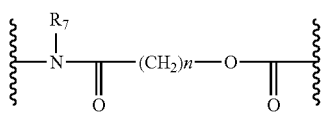

C15 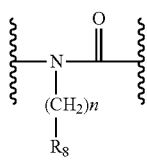

C16 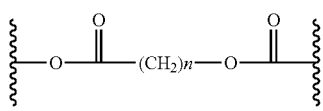

C17 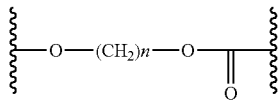

C18 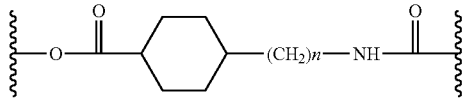

wherein $R_7$ is H or is selected from the group consisting of linear or branched $(C_1-C_8)$alkyl, $(C_3-C_8)$cycloalkyl, $(C_3-C_8)$heterocycloalkyl, aryl, aryl$(C_1-C_6)$alkyl, $(C_1-C_6)$alkoxy$(C_1-C_6)$alkyl, and heteroaryl and $R_8$ is $(C_1-C_8)$alkoxycarbonyl;

D is absent or is selected from the group consisting of $(C_1-C_{12})$alkylene, —C(CH$_3$)$_2$—, arylene, $(C_2-C_{12})$alkenylene, heteroarylene, $(C_3-C_8)$heterocycloalkylene, and $(C_2-C_6)$alkynylene;

n is 0 or an integer from 1 to 3;

E is absent or is selected from —O—, —NR$_7$—, —OC(O)— and —S—;

G is arylene or heteroarylene, optionally substituted by one or more substituents selected from the group consisting of halogen atoms, —OH, oxo (=O), —SH, —NO$_2$, —CN, —CON(R$_6$)$_2$, —NH$_2$, —NHCOR$_6$, —CO$_2$R$_6$, $(C_1-C_{10})$alkylsulfanyl, $(C_1-C_{10})$alkylsulfinyl, $(C_1-C_{10})$alkylsulfonyl, $(C_1-C_{10})$alkyl, aryl, haloaryl, heteroaryl, and $(C_1-C_{10})$alkoxy;

$R_1$ and $R_2$ are independently H or selected from the group consisting of $(C_1-C_8)$alkyl, $(C_3-C_8)$cycloalkyl, $(C_3-C_8)$heterocycloalkyl, aryl, heteroaryl, aryl$(C_1-C_6)$alkyl, heteroaryl$(C_1-C_6)$alkyl, and $(C_3-C_8)$cycloalkyl$(C_1-C_6)$alkyl, optionally substituted by one or more halogen atoms or $(C_1-C_8)$alkyl groups or, taken together with the carbon atom to which they are bounded, $R_1$ and $R_2$ may form a $(C_3-C_8)$cycloalkyl, wherein $R_1$ and $R_2$ are not simultaneously H;

M is —O— or —N(R$_3$)—;

$R_3$ is H or is selected from the group consisting of $(C_1-C_8)$alkyl, $(C_3-C_8)$cycloalkyl, aryl and heteroaryl;

$R_4$ is a group of formula J1, J2, J3, J4 or J5:

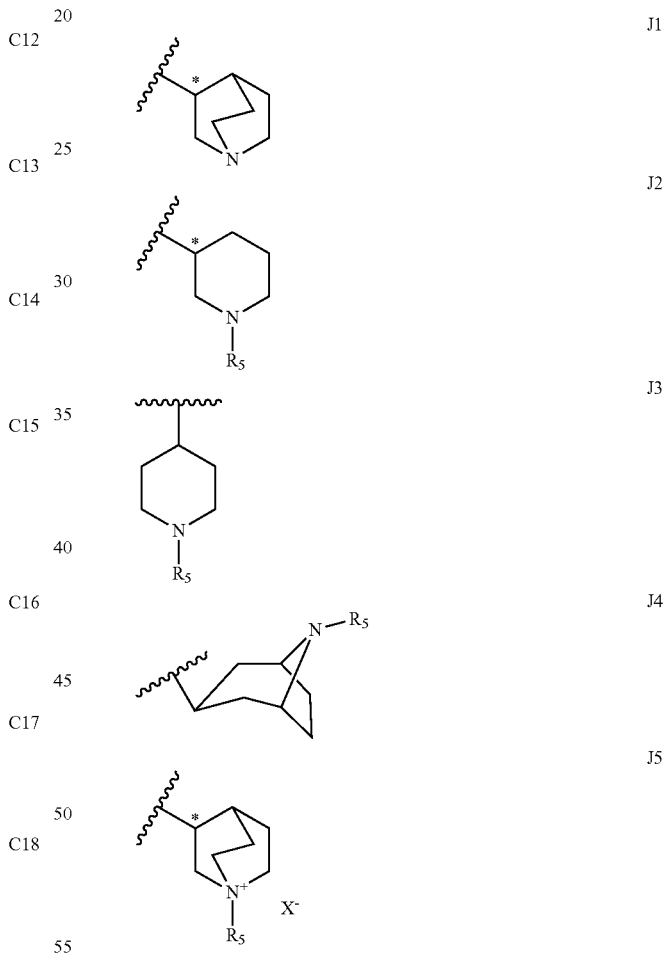

$R_5$ is a group of formula K:

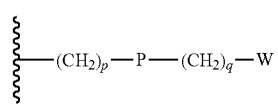

K wherein p is 0 or an integer from 1 to 4; q is 0 or an integer from 1 to 4;

P is absent or is selected from the divalent group consisting of O, S, SO, $SO_2$, CO, $NR_6$ CH=CH, $N(R_6)SO_2$, $N(R_6)COO$, $N(R_6)C(O)$, $SO_2N(R_6)$, $CO(O)N(R_6)$ and $C(O)N(R_6)$;

W is selected from the group consisting of H, $(C_1-C_6)$alkyl, $(C_3-C_8)$cycloalkyl, aryl and heteroaryl, optionally substituted by one or more substituents selected from the group consisting of halogen atoms, —OH, oxo (=O), —SH, —$NO_2$, —CN, —$CON(R_6)_2$, —$NH_2$, —$NHCOR_6$, —$CO_2R_6$, $(C_1-C_{10})$alkylsulfanyl, $(C_1-C_{10})$alkylsulfinyl, $(C_1-C_{10})$alkylsulfonyl, $(C_1-C_{10})$alkyl and $(C_1-C_{10})$alkoxy;

$X^-$ is a physiological acceptable anion;

$R_6$ is H or is selected from the group consisting of $(C_1-C_{10})$ alkyl, $(C_1-C_6)$haloalkyl, $(C_2-C_6)$alkynyl, $(C_2-C_6)$alkenyl, $(C_3-C_8)$cycloalkyl, $(C_3-C_8)$cycloalkyl$(C_1-C_6)$alkyl, heteroaryl, and aryl optionally substituted by one or more substituents selected from the group consisting of halogen atoms, —OH, oxo (=O), —SH, —$NO_2$, —CN, —$CONH_2$, —COOH, $(C_1-C_{10})$alkoxycarbonyl, $(C_1-C_{10})$alkylsulfanyl, $(C_1-C_{10})$alkylsulfinyl, $(C_1-C_{10})$alkylsulfonyl, $(C_1-C_{10})$alkyl and $(C_1-C_{10})$alkoxy;

and pharmaceutically acceptable salts or solvates thereof.

The expression "$(C_1-C_x)$alkyl" refers to straight or branched chain alkyl groups wherein the number of carbon atoms is from 1 to x. Examples of groups are methyl, ethyl, n-propyl, isopropyl, t-butyl, pentyl, hexyl, octyl, nonyl, decyl, undecyl, dodecyl, and the like.

In an analogous manner, the expression "$(C_1-C_x)$alkylene" refers to divalent groups, such as methylene, ethylene, n-propylene, isopropylene, t-butylene, pentylene, hexylene, octylene, nonylene, decylene, undecylene, dodecylene, and the like.

The expression "$(C_1-C_6)$haloalkyl" refers to the above "$(C_1-C_6)$alkyl" group wherein one or more hydrogen atoms are replaced by one or more halogen atoms, which can be the same or different from each other. Examples of said $(C_1-C_6)$ haloalkyl groups include halogenated, poly-halogenated and fully halogenated alkyl groups wherein one or more of the hydrogen atoms are replaced by halogen atoms, e.g. trifluoromethyl group.

The expressions "$(C_1-C_{10})$alkylsulfanyl", "$(C_1-C_{10})$alkylsulfinyl" or "$(C_1-C_{10})$alkylsulfonyl" refer, respectively, to alkyl-S—, alkyl-SO— or alkyl-$SO_2$— groups.

The expression "hydroxy$(C_1-C_6)$alkyl" refers to -alkyl-OH groups.

The expression "$(C_2-C_x)$alkenyl" refers to straight or branched carbon chains with one or more double bonds, wherein the number of carbon atoms is from 1 to x. Examples of said groups comprise ethenyl, propenyl, butenyl, pentenyl, hexenyl, heptenyl, octenyl, nonenyl, decenyl, undecenyl, dodecenyl, and the like.

In an analogous manner, the expression "$(C_2-C_x)$alkenylene" refers to divalent groups, such as ethenylene, propenylene, butenylene, pentenylene, hexenylene, heptenylene, octenylene, nonenylene, decenylene, undecenylene, dodecenylene, and the like.

The expression "$(C_2-C_x)$alkynyl" refers to straight or branched carbon chains with one or more triple bonds, wherein the number of carbon atoms is from 1 to x. Examples of said groups comprise ethynyl, propynyl, butynyl, pentynyl, hexynyl, and the like.

In an analogous manner, the expression "$(C_2-C_x)$alkynylene" refers to divalent groups, such as ethynylene, propynylene, butynylene, pentynylene, hexynylene, and the like.

The expression "$(C_1-C_{10})$alkoxy" refers to alkyl-oxy (e.g. alkoxy) groups, with the alkyl portion as above defined. Examples of said groups comprise methoxy, ethoxy, n-propoxy, isopropoxy, n-butoxy, isobutoxy, sec-butoxy, tert-butoxy, pentoxy, hexoxy, and the like.

The expression "$(C_3-C_8)$cycloalkyl" refers to mono- or bi-cycloaliphatic hydrocarbon groups with 3 to 8 carbon atoms. Examples include cyclopropyl, cyclobutyl, cyclopentyl, cyclohexyl, cycloheptyl, bicyclo[2.2.1]hept-2-yl, and the like.

The expression "$(C_3-C_8)$heterocycloalkyl" refers to $(C_3-C_8)$cycloalkyl groups, in which at least one ring carbon atom is replaced by a heteroatom or heteroaromatic group (e.g. N, NH, S or O). Examples include quinuclidinyl, pyrrolidinyl, piperidinyl, azabicyclo[3.2.1]octan-3-yl and azoniabicyclo [2.2.2]octanyl and the like.

In an analogous manner, the expressions "$(C_3-C_8)$cycloalkylene" and "$(C_3-C_8)$heterocycloalkylene" refer to divalent groups, such as, respectively, cyclopropylene, cyclobutylene, cyclopentylene, cyclohexylene, cycloheptylene, bicyclo[2.2.1]hept-2-ylene and quinuclidinylene, pyrrolidinylene, piperidinylene, azabicyclo[3.2.1]octan-3-ylene, azoniabicyclo[2.2.2]octanylene, and the like.

The expression "aryl" refers to mono-, bi- or tricyclic ring systems having 5 to 20, preferably from 5 to 15, ring atoms, and wherein at least one ring is aromatic.

The expression "heteroaryl" refers to mono-, bi- or tricyclic systems with 5 to 20 ring atoms, preferably from 5 to 15, in which at least one ring is aromatic and in which at least one carbon ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydro-indene, dihydrobenzo dioxepin, benzo oxazin radicals, and the like.

Examples of suitable aryl or heteroaryl tricyclic systems include fluorene radicals as well as benzocondensed derivatives of the aforementioned heteroaryl bicyclic systems.

In an analogous manner, the expressions "arylene" and "heteroarylene" refer to divalent groups, such a phenylene, biphenylene and thienylene.

The expressions "aryl$(C_1-C_6)$alkyl", "heteroaryl$(C_1-C_6)$ alkyl", and "$(C_3-C_8)$cycloalkyl$(C_1-C_6)$alkyl" refer to a "$(C_1-C_6)$alkyl" respectively substituted by one or more aryl, heteroaryl, or $(C_3-C_8)$cycloalkyl groups, as defined above.

Examples of aryl$(C_1-C_6)$alkyl include triphenylmethyl.

Whenever basic amino or quaternary ammonium groups are present in the compounds of formula I, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphtalene disulfonate may be present. Likewise, in the presence of acidic groups such as COOH groups, corresponding physiological cation salts may be present as well, for instance including alkaline or alkaline earth metal ions.

It will be apparent that the compounds of general formula I may contain asymmetric centers. Therefore, the invention also includes any of the optical stereoisomers, diastereoisomers and mixtures thereof, in any proportion.

In particular, the carbon atom linked to $R_1$, $R_2$, G and M groups, depending on the meanings provided to $R_1$ and $R_2$ among those formerly reported, may represent a chiral center.

In an embodiment, the configuration is (S).

In another embodiment, the absolute configuration of this chiral center is preferably (R).

In another preferred embodiment, the compounds of general formula I described in the present invention are present as mixtures of diastereoisomers.

In another embodiment, when in the compounds of general formula I, $R_4$ is a group of formula J1, J2 or J5:

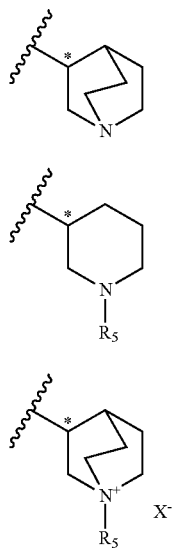

the carbon atom marked with an asterisk represents a chiral center.

In a preferred embodiment, this chiral center has (R) configuration.

It is to be understood that all preferred groups or embodiments described herebelow for compounds of formula I may be combined among each other and apply as well mutatis mutandis.

A first preferred group of compounds is that of general formula I wherein Q is a group of formula Q1, Q2, Q3, Q4, Q5 or Q6:

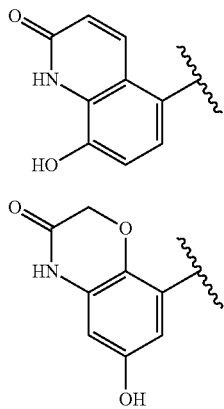

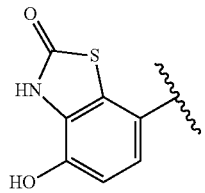

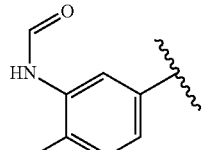

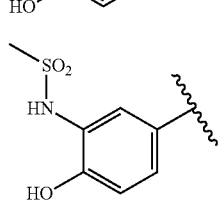

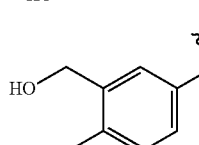

Z is H or OH;
Y is a group of formula

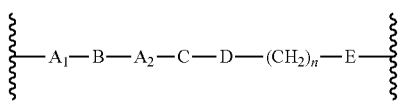

wherein
A1 and A2 are, each independently, absent or are selected from the group consisting of ($C_1$-$C_{12}$)alkylene, ($C_3$-$C_8$)cycloalkylene, and ($C_3$-$C_8$)heterocycloalkylene; B is absent or is selected from the group consisting of ($C_3$-$C_8$)cycloalkylene, ($C_3$-$C_8$)heterocycloalkylene, arylene, and heteroarylene; C is absent or is selected from the group consisting of —O—, —CO—, —OC(O)—, —C(O)—, —S—, —S(O)—, —S(O)$_2$— and —N($R_7$)— wherein $R_7$ is H or is selected from the group consisting of ($C_1$-$C_8$)alkyl, ($C_3$-$C_8$)cycloalkyl, ($C_3$-$C_8$)heterocycloalkyl, aryl, aryl($C_1$-$C_8$)alkyl, ($C_1$-$C_8$)alkoxy($C_1$-$C_8$)alkyl, and heteroaryl; D is absent or is selected from the group consisting of ($C_1$-$C_{12}$)alkylene, arylene, ($C_2$-$C_{12}$)alkenylene, heteroarylene, ($C_3$-$C_8$)heterocycloalkylene, and ($C_2$-$C_6$)alkynylene; n is 0;

E is absent or is selected from —O—, —$NR_7$— and —S—; G is arylene or heteroarylene, optionally substituted by one or more substituents selected from the group consisting of halogen atoms, —OH, oxo (=O), —SH, —NO$_2$, —CN, —CON($R_6$)$_2$, —NH$_2$, —NHCOR$_6$, —CO$_2$R$_6$, ($C_1$-$C_{10}$)alkylsulfanyl, ($C_1$-$C_{10}$)alkylsulfinyl, ($C_1$-$C_{10}$)alkylsulfonyl, ($C_1$-$C_{10}$)alkyl, aryl, haloaryl, heteroaryl, and ($C_1$-$C_{10}$)alkoxy; and $R_1$, $R_2$, M, $R_4$ and $R_6$ are as defined above.

Still more preferred within this first group, are the compounds of general formula I, wherein Q is Q1:

Q1

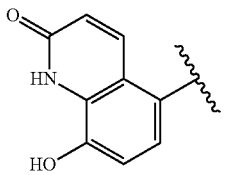

Z is —OH, A1 is absent or is selected from the group consisting of (C$_3$-C$_8$)heterocycloalkylene and (C$_1$-C$_{12}$)alkylene, A2 is absent or is selected from the group consisting of (C$_1$-C$_6$)alkylene, B is absent or arylene, C is absent, D is absent or is selected from the group consisting of (C$_1$-C$_{12}$)alkylene, heteroarylene, and arylene, n is 0, E is absent or is —O—, G is arylene optionally substituted by one or more halogen atoms.

Still more preferred within this class, are the compounds of general formula I, wherein A1 is absent or is selected from the group consisting of methylene, ethylene, propylene, butylene, pentylene, hexylene, hepthylene, octylene, and nonylene, A2 is absent or is selected from the group consisting of methylene and oxadiazolene, B is selected from the group consisting of phenylene and cyclohexylene or is absent, C is absent, D is absent or is selected from methylene, ethylene, propylene, butylene, pentylene, hexylene, hepthylene, octylene, nonylene, phenylene, and oxadiazolene; n is 0, G is selected from the group consisting of fluoro-biphenylene and phenylene.

Even still more preferred within this class are the compounds of general formula I, wherein A1 is selected from the group consisting of ethylene, pentylene, hexylene, heptylene, octylene, and nonylene, D is absent, n is 0, R$_1$ is H, R$_2$ is selected from the group consisting of phenyl, biphenyl, napthyl, pyridinyl, difluorophenyl, methylphenyl, fluorophenyl, and thiophenyl, M is —N(H)—, R$_4$ is a group of formula J1

J1

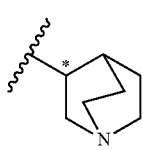

or J3

J3

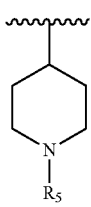

or J4

J4

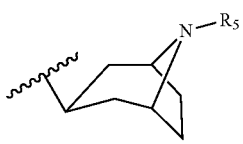

or J5

J5

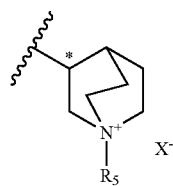

wherein R$_5$ is a group of formula K, wherein p is 0 or 1, P is absent or is CO, q is absent or is 1 and W is H or is selected from the group consisting of (C$_1$-C$_6$)alkyl and aryl.

Another class of preferred compounds of general formula I is that wherein Q is Q3

Q3

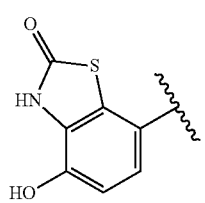

Z is H, A1 is absent or is (C$_1$-C$_{12}$)alkylene, A2 is absent, B is absent, C is absent, D is absent or (C$_1$-C$_{12}$)alkylene, E is —O—, G is arylene.

Still more preferred within this class, are the compounds of general formula I, wherein A1 is absent or is selected from the group consisting of methylene, ethylene, propylene, butylene, pentylene, hexylene, hepthylene, octylene, and nonylene, A2 is absent, B is absent, C is absent, D is absent or is selected from methylene, ethylene, propylene, butylene, pentylene, hexylene, hepthylene, octylene, and nonylene; n is 0, G is phenylene.

Even still more preferred within this class, are the compounds of general formula I, wherein A1 is nonylene, A2, B and C are absent, D is a absent, n is 0, R$_1$ is H, R$_2$ is phenyl, M is —N(H)— and R$_4$ is J1.

Another preferred group of compounds is that of general formula I wherein R$_1$ and R$_2$ are independently H or selected from the group consisting of (C$_1$-C$_8$)alkyl, (C$_3$-C$_8$)cycloalkyl, (C$_3$-C$_8$)heterocycloalkyl, aryl, heteroaryl, aryl(C$_1$-C$_6$)alkyl, heteroaryl(C$_1$-C$_6$)alkyl, and (C$_3$-C$_8$)cycloalkyl(C$_1$-C$_6$)alkyl, optionally substituted by one or more halogen atoms or (C$_1$-C$_8$)alkyl groups or, taken together with the carbon atom they are linked to, R$_1$ and R$_2$ may form a (C$_3$-C$_8$)cycloalkyl group, wherein R$_1$ and R$_2$ are not simultaneously H; M is —O— or —N(R$_3$)—; R$_3$ is H or is selected from the group consisting of (C$_1$-C$_8$)alkyl, (C$_3$-C$_8$)cycloalkyl, aryl and heteroaryl; R$_4$ is a group of formula J1, J2, J3, J4 or J5

J1

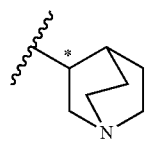

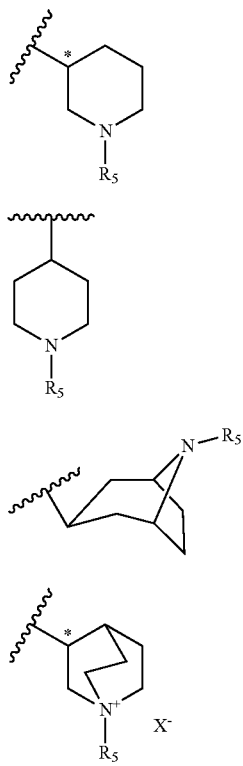

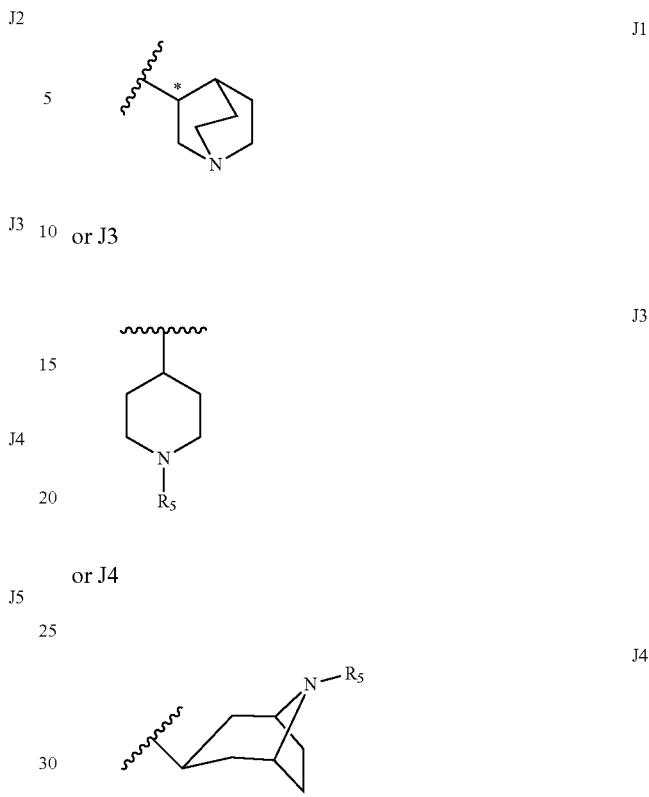

$R_5$ is a group of formula K

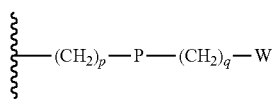

K wherein p is 0 or an integer from 1 to 4; q is 0 or an integer from 1 to 4; P is absent or is selected from the group consisting of —O—, —S—, —S(O)—, —S(O$_2$)—, —C(O)—, —N(R$_6$)—, —CH═CH—, —N(R$_6$)S(O$_2$)—, —N(R$_6$)CO(O)—, —N(R$_6$)C(O)—, —SO$_2$N(R$_6$)—, —CO(O)N(R$_6$)— and —C(O)N(R$_6$)—; W is selected from the group consisting of (C$_1$-C$_6$)alkyl, (C$_3$-C$_8$)cycloalkyl, aryl, and heteroaryl, optionally substituted by one or more substituents selected from the group consisting of halogen atoms, —OH, oxo (═O), —SH, —NO$_2$, —CN, —CON(R$_6$)$_2$, —NH$_2$, —NH-COR$_6$, —CO$_2$R$_6$, (C$_1$-C$_{10}$)alkylsulfanyl, (C$_1$-C$_{10}$)alkylsulfinyl, (C$_1$-C$_{10}$)alkylsulfonyl, (C$_1$-C$_{10}$)alkyl, and (C$_1$-C$_{10}$)alkoxy; R$_6$ is selected from the group consisting of H, (C$_1$-C$_{10}$)alkyl, (C$_1$-C$_6$)haloalkyl, (C$_3$-C$_8$)cycloalkyl, heteroaryl, and aryl; and G, Y, Z and Q are as defined above.

Still more preferred within this class, are the compounds of general formula I wherein R$_1$ and R$_2$ are independently H or selected from the group consisting of (C$_1$-C$_8$)alkyl, (C$_3$-C$_8$)cycloalkyl, aryl, and heteroaryl, optionally substituted by one or more halogen atoms or (C$_1$-C$_8$)alkyl groups or, taken together with the carbon atom to which they are bounded, R$_1$ and R$_2$ may form a (C$_3$-C$_8$)cycloalkyl group, wherein R$_1$ and R$_2$ are not simultaneously H; M is —N(R$_3$)—; R$_3$ is H; R$_4$ is a group of formula J1 wherein R$_5$ is a group of formula K, wherein p is 0, P is absent, q is 1 and W is H or is selected from the group consisting of (C$_1$-C$_6$)alkyl and aryl.

Still more preferred within this class are the compounds of general formula I wherein W is H or phenyl; R$_1$ is H, R$_2$ is selected from the group consisting of phenyl, biphenyl, napthyl, thiophenyl, pyridinyl, difluorophenyl, methylphenyl, and fluorophenyl; M is —N(H)—; and R$_4$ is selected from the group consisting of quinuclidinyl, benzylpiperidinyl, methylpiperidinyl, benzyl-8-azabicyclo[3.2.1]octan-3-yl and azoniabicyclo[2.2.2]octanyl.

A second group of preferred compounds is that of general formula I wherein Q is a group of formula Q1, Q2, Q3, Q4, Q5 or Q6:

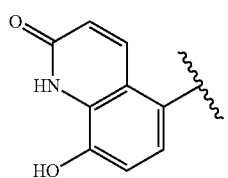

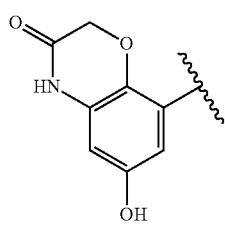

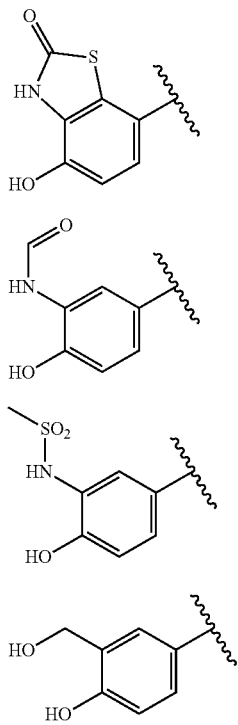
Z is H or OH;
Y1 is a group of formula
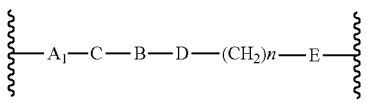
wherein
A1 is $(C_1\text{-}C_{12})$alkylene; C is absent or is selected from the group consisting of —O—, —CO—, —OC(O)— or is a group of formula C1-C18:
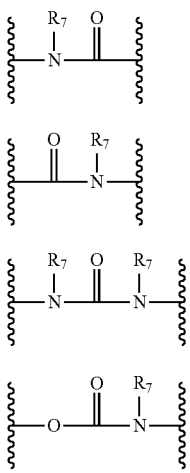
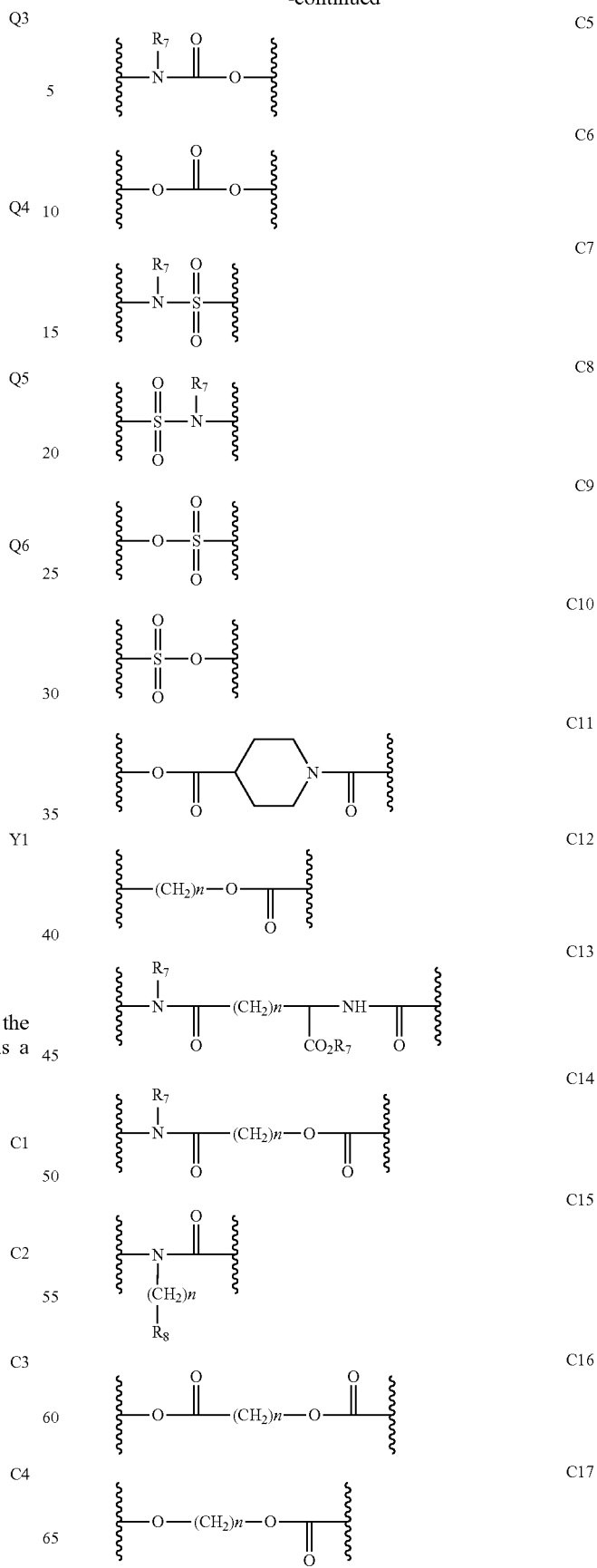

-continued

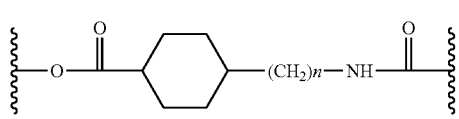
C18 wherein $R_7$ is H or is selected from the group consisting of linear or branched $(C_1-C_8)$alkyl, $(C_3-C_8)$cycloalkyl, $(C_3-C_8)$ heterocycloalkyl, aryl, $(C_1-C_6)$arylalkyl, $(C_1-C_6)$alkoxy$(C_1-C_6)$alkyl, and heteroaryl and $R_8$ is $(C_1-C_8)$alkoxycarbonyl; B is absent or is selected from the group consisting of $(C_3-C_8)$ cycloalkylene, arylene, and heteroarylene, optionally substituted by one or more groups selected from halogens, nitrile, $(C_1-C_6)$alkyl, $(C_1-C_6)$alkoxy, and aryl$(C_1-C_6)$alkyl; D is absent or is selected from the group consisting of $(C_1-C_{12})$ alkylene, $-C(CH_3)_2-$, heteroarylene, and arylene; n is 0 or an integer from 1 to 2; E is $-O-$; G is arylene or heteroarylene, optionally substituted by one or more substituents selected from the group consisting of halogen atoms, $-OH$, oxo $(=O)$, $-SH$, $-NO_2$, $-CN$, $-CON(R_6)_2$, $-NH_2$, $-NHCOR_6$, $-CO_2R_6$, $(C_1-C_{10})$alkylsulfanyl, $(C_1-C_{10})$ alkylsulfinyl, $(C_1-C_{10})$alkylsulfonyl, $(C_1-C_{10})$alkyl, aryl, haloaryl, heteroaryl, and $(C_1-C_{10})$alkoxy; and $R_1$, $R_2$, M and $R_4$ are as defined above.

Still more preferred within this second group, are the compounds of general formula I, wherein Q is Q1

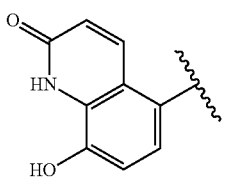
Q1

Z is $-OH$, A1 is selected from $(C_1-C_{12})$alkylene and $(C_3-C_8)$ heterocycloalkylene; C is absent or is selected from the group consisting of $-O-$, $-CO-$, $-OC(O)-$, C11, C13, C14, C16, C17, C18 wherein $R_7$ is H or linear or branched $(C_1-C_8)$ alkyl, C7 wherein $R_7$ is H and C15 wherein $R_8$ is $(C_1-C_8)$ alkoxycarbonyl; B is absent or is selected from the group consisting of $(C_3-C_8)$cycloalkylene, $(C_3-C_8)$heterocycloalkylene, arylene, and heteroarylene, optionally substituted by one or more halogens; D is absent or is selected from the group consisting of $(C_1-C_{12})$alkylene, $-C(CH_3)_2-$, arylene, and heteroarylene; n is 0 or an integer from 1 to 2; E is $-O-$; G is arylene, optionally substituted by one or more substituents selected from the group consisting of halogen atoms, aryl, and heteroaryl.

Still more preferred within this class, are the compounds of general formula I, wherein A1 is selected from the group consisting of methylene, ethylene, propylene, butylene, pentylene, and hexylene; C is absent or is selected from the group consisting of $-O-$, $-CO-$, $-OC(O)-$, C11, C13, C14, C16, C17, C18 wherein $R_7$ is H or is selected from the group consisting of methyl, ethyl, and isopropyl and C15 wherein n is 0 or 1 and $R_8$ is ethoxycarbonyl; B is absent or is selected from phenylene, piperidinylene, cyclopropylene, cyclohexylene, piridinediyl, furanediyl, and oxazolediyl, optionally substituted by one or more halogens; D is absent or is selected from methylene, $-C(CH_3)_2-$, phenylene, and oxadiazolylene; n is 0 or an integer from 1 to 2; E is $-O-$; G is selected from phenylene and biphenylene, optionally substituted by one or more substituents selected from the group consisting of fluorine, phenyl, and 2-thiophenyl.

Even still more preferred within this class are the compounds of general formula I, wherein A1 is selected from the group consisting of methylene, ethylene, propylene, butylene, pentylene, and hexylene; C is absent or is selected from the group consisting of $-O-$, $-CO-$, $-OC(O)-$, C11, C13, C14, C16, C17, C18 wherein $R_7$ is H or is selected from the group consisting of methyl, ethyl, and isopropyl and C15 wherein n is 0 or 1 and $R_8$ is ethoxycarbonyl; B is absent or is selected from phenylene, piperidinylene, cyclopropylene, cyclohexylene, piridinediyl, furanediyl, and oxazolediyl, optionally substituted by one or more halogens; D is absent or is selected from methylene, $-C(CH_3)_2-$, phenylene, and oxadiazolylene; n is 0 or an integer from 1 to 2; E is $-O-$; G is selected from phenylene and biphenylene, optionally substituted by one or more substituents selected from the group consisting of fluorine, phenyl, and 2-thiophenyl; $R_1$ is H, $R_2$ is selected from the group consisting of phenyl, cyclohexyl, fluorophenyl, and chlorophenyl, M is $-N(H)-$, $R_4$ is a group of formula J1

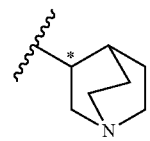
J1 or J3

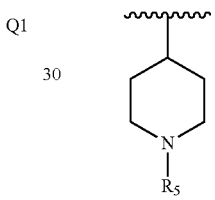
J3 or J4

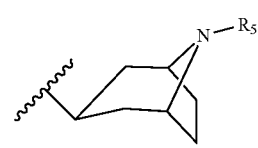
J4 or J5

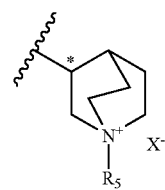
J5 wherein $R_5$ is a group of formula K

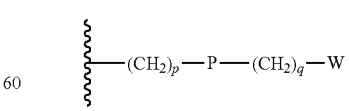
K wherein p is 0 or 1, P is absent or is CO, q is absent or is 1 and W is H or is selected from the group consisting of $(C_1-C_6)$ alkyl and aryl.

Even still more preferred within this class, are the compounds of general formula I, wherein A1 is selected from the group consisting of methylene, ethylene, propylene, butylene, pentylene, and hexylene; C is absent or is selected from the group consisting of —O—, —CO—, —OC(O)—, C11, C13, C14, C16, C17 and C18 wherein $R_7$ is H or is selected from the group consisting of methyl, ethyl, and isopropyl and C15 wherein n is 0 or 1 and $R_8$ is ethoxycarbonyl; B is absent or is selected from phenylene, piperidinylene, cyclopropylene, cyclohexylene, piridinediyl, furanediyl, and oxazolediyl, optionally substituted by one or more halogens; D is absent or is selected from methylene, —C(CH$_3$)$_2$—, phenylene, and oxadiazolylene; n is 1; E is —O—; G is phenylene optionally substituted by one or more substituents selected from the group consisting of phenyl and 2-thiophenyl; $R_1$ is H, $R_2$ is selected from the group consisting of phenyl, cyclohexyl, fluorophenyl, and chlorophenyl, M is —N(H)—, $R_4$ is a group of formula J1 or J5, wherein $R_5$ is a group of formula K, wherein p is 0 or an integer from 1 to 4; q is 0 or an integer from 1 to 4; P is absent or is selected from the group consisting of —O and —C(O)—; W is aryl; and G, Y, Z and Q are as defined above.

The present invention is also directed to a process for the preparation of the compounds of general formula I, which process comprises the reaction of a compound of general formula XIX:

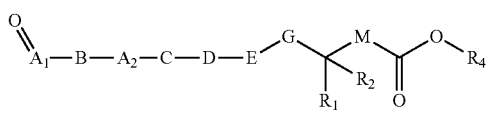

XIX with a compound of general formula XX

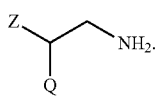

XX

The present invention is also directed to a process for the preparation of the compounds of general formula I

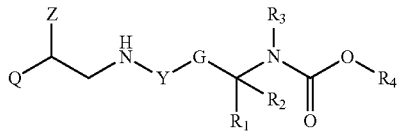

I which process comprises the reaction of a compound of general formula XXVII

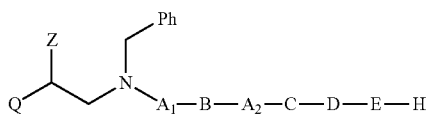

XXVII with a compound of formula XXIX

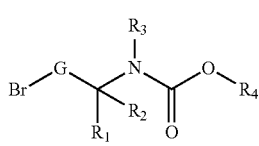

XXIX under the transition metal catalyzed cross-coupling reaction condition.

The present invention is also directed to a process for the preparation of the compounds of general formula I, which process comprises the reaction of a compound of general formula XXIV

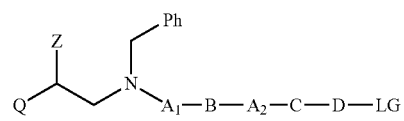

XXIV with a compound of formula XXX

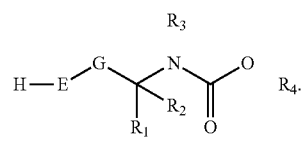

XXX

The present invention is also directed to a process for the preparation of the compounds of general formula I wherein $R_4$ is J5

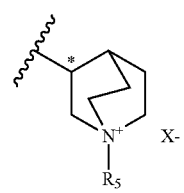

J5 this process comprising the reaction of the corresponding tertiary amine precursor of formula I wherein $R_5$ is a J1-J4 group

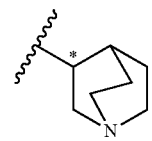

J1

J2

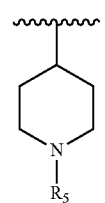

J3

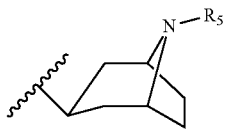

with a compound of formula XXXI

R$_5$-LG  XXXI

The present invention is also directed to a process for the preparation of the compounds of general formula I wherein M is —NR$_3$—, this process comprising the treatment of a compound of general formula XV

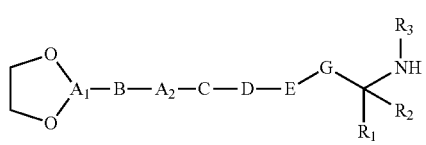

XV with a compound of general formula XVII

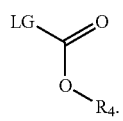

XVII

The present invention is also directed to a process for the preparation of the compounds of general formula I wherein M is —NR$_3$—, this process comprising the treatment of a compound of general formula XXXIX

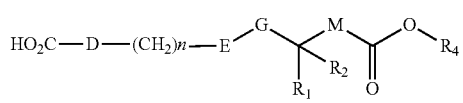

XXXIX with a compound of general formula XL followed by removal of the protecting group (PG)

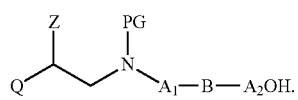

XL

The present invention is also directed to a process for the preparation of a compound of general formula XXXIV $$H-E-G \atop R_2 -NH_2$$

XXXIV in its two enantiomeric forms, by mean of crystallization of the corresponding diasteromeric salt, obtained by salification of the racemic mixture with an enantiomerically pure carboxylic acid.

The present invention also provides pharmaceutical compositions of compounds of formula I alone or in combination with or in admixture with one or more pharmaceutically acceptable carriers and/or excipients.

The present invention also provides the use of compounds of formula I for preparing a medicament.

In a further aspect, the present invention provides the use of compounds of formula I for the prevention and/or treatment of any broncho-obstructive or inflammatory disease, preferably asthma or chronic bronchitis or chronic obstructive pulmonary disease (COPD).

In a further aspect, the present invention provides the use of compounds of formula I for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a compound of general formula I.

The present invention also provides pharmaceutical compositions suitable for administration by inhalation. Inhalable preparations include inhalable powders, propellant-containing metering aerosols or propellant-free inhalable formulations.

The present invention is also directed to a device which may be a single- or multi-dose dry powder inhaler, a metered dose inhaler and a soft mist nebulizer comprising the compounds of formula I.

The present invention is also directed to kit comprising a pharmaceutical composition of a compound of formula I alone or in combination with or in admixture with one or more pharmaceutically acceptable carriers and/or excipients and a device which may be a single- or multi-dose dry powder inhaler, a metered dose inhaler and a soft mist nebulizer comprising the compounds of general formula I.

According to specific embodiments, the present invention provides the compounds reported below:

| Compound | Chemical Name |
|---|---|
| 1 | (R)-quinuclidin-3-yl (3-(9-((R)-2-hydroxy-2-(8-hydroxy-2-oxo-1,2-dihydroquinolin-5-yl)ethylamino)nonyloxy)phenyl)(phenyl)methylcarbamate |
| 2 | (R)-quinuclidin-3-yl (3-(8-((R)-2-hydroxy-2-(8-hydroxy-2-oxo-1,2-dihydroquinolin-5-yl)ethylamino)octyloxy)phenyl)(phenyl)methylcarbamate |
| 3 | (R)-quinuclidin-3-yl(3-(7-((R)-2-hydroxy-2-(8-hydroxy-2-oxo-1,2-dihydroquinolin-5-yl)ethylamino)heptyloxy)phenyl)(phenyl)methylcarbamate |

-continued

| Compound | Chemical Name |
|---|---|
| 4 | (R)-quinuclidin-3-yl (3-(6-((R)-2-hydroxy-2-(8-hydroxy-2-oxo-1,2-dihydroquinolin-5-yl)ethylamino)hexyloxy)phenyl)(phenyl)methylcarbamate |
| 5 | (R)-quinuclidin-3-yl (3-(5-((R)-2-hydroxy-2-(8-hydroxy-2-oxo-1,2-dihydroquinolin-5-yl)ethylamino)pentyloxy)phenyl)(phenyl)methylcarbamate |
| 6 | 1-benzylpiperidin-4-yl (3-(9-((R)-2-hydroxy-2-(8-hydroxy-2-oxo-1,2-dihydroquinolin-5-yl)ethylamino)nonyloxy)phenyl)(phenyl)methylcarbamate |
| 7 | 1-methylpiperidin-4-yl (3-(9-((R)-2-hydroxy-2-(8-hydroxy-2-oxo-1,2-dihydroquinolin-5-yl)ethylamino)nonyloxy)phenyl)(phenyl)methylcarbamate |
| 8 | 8-benzyl-8-azabicyclo[3.2.1]octan-3-yl (3-(9-((R)-2-hydroxy-2-(8-hydroxy-2-oxo-1,2-dihydroquinolin-5-yl)ethylamino)nonyloxy)phenyl)(phenyl)methylcarbamate |
| 9 | (R)-quinuclidin-3-yl (4-(9-((R)-2-hydroxy-2-(8-hydroxy-2-oxo-1,2-dihydroquinolin-5-yl)ethylamino)nonyloxy)phenyl)(phenyl)methylcarbamate |
| 10 | (R)-quinuclidin-3-yl (3-(9-((R)-2-hydroxy-2-(8-hydroxy-2-oxo-1,2-dihydroquinolin-5-yl)ethylamino)nonyloxy)phenyl)(thiophen-2-yl)methylcarbamate |
| 11 | (R)-quinuclidin-3-yl biphenyl-4-yl(3-(9-((R)-2-hydroxy-2-(8-hydroxy-2-oxo-1,2-dihydroquinolin-5-yl)ethylamino)nonyloxy)phenyl)methylcarbamate |
| 12 | (R)-quinuclidin-3-yl (3-(9-((R)-2-hydroxy-2-(8-hydroxy-2-oxo-1,2-dihydroquinolin-5-yl)ethylamino)nonyloxy)phenyl)(naphthalen-1-yl)methylcarbamate |
| 13 | (R)-quinuclidin-3-yl biphenyl-3-yl(3-(9-((R)-2-hydroxy-2-(8-hydroxy-2-oxo-1,2-dihydroquinolin-5-yl)ethylamino)nonyloxy)phenyl)methylcarbamate |
| 14 | (R)-quinuclidin-3-yl (3-(9-((R)-2-hydroxy-2-(8-hydroxy-2-oxo-1,2-dihydroquinolin-5-yl)ethylamino)nonyloxy)phenyl)(pyridin-2-yl)methylcarbamate |
| 15 | (R)-quinuclidin-3-yl (3,5-difluorophenyl)(3-(9-((R)-2-hydroxy-2-(8-hydroxy-2-oxo-1,2-dihydroquinolin-5-yl)ethylamino)nonyloxy)phenyl)methylcarbamate |
| 16 | (R)-quinuclidin-3-yl (3,4,5-difluorophenyl)(3-(9-((R)-2-hydroxy-2-(8-hydroxy-2-oxo-1,2-dihydroquinolin-5-yl)ethylamino)nonyloxy)phenyl)methylcarbamate |
| 17 | (R)-quinuclidin-3-yl (3-(9-((R)-2-hydroxy-2-(8-hydroxy-2-oxo-1,2-dihydroquinolin-5-yl)ethylamino)nonyloxy)phenyl)(o-tolyl)methylcarbamate |
| 18 | (R)-quinuclidin-3-yl (3-(9-((R)-2-hydroxy-2-(8-hydroxy-2-oxo-1,2-dihydroquinolin-5-yl)ethylamino)nonyloxy)phenyl)(m-tolyl)methylcarbamate |
| 19 | (R)-quinuclidin-3-yl (3-(9-((R)-2-hydroxy-2-(8-hydroxy-2-oxo-1,2-dihydroquinolin-5-yl)ethylamino)nonyloxy)phenyl)(p-tolyl)methylcarbamate |
| 20 | (R)-quinuclidin-3-yl (4-difluorophenyl)(3-(9-((R)-2-hydroxy-2-(8-hydroxy-2-oxo-1,2-dihydroquinolin-5-yl)ethylamino)nonyloxy)phenyl)methylcarbamate |
| 1B | (R)-quinuclidin-3-yl (3-fluorophenyl)(3-(9-((R)-2-hydroxy-2-(8-hydroxy-2-oxo-1,2-dihydroquinolin-5-yl)ethylamino)nonyloxy)phenyl)methylcarbamate |
| 2B | (R)-quinuclidin-3-yl (3-chlorophenyl)(3-(9-((R)-2-hydroxy-2-(8-hydroxy-2-oxo-1,2-dihydroquinolin-5-yl)ethylamino)nonyloxy)phenyl)methylcarbamate |
| 1C | (R)-quinuclidin-3-yl (cyclohexyl(3-((9-(((R)-2-hydroxy-2-(8-hydroxy-2-oxo-1,2-dihydroquinolin-5-yl)ethyl)amino)nonyl)oxy)phenyl)methyl)carbamate |
| 2C | (R)-quinuclidin-3-yl ((3-((6-(((R)-2-hydroxy-2-(8-hydroxy-2-oxo-1,2-dihydroquinolin-5-yl)ethyl)amino)hexyl)oxy)phenyl)(thiophen-2-yl)methyl)carbamate |
| 3C | (R)-quinuclidin-3-yl ((3-((6-(((R)-2-hydroxy-2-(8-hydroxy-2-oxo-1,2-dihydroquinolin-5-yl)ethyl)amino)hexyl)oxy)phenyl)(thiophen-3-yl)methyl)carbamate |
| 21 | (R)-quinuclidin-3-yl (3-(9-(2-(4-hydroxy-2-oxo-2,3-dihydrobenzo[d]thiazol-7-yl)ethylamino)nonyloxy)phenyl)(phenyl)methylcarbamate |
| 22 | (R)-quinuclidin-3-yl (3-(4-(2-((R)-2-hydroxy-2-(8-hydroxy-2-oxo-1,2-dihydroquinolin-5-yl)ethylamino)ethyl)benzyloxy)phenyl)(phenyl)methylcarbamate |
| 23 | (R)-quinuclidin-3-yl (3-(2-((R)-2-hydroxy-2-(8-hydroxy-2-oxo-1,2-dihydroquinolin-5-yl)ethylamino)ethyl)phenyl)(phenyl)methylcarbamate |
| 24 | (3R)-3-((3-(6-((R)-2-hydroxy-2-(8-hydroxy-2-oxo-1,2-dihydroquinolin-5-yl)ethylamino)hexyloxy)phenyl)(phenyl)methylcarbamoyloxy)-1-(2-oxo-2-phenylethyl)-1-azoniabicyclo[2.2.2]octane |

-continued

| Compound | Chemical Name |
|---|---|
| 3B | (R)-quinuclidin-3-yl (3-(3-(2-((R)-2-hydroxy-2-(8-hydroxy-2-oxo-1,2-dihydroquinolin-5-yl)ethylamino)ethyl)benzyloxy)phenyl)(phenyl)methylcarbamate formate |
| 4B | (3R)-3-((((3-((4-(2-(((R)-2-hydroxy-2-(((8-hydroxy-2-oxo-1,2-dihydroquinolin-5-yl)ethyl)amino)ethyl)benzyl)oxy)phenyl)(phenyl)methyl)carbamoyl)oxy)-1-(2-oxo-2-phenylethyl)quinuclidin-1-ium |
| 5B | (3R)-3-((((3-chlorophenyl)(3-((9-(((R)-2-hydroxy-2-(8-hydroxy-2-oxo-1,2-dihydroquinolin-5-yl)ethyl)amino)nonyl)oxy)phenyl)methyl)carbamoyl)oxy)-1-(2-oxo-2-phenylethyl)quinuclidin-1-ium |
| 6B | (3R)-3-((((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium |
| 7B | (R)-quinuclidin-3-yl (2-chloro-3-(9-((R)-2-hydroxy-2-(8-hydroxy-2-oxo-1,2-dihydroquinolin-5-yl)ethylamino)nonyloxy)phenyl)(phenyl)methylcarbamate |
| 8B | (R)-quinuclidin-3-yl ((2,6-difluoro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamate |
| 9B | (R)-quinuclidin-3-yl ((2-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate |
| 10B | (3R)-3-((((2-chloro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium |
| 11B | (3R)-3-((((2,6-difluoro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium |
| 12B | (3R)-3-((((2-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium |
| 13B | (3R)-3-((((3-((9-(((R)-2-hydroxy-2-(8-hydroxy-2-oxo-1,2-dihydroquinolin-5-yl)ethyl)amino)nonyl)oxy)-4-methylphenyl)(phenyl)methyl)carbamoyl)oxy)-1-(2-oxo-2-phenylethyl)quinuclidin-1-ium |
| 14B | (R)-quinuclidin-3-yl ((3-((9-(((R)-2-hydroxy-2-(8-hydroxy-2-oxo-1,2-dihydroquinolin-5-yl)ethyl)amino)nonyl)oxy)-4-methoxyphenyl)(phenyl)methyl)carbamate |
| 15B | (R)-quinuclidin-3-yl ((3-((9-(((R)-2-hydroxy-2-(8-hydroxy-2-oxo-1,2-dihydroquinolin-5-yl)ethyl)amino)nonyl)oxy)-5-methoxyphenyl)(phenyl)methyl)carbamate |
| 16B | (3R)-3-((((3-((9-(((R)-2-hydroxy-2-(8-hydroxy-2-oxo-1,2-dihydroquinolin-5-yl)ethyl)amino)nonyl)oxy)-4-methoxyphenyl)(phenyl)methyl)carbamoyl)oxy)-1-(2-oxo-2-phenylethyl)quinuclidin-1-ium |
| 17B | (3R)-3-((((3-((9-(((R)-2-hydroxy-2-(8-hydroxy-2-oxo-1,2-dihydroquinolin-5-yl)ethyl)amino)nonyl)oxy)-5-methoxyphenyl)(phenyl)methyl)carbamoyl)oxy)-1-(2-oxo-2-phenylethyl)quinuclidin-1-ium |
| 18B | (3R)-3-((((5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)methyl)carbamoyl)oxy)-1-(2-oxo-2-phenylethyl)quinuclidin-1-ium |
| 19B | (R)-quinuclidin-3-yl (3-(9-((R)-2-hydroxy-2-(8-hydroxy-2-oxo-1,2-dihydroquinolin-5-yl)ethylamino)nonyloxy)-5-(thiophen-2-yl)phenyl)(phenyl)methylcarbamate |
| 20B | (3R)-3-((((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamoyl)oxy)-1-(2-oxo-2-phenylethyl)quinuclidin-1-ium |
| 21B | (3R)-3-((((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamoyl)oxy)-1-(2-phenoxyethyl)quinuclidin-1-ium |
| 22B | (3R)-3-((((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)carbamoyl)oxy)-1-(2-oxo-2-phenylethyl)quinuclidin-1-ium |
| 23B | (3R)-3-((((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)carbamoyl)oxy)-1-(2-phenoxyethyl)quinuclidin-1-ium |

| Compound | Chemical Name |
|---|---|
| 24B | (R)-quinuclidin-3-yl (3-fluorophenyl)(3-(6-((R)-2-hydroxy-2-(8-hydroxy-2-oxo-1,2-dihydroquinolin-5-yl)ethylamino)hexyloxy)phenyl)methylcarbamate |
| 25B | (3R)-3-((((3-((5-(((R)-2-hydroxy-2-(8-hydroxy-2-oxo-1,2-dihydroquinolin-5-yl)ethyl)amino)pentyl)oxy)phenyl)(phenyl)methyl)carbamoyl)oxy)-1-(4-phenylbutyl)quinuclidin-1-ium |
| 26B | (R)-Quinuclidin-3-yl (3-fluorophenyl)(3-(3-(2-((R)-2-hydroxy-2-(8-hydroxy-2-oxo-1,2-dihydroquinolin-5-yl)ethylamino)ethyl)benzyloxy)phenyl)methylcarbamate |
| 27B | (3R)-3-((((3-fluorophenyl)(3-((3-(2-(((R)-2-hydroxy-2-(8-hydroxy-2-oxo-1,2-dihydroquinolin-5-yl)ethyl)amino)ethyl)benzyl)oxy)phenyl)methyl)carbamoyl)oxy)-1-(2-oxo-2-phenylethyl)quinuclidin-1-ium |
| 28B | (3R)-3-((((3-((4-(((((R)-2-hydroxy-2-(8-hydroxy-2-oxo-1,2-dihydroquinolin-5-yl)ethyl)amino)methyl)benzyl)oxy)phenyl)(phenyl)methyl)carbamoyl)oxy)-1-(2-oxo-2-phenylethyl)quinuclidin-1-ium |
| 29B | (R)-Quinuclidin-3-yl (3-((4'-(2-((R)-2-hydroxy-2-(8-hydroxy-2-oxo-1,2-dihydroquinolin-5-yl)ethylamino)ethyl)biphenyl-3-yl)methoxy)phenyl)(phenyl)methylcarbamate |
| 30B | (R)-quinuclidin-3-yl ((3-((4-((4-(((R)-2-hydroxy-2-(8-hydroxy-2-oxo-1,2-dihydroquinolin-5-yl)ethyl)amino)butyl)carbamoyl)benzyl)oxy)phenyl)(phenyl)methyl)carbamate |
| 31B | (R)-quinuclidin-3-yl (3-(4-(3-((R)-2-hydroxy-2-(8-hydroxy-2-oxo-1,2-dihydroquinolin-5-yl)ethylamino)propylcarbamoyl)benzyloxy)phenyl)(phenyl)methylcarbamate |
| 32B | (3R)-3-((((3-((4-((3-(((R)-2-hydroxy-2-(8-hydroxy-2-oxo-1,2-dihydroquinolin-5-yl)ethyl)amino)propyl)carbamoyl)benzyl)oxy)phenyl)(phenyl)methyl)carbamoyl)oxy)-1-(2-oxo-2-phenylethyl)quinuclidin-1-ium |
| 33B | 4-(((R)-2-Hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)phenoxy)methyl)benzoate |
| 34B | 5-((R)-2-hydroxy-2-(8-hydroxy-2-oxo-1,2-dihydroquinolin-5-yl)ethylamino)pentyl 4-((3-(phenyl(((R)-quinuclidin-3-yloxy)carbonylamino)methyl)phenoxy)methyl)benzoate |
| 35B | 6-((R)-2-hydroxy-2-(8-hydroxy-2-oxo-1,2-dihydroquinolin-5-yl)ethylamino)hexyl 4-((3-(phenyl(((R)-quinuclidin-3-yloxy)carbonylamino)methyl)phenoxy)methyl)benzoate |
| 4C | 7-(((R)-2-hydroxy-2-(8-hydroxy-2-oxo-1,2-dihydroquinolin-5-yl)ethyl)amino)heptyl 4-((3-(phenyl((((R)-quinuclidin-3-yloxy)carbonyl)amino)methyl)phenoxy)methyl)benzoate |
| 5C | 4-((((R)-2-hydroxy-2-(8-hydroxy-2-oxo-1,2-dihydroquinolin-5-yl)ethyl)amino)methyl)benzyl 4-((3-(phenyl((((R)-quinuclidin-3-yloxy)carbonyl)amino)methyl)phenoxy)methyl)benzoate |
| 6C | 4-(2-(((R)-2-hydroxy-2-(8-hydroxy-2-oxo-1,2-dihydroquinolin-5-yl)ethyl)amino)ethyl)phenyl 4-((3-(phenyl((((R)-quinuclidin-3-yloxy)carbonyl)amino)methyl)phenoxy)methyl)benzoate |
| 7C | 4-((((R)-2-hydroxy-2-(8-hydroxy-2-oxo-1,2-dihydroquinolin-5-yl)ethyl)amino)methyl)phenyl 4-((3-(phenyl((((R)-quinuclidin-3-yloxy)carbonyl)amino)methyl)phenoxy)methyl)benzoate |
| 8C | 4-(2-(((R)-2-hydroxy-2-(8-hydroxy-2-oxo-1,2-dihydroquinolin-5-yl)ethyl)amino)ethyl)benzyl 4-((3-(phenyl((((R)-quinuclidin-3-yloxy)carbonyl)amino)methyl)phenoxy)methyl)benzoate |
| 36B | (3R)-3-((((3-((4-(1-((4-(((R)-2-hydroxy-2-(8-hydroxy-2-oxo-1,2-dihydroquinolin-5-yl)ethyl)amino)butoxy)carbonyl)-cyclopropyl)benzyl)oxy)phenyl)(phenyl)methyl)carbamoyl)oxy)-1-(2-oxo-2-phenylethyl)quinuclidin-1-ium |
| 37B | (R)-quinuclidin-3-yl (3-(2-(3'-(((R)-2-hydroxy-2-(8-hydroxy-2-oxo-1,2-dihydroquinolin-5-yl)ethylamino)methyl)biphenyl-4-yl)ethoxy)phenyl)(phenyl)methylcarbamate |
| 38B | (R)-quinuclidin-3-yl (3-(2-(3'-(((R)-2-hydroxy-2-(8-hydroxy-2-oxo-1,2-dihydroquinolin-5-yl)ethylamino)methyl)biphenyl-4-yl)ethoxy)phenyl)(phenyl)methylcarbamate |
| 39B | 6-((R)-2-hydroxy-2-(8-hydroxy-2-oxo-1,2-dihydroquinolin-5-yl)ethylamino)hexyl 2-(3-(phenyl(((R)-quinuclidin-3-yloxy)carbonylamino)methyl)phenoxy)acetate |
| 40B | (R)-quinuclidin-3-yl ((3-((6-(((R)-2-hydroxy-2-(8-hydroxy-2-oxo-1,2-dihydroquinolin-5-yl)ethyl)amino)hexyl)oxy)phenyl)(phenyl)methyl)carbamate |
| 41B | (R)-quinuclidin-3-yl ((3-((6-(((R)-2-hydroxy-2-(8-hydroxy-2-oxo-1,2-dihydroquinolin-5-yl)ethyl)amino)hexyl)oxy)phenyl)(phenyl)methyl)carbamate |
| 42B | (3R)-3-((((3-((6-(((R)-2-hydroxy-2-(8-hydroxy-2-oxo-1,2-dihydroquinolin-5-yl)ethyl)amino)hexyl)oxy)phenyl)(phenyl)methyl)carbamoyl)oxy)-1-(2-oxo-2-phenylethyl)quinuclidin-1-ium |

| Compound | Chemical Name |
|---|---|
| 43B | (3R)-3-((((3-((6-(((R)-2-hydroxy-2-(8-hydroxy-2-oxo-1,2-dihydroquinolin-5-yl)ethyl)amino)hexyl)oxy)phenyl)(phenyl)methyl)carbamoyl)oxy)-1-(2-oxo-2-phenylethyl)quinuclidin-1-ium |
| 44B | 4-(((R)-2-hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)phenoxy)methyl)benzoate |
| 45B | 4-(((R)-2-hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)phenoxy)methyl)benzoate |
| 9C | 5-(((R)-2-hydroxy-2-(8-hydroxy-2-oxo-1,2-dihydroquinolin-5-yl)ethyl)amino)pentyl 2-(3-(phenyl((((R)-quinuclidin-3-yloxy)carbonyl)amino)methyl)phenoxy)acetate |
| 10C | 4-(((R)-2-hydroxy-2-(8-hydroxy-2-oxo-1,2-dihydroquinolin-5-yl)ethyl)amino)butyl 2-(3-(phenyl(((((R)-quinuclidin-3-yloxy)carbonyl)amino)methyl)phenoxy)acetate |
| 11C | 5-(((R)-2-hydroxy-2-(8-hydroxy-2-oxo-1,2-dihydroquinolin-5-yl)ethyl)amino)pentyl 2-methyl-2-(3-(phenyl(((((R)-quinuclidin-3-yloxy)carbonyl)amino)methyl)phenoxy)propanoate |
| 12C | 4-(((R)-2-hydroxy-2-(8-hydroxy-2-oxo-1,2-dihydroquinolin-5-yl)ethyl)amino)butyl 2-methyl-2-(3-(phenyl((((R)-quinuclidin-3-yloxy)carbonyl)amino)methyl)phenoxy)propanoate |
| 13C | 5-(((R)-2-hydroxy-2-(8-hydroxy-2-oxo-1,2-dihydroquinolin-5-yl)ethyl)amino)pentyl 2,2-dimethyl-3-(3-(phenyl(((((R)-quinuclidin-3-yloxy)carbonyl)amino)methyl)phenoxy)propanoate |
| 14C | 4-(((R)-2-hydroxy-2-(8-hydroxy-2-oxo-1,2-dihydroquinolin-5-yl)ethyl)amino)butyl 1-(2-(3-(phenyl(((((R)-quinuclidin-3-yloxy)carbonyl)amino)methyl)phenoxy)acetyl)piperidine-4-carboxylate |
| 15C | 4-(2-(((R)-2-hydroxy-2-(8-hydroxy-2-oxo-1,2-dihydroquinolin-5-yl)ethyl)amino)ethyl)benzyl 2-(3-(phenyl(((((R)-quinuclidin-3-yloxy)carbonyl)amino)methyl)phenoxy)acetate |
| 16C | (R)-quinuclidin-3-yl ((3-((9-(((R)-2-hydroxy-2-(8-hydroxy-2-oxo-1,2-dihydroquinolin-5-yl)ethyl)amino)nonyl)oxy)-4-methylphenyl)(phenyl)methyl)carbamate |
| 17C | (R)-Quinuclidin-3-yl ((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate |
| 18C | (R)-quinuclidin-3-yl ((5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)methyl)carbamate |
| 19C | (R)-quinuclidin-3-yl ((2-bromo-3-((9-(((R)-2-hydroxy-2-(8-hydroxy-2-oxo-1,2-dihydroquinolin-5-yl)ethyl)amino)nonyl)oxy)phenyl)(phenyl)methyl)carbamate |
| 20C | (R)-quinuclidin-3-yl ((3'-fluoro-5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)methyl)carbamate |
| 21C | (R)-quinuclidin-3-yl ((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamate |
| 22C | (R)-quinuclidin-3-yl ((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)carbamate |
| 23C | (3R)-3-((((cyclohexyl(3-((9-(((R)-2-hydroxy-2-(8-hydroxy-2-oxo-1,2-dihydroquinolin-5-yl)ethyl)amino)nonyl)oxy)phenyl)methyl)carbamoyl)oxy)-1-(2-oxo-2-phenylethyl)quinuclidin-1-ium |
| 24C | (3R)-3-((((3-((6-(((R)-2-hydroxy-2-(8-hydroxy-2-oxo-1,2-dihydroquinolin-5-yl)ethyl)amino)hexyl)oxy)phenyl)(thiophen-2-yl)methyl)carbamoyl)oxy)-1-(2-oxo-2-phenylethyl)quinuclidin-1-ium |
| 25C | (3R)-3-((((3-fluorophenyl)(3-((6-(((R)-2-hydroxy-2-(8-hydroxy-2-oxo-1,2-dihydroquinolin-5-yl)ethyl)amino)hexyl)oxy)phenyl)methyl)carbamoyl)oxy)-1-(2-oxo-2-phenylethyl)quinuclidin-1-ium |
| 26C | (3R)-3-((((3-((6-(((R)-2-hydroxy-2-(8-hydroxy-2-oxo-1,2-dihydroquinolin-5-yl)ethyl)amino)hexyl)oxy)phenyl)(thiophen-3-yl)methyl)carbamoyl)oxy)-1-(2-oxo-2-phenylethyl)quinuclidin-1-ium |
| 27C | (3R)-3-((((3-((4-((4-(((R)-2-hydroxy-2-(8-hydroxy-2-oxo-1,2-dihydroquinolin-5-yl)ethyl)amino)butyl)carbamoyl)benzyl)oxy)phenyl)(phenyl)methyl)carbamoyl)oxy)-1-(2-oxo-2-phenylethyl)quinuclidin-1-ium |
| 28C | (3R)-3-((((3-((7-(((R)-2-hydroxy-2-(8-hydroxy-2-oxo-1,2-dihydroquinolin-5-yl)ethyl)amino)heptyl)oxy)phenyl)(phenyl)methyl)carbamoyl)oxy)-1-(2-oxo-2-phenylethyl)quinuclidin-1-ium |
| 29C | (3R)-3-((((3-((7-(((R)-2-hydroxy-2-(8-hydroxy-2-oxo-1,2-dihydroquinolin-5-yl)ethyl)amino)heptyl)oxy)phenyl)(phenyl)methyl)carbamoyl)oxy)-1-(3-phenylpropyl)quinuclidin-1-ium |

-continued

| Compound | Chemical Name |
|---|---|
| 30C | (3R)-3-((((3-((5-(((R)-2-hydroxy-2-(8-hydroxy-2-oxo-1,2-dihydroquinolin-5-yl)ethyl)amino)pentyl)oxy)phenyl)(phenyl)methyl)carbamoyl)oxy)-1-(2-oxo-2-phenylethyl)quinuclidin-1-ium |
| 31C | 4-(((R)-2-hydroxy-2-(8-hydroxy-2-oxo-1,2-dihydroquinolin-5-yl)ethyl)amino)butyl 1-(4-((3-(phenyl((((R)-quinuclidin-3-yloxy)carbonyl)amino)methyl)phenoxy)methyl)phenyl)cyclopentanecarboxylate |
| 32C | 4-(((R)-2-hydroxy-2-(8-hydroxy-2-oxo-1,2-dihydroquinolin-5-yl)ethyl)amino)butyl 1-(4-((3-(phenyl((((R)-quinuclidin-3-yloxy)carbonyl)amino)methyl)phenoxy)methyl)phenyl)cyclohexanecarboxylate |
| 33C | 4-(((R)-2-hydroxy-2-(8-hydroxy-2-oxo-1,2-dihydroquinolin-5-yl)ethyl)amino)butyl 2-methyl-2-(4-((3-(phenyl((((R)-quinuclidin-3-yloxy)carbonyl)amino)methyl)phenoxy)methyl)phenyl)propanoate |
| 34C | 8-(((R)-2-hydroxy-2-(8-hydroxy-2-oxo-1,2-dihydroquinolin-5-yl)ethyl)amino)octyl 3-(phenyl((((R)-quinuclidin-3-yloxy)carbonyl)amino)methyl)benzoate |
| 35C | 9-(((R)-2-hydroxy-2-(8-hydroxy-2-oxo-1,2-dihydroquinolin-5-yl)ethyl)amino)nonyl 3-(phenyl((((R)-quinuclidin-3-yloxy)carbonyl)amino)methyl)benzoate |
| 36C | 7-(((R)-2-hydroxy-2-(8-hydroxy-2-oxo-1,2-dihydroquinolin-5-yl)ethyl)amino)heptyl 3-(phenyl((((R)-quinuclidin-3-yloxy)carbonyl)amino)methyl)benzoate |
| 37C | 6-(((R)-2-hydroxy-2-(8-hydroxy-2-oxo-1,2-dihydroquinolin-5-yl)ethyl)amino)hexyl 3-(phenyl((((R)-quinuclidin-3-yloxy)carbonyl)amino)methyl)benzoate |
| 38C | 5-(((R)-2-hydroxy-2-(8-hydroxy-2-oxo-1,2-dihydroquinolin-5-yl)ethyl)amino)pentyl 3-(phenyl((((R)-quinuclidin-3-yloxy)carbonyl)amino)methyl)benzoate |
| 39C | 4-((4-(((R)-2-hydroxy-2-(8-hydroxy-2-oxo-1,2-dihydroquinolin-5-yl)ethyl)amino)butyl)carbamoyl)benzyl 3-(phenyl((((R)-quinuclidin-3-yloxy)carbonyl)amino)methyl)benzoate |
| 40C | 4-(N-(4-(((R)-2-hydroxy-2-(8-hydroxy-2-oxo-1,2-dihydroquinolin-5-yl)ethyl)amino)butyl)sulfamoyl)benzyl 3-(phenyl((((R)-quinuclidin-3-yloxy)carbonyl)amino)methyl)benzoate |
| 41C | 4-(2-(((R)-2-hydroxy-2-(8-hydroxy-2-oxo-1,2-dihydroquinolin-5-yl)ethyl)amino)ethyl)benzyl 3-(phenyl((((R)-quinuclidin-3-yloxy)carbonyl)amino)methyl)benzoate |
| 42C | 4-(((R)-2-hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)benzamido)methyl)benzoate |
| 43C | (2S)-4-(((R)-2-hydroxy-2-(8-hydroxy-2-oxo-1,2-dihydroquinolin-5-yl)ethyl)amino)butyl 3-phenyl-2-(4-((3-(phenyl((((R)-quinuclidin-3-yloxy)carbonyl)amino)methyl)phenoxy)methyl)benzamido)propanoate |
| 44C | (R)-quinuclidin-3-yl ((3-((3-(4-(2-(((R)-2-hydroxy-2-(8-hydroxy-2-oxo-1,2-dihydroquinolin-5-yl)ethyl)amino)ethyl)phenyl)-1,2,4-oxadiazol-5-yl)methoxy)phenyl)(phenyl)methyl)carbamate |
| 45C | (R)-quinuclidin-3-yl ((5-((9-(((R)-2-hydroxy-2-(8-hydroxy-2-oxo-1,2-dihydroquinolin-5-yl)ethyl)amino)nonyl)oxy)pyridin-3-yl)(phenyl)methyl)carbamate |
| 46C | (R)-quinuclidin-3-yl ((3-fluorophenyl)(5-((9-(((R)-2-hydroxy-2-oxo-1,2-dihydroquinolin-5-yl)ethyl)amino)nonyl)oxy)pyridin-3-yl)methyl)carbamate |
| 47C | 4-(((R)-2-hydroxy-2-(8-hydroxy-2-oxo-1,2-dihydroquinolin-5-yl)ethyl)amino)butyl 2-chloro-4-((3-(phenyl((((R)-quinuclidin-3-yloxy)carbonyl)amino)methyl)phenoxy)methyl)benzoate |
| 48C | 4-(((R)-2-hydroxy-2-(8-hydroxy-2-oxo-1,2-dihydroquinolin-5-yl)ethyl)amino)butyl 2-fluoro-4-((3-(phenyl((((R)-quinuclidin-3-yloxy)carbonyl)amino)methyl)phenoxy)methyl)benzoate |
| 49C | 4-(((R)-2-hydroxy-2-(8-hydroxy-2-oxo-1,2-dihydroquinolin-5-yl)ethyl)amino)butyl 6-((3-(phenyl((((R)-quinuclidin-3-yloxy)carbonyl)amino)methyl)phenoxy)methyl)nicotinate |
| 50C | 4-(((R)-2-hydroxy-2-(8-hydroxy-2-oxo-1,2-dihydroquinolin-5-yl)ethyl)amino)butyl 5-((3-(phenyl((((R)-quinuclidin-3-yloxy)carbonyl)amino)methyl)phenoxy)methyl)furan-2-carboxylate |
| 51C | 4-(((R)-2-hydroxy-2-(8-hydroxy-2-oxo-1,2-dihydroquinolin-5-yl)ethyl)amino)butyl 2-((3-(phenyl((((R)-quinuclidin-3-yloxy)carbonyl)amino)methyl)phenoxy)methyl)oxazole-4-carboxylate |
| 52C | 4-(((R)-2-hydroxy-2-(8-hydroxy-2-oxo-1,2-dihydroquinolin-5-yl)ethyl)amino)butyl 3-((3-(phenyl((((R)-quinuclidin-3-yloxy)carbonyl)amino)methyl)phenoxy)methyl)benzoate |
| 53C | 5-(((R)-2-hydroxy-2-(8-hydroxy-2-oxo-1,2-dihydroquinolin-5-yl)ethyl)amino)pentyl 2-(3-(phenyl((((R)-quinuclidin-3-yloxy)carbonyl)amino)methyl)phenoxy)acetate |
| 54C | 5-(((R)-2-hydroxy-2-(8-hydroxy-2-oxo-1,2-dihydroquinolin-5-yl)ethyl)amino)pentyl 2-(3-(phenyl((((R)-quinuclidin-3-yloxy)carbonyl)amino)methyl)phenoxy)acetate |

-continued

| Compound | Chemical Name |
|---|---|
| 55C | 5-(((R)-2-hydroxy-2-(8-hydroxy-2-oxo-1,2-dihydroquinolin-5-yl)ethyl)amino)hexyl 2-(3-(phenyl((((R)-quinuclidin-3-yloxy)carbonyl)amino)methyl)phenoxy)acetate |
| 56C | 5-(((R)-2-hydroxy-2-(8-hydroxy-2-oxo-1,2-dihydroquinolin-5-yl)ethyl)amino)hexyl 2-(3-(phenyl((((R)-quinuclidin-3-yloxy)carbonyl)amino)methyl)phenoxy)acetate |
| 57C | (R)-quinuclidin-3-yl ((3-((4-((3-(((R)-2-hydroxy-2-(8-hydroxy-2-oxo-1,2-dihydroquinolin-5-yl)ethyl)amino)propyl)carbamoyl)benzyl)oxy)phenyl)(phenyl)methyl)carbamate |
| 58C | (R)-quinuclidin-3-yl ((3-((4-((3-(((R)-2-hydroxy-2-(8-hydroxy-2-oxo-1,2-dihydroquinolin-5-yl)ethyl)amino)ethyl)carbamoyl)benzyl)oxy)phenyl)(phenyl)methyl)carbamate |
| 59C | (R)-quinuclidin-3-yl ((3-((4-(ethyl(3-(((R)-2-hydroxy-2-(8-hydroxy-2-oxo-1,2-dihydroquinolin-5-yl)ethyl)amino)propyl)carbamoyl)benzyl)oxy)phenyl)(phenyl)methyl)carbamate |
| 60C | (R)-quinuclidin-3-yl ((3-((4-((3-(((R)-2-hydroxy-2-(8-hydroxy-2-oxo-1,2-dihydroquinolin-5-yl)ethyl)amino)propyl)(methyl)carbamoyl)benzyl)oxy)phenyl)(phenyl)methyl)carbamate |
| 61C | (R)-quinuclidin-3-yl ((3-((4-((3-(((R)-2-hydroxy-2-(8-hydroxy-2-oxo-1,2-dihydroquinolin-5-yl)ethyl)amino)propyl)(isopropyl)carbamoyl)benzyl)oxy)phenyl)(phenyl)methyl)carbamate |
| 62C | (1R,4R)-4-(((R)-2-hydroxy-2-(8-hydroxy-2-oxo-1,2-dihydroquinolin-5-yl)ethyl)amino)butyl 4-((4-((3-(phenyl((((R)-quinuclidin-3-yloxy)carbonyl)amino)methyl)phenoxy)methyl)benzamido)methyl)cyclohexanecarboxylate |
| 63C | (2S)-methyl 4-((2-(((R)-2-hydroxy-2-(8-hydroxy-2-oxo-1,2-dihydroquinolin-5-yl)ethyl)amino)ethyl)(methyl)amino)-4-oxo-2-(4-((3-(phenyl((((R)-quinuclidin-3-yloxy)carbonyl)amino)methyl)phenoxy)methyl)benzamido)butanoate |
| 64C | ((1R,4R)-4-((((R)-2-hydroxy-2-(8-hydroxy-2-oxo-1,2-dihydroquinolin-5-yl)ethyl)amino)methyl)cyclohexyl)methyl 4-((3-(phenyl(((quinuclidin-4-yloxy)carbonyl)amino)methyl)phenoxy)methyl)benzoate |
| 65C | 2-((4-(((R)-2-hydroxy-2-(8-hydroxy-2-oxo-1,2-dihydroquinolin-5-yl)ethyl)amino)butyl)amino)-2-oxoethyl 4-((3-(phenyl((((R)-quinuclidin-3-yloxy)carbonyl)amino)methyl)phenoxy)methyl)benzoate |
| 66C | 2-((3-(((R)-2-hydroxy-2-(8-hydroxy-2-oxo-1,2-dihydroquinolin-5-yl)ethyl)amino)propyl)amino)-2-oxoethyl 4-((3-(phenyl(((((R)-quinuclidin-3-yloxy)carbonyl)amino)methyl)phenoxy)methyl)benzoate |
| 67C | 2-(4-(((R)-2-hydroxy-2-(8-hydroxy-2-oxo-1,2-dihydroquinolin-5-yl)ethyl)amino)butoxy)-2-oxoethyl 4-((3-(phenyl((((R)-quinuclidin-3-yloxy)carbonyl)amino)methyl)phenoxy)methyl)benzoate |
| 68C | 2-(5-(((R)-2-hydroxy-2-(8-hydroxy-2-oxo-1,2-dihydroquinolin-5-yl)ethyl)amino)pentyl)oxy)-2-oxoethyl 4-((3-(phenyl((((R)-quinuclidin-3-yloxy)carbonyl)amino)methyl)phenoxy)methyl)benzoate |
| 69C | 2-(2-(((R)-2-hydroxy-2-(8-hydroxy-2-oxo-1,2-dihydroquinolin-5-yl)ethyl)amino)ethoxy)ethyl 4-((3-(phenyl((((R)-quinuclidin-3-yloxy)carbonyl)amino)methyl)phenoxy)methyl)benzoate |
| 70C | 2-(4-(((R)-2-hydroxy-2-(8-hydroxy-2-oxo-1,2-dihydroquinolin-5-yl)ethyl)amino)butoxy)ethyl 4-((3-(phenyl((((R)-quinuclidin-3-yloxy)carbonyl)amino)methyl)phenoxy)methyl)benzoate |
| 71C | 2-((5-(((R)-2-hydroxy-2-(8-hydroxy-2-oxo-1,2-dihydroquinolin-5-yl)ethyl)amino)pentyl)oxy)-2-oxoethyl 4-((3-(phenyl((((R)-quinuclidin-3-yloxy)carbonyl)amino)methyl)phenoxy)methyl)benzoate |
| 72C | 2-(2-(((R)-2-hydroxy-2-(8-hydroxy-2-oxo-1,2-dihydroquinolin-5-yl)ethyl)amino)ethoxy)ethyl 4-((3-(phenyl((((R)-quinuclidin-3-yloxy)carbonyl)amino)methyl)phenoxy)methyl)benzoate |
| 73C | 2-(4-(((R)-2-hydroxy-2-(8-hydroxy-2-oxo-1,2-dihydroquinolin-5-yl)ethyl)amino)butoxy)ethyl 4-((3-(phenyl((((R)-quinuclidin-3-yloxy)carbonyl)amino)methyl)phenoxy)methyl)benzoate |
| 74C | 3-(2-(((R)-2-hydroxy-2-(8-hydroxy-2-oxo-1,2-dihydroquinolin-5-yl)ethyl)amino)ethyl)benzyl 4-((3-(phenyl((((R)-quinuclidin-3-yloxy)carbonyl)amino)methyl)phenoxy)methyl)benzoate |
| 75C | 3-(3-(phenyl((((R)-quinuclidin-3-yloxy)carbonyl)amino)methyl)phenoxy)propyl 4-(2-(((R)-2-hydroxy-2-(8-hydroxy-2-oxo-1,2-dihydroquinolin-5-yl)ethyl)amino)ethyl)benzoate |
| 76C | 4-(((R)-2-hydroxy-2-(8-hydroxy-2-oxo-1,2-dihydroquinolin-5-yl)ethyl)amino)butyl 4-(2-(3-(phenyl((((R)-quinuclidin-3-yloxy)carbonyl)amino)methyl)phenoxy)ethyl)benzoate |
| 77C | 4-(((R)-2-hydroxy-2-(8-hydroxy-2-oxo-1,2-dihydroquinolin-5-yl)ethyl)amino)butyl 4-(5-((3-(phenyl((((R)-quinuclidin-3-yloxy)carbonyl)amino)methyl)phenoxy)methyl)-1,2,4-oxadiazol-3-yl)benzoate |
| 78C | 4-(((R)-2-hydroxy-2-(8-hydroxy-2-oxo-1,2-dihydroquinolin-5-yl)ethyl)amino)butyl 4-((4-((3-(phenyl((((R)-quinuclidin-3-yloxy)carbonyl)amino)methyl)phenoxy)methyl)piperidin-1-yl)methyl)benzoate |

| Compound | Chemical Name |
|---|---|
| 79C | 2-(4-(((R)-2-hydroxy-2-(8-hydroxy-2-oxo-1,2-dihydroquinolin-5-yl)ethyl)amino)butoxy)ethyl 4-((3-(phenyl((((R)-quinuclidin-3-yloxy)carbonyl)amino)methyl)phenoxy)methyl)benzoate |
| 80C | 4-(2-(((R)-2-hydroxy-2-(8-hydroxy-2-oxo-1,2-dihydroquinolin-5-yl)ethyl)amino)ethyl)benzyl 4-((3-(phenyl((((R)-quinuclidin-3-yloxy)carbonyl)amino)methyl)phenoxy)methyl)benzoate |
| 81C | 2-(2-(((R)-2-hydroxy-2-(8-hydroxy-2-oxo-1,2-dihydroquinolin-5-yl)ethyl)amino)ethoxy)ethyl 4-((3-(phenyl((((R)-quinuclidin-3-yloxy)carbonyl)amino)methyl)phenoxy)methyl)benzoate |
| 82C | 4-(((R)-2-hydroxy-2-(8-hydroxy-2-oxo-1,2-dihydroquinolin-5-yl)ethyl)amino)butyl 2-chloro-4-((3-(phenyl((((R)-quinuclidin-3-yloxy)carbonyl)amino)methyl)phenoxy)methyl)benzoate |
| 83C | 4-(((R)-2-hydroxy-2-(8-hydroxy-2-oxo-1,2-dihydroquinolin-5-yl)ethyl)amino)butyl 2-fluoro-4-((3-(phenyl((((R)-quinuclidin-3-yloxy)carbonyl)amino)methyl)phenoxy)methyl)benzoate |

The compounds of the present invention can be prepared from readily available starting materials using the following general methods and procedures or by using other information readily available to those of ordinary skill in the art. Although a particular embodiment of the present invention may be shown or described herein, those skilled in the art will recognize that all embodiments or aspects of the present invention can be prepared using the methods described herein or by using other methods, reagents, and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimisation procedures.

Compounds of general formula I may be prepared according to the following synthetic Scheme.

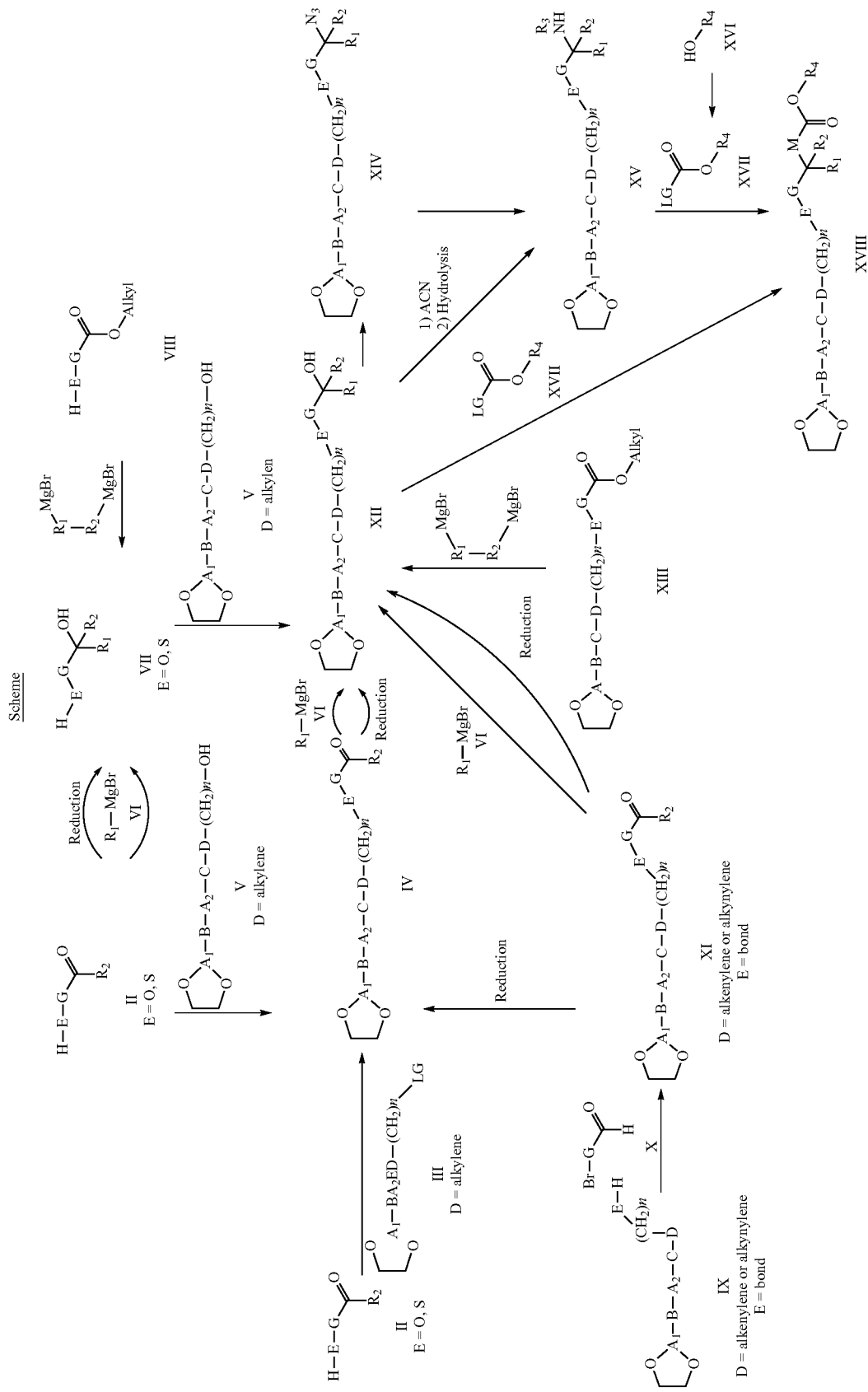

-continued
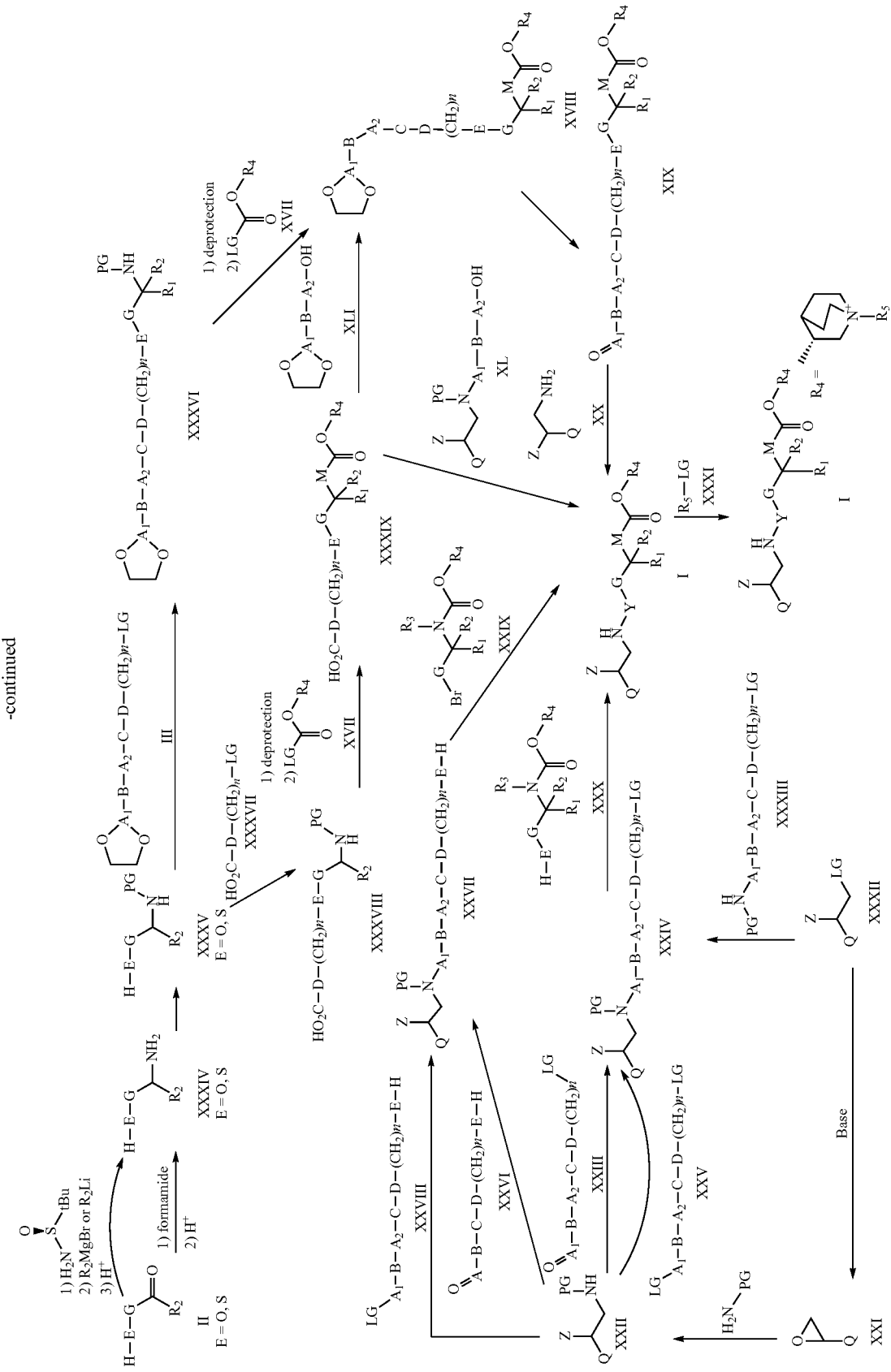

General Procedure for the Preparation of Compounds of Formula I.

The compounds of general formula IX represent a compound wherein A1 is alkylene, cycloalkylene, or heterocycloalkylene substituted with oxo, leading to an aldehyde or ketone protected as cyclic acetal. The cyclic acetal protecting group (PG) can be removed leading to a compound of general formula XXVI.

In the case when A1 is absent and B is a cycloalkylene, heterocycloalkylene, or a group of formula B1, the carbonyl moiety, as such or protected, must be considered on group B.

The synthesis of compounds of general formula I may require the protection of potential reactive functionality in addition to those methods already described. In such a case, examples of compatible protecting groups (PG) and their particular methods of protection and deprotection are described in "Protecting groups in organic Synthesis" by T. W. Green and P. Wutz (Wiley-Interscience publication, 1999, which is incorporated herein by reference in its entirety). Compounds of general formula I can be prepared for example by reaction of a compound of general formula XIX with a compound of general formula XX. This reductive amination reaction can be performed following several different protocols described in the literature and well known for those skilled in the art. For example, it can be performed in solvent such as methanol, ethanol, tetrahydrofuran (THF), or dichloromethane (DCM) using a reducing agent such as $NaBH_4$, $NaCNBH_3$, or $NaBAcO_3H$. It could be useful to obtain the imine before adding the reducing agent. The reaction proceeds smoothly at room temperature (RT) over 1 to 12 hours.

The intermediate of general formula XIX can be easily prepared by reaction of a compound of general formula XIV with a compound of general formula XVII. The reaction occurs smoothly at RT or lower temperature in a solvent such as DCM or pyridine over 1-16 hours leading to compounds of formula XVIII, that can be easily deprotected in aqueous acidic solution, leading to a compound of general formula XIX.

Compounds of general formula XVII are either commercially available or can be prepared by reacting an alcohol of general formula XVI with for example diphosgene in a solvent such as DCM, THF, or acetonitrile (ACN) at RT or lower temperature, over a period of time ranging from 0.5 to 12 hours, leading to a compound of general formula XVII wherein the leaving group LG is chlorine. Alternatively an alcohol of general formula XVI can be reacted with for example carbonyldiimidazole (CDI) leading to the same intermediate wherein LG is imidazole. Other possible intermediates with other known LGs can be prepared as described in the literature.

Compounds of general formula XV, wherein $R_3$ is hydrogen, may be prepared from a compound of general formula XII via a Ritter reaction (acetonitrile and sulphuric acid at RT) followed by hydrolysis of the intermediate acetamide performed under basic condition.

Alternatively, compounds of general formula XV can be prepared by reduction of azide formula XIV via hydrogenation under hydrogen atmosphere or hydrogen transfer conditions. The reaction occurs in alcohols at RT or higher temperature and is completed in 1 to 12 hours. An alternative reduction method could be the Staudinger reaction, which involves treatment of the azide, first with for example triphenylphosphine, followed by hydrolysis of the iminophosphorane intermediate with water. This reaction occurs at RT in a water miscible solvent such as for example THF. The use of a strong reducing agent such as for example $LiAlH_4$ in THF or ether at $-40°$ C. or lower temperature could easily effect the required conversion of compound XIV into XV.

Azide XIV is obtained from compound of formula XII by reaction with diphenyl phosphoryl azide. The reaction is performed in a high boiling point solvent such as toluene or xylene in the presence of a strong base such as, but not limited to 1,8-diazabicyclo[5.4.0]undec-7-ene (DBU) at a temperature ranging from 80 to 120° C. and it is completed over 12 to 24 hour. Alternatively the hydroxyl moiety of intermediate of formula XII can be converted into a suitable leaving group (LG), such as for example mesyl, tosyl, or halogen and then reacted with an alkaline azide in a polar solvent such as acetonitrile, DMF, or N-Methyl-2-pyrrolidone (NMP) at RT or higher temperature.

Compounds of general formula XV wherein $R_3$ is alkyl, can be prepared from compounds of formula XV wherein $R_3$ is hydrogen, by reductive amination with a suitable aldehyde or ketone. The reaction can be conducted under the same reaction conditions described for the preparation of compounds of formula I from compounds of formula XIX and XX. Alternatively the alkylation of amine with alkyl halides, alkyl tosylates or mesylates under standard reaction conditions, well known to those skilled in the art, can be considered to achieve the described conversion.

Compounds of general formula I wherein M is —O—, can be prepared by treating a compound of general formula XII with a compound of general formula XVII. The reaction occurs in an aprotic solvent such as THF, DCM, or DMF and requires the use of a strong base such as alkyl lithium or sodium hydride. It proceeds rapidly at 0° C. or lower temperature over a period of time ranging from 1 to 12 hours. The reaction can be performed using the compound of general formula XVII or alternatively an analogue compound in which the chlorine atom is substituted with another usual leaving group, such as imidazole or p-nitro phenol, typical reactant for the preparation of organic asymmetric carbonates or carbamates.

Intermediates of general formula XII can be prepared in several different ways. For example they can be prepared from reaction of a compound of general formula VII, wherein E is —O— or —S—, and an aldehyde of general formula V wherein D is functionalized with an hydroxyl group that can conveniently react under standard Mitsunobu conditions. The reaction is done in solvents such as THF or N-methyl-morpholine (NMM) at a temperature from $-10°$ C. to RT and is completed in 1 to 24 hours. It occurs in the presence of diethyl azodicarboxylate (DEAD) or diisopropyl azodicarboxylate (DIAD) and an organic phosphine such as triphenylphosphine.

Alcohols of general formula VII are either commercially available or can be prepared from compound of formula II by addition of a Grignard reagent of formula VI. The reaction is normally done in an aprotic solvent such as ether or THF at RT or lower temperature and is completed over 0.5 to 12 hours. Alternatively, it can be prepared by reduction of a compound of general formula II, wherein $R_2$ is not hydrogen, with a reducing agent such as, but not limited to, $NaBH_4$, leading in this case to a compound of formula VII wherein $R_1$ is hydrogen. The reaction is performed in a solvent such as methanol, ethanol, or THF and is completed over a period of time ranging from 1 to 12 hours. A similar synthetic protocol can be used for the preparation of intermediate XII from compounds of general formula IV or XI.

It is clear to a person skilled in the art that the preparation of compounds of general formula VII or XII can be accomplished via inverse Grignard reaction in which a Grignard reagent of formula G-MgBr reacts with a compound of formula R₁C(O)R₂ under the same reaction conditions described above.

If the reaction is performed on a compound of general formula XIII with a bi-functional Grignard reagent such as for example BrMg—R₁—R₂—MgBr, a compound of general formula XII, wherein R₁ and R₂ are connected to form a cycle, can be obtained. A similar synthetic protocol can be used for the preparation of intermediates of formula VII, wherein R₁ and R₂ are connected to form a cycle, from compounds of general formula VIII.

Compounds of general formula IV wherein E is —O— or —S—, can be prepared from a compound of general formula II, following an approach similar to that described for the preparation of compounds of formula XII from VII. Alternatively, the compounds of general formula IV can be obtained by alkylation of a compound of general formula II, with a compound of general formula III wherein LG is a suitable leaving group such as tosyl, mesyl, or halogen. The reaction is normally done in polar solvents such as acetonitrile or DMF, occurs in a presence of a base such as for example alkaline carbonate, bicarbonates or organic bases, and is completed over a period of time varying from 1 to 24 hours.

Compounds of general formula XII, wherein D is alkenylene or alkynylene, n is 0 and E is absent, can be prepared by reacting a compound of formula XI under the same reaction condition described for the addition of a Grignard reagent of formula VI to a compound of formula II.

Preparation of compounds of formula XI can be achieved by reaction of a compound of general formula X, or the analogue wherein the bromine is substituted by iodine or triflate, with a compound of general formula IX, under transition metal catalyzed cross-coupling reaction conditions. A great number of protocols, reagents, and catalysts can be conveniently used to achieve the desired conversion, as it is known to a person skilled in the art. It is clear that a compound of formula XI, wherein n is 0, E is absent and D is alkenylene or alkynylene, can be easily hydrogenated leading to the a compound of formula IV wherein D is the alkyl group derived from reduction of the unsaturated bond.

Alternatively, compounds of general formula I wherein M is —O—, can be prepared by treating a compound of general formula XXXIX with a compound of general formula XL.

In another embodiment of the present invention, compounds of general formula I can be prepared following a different synthetic approach in which a compound of general formula XXVII is reacted with a compound of formula XXIX under the transition metal catalyzed cross-coupling reaction condition. Alternatively, it can be prepared by reaction of a compound of formula XXIV with a compound of formula XXX under the conditions described above for the reaction of a compound of formula II with a compound of formula III.

Intermediates of formula XXVII and XXIV can be prepared by reaction of compound of formula XXII under reductive amination conditions, described above for the reaction of compound of formula XIX with XX, with compound of formula XXVI and XXIII respectively. Alternatively compounds of formula XXVII and XXIV can be prepared by alkylation of compound XXII with compound of formula XXVIII and XXV respectively under alkylation condition described above for the preparation of compound IV by reaction of compound II with compound III.

Compounds of general formula XXII can be obtained by opening the epoxide intermediates XXI with a benzyl amine optionally substituted on the phenyl ring. The reaction can be performed neat or in high boiling point solvent such as toluene, xylene, isopropanol, or butanol and occurs at temperature ranging from 80 to 120° C. Classical thermal or microwave heating is efficacious to drive the reaction to completion over 1 to 24 hours.

In an additional embodiment of the present invention, compounds of formula I, wherein R₄ is J5 or another group featuring a quaternary ammonium salt, can be prepared reacting the corresponding tertiary amine precursor of formula I where R₅ is J1-J4 with a compound of formula XXXI. The reaction proceeds smoothly at RT or higher temperature in solvent such as DCM, acetonitrile, methanol, or AcOEt over a period of time ranging from 1 to 24 hours.

In another embodiment of the present invention, compounds of general formula XXIV can be prepared by reacting an intermediate of general formula XXXII with an amine of general formula XXXIII. This reaction is a common alkylation of an amine in which the leaving group LG (normally chlorine, bromine, or sulfate) is displaced by a nucleophile like the amine XXXIII wherein R3 is H or an alkylic group that can increase the selectivity and it can be removed after the reaction. Several methods to perform this reaction, that normally occurs in a polar solvent at a temperature higher than room temperature, are described in the literature.

It is apparent for those skilled in the art that compounds of general formula I wherein R4 is J1 or J2 contain three stereogenic centers, as indicated below with the symbol *. This means that the structure of formula I is characterized by eight different stereoisomers.

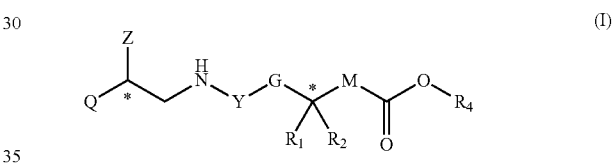

(I)

Each diastereoisomer can be obtained theoretically by chromatographic separation of the mixture obtained by reacting racemic mixtures of the required intermediates. It is clear that this approach it is not convenient and that it can be used only for the separation of mixtures containing few diastereoisomers.

In a more convenient approach, the synthesis of each single stereoisomer can be accomplished using, in the reactions described above, only enantiomerically pure intermediates.

The enantiomerically pure alcohol required for the preparation of compounds of general formula I wherein R4 is J1, J2 or J5 are commercially available.

The preparation of single enantiomerically pure compounds of general formula XXXII wherein LG is bromine are described in WO 2005/080324, US 2005/2222128, WO 2004/032921, US 2005/215590, and WO 2005/092861 (citato da WO2007/107228), all of which are incorporated herein by reference in their entireties. This compound can be easily converted into the epoxide XXI by heating the precursor (wherein Z is oxygen) in a suitable solvent in the presence of a base that catalyzes the epoxide formation.

Enantiomerically pure compounds of general formula XXXV can be obtained by chiral chromatographic separation of the racemic mixture or starting from enantiomerically pure amine compounds of general formula XXXIV. As intermediate compounds of formula XXXIV contains a basic group, it is possible to obtain the two enantiomers by mean of crystallization of the diasteromeric salt, obtained by salification of the racemic mixture with an enantiomerically pure carboxylic acid. Widely used carboxylic acids used for this purpose are for example mandelic acid, tartaric acid and its derivatives.

The base XXXIV is dissolved in a suitable polar solvent and then treated with of the carboxylic acid causing precipitation of one of the two diateroisomeric salts. It could be required to repeat the procedure several times to obtain the desired level of optical purity.

Alternatively, the amines of formula XXXIV can be obtained via enantioselective synthesis following for example the approach described in the literature (Tetrahedron: Asymmetry 13 (2002) 303-310, which is incorporated herein by reference in its entirety) in which the aldehyde of formula II, wherein $R_2$ is H, is treated first with a enantiomerically pure tert-butyl sulfiniimide and then with $R_2MgBr$ or $R_2Li$ (wherein $R_2$ is not H), followed by hydrolysis of the intermediate leading to the formation of enantiomerically enriched compounds of formula XXXIV that can be used as such or further purified to increase the optical purity.

The available amines of formula XXXIV can be easily further derivatized under the reaction conditions described above. For example it can be treated with a protected aldehyde of formula III, under the conditions described for the alkylation of compounds of formula II with compounds of formula III, leading to compound or general formula XXXVI. Deprotection of the aminic group and reaction of compounds of formula XVII, lead to the preparation of a compound of general formula XVIII.

Alternatively, compounds of general formula I can be prepared coupling a compound of general formula XXXIX with a compound of general formula XL leading to a compound of general formula I wherein C is —OCO—. This ester can be obtained under different reaction condition well known to those skilled in the art. The reaction requires the activation of the acid XXXIX with reactant such as DCC, EDC, HBTU, or HATU or it may be converted into the corresponding acyl chloride. The activated ester can smoothly react, in DCM, pyridine or other apolar solvents, with the alcohol of formula XL.

Compounds of formula XXXIX can be prepared starting from XXXV via alkylation with a compound of formula XXXVII, deprotection, and reaction with a compound of formula XVII. The reaction conditions for this conversion are described above and well described in the literature. Acid XXXIX can be easily reacted with a compound of formula XLI, as described above for the reaction with a compound of formula XL, leading to compound of formula XVIII.

A compound of general formula XL can be prepared by reaction of a compound of general formula XXXII with an amine of formula PG-NH-$A_1$-B-$A_2$-OH, under the reaction conditions described for the reaction of compounds of general formula XXXII with compounds of general formula XXXIII.

For all the above, the synthesis of compounds of general formula I can be performed following several different approaches. In particular it must be noted that the sequence of reactions required, strongly depends on the nature of the linkers Y and Y1 and on the functional groups present on the linker. The example given above for the preparation of compounds of formula I wherein C is —OCO— illuminates this aspect of the invention.

The invention also provides pharmaceutical compositions of compounds of formula I in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the present invention including such solid forms as tablets, gelcaps, capsules, caplets, granules, lozenges, and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants, and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the present invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates, and polyethylene glycols.

Formulations for vaginal administration can be in the form of a cream, gel, paste, foam, or spray formula containing, in addition to the active ingredient, such suitable carriers, as are also known.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the present invention are preferably administered by inhalation. Inhalable preparations include inhalable powders, propellant-containing metering aerosols, or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the present invention.

Inhalation aerosols containing propellant gas such as a hydrofluoroalkane may contain the compounds of the invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic, or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. corticosteroids, P38 MAP kinase inhibitors, IKK2, HNE inhibitors, PDE4 inhibitors, leukotriene modulators, NSAIDs, and mucus regulators.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula I can be administered for example, at a dosage of 0.001 to 1000 mg/day, preferably 0.1 to 500 mg/day.

When the compounds of formula I are administered by the inhalation route, they are preferably given at a dosage of 0.001 to 500 mg/day, preferably 0.1 to 200 mg/day.

The compounds of formula I may be administered for the prevention and/or treatment of broncho-obstructive or inflammatory diseases, such as asthma, chronic bronchitis, chronic obstructive pulmonary disease (COPD), bronchial hyperreactivity, cough, emphysema or rhinitis; urological disorders such as urinary incontinence, pollakiuria, cystospasm, chronic cystitis and overactive bladder (OAB); gastrointestinal disorders such as bowel syndrome, spastic colitis, diverticulitis, peptic ulceration, gastrointestinal motility or gastric acid secretion; dry mouth; mydriasis, tachycardia; ophthalmic interventions cardiovascular disorders such as vagally induced sinus bradycardia.

Other features of the invention will become apparent in the course of the following descriptions of exemplary embodiments which are given for illustration of the invention and are not intended to be limiting thereof.

EXAMPLES

The LCMS methods A, B, and C, used for the characterization of the compounds of the present invention, are described in the following:

| Method A (IS 10 cm__ESCI__Formic__MeCN) HPLC Setup | | |
|---|---|---|
| Solvents: | Acetonitrile (Far UV grade) with 0.1% (V/V) formic acid Water (High purity via PureLab Option unit) with 0.1% formic acid | |
| Column: | Phenomenex Luna 5μ C18 (2), 100 × 4.6 mm. (Plus guard cartridge) | |
| Flow Rate: | 2 ml/min | |
| Gradient: | A: Water/formic    B: MeCN/formic | |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

Typical Injections 2-7 ul
UV detection via HP or Waters DAD
Start Range (nm) 210  End Range (nm) 400  Range interval (nm) 4.0
Optional ELS detection using Polymer Labs ELS-1000.
MS detection: Micromass ZQ, single quadrapole LC-MS instrument.
Scan range for MS Data (m/z)
Start (m/z) 100
End (m/z) 650 or 1000 when required
With +ve/−ve switching Ionisation is either electrospray (ESI) or atmospheric-pressure chemical ionization (APCI) dependent on compound types.

| Method B (IS 15 cm__Formic__ASCENTIS__HPLC__CH₃CN) HPLC Setup | | |
|---|---|---|
| Solvents: | Acetonitrile (Far UV grade) with 0.1% (V/V) formic acid Water (High purity via PureLab Ultra unit) with 0.1% formic acid | |
| Column: | Supelco, Ascentis ® Express C18 or Hichrom Halo C18, 2.7 μm C18, 150 × 4.6 mm. | |
| Flow Rate: | 1 ml/min | |
| Gradient: | A: Water/formic    B: MeCN/formic | |

| Time | A % | B % |
|---|---|---|
| 0.00 | 96 | 4 |
| 3.00 | 96 | 4 |
| 9.00 | 0 | 100 |
| 13.6 | 0 | 100 |
| 13.7 | 96 | 4 |
| 15 | 96 | 4 |

Typical Injections 0.2-10 ul
Maximum pressure setting 400 bar.
Instrument: Agilent 1100, Binary Pump, Agilent Sampler and Agilent DAD detector
Diode array detection: (300 nm, Band Width 200 nm; Ref. 450 nm, Band Width 100 nm)

| Method C (IS 10 cm__ESCI__Formic__MeCN) HPLC Setup | | |
|---|---|---|
| Solvents: | Acetonitrile (Far UV grade) with 0.1% (V/V) formic acid Water (High purity via PureLab Ultra unit) with 0.1% formic acid | |
| Column: | Hichrom ACE 3 C18-AR mixed mode column 100 × 4.6 mm | |
| Flow Rate: | ml/min | |
| Gradient: | A: Water/formic    B: MeCN/formic | |

| Time | A % | B % |
|---|---|---|
| 0.00 | 98 | 2 |
| 3.00 | 98 | 2 |
| 12.00 | 0 | 100 |
| 15.4 | 0 | 100 |
| 15.5 | 98 | 2 |
| 17 | 98 | 2 |

Typical Injections 0.2-10 ul
Maximum pressure setting 400 bar.
Instrument: Agilent 1100, Binary Pump, Agilent Sampler and Agilent DAD detector
Diode array detection: (300 nm, Band Width 200 nm; Ref 450 nm, Band Width The intermediate compounds for the synthesis of final compounds of general formula (I) were obtained through the preparations herebelow described.

Preparation of 9-Bromononanoic acid

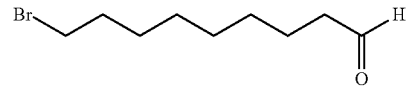 [SMILES: O=CCCCCCCCCBr]

Pyridinium chlorochromate (38.7 g, 180 mmol) and silica 60A (39 g, particle size 35-70 micron) suspended in DCM (250 mL) were stirred at RT for 45 minutes. 9-Bromononanol (26.7 g, 120 mmol) was added, in one portion, and the suspension was stirred at RT for 18 hours. The reaction mixture was filtered through a celite plug, and the resulting filtrate concentrated under vacuum affording the title compound (28.0 g, >100%). The material was used without further purification in the next step.

$^1$H NMR (400 MHz, CDCl$_3$): δ 9.77 (s, 1H), 3.41 (t, 2H), 2.43 (t, 2H), 1.90-1.80 (m, 2H), 1.63 (s, 2H), 1.43 (s, 2H), 1.32 (s, 6H).

Preparation of 2-(8-Bromooctyl)-1,3-dioxolane

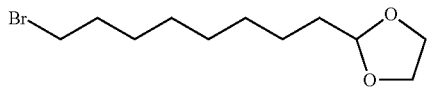 [SMILES: BrCCCCCCCCC1OCCO1]

9-Bromononanal (28.0 g, assumed 120 mmol), ethylene glycol (33.6 mL, 600 mmol) and para-toluenesulphonic acid (2.7 g, 13 mmol) in toluene (210 mL) were heated at reflux for 20 hours. The reaction was cooled to RT and quenched with saturated aqueous sodium bicarbonate solution (300 mL). The resulting mixture was extracted with diethyl ether (2×500 mL). The combined organic extracts were washed with saturated aqueous sodium bicarbonate solution (300 mL), water (300 mL), brine (100 mL), dried (magnesium sulfate), filtered and evaporated under reduced pressure to afford the title compound (25.2 g, 79%).

$^1$H NMR (400 MHz, CDCl$_3$): δ 4.84 (t, J=4.8 Hz, 1H), 3.95-3.78 (m, 4H), 3.43-3.37 (m, 2H), 1.90-1.79 (m, 2H), 1.69-1.54 (m, 2H), 1.42 (s, 3H), 1.32 (s, 7H).

Alternatively 9-Bromononanal could be prepared as follows:

To a cooled (−78° C.) solution of oxalyl chloride (11.66 g, 92 mmol) in DCM (250 mL), a solution of dimethylsulfoxide (DMSO) (13.0 mL, 183 mmol) in DCM (50 mL) was added over 15 minutes. After a further 5 minutes, a solution of 9-bromononanol (10.25 g, 45.9 mmol) in DCM (50 mL) was added dropwise over 15 minutes. The resulting reaction mixture was stirred at this temperature for 45 minutes. Triethylamine (32 mL, 230 mmol) was added, and the reaction mixture stirred at this temperature for 10 minutes. The coolant was removed and allowed to warm to RT. The reaction mixture was stirred at RT for 40 minutes and then diluted with water. The organic phase was removed and washed with 10% aqueous potassium hydrogen sulfate and dried (magnesium sulfate). The suspension was filtered and the filtrate evaporated under reduced pressure to afford the title compound.

All other 1,3-dioxalanes (i.e. 2-(7-bromoheptyl)-1,3-dioxolane; 2-(6-bromohexyl)-1,3-dioxolane; 2-(5-bromopentyl)-1,3-dioxolane, and 2-(4-bromobutyl)-1,3-dioxolane) were prepared by the same method.

Preparation of 8-(Benzyloxy)-5-(2-bromoacetyl)quinolin-2(1H)-one

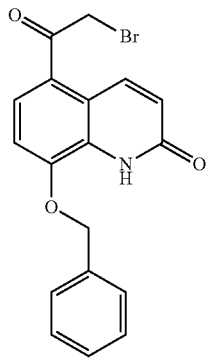 [SMILES: O=C(CBr)c1ccc(OCc2ccccc2)c2[nH]c(=O)ccc12]

To a suspension of 5-acetyl-8-(benzyloxy)quinolin-2(1H)-one (19.4 g, 66.4 mmol) in anhydrous THF (240 mL) and anhydrous methanol (165 mL) was added a solution of tetra-n-butylammonium tribromide (54.5 g, 113.0 mmol) in anhydrous THF (130 mL) dropwise over 1.5 hours. The resulting solution was stirred at RT overnight before concentrating under reduced pressure without heating. The residue was re-dissolved in methanol (200 mL). Saturated aqueous ammonium chloride solution (390 mL) was added with ice-cooling. The resulting suspension was filtered, and the solid washed with water and air-dried under vacuum. The solid was suspended in DCM and methanol (1:1 v/v, 100 mL) for 90 minutes. The solid was collected by filtration, washed with DCM and air-dried to afford the title compound (18.0 g, 73%).

$^1$H NMR (400 MHz, DMSO-d$_6$): δ 11.07 (s, 1H), 8.51 (d, J=10.0 Hz, 1H), 7.94-7.83 (m, 1H), 7.60 (d, J=7.5 Hz, 2H), 7.44-7.27 (m, 4H), 6.79-6.65 (m, 1H), 5.53-5.39 (s, 2H); 4.93 (s, 2H)

Preparation of (R)-8-(Benzyloxy)-5-(2-bromo-1-hydroxyethyl)-quinolin-2(1H)-one

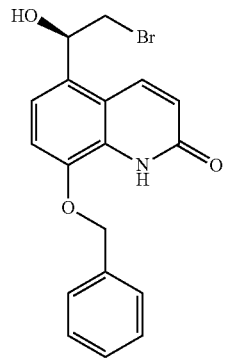 [SMILES: O=c1ccc2c([C@@H](O)CBr)ccc(OCc3ccccc3)c2[nH]1]

8-(Benzyloxy)-5-(2-bromoacetyl)quinolin-2(1H)-one (26.0 g, 69.9 mmol) and (R)-3,3-diphenyl-1-methyltetrahydro-3H-pyrrolo[1,2-c][1,3,2]oxazaborole (21.3 g, 76.8 mmol) were azeotroped with toluene (×3) and then suspended in anhydrous THF (400 mL) under an atmosphere of nitrogen. The suspension was cooled to −20° C. (external temperature), and borane dimethyl sulfide complex solution (45.4 mL, 90.8 mmol, 2.0 M solution in THF) was added by syringe pump over 3 hours. After complete addition, the reaction mixture was stirred for one hour before quenching with methanol (25 mL). The reaction was warmed to RT over 20 minutes. The mixture was concentrated under reduced pressure, and the residue was suspended in aqueous hydrochloric acid (500 mL, 1 M solution) and stirred at RT for 18 hours. After this time, the solid was collected by filtration and washed with water (3×100 mL). The solid was partially dissolved in ethyl acetate and heated at reflux for 2 hours. The remaining solid was removed by hot filtration, and the filtrate was evaporated to afford the title compound. The solid collected from the hot ethyl acetate was again partially dissolved in ethyl acetate and heated at reflux for 2 hours then filtered to give filtrate containing pure product. This process was repeated four more times. The combined solid was recrystallised from ethyl acetate and petroleum ether to afford the title compound (20.0 g, 76%).

$^1$H NMR (400 MHz, DMSO-d$_6$): δ 10.68 (s, 1H); 8.19 (d, J=9.9 Hz, 1H); 7.58 (d, J=7.5 Hz, 2H); 7.41-7.36 (m, 2H);

7.34-7.29 (m, 1H); 7.23-7.19 (m, 2H); 6.57 (d, J=9.8 Hz, 1H); 5.94 (d, J=4.7 Hz, 1H); 5.31 (s, 2H); 5.25-5.19 (m, 1H); 3.71-3.58 (m, 2H).

Preparation of (R)-8-(Benzyloxy)-5-(2-bromo-1-(tert-butyldimethylsilyloxy)-ethyl)quinolin-2(1H)-one

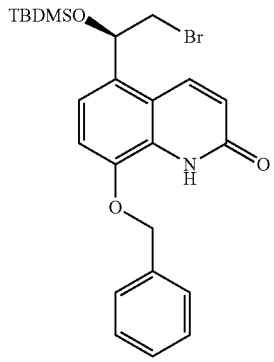 [SMILES: CC(C)(C)[Si](C)(C)O[C@@H](CBr)c1ccc(OCc2ccccc2)c2[nH]c(=O)ccc12]

2,6-Lutidine (6.9 mL, 59.5 mmol) was added to a solution of (R)-8-(benzyloxy)-5-(2-bromo-1-hydroxyethyl)quinolin-2(1H)-one (10.1 g, 27.0 mmol) in DCM (100 mL) at 0° C. The reaction mixture was stirred for 5 minutes and then tert-butyldimethylsilyl trifluoromethanesulfonate (13.0 mL, 56.8 mmol) was added dropwise over 15 minutes. The mixture was stirred at 0° C. for 30 minutes, followed by RT overnight. After this time the reaction was quenched with saturated aqueous sodium bicarbonate solution and extracted with DCM (×3). The combined organic extracts were dried (magnesium sulfate), filtered and concentrated under reduced pressure. Iso-hexane (500 mL) was added to the crude material and the resulting solid collected by filtration. The solid was recrystallised from ethyl acetate and petroleum ether (40:60) to afford the title compound (11.3 g, 85%).
$^1$H NMR (400 MHz, CDCl$_3$): δ 9.19 (s, 1H), 8.23 (dd, J=9.9, 4.4 Hz, 1H), 7.43 (d, J=4.6 Hz, 5H), 7.17 (dd, J=8.3, 4.5 Hz, 1H), 7.03 (dd, J=8.2, 4.4 Hz, 1H), 6.71 (dd, J=9.9, 3.7 Hz, 1H), 5.18 (d, J=4.5 Hz, 3H), 3.63-3.56 (m, 1H), 3.49 (dd, J=10.4, 4.8 Hz, 1H), 0.88 (t, J=4.4 Hz, 9H), 0.14 (d, J=4.4 Hz, 3H), −0.11 (d, J=4.4 Hz, 3H).

Preparation of (R)-5-(2-Azido-1-(tert-butyldimethyl-silyloxy)ethyl)-8-(benzyloxy)quinolin-2(1H)-one

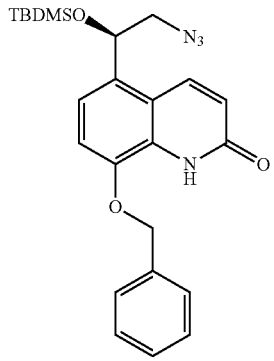 [SMILES: CC(C)(C)[Si](C)(C)O[C@@H](CN=[N+]=[N-])c1ccc(OCc2ccccc2)c2[nH]c(=O)ccc12]

(R)-8-(Benzyloxy)-5-(2-bromo-1-(tert-butyldimethylsilyloxy)ethyl)quinolin-2(1H)-one (5.0 g, 10.2 mmol) was dissolved in dimethyl formamide (90 mL) and water (10 mL). Sodium iodide (1.7 g, 11.3 mmol) and sodium azide (0.7 g, 11.3 mmol) were added sequentially. The reaction mixture was stirred at RT until all the solid was in solution. The solution was heated at 80° C. for 40 hours and then cooled to RT and diluted with water (300 mL). The aqueous layer was extracted with DCM, and the combined organic extracts were dried (magnesium sulfate), filtered, and concentrated under reduced pressure. The crude residue was recrystallised from ethyl acetate and iso-hexane to afford the desired compound (3.6 g, 78%), which was used without further purification in the next step.
$^1$H NMR (400 MHz, CDCl$_3$): δ 9.19 (s, 1H), 8.18 (d, J=9.9 Hz, 1H), 7.45-7.36 (m, 4H), 7.20 (d, J=8.3 Hz, 1H), 7.04 (d, J=8.3 Hz, 1H), 6.70 (dd, J=9.9, 2.2 Hz, 1H), 5.19-5.13 (m, 3H), 3.48 (dd, J=12.7, 8.1 Hz, 1H), 3.26 (dd, J=12.7, 3.8 Hz, 1H), 0.89 (s, 9H), 0.14 (s, 3H), −0.11 (s, 3H).

Preparation of (R)-5-(2-Amino-1-(tert-butyldimethylsilyloxy)ethyl)-8-hydroxyquinolin-2(1H)-one formate

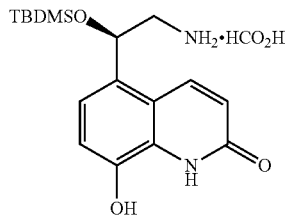

Palladium on activated carbon (0.4 g, 10% w/w) was added to a suspension of (R)-5-(2-azido-1-(tert-butyldimethylsilyloxy)ethyl)-8-(benzyloxy)quinolin-2(1H)-one (2.05 g, 4.60 mmol) and ammonium formate (2.87 g, 63 mmol) in methanol (50 mL). The reaction mixture was heated at 80° C. for 1 hour. If after this time, the reaction had not reached completion; the reaction mixture was filtered through celite, washing with methanol. The reaction mixture was concentrated to approximately 50 mL then ammonium formate (2.87 g, 63.0 mmol) and Palladium on activated carbon (0.40 g, 10% w/w) were added. The reaction mixture was heated at 80° C. for 20 minutes, and then filtered through celite, washing with water. The reaction mixture was concentrated under reduced pressure. The resulting solid was washed with water, triturated with ethyl acetate and collected by filtration to afford the title compound (1.32 g, 86%).
$^1$H NMR (400 MHz, DMSO-d$_6$): δ 8.34 (s, 1H), 8.31-8.22 (m, 1H), 7.03 (d, J=8.1 Hz, 1H), 6.98-6.90 (m, 1H), 6.53 (d, J=9.9 Hz, 1H), 5.13 (t, J=6.0 Hz, 1H), 3.18 (s, 1H), 2.84-2.73 (m, 2H), 0.83 (s, 9H), 0.06 (s, 3H), −0.17 (s, 3H).

Preparation of (R)-5-(2-Amino-1-(tert-butyldimethylsilyloxy)ethyl)-8-hydroxyquinolin-2(1H)-one

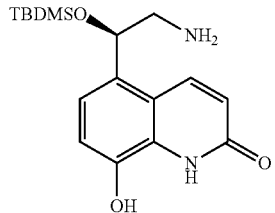 [SMILES: CC(C)(C)[Si](C)(C)O[C@@H](CN)c1ccc(O)c2[nH]c(=O)ccc12]

To an ice-cooled suspension of (R)-5-(2-azido-1-(tert-butyldimethylsilyloxy)-ethyl)-8-(benzyloxy)quinolin-2(1H)-one (5.77 g, 12.8 mmol) and palladium on activated charcoal (5.8 g, 10% w/w wet) in ethanol (50 mL), 1,4-cyclohexadiene (12.0 mL, 126 mmol) was added dropwise. After stirring at this temperature for 30 minutes, the coolant was removed and replaced with a water bath at 30° C. The reaction was stirred at this temperature for 1 hour. The suspension was filtered and the filter cake washed with further ethanol. The filtrate was evaporated under reduced pressure to dryness. The resulting solid was suspended in acetonitrile and stirred for 1 hour. The suspension was filtered and the resulting solid air-dried under vacuum to afford the title compound (2.90 g, 87%).

$^1$H NMR (400 MHz, DMSO-d$_6$): δ 8.43 (d, J=10 Hz, 1H), 7.18 (d, J=8.0 Hz, 1H), 7.08 (d, J=8.4 Hz, 1H), 6.68 (d, J=10 Hz, 1H), 5.14 (m, 1H), 2.84-2.82 (m, 2H), 0.96 (s, 9H), 0.19 (s, 3H), 0.00 (s, 3H).

Preparation of (R)-5-(2-Amino-1-hydroxyethyl)-8-hydroxyquinolin-2(1H)-one hydrochloride

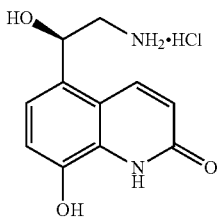

(R)-5-(2-Amino-1-(tert-butyldimethylsilyloxy)ethyl)-8-hydroxyquinolin-2(1H)-one formate (0.23 g, 0.61 mmol) was dissolved in hydrochloric acid (5 mL, 4 M solution in dioxane) and methanol (5 mL). The reaction mixture was stirred at RT for 16 hours before concentrating in vacuo. The resulting residue was washed with ethyl acetate and dried in a vacuum oven for 18 hours to afford the title compound (0.15 g, 99%).

$^1$H NMR (400 MHz, MeOD): δ 7.71 (d, J=9.8 Hz, 1H), 6.57 (d, J=8.2 Hz, 1H), 6.31 (d, J=8.2 Hz, 1H), 6.02 (dd, J=9.8, 6.5 Hz, 1H), 4.58 (dd, J=9.6, 3.5 Hz, 1H), 2.47-2.31 (m, 2H).

Preparation of (R)-Quinuclidin-3-yl carbonochloridate hydrochloride

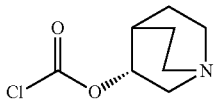 [SMILES: O=C(Cl)O[C@H]1CN2CCC1CC2]

To a stirred solution of (R)-3-quinuclidinol (2.5 g, 19.66 mmol) in acetonitrile (200 mL), trichloromethyl chloroformate (3.06 mL, 25.57 mmol) was added dropwise at 0° C. and stirred for 1 hour. The reaction mixture was stirred at RT for 16 hours before concentrating in vacuo to afford the title compound (4.39 g, 98%).

$^1$H NMR (400 MHz, DMSO-d$_6$): δ 10.29 (s, 1H), 4.05-3.95 (m, 1H), 3.43 (t, J=10.78 Hz, 1H), 3.12 (m, 3H), 3.10-2.95 (m, 1H), 2.79 (d, J=13.27 Hz, 1H), 2.12-2.02 (m, 1H), 1.98 (m, J=3.36 Hz, 1H), 1.89-1.78 (m, 1H), 1.75-1.59 (m, 2H).

Preparation of 1-Benzylpiperidin-4-yl carbonochloridate hydrochloride

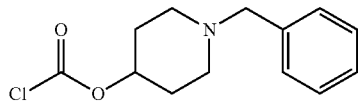 [SMILES: O=C(Cl)OC1CCN(Cc2ccccc2)CC1]

The title compound was prepared as described above for (R)-quinuclidin-3-yl carbonochloridate to afford the title compound (0.6 g, 99%) which was used without further purification.

$^1$H NMR (400 MHz, DMSO-d$_6$): δ 10.33 (s, 1H), 7.60 (d, J=13.85 Hz, 2H), 7.47-7.44 (m, 3H), 4.27 (dd, J=16.57, 5.30 Hz, 2H), 3.66-3.56 (m, 1H), 3.28 (d, J=12.34 Hz, 1H), 3.12 (s, 2H), 2.91 (q, J=11.35 Hz, 1H), 1.94 (d, J=13.65 Hz, 2H), 1.77-1.62 (m, 2H).

Preparation of 1-Methylpiperidin-4-yl carbonochloridate hydrochloride

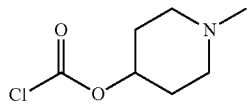

The title compound was prepared as described above for (R)-quinuclidin-3-yl carbonochloridate to afford the title compound (0.42 g, 90%) which was used without further purification.

$^1$H NMR (400 MHz, DMSO-d$_6$): δ 10.63 (s, 1H); 3.93-3.89 (m, 1H), 3.36-3.27 (m, 1H), 3.19-3.04 (m, 2H), 2.97-2.86 (m, 1H), 2.70-2.63 (m, 3H), 2.00-1.85 (m, 2H), 1.76-1.61 (m, 2H).

Preparation of 8-Benzyl-8-azabicyclo[3.2.1]octan-3-yl carbonochloridate hydrochloride

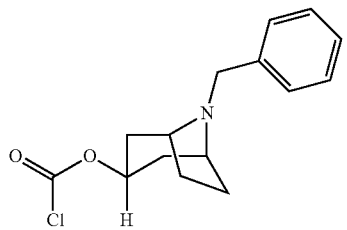 [SMILES: O=C(Cl)OC1CC2CCC(C1)N2Cc1ccccc1]

The title compound was prepared as described above for (R)-quinuclidin-3-yl carbonochloridate to afford the title compound (0.31 g, 84%) which was used without further purification.

$^1$H NMR (400 MHz, DMSO-d$_6$): δ 7.68 (s, 2H), 7.47 (s, 3H), 4.13 (d, J=6.31 Hz, 1H), 3.99-3.90 (m, 2H), 3.72 (s, 2H), 2.27 (s, 2H), 1.88 (t, J=11.52 Hz, 6H).

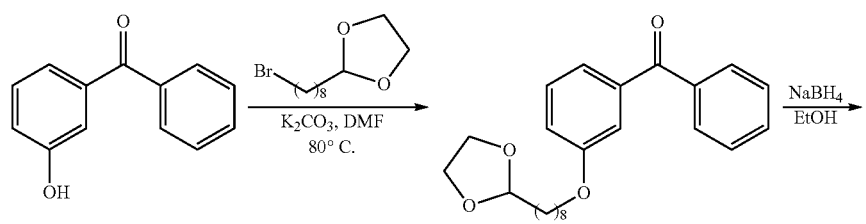
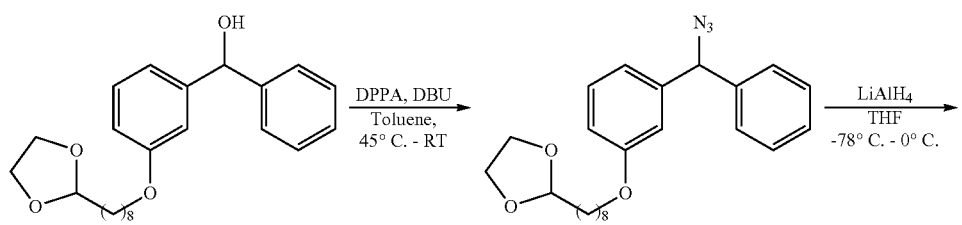
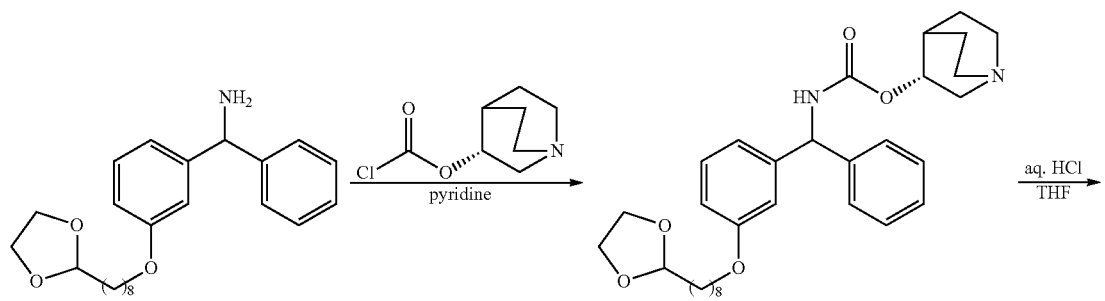
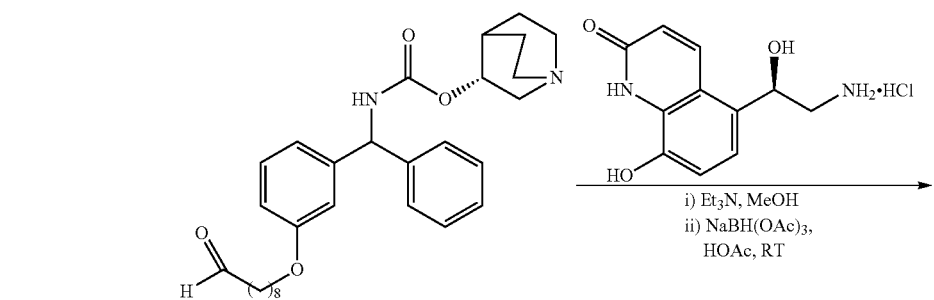
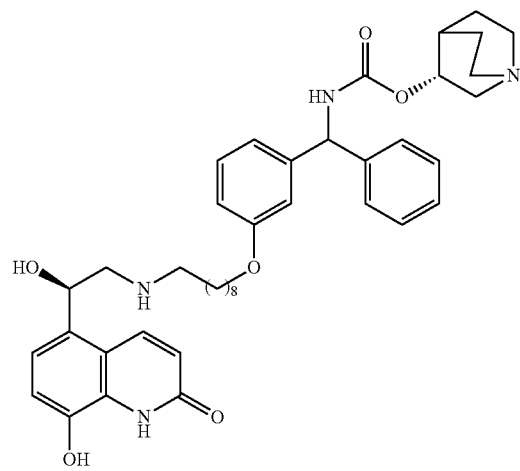

Example 1

(R)-Quinuclidin-3-yl(3-(9-((R)-2-hydroxy-2-(8-hydroxy-2-oxo-1,2-dihydroquinolin-5-yl)ethylamino)nonyloxy)phenyl)(phenyl)-methylcarbamate (compound 1)

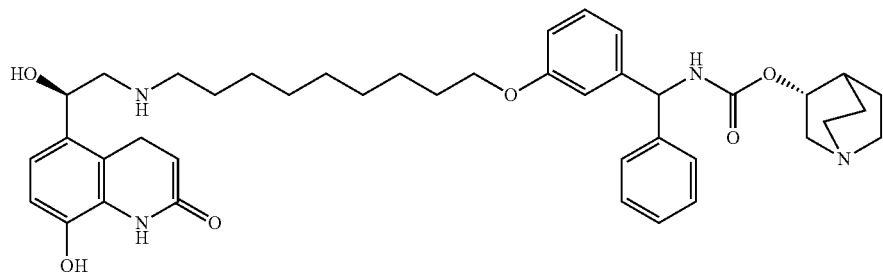

Step 1. (3-(8-(1,3-Dioxolan-2-yl)octyloxy)phenyl)(phenyl)methanone

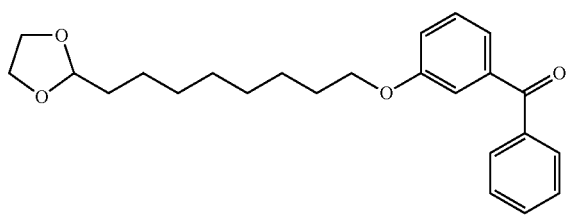 [SMILES: O=C(c1ccccc1)c1cccc(OCCCCCCCCC2OCCO2)c1]

2-(8-Bromooctyl)-1,3-dioxolane (3.89 g, 14.69 mmol) was added to a mixture of 3-hydroxybenzophenone (3 g, 15.13 mmol) and potassium carbonate (4.17 g, 30.21 mmol) in dimethyl formamide (50 mL). The reaction mixture was stirred at 80° C. for 16 hours. The reaction mixture was diluted with water and extracted with ethyl acetate (×3). The combined organic extracts were washed with saturated aqueous sodium bicarbonate solution, saturated aqueous ammonium chloride solution and dried (sodium sulfate), filtered, and concentrated under reduced pressure. The crude material was purified by silica gel column chromatography eluting with 0-100% ethyl acetate in iso-hexane to afford the title compound (4.73 g, 84%).

$^1$H NMR (400 MHz, DMSO-d$_6$): δ 7.74 (d, J=7.53 Hz, 2H), 7.69-7.66 (m, 1H), 7.60-7.53 (m, 2H), 7.46-7.43 (m, 1H), 7.28-7.20 (m, 3H), 4.77-4.71 (m, 1H), 4.04-3.97 (m, 2H), 3.90-3.80 (m, 2H), 3.79-3.69 (m, 2H), 1.77-1.66 (m, 2H), 1.57-1.50 (m, 2H), 1.54-1.15 (m, 10H).

Step 2. (3-(8-(1,3-Dioxolan-2-yl)octyloxy)phenyl)(phenyl)methanol

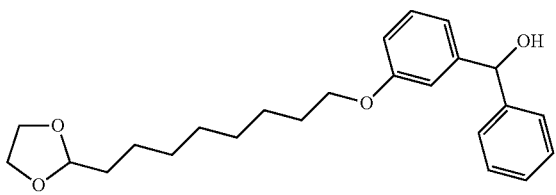 [SMILES: OC(c1ccccc1)c1cccc(OCCCCCCCCC2OCCO2)c1]

To a solution of (3-(8-(1,3-dioxolan-2-yl)octyloxy)phenyl)(phenyl)methanone (4.73 g, 12.35 mmol) in ethanol (100 mL) at 0° C., sodium borohydride (1.88 g, 49.42 mmol) was added portion wise. The coolant was removed, and the reaction mixture was allowed to warm to RT and stirred for 1 hour. The reaction mixture was quenched with water (30 mL) at 0° C. and then concentrated under reduced pressure. The crude material was dissolved in DCM and washed with saturated aqueous ammonium chloride, dried (sodium sulfate), filtered, and concentrated under reduced pressure to afford the title compound (4.33 g, 91%).

$^1$H NMR (400 MHz, DMSO-d$_6$): δ 7.37 (d, J=1.27 Hz, 2H), 7.32-7.28 (m, 2H), 7.23-7.16 (m, 2H), 6.96-6.90 (m, 2H), 6.75 (dd, J=8.11, 2.58 Hz, 1H), 5.85 (d, J=4.08 Hz, 1H), 5.65 (d, J=4.05 Hz, 1H), 4.79-4.73 (m, 1H), 3.93-3.80 (m, 4H), 3.79-3.70 (m, 2H), 1.73-1.62 (m, 2H), 1.59-1.51 (m, 2H), 1.73-0.95 (m, 10H).

Step 3. 2-(8-(3-(Azido(phenyl)methyl)phenoxy)octyl)-1,3-dioxolane

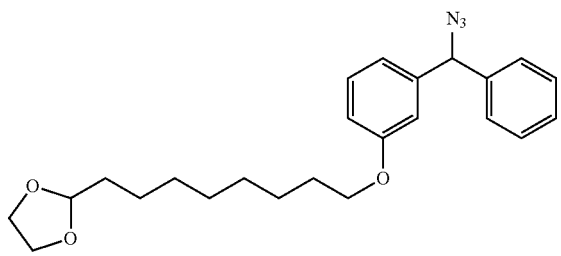 [SMILES: [N-]=[N+]=NC(c1ccccc1)c1cccc(OCCCCCCCCC2OCCO2)c1]

To a stirred solution of (3-(8-(1,3-dioxolan-2-yl)octyloxy)phenyl)-(phenyl)methanol (1.63 g, 4.24 mmol) in toluene (10 mL) under an atmosphere of nitrogen, diphenylphosphoryl azide (1.10 mL, 5.10 mmol) and DBU (0.77 mL, 5.11 mmol) was added. The reaction mixture was stirred at 45° C. for 3 hours and then at RT for 16 hours. The reaction mixture was concentrated under reduced pressure. The crude material was purified by silica gel chromatography eluting with 0-100% ethyl acetate in iso-hexane to afford impure title compound (1.11 g, 64%). This material was used directly in the next step.

Step 4. (3-(8-(1,3-Dioxolan-2-yl)octyloxy)phenyl) (phenyl)methanamine

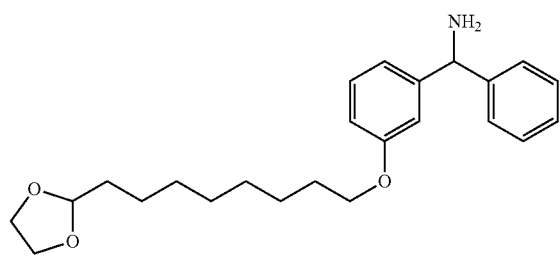 [SMILES: NC(c1ccccc1)c1cccc(OCCCCCCCCC2OCCO2)c1]

To a stirred solution of 2-(8-(3-(azido(phenyl)methyl)phenoxy)octyl)-1,3-dioxolane (1.11 g, 2.71 mmol) in THF (15 mL) at −78° C. under an atmosphere of nitrogen, a solution of lithium aluminium hydride (2.0M in THF, 2.8 mL, 5.60 mmol) was added drop wise. After stirring the reaction at −78° C. for 1 hour, the reaction mixture was warmed up to 0° C. for 1 hour. The reaction mixture was quenched with water (304 mL), 2M sodium hydroxide (304 mL) and water (304 mL×3). Anhydrous magnesium sulphate and ethyl acetate were added, and the reaction mixture filtered and concentrated under reduced pressure. The crude material was purified by column chromatography eluting with 100% iso-hexane to 100% DCM to 25:1 DCM:methanol (0.63 g, 39% based on (3-(8-(1,3-dioxolan-2-yl)octyloxy)phenyl)(phenyl) methanol).

$^1$H NMR (400 MHz, CDCl$_3$): δ 7.39-7.18 (m, 6H), 7.00-6.91 (m, 2H), 6.76-6.73 (m, 1H), 5.17 (s, 1H), 4.84 (t, J=4.8 Hz, 1H), 4.00-3.83 (m, 6H), 1.79-1.53 (m, 8H), 1.43-1.33 (m, 8H).

Step 5. (R)-Quinuclidin-3-yl(3-(8-(1,3-dioxolan-2-yl)octyloxy)-phenyl)(phenyl)-methylcarbamate

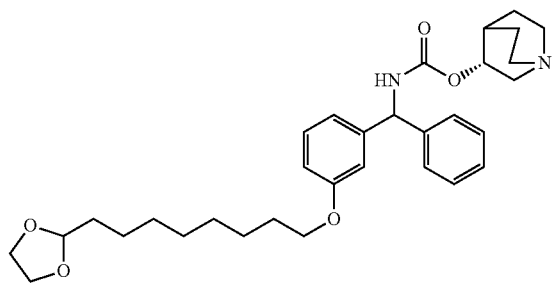 [SMILES: O=C(NC(c1ccccc1)c1cccc(OCCCCCCCCC2OCCO2)c1)O[C@H]1CN2CCC1CC2]

To a stirred solution of (3-(8-(1,3-dioxolan-2-yl)octyloxy) phenyl)-(phenyl)-methanamine (0.62 g, 1.62 mmol) in pyridine (10 mL) at 0° C., (R)-quinuclidin-3-yl carbonochloridate (0.48 g, 2.1 mmol) was added. The reaction was stirred at 0° C. for 1 hour and then allowed to warm to RT for 16 hours. Water was added to the reaction mixture and extracted with ethyl acetate (×3). The combined extracts were washed with brine, dried (sodium sulfate), filtered, and concentrated under reduced pressure. The crude material was purified by chromatography on a KP-NH Biotage cartridge eluting with 0-20% methanol in ethyl acetate to afford the title compound (0.67 g, 78%).

H NMR (400 MHz, CDCl$_3$): δ 7.41-7.18 (m, 6H), 6.87-6.74 (m, 3H), 5.96-5.82 (br m, 1H), 5.32 (br s, 1H), 4.86-4.82 (m, 1H), 4.76-4.69 (m, 1H), 4.01-3.81 (m, 6H), 3.20 (br s, 1H), 2.96-2.60 (m, 5H), 2.00 (br s, 1H), 1.79-1.19 (m, 17H).

Step 6. (R)-Quinuclidin-3-yl(3-(9-oxononyloxy)phenyl)(phenyl)-methylcarbamate

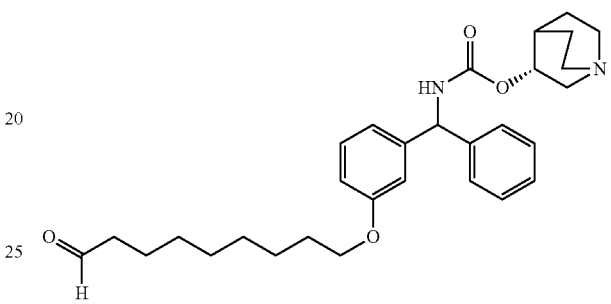

To a stirred solution of (R)-quinuclidin-3-yl(3-(8-(1,3-dioxolan-2-yl)octyloxy)phenyl)(phenyl)methylcarbamate (0.66 g, 1.23 mmol) in THF (10 mL), 2M hydrochloric acid was added (20 mL). The reaction mixture was stirred at RT for 3 hours. To the reaction mixture was added 10% aqueous potassium carbonate, and the mixture extracted with DCM (×3). The combined organic extracts were washed poured through a hydrophobic cartridge, and concentrated under reduced pressure to afford the title compound (0.64 g, quantitative yield). The material was used directly in the next step with no further purification.

Step 7. (R)-Quinuclidin-3-yl(3-(9-((R)-2-hydroxy-2-(8-hydroxy-2-oxo-1,2-dihydroquinolin-5-yl)ethylamino)nonyloxy)phenyl)(phenyl)methylcarbamate To a suspension of (R)-5-(2-amino-1-hydroxyethyl)-8-hydroxyquinolin-2(1H)-one hydrochloride (0.17 g, 0.66 mmol) in methanol (2.5 mL), triethylamine (0.18 mL, 1.32 mmol) was added and the reaction mixture stirred for 10 minutes at RT. To the reaction mixture was then added a solution of (R)-quinuclidin-3-yl(3-(9-oxononyloxy)phenyl) (phenyl)-methylcarbamate (0.33 g, 0.66 mmol) in methanol (2.5 mL), and the reaction mixture was stirred at RT for 1 hour. To the reaction mixture was added sodium triacetoxyborohydride (0.26 g, 1.23 mmol) followed by acetic acid (0.15 mL, 2.64 mmol). The reaction mixture was stirred at RT for 16 hours. Water was added, and the reaction mixture concentrated under reduced pressure. The crude material was purified by reverse phase preparative HPLC to afford the title compound (0.041 g, 9%).

The following compounds were prepared using the procedure described for the preparation of compound 1:

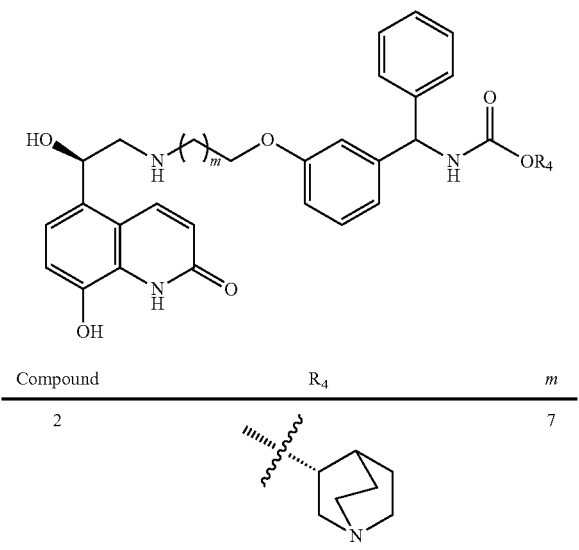
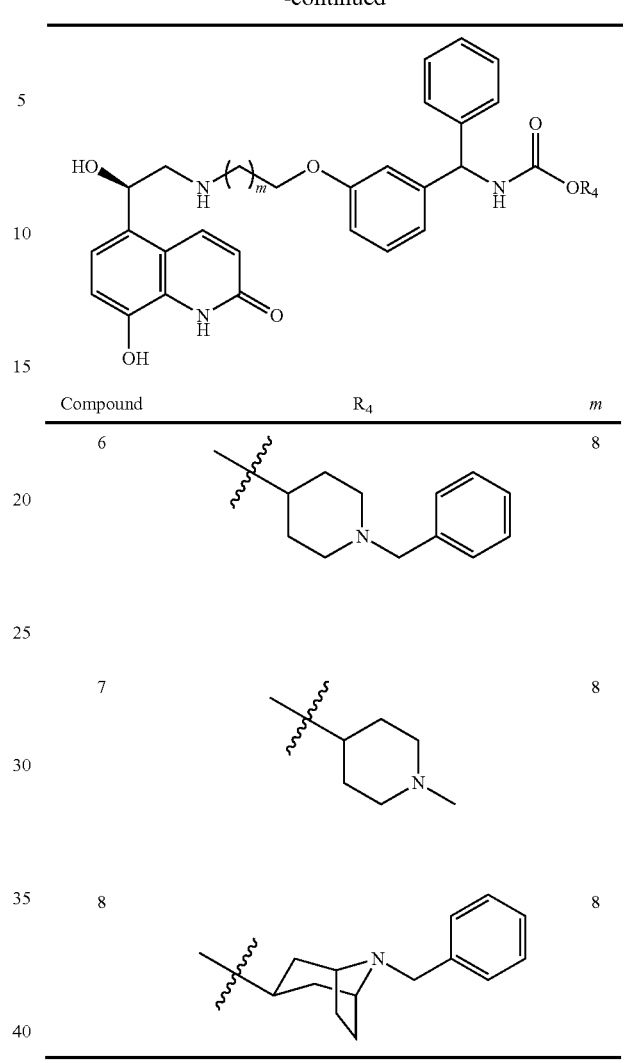
Example 9
(R)-Quinuclidin-3-yl(4-(9-((R)-2-hydroxy-2-(8-hydroxy-2-oxo-1,2-dihydroquinolin-5-yl)ethylamino)nonyloxy)phenyl)(phenyl)-methylcarbamate (compound 9)
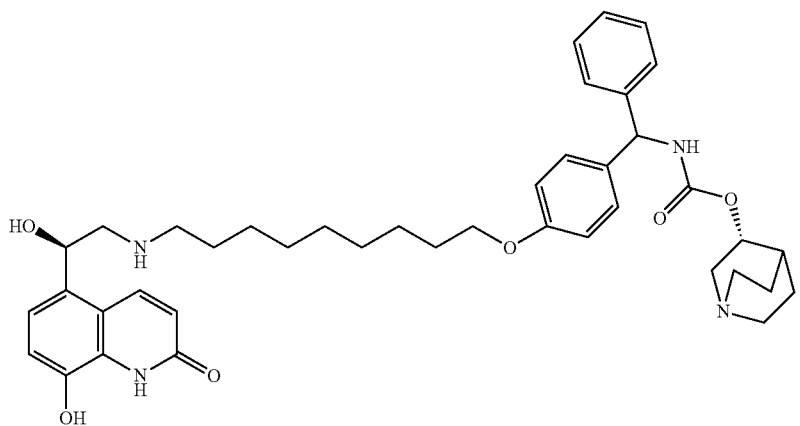 [SMILES: O=C(NC(c1ccccc1)c1ccc(OCCCCCCCCCNC[C@H](O)c2ccc(O)c3[nH]c(=O)ccc23)cc1)O[C@H]1CN2CCC1CC2]

The title compound was prepared as in Example 1 with 4-hydroxybenzophenone replacing 3-hydroxybenzophenone in Step 1. The additional steps required to make the target compound are described in the preparation of Example 1.
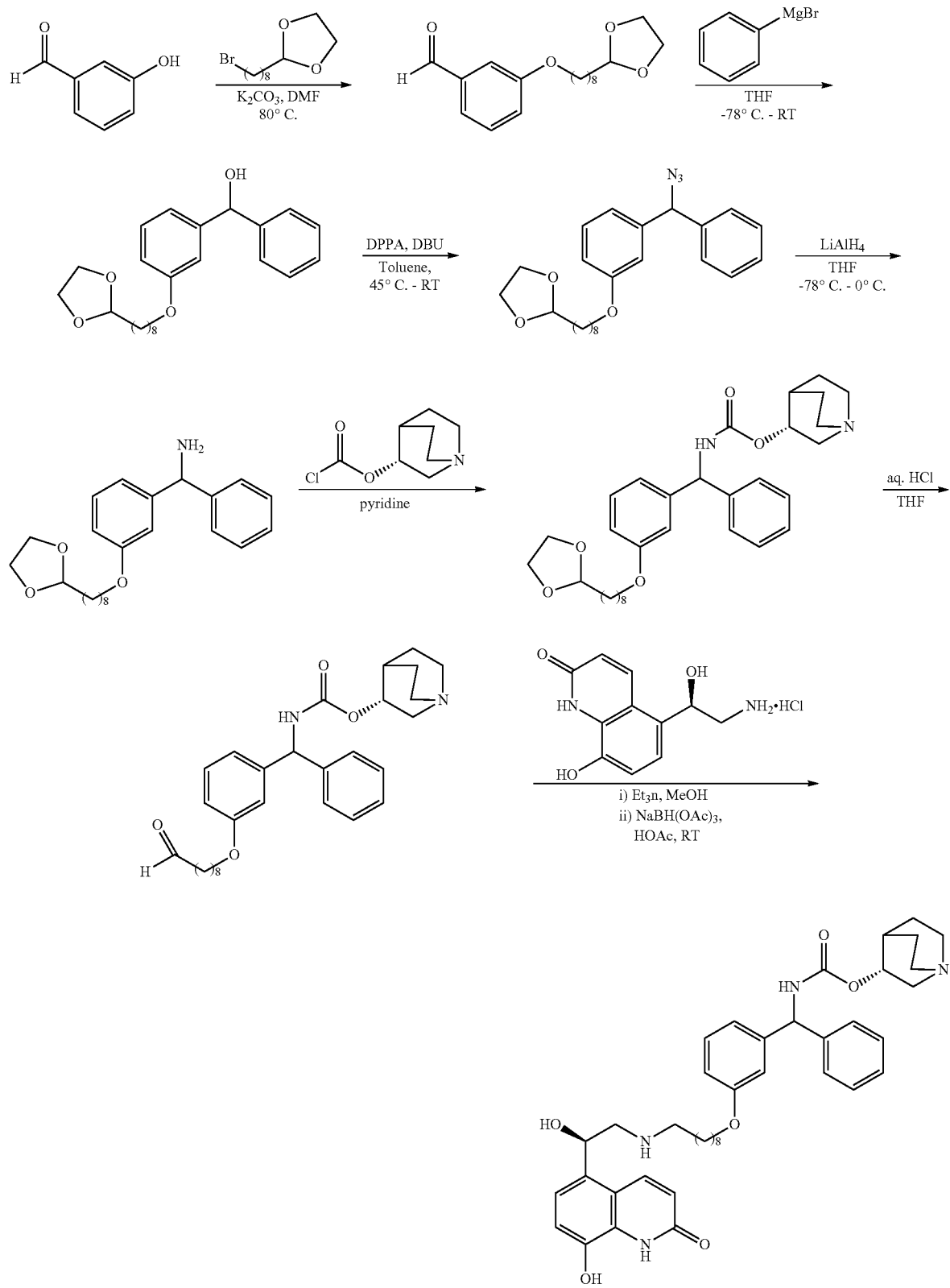

Example 10

(R)-Quinuclidin-3-yl(3-(9-((R)-2-hydroxy-2-(8-hydroxy-2-oxo-1,2-dihydroquinolin-5-yl)ethylamino)nonyloxy)phenyl)(thiophen-2-yl)methylcarbamate (compound 10)

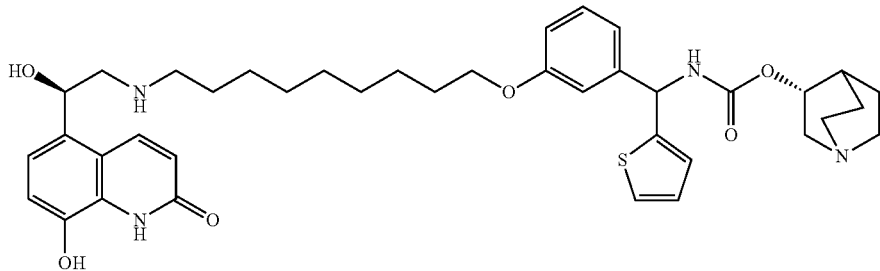 [SMILES: O=C(NC(c1cccc(OCCCCCCCCCNC[C@H](O)c2ccc(O)c3[nH]c(=O)ccc23)c1)c1cccs1)O[C@H]1CN2CCC1CC2]

Step 1. 3-(8-(1,3-Dioxolan-2-yl)octyloxy)benzaldehyde

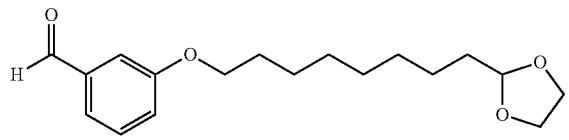 [SMILES: O=Cc1cccc(OCCCCCCCCC2OCCO2)c1]

To a stirred solution of 2-(8-bromooctyl)-1,3-dioxolane (5 g, 18.85 mmol) in dimethyl formamide (100 mL) was added 3-hydroxybenzaldehyde (2.37 g, 19.42 mmol) and potassium carbonate (5.37 g, 38.83 mmol). The reaction mixture was stirred at 80° C. for 16 hours. The reaction mixture was diluted with water and extracted with ethyl acetate (×3). The combined organic extracts were washed with saturated aqueous sodium hydrogen carbonate solution and brine, dried (sodium sulfate), filtered, and concentrated under reduced pressure. The crude material was purified by silica gel column chromatography eluting with 0-100% ethyl acetate in isohexane to afford the title compound (4.66 g, 78%).

$^1$H NMR (400 MHz, CDCl$_3$): δ 9.97 (s, 1H); 7.46-7.40 (m, 2H); 7.38 (d, J=2.59 Hz, 1H); 7.20-7.14 (m, 1H); 4.84 (t, J=4.82 Hz, 1H); 4.05-3.93 (m, 4H); 3.89-3.81 (m, 2H); 1.85-1.74 (m, 2H); 1.55-1.27 (m, 12H).

Step 2. (3-(8-(1,3-Dioxolan-2-yl)octyloxy)phenyl)(thiophen-2-yl)methanol

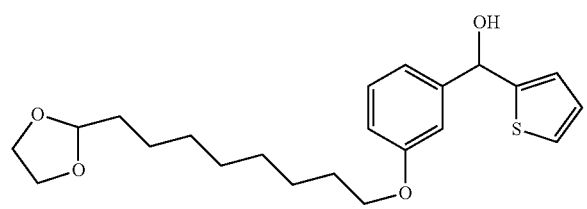 [SMILES: OC(c1cccc(OCCCCCCCCC2OCCO2)c1)c1cccs1]

To a stirred solution of 3-(8-(1,3-dioxolan-2-yl)octyloxy)benzaldehyde (1.0 g, 3.25 mmol) in THF (30 mL) at −78° C. under an atmosphere of nitrogen, a solution of 2-thienylmagnesium bromide (1M in THF, 4.23 mL, 4.23 mmol) was added over 10 minutes. After stirring at −78° C. for 1 hour, the reaction was allowed to warm to RT and stirred for 16 hours. The reaction was quenched with saturated aqueous ammonium chloride solution and extracted with ethyl acetate (×3). The combined organic extracts were washed with brine, dried (magnesium sulfate), filtered, and concentrated under reduced pressure. The crude material was purified by silica gel chromatography eluting with 0-50% ethyl acetate in isohexane to afford the title compound (1.12 g, 87%).

$^1$H NMR (400 MHz, CDCl$_3$): δ 7.29-7.22 (m, 2H), 7.05-6.95 (m, 2H), 6.96-6.92 (m, 1H), 6.89 (dt, J=3.58, 1.09 Hz, 1H), 6.85-6.81 (m, 1H), 6.02 (s, 1H), 4.83 (t, J=4.83 Hz, 1H), 4.06-3.89 (m, 4H), 3.89-3.81 (m, 2H), 2.47 (s, 1H), 1.81-1.69 (m, 2H), 1.70-1.58 (m, 2H), 1.49-1.21 (m, 10H).

The title compound was prepared as described in Example 1 with (3-(8-(1,3-dioxolan-2-yl)octyloxy)phenyl)(thiophen-2-yl)methanol replacing (3-(8-(1,3-dioxolan-2-yl)octyloxy)phenyl)(phenyl)methanol in Step 3. The additional steps required to make the target compound are described in the preparation of Example 1.

The following compounds were prepared using the methodology described for the preparation of compound 10 using the appropriate Grignard reagent to introduce suitable bromoacetals to generate alternate chain lengths (m)

| Compound | R$_2$ | m |
|---|---|---|
| 11 | 4-biphenyl | 8 |
| 12 | napthyl | 8 |
| 13 | 3-biphenyl | 8 |
| 14 | 2-pyridinyl | 8 |
| 15 | 3,5-difluorophenyl | 8 |
| 16 | 3,4,5-trflurophenyl | 8 |
| 17 | 2-methylphenyl | 8 |
| 18 | 3-methylphenyl | 8 |
| 19 | 4-methylphenyl | 8 |
| 20 | 4-fluorophenyl | 8 |
| 1B | 3-fluorophenyl | 8 |
| 2B | 3-chlorophenyl | 8 |
| 1C | cyclohexyl | 8 |
| 2C | 2-thienyl | 5 |
| 3C | 3-thienyl | 5 |

Example 21

(R)-Quinuclidin-3-yl(3-(9-(2-(4-hydroxy-2-oxo-2,3-dihydrobenzo[d]thiazol-7-yl)ethylamino)nonyloxy)phenyl)(phenyl)methylcarbamate (compound 21)

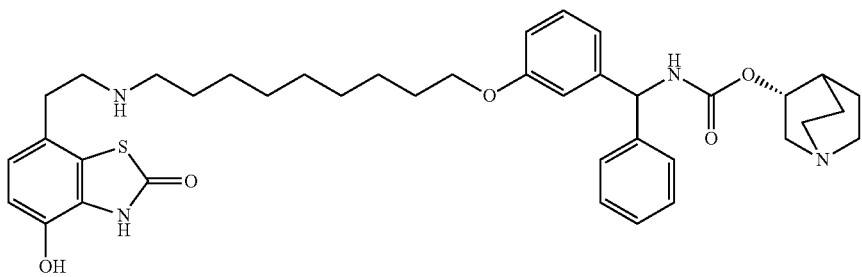 [SMILES: O=C(NC(c1ccccc1)c1cccc(OCCCCCCCCCNCCc2ccc(O)c3[nH]c(=O)sc23)c1)O[C@H]1CN2CCC1CC2]

The preparation of compound 21 requires 7-(2-aminoethyl)-4-hydroxybenzo-[d]thiazol-2(3H)-one hydrobromide (prepared as described in Organic Process Research & Development 2004, 8, 628-642, which is incorporated herein by reference in its entirety) replacing (R)-5-(2-amino-1-hydroxyethyl)-8-hydroxyquinolin-2(1H)-one hydrochloride in Example 1 Step 7. The additional steps required to make the title compound are described in Example 1.

Scheme for Example 22
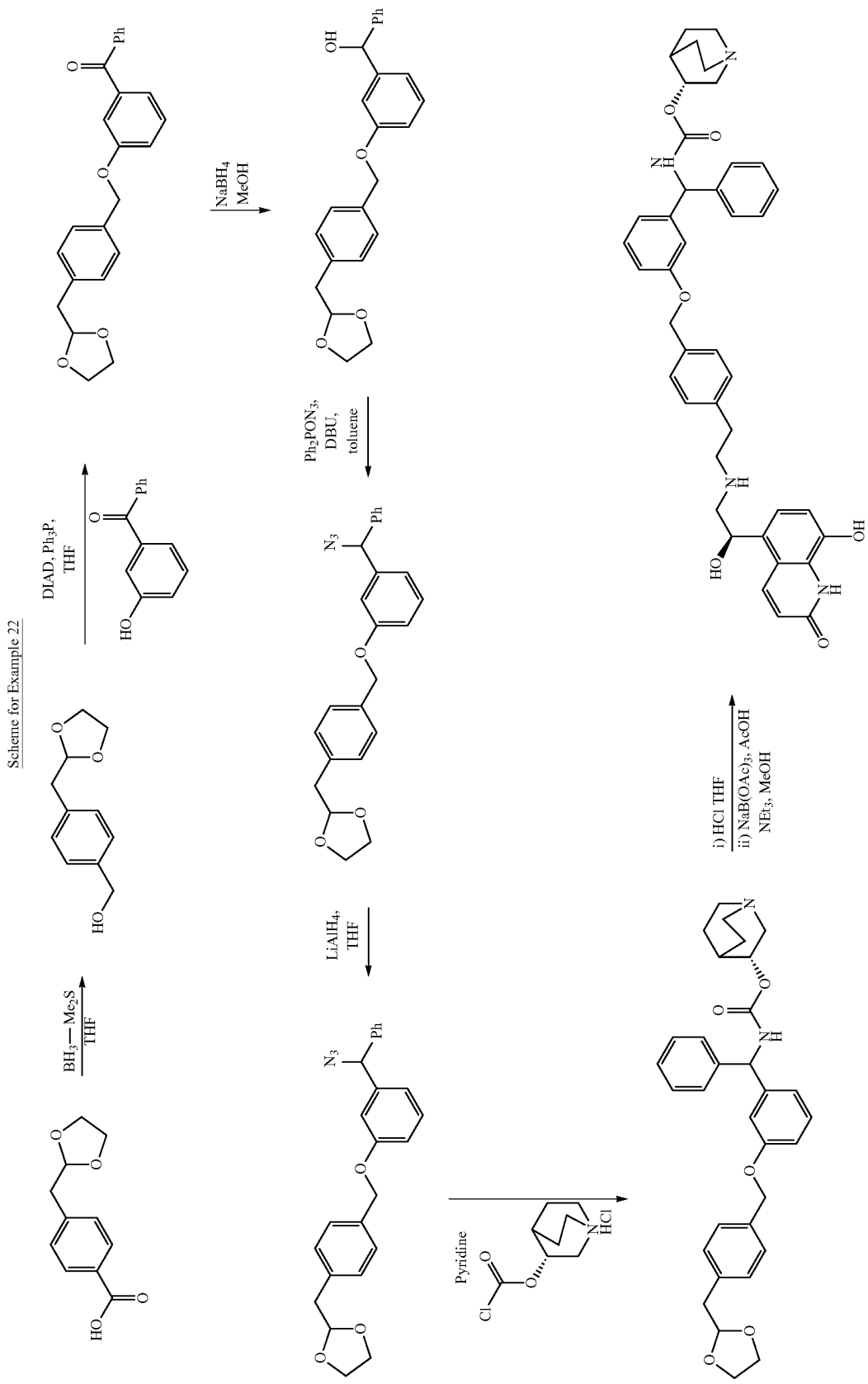

Example 22

(R)-Quinuclidin-3-yl(3-(4-(2-((R)-2-hydroxy-2-(8-hydroxy-2-oxo-1,2-dihydroquinolin-5-yl)ethylamino)ethyl)benzyloxy)phenyl)(phenyl)-methylcarbamate (compound 22)

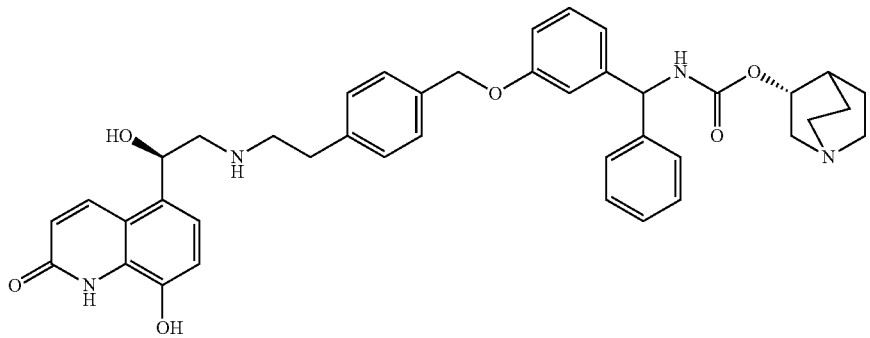 [SMILES: O=C(NC(c1ccccc1)c1cccc(OCc2ccc(CCNC[C@H](O)c3ccc(O)c4[nH]c(=O)ccc34)cc2)c1)O[C@H]1CN2CCC1CC2]

Step 1.
(4-((1,3-Dioxolan-2-yl)methyl)phenyl)methanol

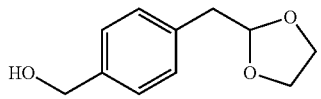 [SMILES: OCc1ccc(CC2OCCO2)cc1]

To a cooled (0° C.) solution of 4-((1,3-dioxolan-2-yl)methyl)benzoic acid (1.02 g, 4.92 mmol) in anhydrous THF (63.5 mL), a solution of borane dimethylsulfide complex (2.0 M in THF, 12.29 mL, 24.59 mmol) was added dropwise. The reaction mixture was stirred at this temperature for 5 minutes and then the coolant removed. The reaction mixture was stirred at RT for 16 hours. The reaction mixture was cooled to 0° C. and methanol (1 mL) was added. The reaction mixture was diluted with water and saturated aqueous sodium hydrogen carbonate and then extracted with ethyl acetate (×2). The combined organic extracts were washed with brine, dried (magnesium sulphate) filtered, and concentrated under reduced pressure. The crude material was purified by silica gel chromatography eluting with 0-50% ethyl acetate in iso-hexane to afford the title compound (0.936 g, 98%).

$^1$H NMR (400 MHz, CDCl$_3$): δ 7.29 (m, 4H), 5.08-5.02 (m, 1H), 4.67 (d, J=5.97 Hz, 2H), 4.00-3.78 (m, 4H), 2.97 (d, J=4.82 Hz, 2H), 1.61-1.58 (m, 1H).

Step 2. (3-(4-((1,3-Dioxolan-2-yl)methyl)benzyloxy)phenyl)-(phenyl)methanone

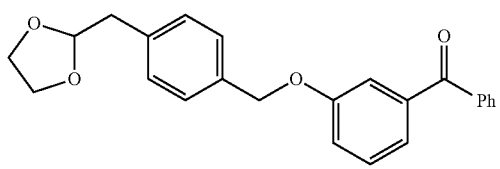 [SMILES: O=C(c1ccccc1)c1cccc(OCc2ccc(CC3OCCO3)cc2)c1]

To a cooled (0° C.) solution of (4-((1,3-dioxolan-2-yl)methyl)phenyl)methanol (0.45 g, 2.317 mmol), 3-hydroxy-benzophenone (0.551 g, 2.78 mmol) and triphenylphosphine (0.729 g, 2.78 mmol) in anhydrous THF, di-iso-propylazodicarboxylate (1.027 mL, 2.78 mmol) was added dropwise. The reaction mixture was allowed to warm to RT and stirred at this temperature for 16 hours. The reaction mixture was diluted with ethyl acetate and washed with 10% aqueous potassium carbonate, brine and dried (magnesium sulfate). The suspension was filtered and concentrated under reduced pressure. The crude material was purified by silica gel chromatography eluting with 100% iso-hexane to 25% ethyl acetate in iso-hexane to afford the title compound (1.022 g, >100%).

$^1$H NMR (400 MHz, CDCl$_3$): δ 7.82-7.76 (m, 2H), 7.63-7.55 (m, 1H), 7.51-7.16 (m, 10H), 5.11-5.05 (m, 3H), 3.98-3.92 (m, 2H), 3.87-3.82 (m, 2H), 2.98 (d, J=4.8 Hz, 2H).

The title compound was prepared as described in Example 1 with (3-(4-((1,3-dioxolan-2-yl)methyl)benzyloxy)phenyl)(phenyl)methanone replacing (3-(8-(1,3-dioxolan-2-yl)octyloxy)phenyl)(phenyl)methanone in Step 2. The additional steps required to make the target compound are described in Example 1.

Example 23

(R)-Quinuclidin-3-yl(3-(2-((R)-2-hydroxy-2-(8-hydroxy-2-oxo-1,2-dihydroquinolin-5-yl)ethylamino)ethyl)phenyl)(phenyl)methylcarbamate (compound 23)

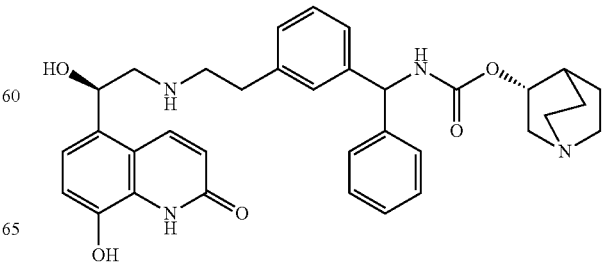

Step 1. 3-((1,3-Dioxolan-2-yl)methyl)benzaldehyde

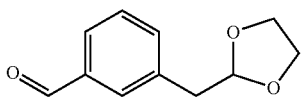 [SMILES: O=Cc1cccc(CC2OCCO2)c1]

To a solution of (3-((1,3-dioxolan-2-yl)methyl)phenyl)methanol (prepared as in Example 22, Step 1 with 3-((1,3-dioxolan-2-yl)methyl)benzoic acid replacing 4-((1,3-dioxolan-2-yl)methyl)benzoic acid; 0.47 g, 2.42 mmol) in 1,4-dioxane (8 mL), manganese (IV) oxide (2.35 g) was added. The resulting suspension was heated at 100° C. for 16 hours. The reaction mixture was allowed to cool, and the suspension was filtered through a pad of celite. The celite pad was washed with ethyl acetate and the filtrate evaporated at reduced pressure to afford the title compound (0.352 g, 76%).

$^1$H NMR (400 MHz, CDCl$_3$): δ 10.01 (s, 1H), 7.79-7.74 (m, 2H), 7.56 (dt, J=7.6, 1.5 Hz, 1H), 7.51-7.43 (m, 1H), 5.13-5.08 (m, 1H), 3.96-3.81 (m, 4H), 3.06 (d, J=4.6 Hz, 2H).

The title compound was prepared as described in Example 2 with 3-((1,3-dioxolan-2-yl)methyl)benzaldehyde replacing 3-(8-(1,3-dioxolan-2-yl)octyloxy)benzaldehyde in Step 2. The additional steps required to make the target compound are described in Example 1.

Example 24

(3R)-3-((((3-((6-(((R)-2-hydroxy-2-(8-hydroxy-2-oxo-1,2-dihydroquinolin-5-yl)ethyl)amino)hexyl)oxy)phenyl)(phenyl)methyl)carbamoyl)oxy)-1-(2-oxo-2-phenylethyl)quinuclidin-1-ium

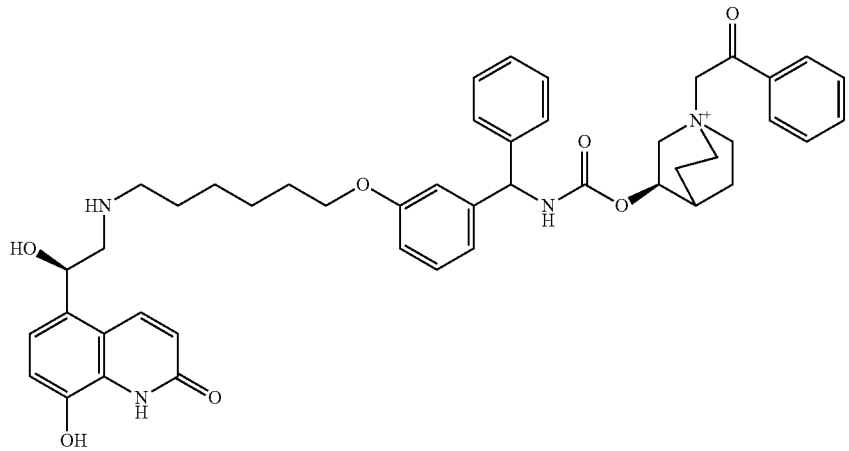 [SMILES: O=C(NC(c1ccccc1)c1cccc(OCCCCCCNC[C@H](O)c2ccc(O)c3[nH]c(=O)ccc23)c1)O[C@H]1C[N+]2(CC(=O)c3ccccc3)CCC1CC2]

To a solution of (R)-quinuclidin-3-yl(3-(6-((R)-2-hydroxy-2-(8-hydroxy-2-oxo-1,2-dihydroquinolin-5-yl)ethylamino)hexyloxy)-phenyl)(phenyl)methylcarbamate (Example 4, 0.02 g, 0.03 mmol) in methanol (0.5 mL), was added a solution of 2-bromoacetophenone (0.007 g, 0.04 mmol) in methanol (0.5 mL). The reaction mixture was stirred at RT for 1 hour. Further 2-bromoacetophenone (0.007 g, 0.04 mmol) added, and the reaction continued for 15 minutes. The solvent was evaporated at reduced pressure. The residue was purified by reverse phase preparative HPLC to afford the title compound (0.010 g, 43%).

Example 25

(R)-quinuclidin-3-yl(3-(3-(2-((R)-2-hydroxy-2-(8-hydroxy-2-oxo-1,2-dihydroquinolin-5-yl)ethylamino)ethyl)benzyloxy)phenyl)(phenyl)methylcarbamate formate (compound 3B)

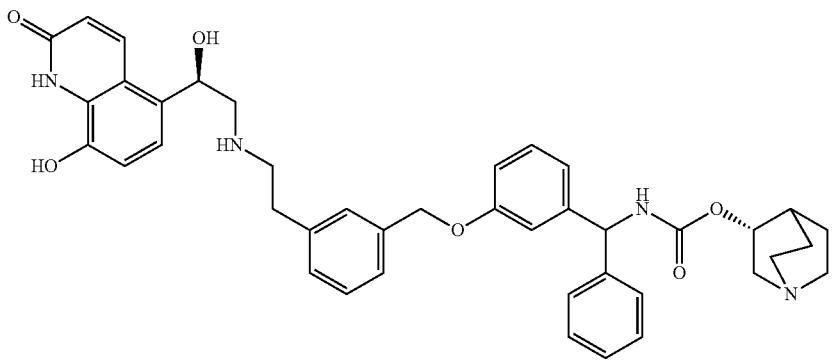 [SMILES: O=C(NC(c1ccccc1)c1cccc(OCc2cccc(CCNC[C@H](O)c3ccc(O)c4[nH]c(=O)ccc34)c2)c1)O[C@H]1CN2CCC1CC2]

The title compound was prepared as described in Example 22 with 3-((1,3-dioxolan-2-yl)methyl)benzoic acid replacing 4-((1,3-dioxolan-2-yl)methyl)benzoic acid in Step 1. The additional steps required to make the target compound are described in the preparation of Example 1.

Example 26

(3R)-3-(((((3-((4-(2-(((R)-2-hydroxy-2-(8-hydroxy-2-oxo-1,2-dihydroquinolin-5-yl)ethyl)amino)ethyl)benzyl)oxy)phenyl)(phenyl)methyl)-carbamoyl)oxy)-1-(2-oxo-2-phenylethyl)quinuclidin-1-ium (compound 4B)

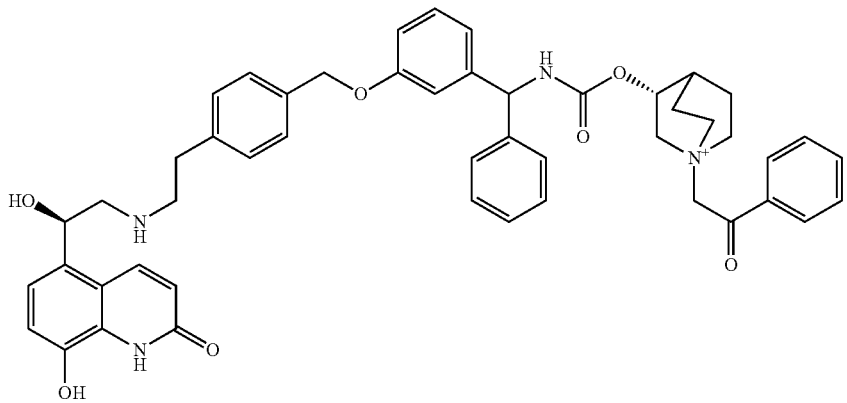 [SMILES: O=C(NC(c1ccccc1)c1cccc(OCc2ccc(CCNC[C@H](O)c3ccc(O)c4[nH]c(=O)ccc34)cc2)c1)O[C@H]1C[N+]2(CC(=O)c3ccccc3)CCC1CC2]

The title compound was prepared as described in Example 24 with (R)-quinuclidin-3-yl(3-(4-(2-((R)-2-hydroxy-2-(8-hydroxy-2-oxo-1,2-dihydroquinolin-5-yl)ethylamino)ethyl)benzyloxy)phenyl)(phenyl)methylcarbamate (Example 22) replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 27

(3R)-3-(((((3-chlorophenyl)(3-((9-(((R)-2-hydroxy-2-(8-hydroxy-2-oxo-1,2-dihydroquinolin-5-yl)ethyl)amino)nonyl)oxy)phenyl)methyl)carbamoyl)oxy)-1-(2-oxo-2-phenylethyl)quinuclidin-1-ium (compound 5B)

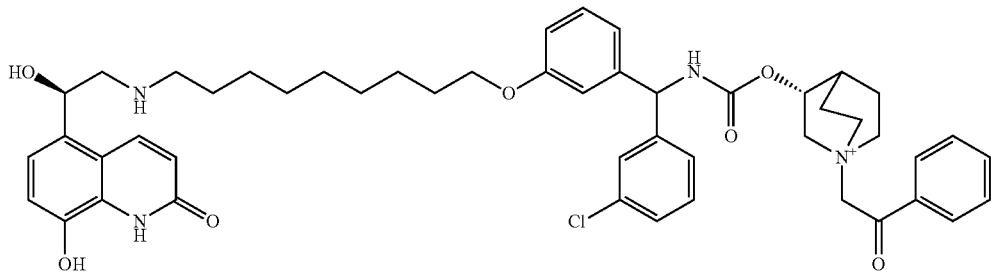 [SMILES: O=C(NC(c1cccc(Cl)c1)c1cccc(OCCCCCCCCCNC[C@H](O)c2ccc(O)c3[nH]c(=O)ccc23)c1)O[C@H]1C[N+]2(CC(=O)c3ccccc3)CCC1CC2]

The title compound was prepared as described in Example 24 with ((R)-quinuclidin-3-yl(3-chlorophenyl)(3-(9-(((R)-2-hydroxy-2-(8-hydroxy-2-oxo-1,2-dihydroquinolin-5-yl)ethylamino)nonyloxy)phenyl)methylcarbamate (Example 26) replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 28

(3R)-3-((((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium (compound 6B)

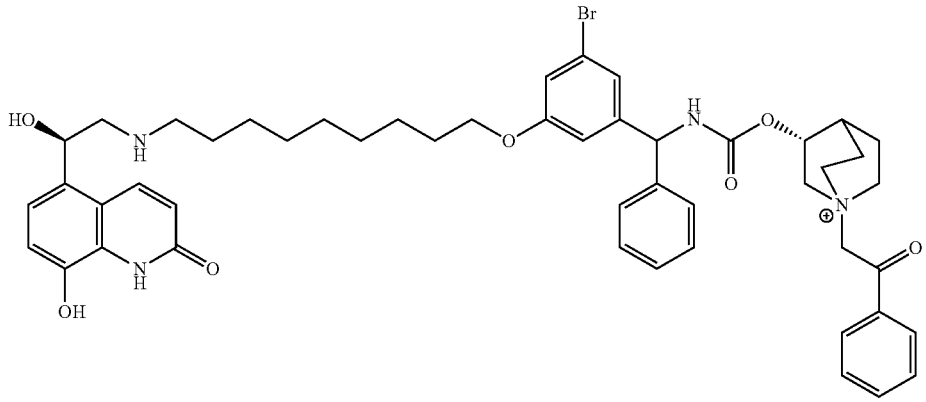 [SMILES: O=C(NC(c1ccccc1)c1cc(Br)cc(OCCCCCCCCCNC[C@H](O)c2ccc(O)c3[nH]c(=O)ccc23)c1)O[C@H]1C[N+]2(CC(=O)c3ccccc3)CCC1CC2]

Step 1. Benzyl 3-bromo-5-hydroxybenzoate

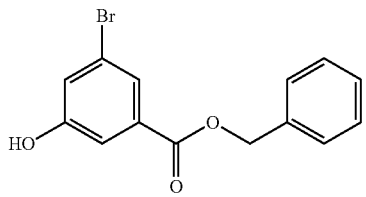 [SMILES: O=C(OCc1ccccc1)c1cc(O)cc(Br)c1]

To a stirred solution of 3-bromo-5-hydroxybenzoic acid (2 g, 9.22 mmol) in dimethyl formamide (50 mL), was added potassium carbonate (1.27 g, 9.21 mmol), and the mixture was stirred at 0° C. for 20 minutes. Benzyl bromide (1.1 mL, 9.25 mmol) was added, and the reaction mixture allowed to warm to room temperature over 16 hours. The reaction mixture was diluted with water and extracted with ethyl acetate (×3). The combined organic extracts were washed with brine, dried (magnesium sulphate), filtered, and concentrated under reduced pressure to afford the title compound (2.85 g, quantitative yield).

$^1$H NMR (400 MHz, CDCl$_3$): δ 7.75-7.72 (m, 1H); 7.51-7.48 (m, 1H); 7.45-7.34 (m, 5H); 7.24-7.21 (m, 1H); 5.34 (s, 2H).

Step 2. Benzyl 3-((8-(1,3-dioxolan-2-yl)octyl)oxy)-5-bromobenzoate

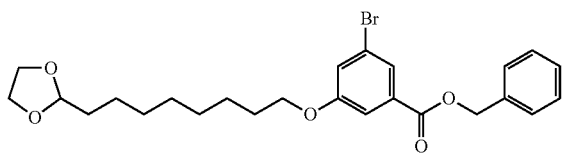 [SMILES: O=C(OCc1ccccc1)c1cc(Br)cc(OCCCCCCCCC2OCCO2)c1]

To a stirred solution of benzyl 3-bromo-5-hydroxybenzoate (2.85 g, 9.22 mmol) in dimethyl formamide (50 mL), was added 2-(8-bromooctyl)-1,3-dioxolane (2.44 g, 9.21 mmol) and potassium carbonate (1.91 g, 13.8 mmol), and the mixture stirred at 80° C. for 16 hours. The reaction mixture was cooled to room temperature, diluted with water and extracted with ethyl acetate (×3). The combined organic extracts were washed with brine, dried (magnesium sulphate), filtered, and concentrated under reduced pressure. The crude material was purified by silica gel chromatography eluting with 0-7% ethyl acetate in iso-hexane to afford the title compound (2.94 g, 65%).

$^1$H NMR (400 MHz, CDCl$_3$): δ 7.76-7.75 (m, 1H); 7.51-7.50 (m, 1H); 7.45-7.34 (m, 5H); 7.23-7.22 (m, 1H); 5.35 (s, 2H); 4.84 (t, J=4.8 Hz; 1H); 4.00-3.94 (m, 4H); 3.86-3.83 (m, 2H); 1.80-1.73 (m 2H); 1.68-1.63 (m, 2H); 1.44-1.22 (m, 10H).

Step 3. (3-((8-(1,3-Dioxolan-2-yl)octyl)oxy)-5-bromophenyl)methanol

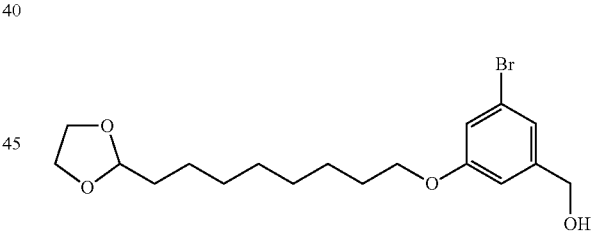

To a solution of benzyl 3-((8-(1,3-dioxolan-2-yl)octyl)oxy)-5-bromobenzoate in tetrahydrofuran (30 mL) at −78° C., was added a solution of lithium aluminium hydride in THF (2.0 M, 3.3 mL, 6.60 mmol). The reaction mixture was stirred for 4 hours, then quenched with water (0.25 mL), 2 M sodium hydroxide (0.25 mL) and water (0.75 mL). The coolant was removed and ethyl acetate and magnesium sulphate was added, and the mixture stirred at room temperature for 20 minutes. The suspension was filtered, washed with ethyl acetate, and the filtrate was concentrated under reduced pressure. The crude material was purified by silica gel chromatography eluting with 0-17% ethyl acetate in iso-hexane to afford the title compound as a 10:7 ratio of product to starting material (1.69 g, 73%).

$^1$H NMR (400 MHz, CDCl$_3$): δ 7.08 (s, 1H); 6.97-6.96 (m, 1H); 6.84 (m, 1H); 4.84 (t, J=4.8 Hz, 1H); 4.66-4.63 (m, 2H); 3.99-3.89 (m, 4H); 3.84-3.81 (m, 2H); 1.79-1.74 (m, 2H); 1.66-1.63 (m, 2H); 1.45-1.42 (m, 10H).

Step 4. 3-((8-(1,3-Dioxolan-2-yl)octyl)oxy)-5-bromobenzaldehyde

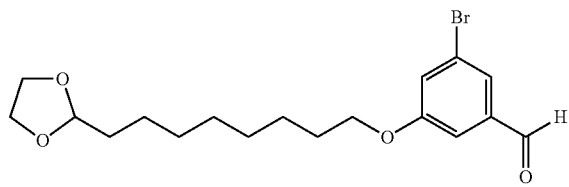 [SMILES: O=Cc1cc(Br)cc(OCCCCCCCCC2OCCO2)c1]

To a stirred solution of (3-((8-(1,3-dioxolan-2-yl)octyl)oxy)-5-bromophenyl)methanol (1.69 g, 4.36 mmol) in 1,4-dioxane (25 mL), was added magnesium (IV) oxide (1.90 g, 21.9 mmol). The reaction mixture was heated to 100° C. for 16 hours. The suspension was filtered, washed with ethyl acetate, and the filtrate was concentrated under reduced pressure to afford the title compound (1.25 g, 74%).

$^{1}$H NMR (400 MHz, CDCl$_{3}$): δ 9.89 (s, 1H); 7.56 (m, 1H); 7.31 (m, 2H); 4.85 (t, J=4.8 Hz, 1H); 4.10-3.95 (m 4H); 3.86-3.83 (m, 2H); 1.82-1.75 (m, 2H); 1.69-1.63 (m, 2H); 1.45-1.34 (m, 10H).

Step 5. (3-((8-(1,3-Dioxolan-2-yl)octyl)oxy)-5-bromophenyl)(phenyl)methanol

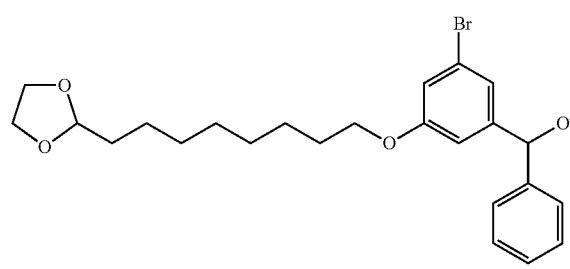

The title compound was prepared as described in Example 10 Step 2 with 3-((8-(1,3-dioxolan-2-yl)octyl)oxy)-5-bromobenzaldehyde and phenylmagnesium bromide replacing 3-(8-(1,3-dioxolan-2-yl)octyloxy)benzaldehyde and 2-thienylmagnesium bromide, respectively.

$^{1}$H NMR (400 MHz, CDCl$_{3}$): δ 7.38-7.27 (m, 5H); 7.10 (d, J=1.52 Hz, 1H); 6.95-6.91 (m, 1H); 6.87 (s, 1H); 5.74 (d, J=3.46 Hz, 1H); 4.84 (t, J=4.83 Hz, 1H); 3.99-3.93 (m, 2H); 3.90 (t, J=6.48 Hz, 2H); 3.87-3.81 (m, 2H); 2.28 (d, J=4.43 Hz, 1H); 1.78-1.60 (m, 4H); 1.37 (d, J=34.79 Hz, 10H).

Step 6. 2-(8-(3-(Azido(phenyl)methyl)-5-bromophenoxy)octyl)-1,3-dioxolane

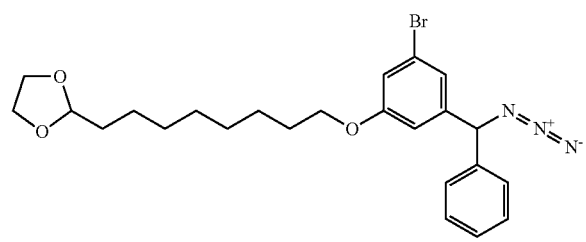 [SMILES: [N-]=[N+]=NC(c1ccccc1)c1cc(Br)cc(OCCCCCCCCC2OCCO2)c1]

The title compound was prepared as described in Example 1 Step 3 with (3-((8-(1,3-dioxolan-2-yl)octyl)oxy)-5-bromophenyl)(phenyl)methanol replacing (3-(8-(1,3-dioxolan-2-yl)octyloxy)phenyl)(phenyl)methanol.

$^{1}$H NMR (400 MHz, CDCl$_{3}$): δ 7.40-7.19 (m, 5H); 7.11-6.91 (m, 1H); 6.97-6.95 (m, 1H); 6.78 (s, 1H); 5.61 (s, 1H); 4.84 (t, J=4.83 Hz, 1H); 3.98-3.93 (m, 2H); 3.92-3.86 (m, 2H); 3.88-3.82 (m, 2H); 1.79-1.61 (m, 4H); 1.53-1.25 (m, 10H).

Step 7. (3-((8-(1,3-Dioxolan-2-yl)octyl)oxy)-5-bromophenyl)(phenyl)methanamine

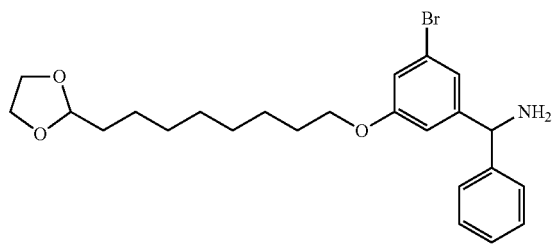 [SMILES: NC(c1ccccc1)c1cc(Br)cc(OCCCCCCCCC2OCCO2)c1]

To a stirred reaction of 2-(8-(3-(azido(phenyl)methyl)-5-bromophenoxy)octyl)-1,3-dioxolane (1.19 g, 2.45 mmol) in tetrahydrofuran (15 mL) and water (0.3 mL), was added triphenylphosphine (0.71 g, 2.69 mmol). The reaction mixture was heated to 60° C. for 16 hours. The reaction mixture was cooled, concentrated and purified by silica gel chromatography eluting with 0-100% ethyl acetate in iso-hexane to afford impure title compound as a colourless oil (0.77 g, 68%).

$^{1}$H NMR (400 MHz, CDCl$_{3}$): δ 7.38-7.29 (m, 5H); 7.11 (t, J=1.55 Hz, 1H); 6.94-6.84 (m, 2H); 5.12 (s, 1H); 4.84 (t, J=4.83 Hz, 1H); 3.99-3.94 (m, 2H); 3.93-3.81 (m, 4H); 1.77-1.60 (m, 4H); 1.48-1.28 (m, 10H).

Step 8. (R)-quinuclidin-3-yl((3-((8-(1,3-dioxolan-2-yl)octyl)oxy)-5-bromophenyl)-(phenyl)methyl)carbamate

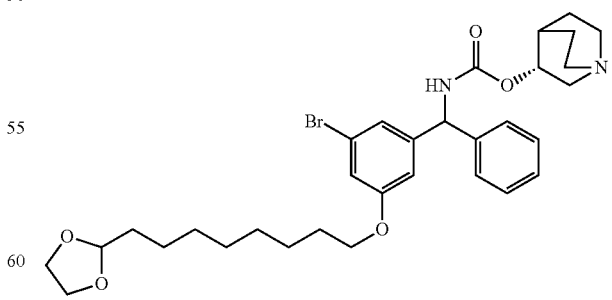

The title compound was prepared as described in Example 1, Step 5 with (3-((8-(1,3-dioxolan-2-yl)octyl)oxy)-5-bromophenyl)(phenyl)methanamine replacing (3-(8-(1,3-dioxolan-2-yl)octyloxy)phenyl)(phenyl)methanamine.

Step 9. (R)-quinuclidin-3-yl((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate The title compound was prepared as described in Example 1 Steps 6 and 7 with (R)-quinuclidin-3-yl((3-((8-(1,3-dioxolan-2-yl)octyl)oxy)-5-bromophenyl)(phenyl)-methyl)carbamate replacing (R)-quinuclidin-3-yl(3-(8-(1,3-dioxolan-2-yl)octyloxy)-phenyl)(phenyl)methylcarbamate in Step 6 and (R)-Quinuclidin-3-yl((3-bromo-5-((9-oxononyl)oxy)phenyl)(phenyl)methyl)carbamate replacing (R)-quinuclidin-3-yl(3-(9-oxononyloxy)phenyl)(phenyl)methylcarbamate in Step 7.

Step 10. (3R)-3-((((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium (compound 6B)

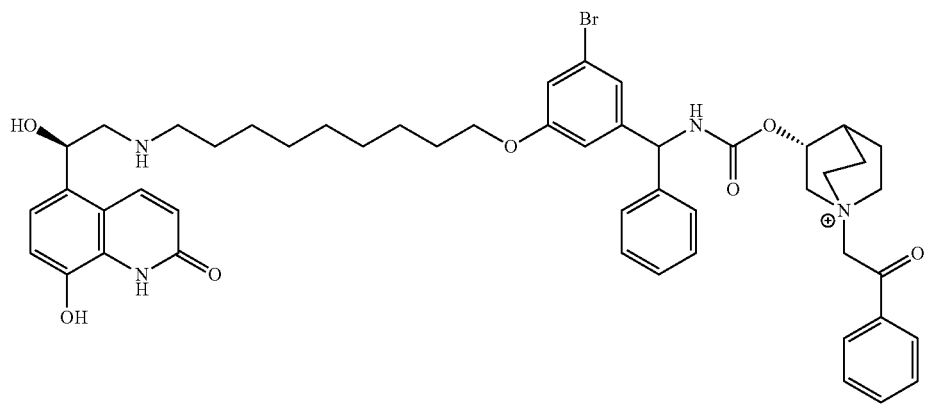 [SMILES: O=C(NC(c1ccccc1)c1cc(Br)cc(OCCCCCCCCCNC[C@H](O)c2ccc(O)c3[nH]c(=O)ccc23)c1)O[C@H]1C[N+]2(CC(=O)c3ccccc3)CCC1CC2]

The title compound was prepared as described in Example 24 with (R)-quinuclidin-3-yl((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 29

(R)-quinuclidin-3-yl(2-chloro-3-(9-((R)-2-hydroxy-2-(8-hydroxy-2-oxo-1,2-dihydroquinolin-5-yl)ethylamino)nonyloxy)phenyl)(phenyl)methylcarbamate (compound 7B)

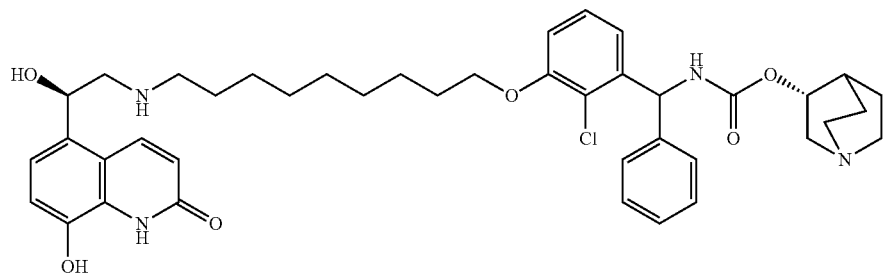 [SMILES: O=C(NC(c1ccccc1)c1cccc(OCCCCCCCCCNC[C@H](O)c2ccc(O)c3[nH]c(=O)ccc23)c1Cl)O[C@H]1CN2CCC1CC2]

Step 1. 3-((8-(1,3-Dioxolan-2-yl)octyl)oxy)-2-chlorobenzaldehyde

The title compound was prepared as described in Example 10 Step 1 with 2-chloro-3-hydroxybenzaldehyde replacing 3-hydroxybenzaldehyde.

$^1$H NMR (400 MHz, CDCl$_3$-d): δ 10.53 (d, J=0.92 Hz, 1H); 7.51 (d, J=7.79 Hz, 1H); 7.35-7.26 (m, 1H); 7.15 (d, J=8.16 Hz, 1H); 4.86-4.81 (m, 1H); 4.09-4.02 (m, 2H); 4.00-3.93 (m, 2H); 3.91-3.81 (m, 2H); 1.91-1.76 (m, 3H); 1.70-1.19 (m, 11H).

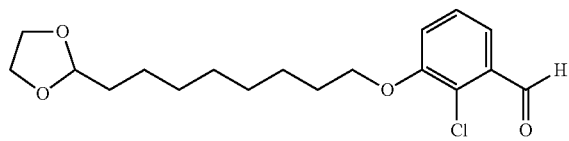 [SMILES: O=Cc1cccc(OCCCCCCCCC2OCCO2)c1Cl]

Step 2. (R)-quinuclidin-3-yl(2-chloro-3-(9-((R)-2-hydroxy-2-(8-hydroxy-2-oxo-1,2-dihydroquinolin-5-yl)ethylamino)nonyloxy)phenyl)(phenyl)methylcarbamate (compound 7B)

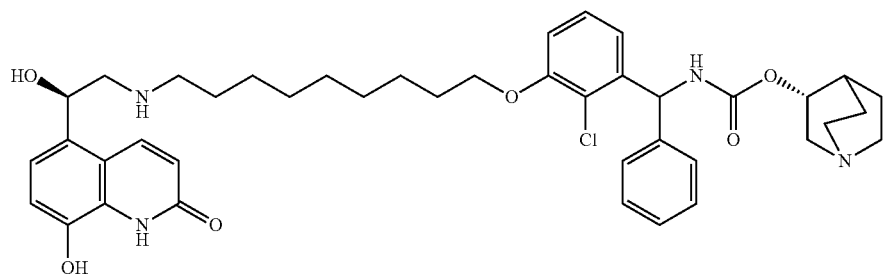 [SMILES: O=C(NC(c1ccccc1)c1cccc(OCCCCCCCCCNC[C@H](O)c2ccc(O)c3[nH]c(=O)ccc23)c1Cl)O[C@H]1CN2CCC1CC2]

The title compound was prepared as in Example 10 with 3-((8-(1,3-dioxolan-2-yl)octyl)oxy)-2-chlorobenzaldehyde replacing 3-((8-(1,3-dioxolan-2-yl)octyl)oxy)-benzaldehyde in Step 2 and using the subsequent steps described in Example 1.

Example 30

(R)-quinuclidin-3-yl((2,6-difluoro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamate (compound 8B)

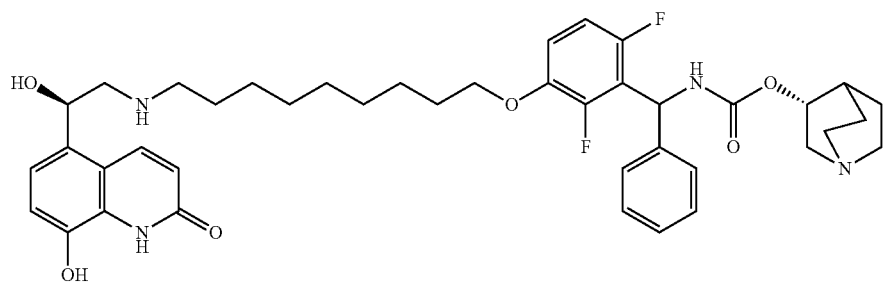 [SMILES: O=C(NC(c1ccccc1)c1c(F)ccc(OCCCCCCCCCNC[C@H](O)c2ccc(O)c3[nH]c(=O)ccc23)c1F)O[C@H]1CN2CCC1CC2]

The title compound was prepared as described for Example 29 from the commercially available 2,6-difluoro-3-hydroxy-benzaldehyde.

Example 31

(R)-quinuclidin-3-yl((2-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate (compound 9B)

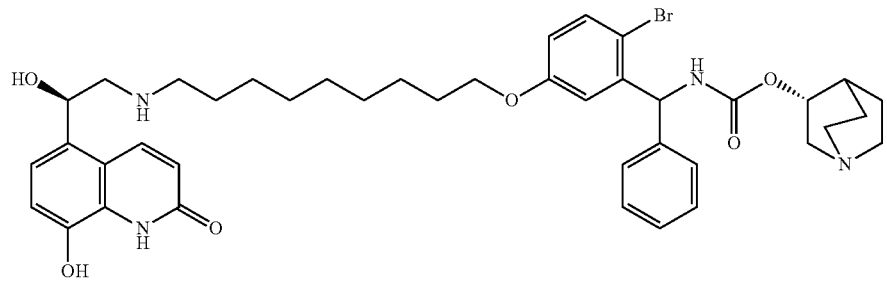 [SMILES: O=C(NC(c1ccccc1)c1cc(OCCCCCCCCCNC[C@H](O)c2ccc(O)c3[nH]c(=O)ccc23)ccc1Br)O[C@H]1CN2CCC1CC2]

The title compound was prepared as described for Example 19 from the commercially available 2-bromo-5-hydroxybenzaldehyde.

Example 32

(3R)-3-((((2-chloro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium (compound 10B)

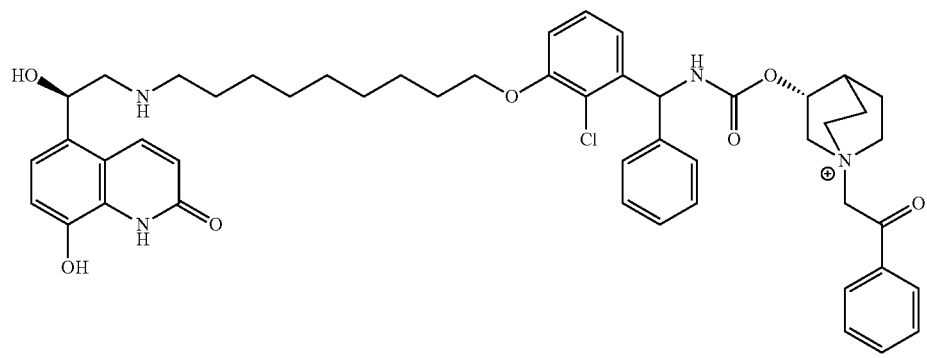 [SMILES: O=C(NC(c1ccccc1)c1cccc(OCCCCCCCCCNC[C@H](O)c2ccc(O)c3[nH]c(=O)ccc23)c1Cl)O[C@H]1C[N+]2(CC(=O)c3ccccc3)CCC1CC2]

The title compound was prepared as described in Example 24 with (R)-quinuclidin-3-yl(2-chloro-3-(9-((R)-2-hydroxy-2-(8-hydroxy-2-oxo-1,2-dihydroquinolin-5-yl)ethylamino)nonyloxy)phenyl)(phenyl)methylcarbamate (Example 31) replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 33

(3R)-3-((((2,6-difluoro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium (compound 11B)

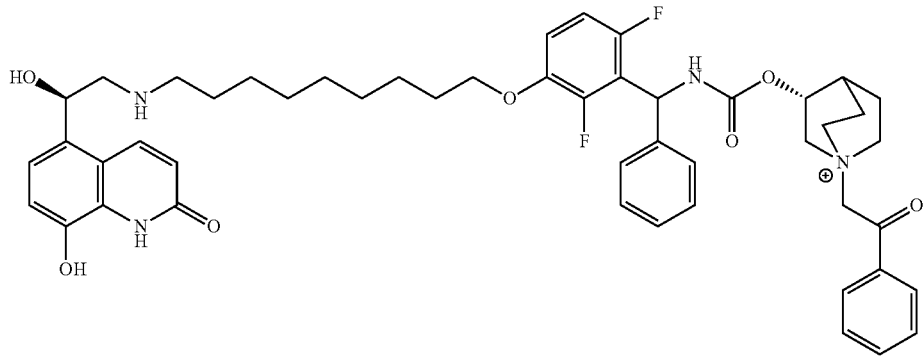 [SMILES: O=C(NC(c1ccccc1)c1c(F)ccc(OCCCCCCCCCNC[C@H](O)c2ccc(O)c3[nH]c(=O)ccc23)c1F)O[C@H]1C[N+]2(CC(=O)c3ccccc3)CCC1CC2]

The title compound was prepared as described in Example 24 with (R)-quinuclidin-3-yl((2,6-difluoro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamate (Example 30) replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 34

(3R)-3-((((2-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium (compound 12B)

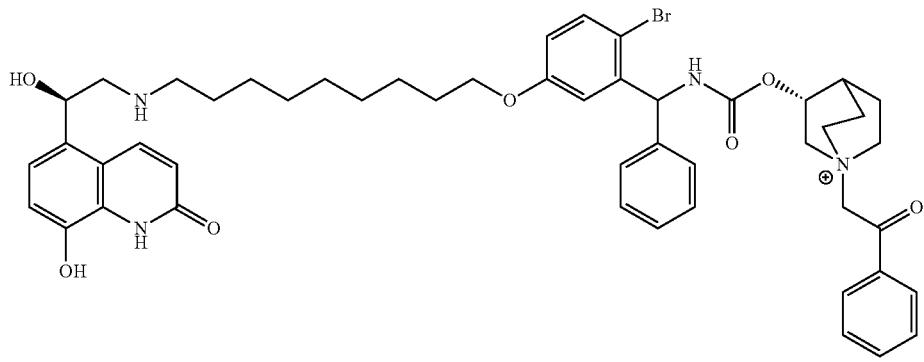 [SMILES: O=C(NC(c1ccccc1)c1cc(OCCCCCCCCCNC[C@H](O)c2ccc(O)c3[nH]c(=O)ccc23)ccc1Br)O[C@H]1C[N+]2(CC(=O)c3ccccc3)CCC1CC2]

The title compound was prepared as described in Example 24 with (R)-quinuclidin-3-yl((2-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 35

(3R)-3-((((3-((9-(((R)-2-hydroxy-2-(8-hydroxy-2-oxo-1,2-dihydroquinolin-5-yl)ethyl)amino)nonyl)oxy)-4-methylphenyl)(phenyl)methyl)carbamoyl)oxy)-1-(2-oxo-2-phenylethyl)quinuclidin-1-ium (compound 13B)

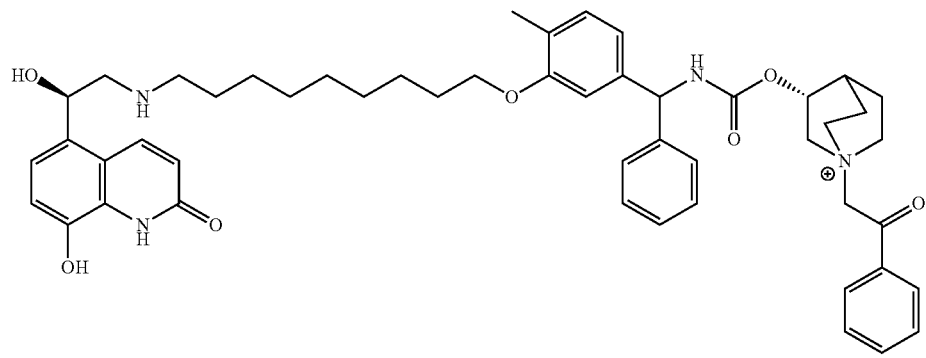 [SMILES: Cc1ccc(C(NC(=O)O[C@H]2C[N+]3(CC(=O)c4ccccc4)CCC2CC3)c2ccccc2)cc1OCCCCCCCCCNC[C@H](O)c1ccc(O)c2[nH]c(=O)ccc12]

Step 1. (3-((8-(1,3-dioxolan-2-yl)octyl)oxy)-4-methylphenyl)methanol

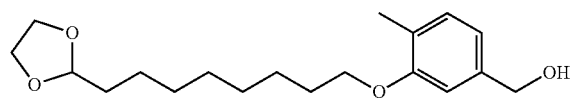 [SMILES: Cc1ccc(CO)cc1OCCCCCCCCC1OCCO1]

To a stirred solution of 5-(hydroxymethyl)-2-methylphenol (0.57 g, 4.15 mmol) in dimethyl formamide (15 mL), was added 2-(8-bromooctyl)-1,3-dioxolane (1.00 g, 3.77 mmol) and potassium carbonate (0.63 g, 4.57 mmol), and the mixture was stirred at 80° C. for 16 hours. The reaction mixture was cooled to room temperature, diluted with water and extracted with ethyl acetate (×3). The combined organic extracts were washed with brine, dried (magnesium sulphate), filtered and concentrated under reduced pressure. The crude material was purified by silica gel chromatography eluting with 0-7% ethyl acetate in iso-hexane to afford the title compound (0.5 g, 41%).

$^1$H NMR (400 MHz, DMSO-d$_6$): δ 7.06 (d, J=8 Hz, 1H); 6.86 (s, 1H); 6.77 (d, J=8 Hz, 1H); 5.10 (d, J=5.6 Hz, 1H); 4.75 (t, J=4.8 Hz, 1H); 4.44 (d, J=5.6 Hz, 2H); 3.94 (t, J=6.4 Hz, 2H); 3.86-3.84 (m, 2H); 3.76-3.74 (m, 2H); 2.11 (s, 3H); 1.73 (m, 2H); 1.53 (m, 2H); 1.35-1.30 (m, 10H).

Step 2. (3R)-3-((((3-((9-(((R)-2-hydroxy-2-(8-hydroxy-2-oxo-1,2-dihydroquinolin-5-yl)ethyl)amino)nonyl)oxy)-4-methylphenyl)(phenyl)methyl)carbamoyl)oxy)-1-(2-oxo-2-phenylethyl)quinuclidin-1-ium (compound 13B)

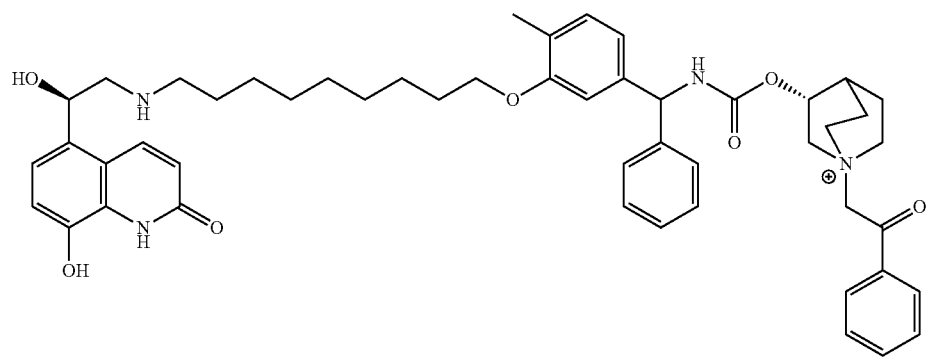 [SMILES: Cc1ccc(C(NC(=O)O[C@H]2C[N+]3(CC(=O)c4ccccc4)CCC2CC3)c2ccccc2)cc1OCCCCCCCCCNC[C@H](O)c1ccc(O)c2[nH]c(=O)ccc12]

The title compound was prepared as described in Example 18 Steps 4 to 9 with (3-((8-(1,3-dioxolan-2-yl)octyl)oxy)-4-methylphenyl)methanol replacing (3-((8-(1,3-dioxolan-2-yl)octyl)oxy)-5-bromophenyl)methanol in Step 4 and the products used in the subsequent steps.

Example 36

(R)-quinuclidin-3-yl((3-((9-(((R)-2-hydroxy-2-(8-hydroxy-2-oxo-1,2-dihydroquinolin-5-yl)ethyl)amino)nonyl)oxy)-4-methoxyphenyl)(phenyl)-methyl)carbamate (compound 14B)

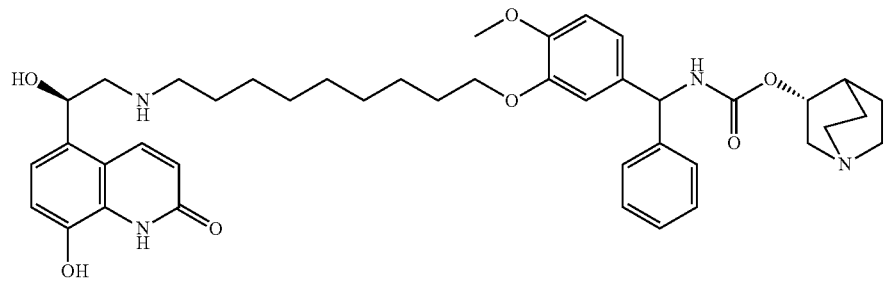 [SMILES: COc1ccc(C(NC(=O)O[C@H]2CN3CCC2CC3)c2ccccc2)cc1OCCCCCCCCCNC[C@H](O)c1ccc(O)c2[nH]c(=O)ccc12]

The title compound was prepared as described for Example 29 from the commercially available 3-hydroxy-4-methoxybenzaldehyde.

Example 37

(R)-quinuclidin-3-yl((3-((9-(((R)-2-hydroxy-2-(8-hydroxy-2-oxo-1,2-dihydroquinolin-5-yl)ethyl)amino)nonyl)oxy)-5-methoxyphenyl)(phenyl)-methyl)carbamate (compound 15B)

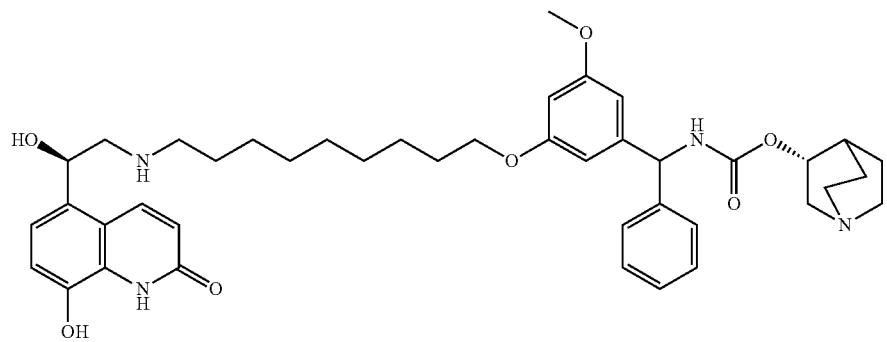 [SMILES: COc1cc(OCCCCCCCCCNC[C@H](O)c2ccc(O)c3[nH]c(=O)ccc23)cc(C(NC(=O)O[C@H]2CN3CCC2CC3)c2ccccc2)c1]

Step 1. Benzyl 3-((8-(1,3-dioxolan-2-yl)octyl)oxy)-5-hydroxybenzoate

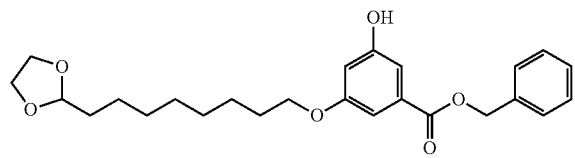 [SMILES: O=C(OCc1ccccc1)c1cc(O)cc(OCCCCCCCCC2OCCO2)c1]

The title compound was prepared as described in Example 28 Step 1 and 2 with 3,5-dihydroxybenzoic acid replacing 5-bromo-3-hydroxybenzoic acid in Step 1 and the product used in the subsequent step.

Step 2. Benzyl 3-((8-(1,3-dioxolan-2-yl)octyl)oxy)-5-methoxybenzoate

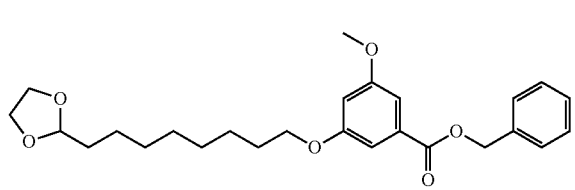 [SMILES: COc1cc(OCCCCCCCCC2OCCO2)cc(C(=O)OCc2ccccc2)c1]

To an ice-cooled solution of benzyl 3-((8-(1,3-dioxolan-2-yl)octyl)oxy)-5-hydroxybenzoate (1.94 g, 4.53 mmol) in dimethyl formamide (25 mL), was added potassium carbonate (0.93 g, 6.75 mmol) followed by iodomethane (0.42 mL, 6.75 mmol). The reaction mixture was allowed to warm to room temperature over 16 hours and stood at room temperature for 3 days. The reaction mixture was diluted with water and extracted with ethyl acetate. The organic extracts were washed with brine, dried (MgSO$_4$), filtered, and concentrated under reduced pressure to afford the title compound (1.76 g, 88%).

$^1$NMR (400 MHz, CDCl$_3$-d): 7.45-7.32 (m, 5H); 7.20-7.18 (m, 2H); 6.64-6.63 (m, 1H); 5.35 (s, 2H); 4.84 (t, J=4.8 Hz, 1H); 4.10-3.92 (m, 4H); 3.86-3.82 (m, 5H); 1.80-1.73 (m, 2H); 1.68-1.63 (m, 2H); 1.46-1.34 (m, 10H).

Step 3. (R)-quinuclidin-3-yl((3-((9-(((R)-2-hydroxy-2-(8-hydroxy-2-oxo-1,2-dihydroquinolin-5-yl)ethyl)amino)nonyl)oxy)-5-methoxyphenyl)(phenyl)-methyl)carbamate (compound 15B)

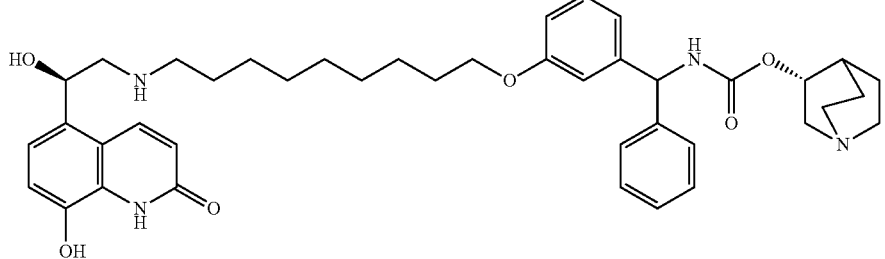

The title compound was prepared as described in Example 28 Steps 3 through 9 with benzyl 3-((8-(1,3-dioxolan-2-yl)octyl)oxy)-5-methoxybenzoate replacing benzyl 3-((8-(1,3-dioxolan-2-yl)octyl)oxy)-5-bromobenzoate in Step 3 and the product used in the subsequent steps.

Example 38

(3R)-3-((((3-((9-(((R)-2-hydroxy-2-(8-hydroxy-2-oxo-1,2-dihydroquinolin-5-yl)ethyl)amino)nonyl)oxy)-4-methoxyphenyl)(phenyl)methyl)carbamoyl)oxy)-1-(2-oxo-2-phenylethyl)quinuclidin-1-ium (compound 16B)

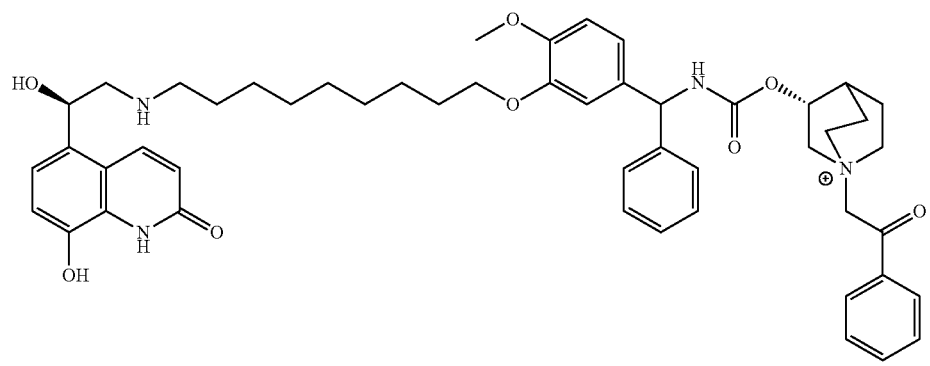 [SMILES: COc1ccc(C(NC(=O)O[C@H]2C[N+]3(CC(=O)c4ccccc4)CCC2CC3)c2ccccc2)cc1OCCCCCCCCCNC[C@H](O)c1ccc(O)c2[nH]c(=O)ccc12]

The title compound was prepared as described in Example 24 with (R)-quinuclidin-3-yl((3-((9-(((R)-2-hydroxy-2-(8-hydroxy-2-oxo-1,2-dihydroquinolin-5-yl)ethyl)amino)nonyl)oxy)-4-methoxyphenyl)(phenyl)methyl)carbamate (Example 36) replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 39

(3R)-3-((((3-((9-(((R)-2-hydroxy-2-(8-hydroxy-2-oxo-1,2-dihydroquinolin-5-yl)ethyl)amino)nonyl)oxy)-5-methoxyphenyl)(phenyl)methyl)carbamoyl)oxy)-1-(2-oxo-2-phenylethyl)quinuclidin-1-ium (compound 17B)

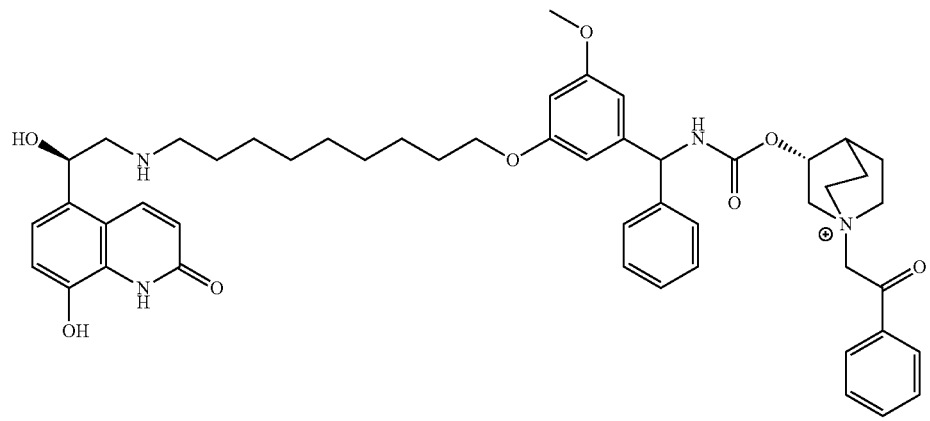 [SMILES: COc1cc(OCCCCCCCCCNC[C@H](O)c2ccc(O)c3[nH]c(=O)ccc23)cc(C(NC(=O)O[C@H]2C[N+]3(CC(=O)c4ccccc4)CCC2CC3)c2ccccc2)c1]

The title compound was prepared as described in Example 24 with (R)-quinuclidin-3-yl((3-((9-(((R)-2-hydroxy-2-(8-hydroxy-2-oxo-1,2-dihydroquinolin-5-yl)ethyl)amino)nonyl)oxy)-5-methoxyphenyl)(phenyl)methyl)carbamate (Example 36) replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 40

(3R)-3-((((5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)methyl)carbamoyl)oxy)-1-(2-oxo-2-phenylethyl)quinuclidin-1-ium (compound 18B)

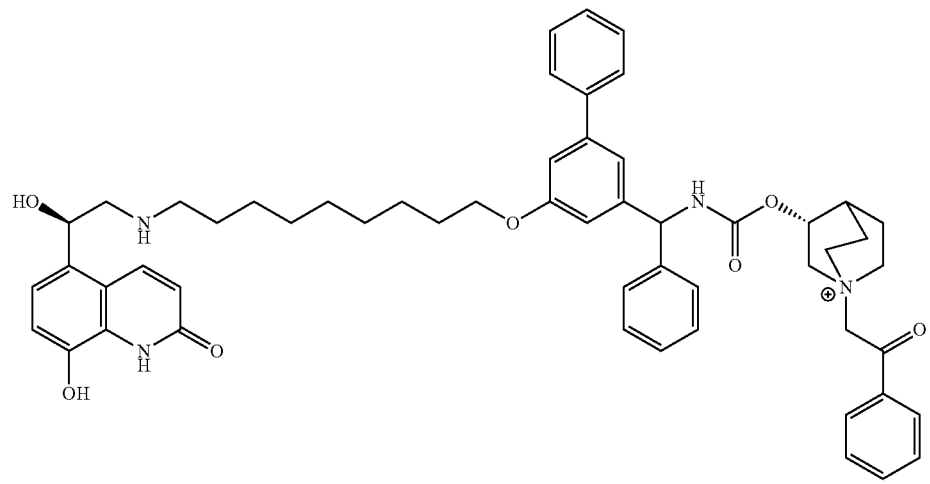 [SMILES: O=C(NC(c1ccccc1)c1cc(OCCCCCCCCCNC[C@H](O)c2ccc(O)c3[nH]c(=O)ccc23)cc(-c2ccccc2)c1)O[C@H]1C[N+]2(CC(=O)c3ccccc3)CCC1CC2]

Step 1. (R)-quinuclidin-3-yl((5-((8-(1,3-dioxolan-2-yl)octyl)oxy)-[1,1'-biphenyl]-3-yl)(phenyl)methyl) carbamate

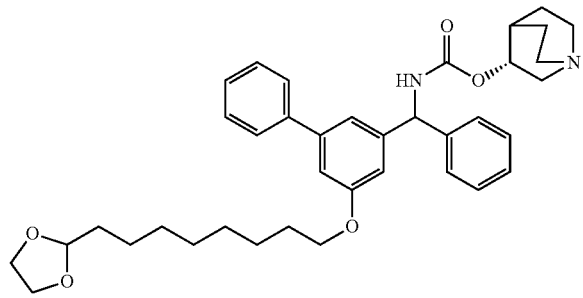 [SMILES: O=C(NC(c1ccccc1)c1cc(OCCCCCCCCC2OCCO2)cc(-c2ccccc2)c1)O[C@H]1CN2CCC1CC2]

To a stirred solution of (R)-quinuclidin-3-yl((3-((8-(1,3-dioxolan-2-yl)octyl)oxy)-5-bromophenyl)(phenyl)methyl) carbamate (0.2 g, 0.33 mmol) (prepared in Example 28 Step 8) in toluene (4 mL) and water (1 mL), was added phenyl boronic acid (0.04 g, 0.33 mmol), sodium carbonate (0.07 g, 0.66 mmol), and tetrakis(triphenylphosphine)palladium (0) (0.04 g, 0.03 mmol). The reaction mixture was heated in the microwave at 120° C. for 30 minutes. The solvent was removed under reduced pressure, diluted with water and extracted with ethyl acetate (×3). The combined organic extracts were dried (sodium sulphate), filtered and solvent removed under reduced pressure. The crude material was purified by silica gel chromatography eluting with 0-10% methanol in ethyl acetate to afford the title compound as a colourless oil (0.14 g, 71%).

$^1$H NMR (400 MHz, CDCl$_3$): δ 7.53 (d, J=7.56 Hz, 2H); 7.44-7.38 (m, 2H); 7.38-7.27 (m, 6H); 7.06 (s, 1H); 7.01 (s, 1H); 6.78 (s, 1H); 5.95 (br s, 1H); 5.4 (br s, 1H); 4.86-4.81 (t, J=4.81 Hz, 1H); 4.77-4.71 (m, 1H); 3.99-3.92 (m, 4H); 3.86-3.81 (m, 2H); 3.2-2.6 (m, 6H); 2.03 (s, 1H); 1.80-1.71 (m, 2H); 1.7-1.3 (m, 15H).

Step 2. 3R)-3-(((((5-((9-(((R)-2-hydroxy-2-(8-hydroxy-2-oxo-1,2-dihydroquinolin-5-yl)ethyl)amino) nonyl)oxy)-[1,1'-biphenyl]-3-yl)(phenyl)methyl) carbamoyl)oxy)-1-(2-oxo-2-phenylethyl)quinuclidin-1-ium (compound 18B)

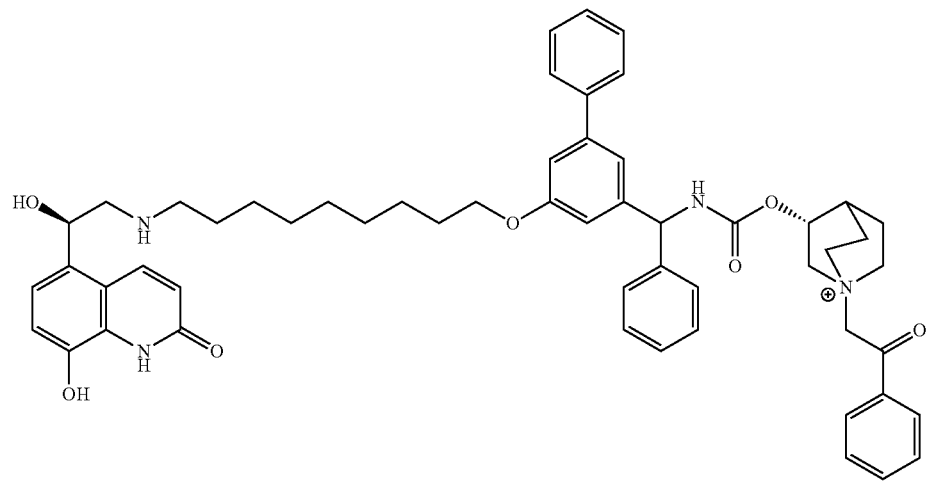 [SMILES: O=C(NC(c1ccccc1)c1cc(OCCCCCCCCCNC[C@H](O)c2ccc(O)c3[nH]c(=O)ccc23)cc(-c2ccccc2)c1)O[C@H]1C[N+]2(CC(=O)c3ccccc3)CCC1CC2]

The title compound was prepared as described in Example 28 Steps 9 and 10 with (R)-quinuclidin-3-yl((5-((8-(1,3-dioxolan-2-yl)octyl)oxy)-[1,1'-biphenyl]-3-yl)(phenyl)methyl)carbamate replacing (R)-quinuclidin-3-yl((3-bromo-5-((9-(((R)-2-hydroxy-2-(8-hydroxy-2-oxo-1,2-dihydroquinolin-5-yl)ethyl)amino)nonyl)oxy)-phenyl)(phenyl)methyl)carbamate in Step 9 and the product used in the subsequent steps.

The following compound was also prepared by the method of Example 40

| Compound | R | R₄ |
|---|---|---|
| 19B | 2-thienyl | 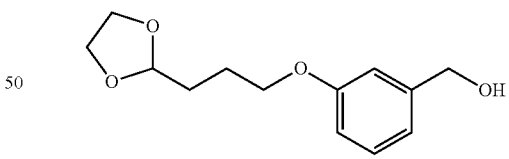 |

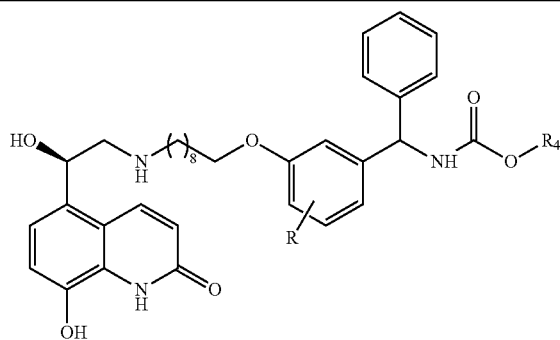

Example 41

(3R)-3-((((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)-carbamoyl)oxy)-1-(2-oxo-2-phenylethyl)quinuclidin-1-ium (compound 20B)

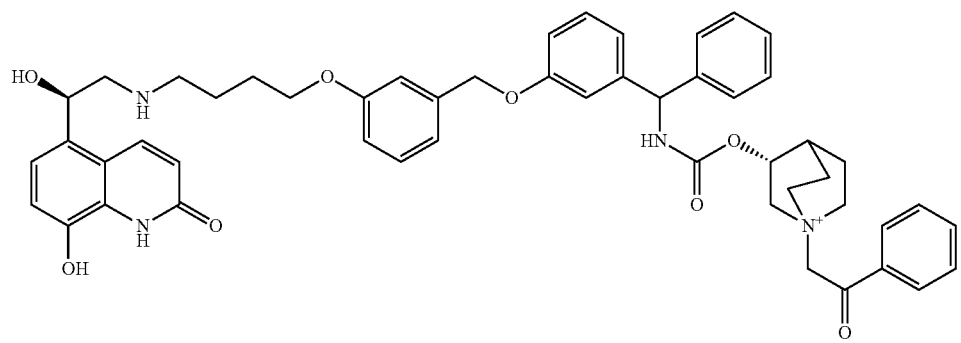 [SMILES: O=C(NC(c1ccccc1)c1cccc(OCc2cccc(OCCCCNC[C@H](O)c3ccc(O)c4[nH]c(=O)ccc34)c2)c1)O[C@H]1C[N+]2(CC(=O)c3ccccc3)CCC1CC2]

Step 1. (3-(3-(1,3-Dioxolan-2-yl)propoxy)phenyl)methanol

To an ice-cooled solution of 3-(3-(1,3-dioxolan-2-yl)propoxy)benzaldehyde (prepared as in Example 10; Step 1) (3.08 g, 13.1 mmol) in ethanol (66 mL), was added sodium borohydride (1.98 g, 52.4 mmol). The reaction mixture was allowed to warm to ambient temperature and stirred at ambient temperature for 16 hours. The reaction mixture was carefully quenched with saturated aqueous ammonium chloride and extracted twice with DCM. The combined organic phases were poured through a hydrophobic column, and the solvent was evaporated at reduced pressure to afford the title compound as a colourless oil (2.96 g, 95%).

$^1$H NMR (400 MHz, CDCl$_3$): δ 7.25 (m, 1H), 6.93-6.88 (m, 2H), 6.82 (m, 1H), 4.93 (m, 1H), 4.66 (m, 2H), 4.02-3.92 (m, 4H), 3.87 (m, 2H), 1.96-1.77 (m, 5H).

Step 2. (R)-Quinuclidin-3-yl((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamate

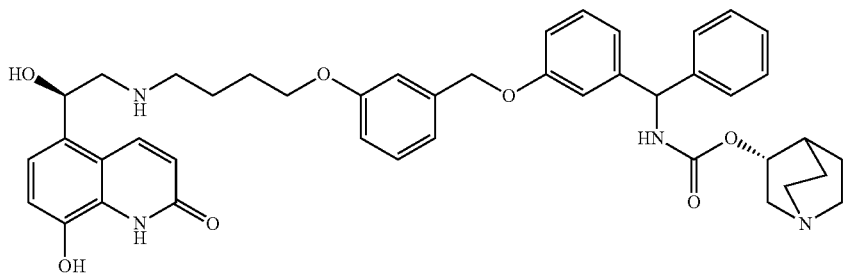 [SMILES: O=C(NC(c1ccccc1)c1cccc(OCc2cccc(OCCCCNC[C@H](O)c3ccc(O)c4[nH]c(=O)ccc34)c2)c1)O[C@H]1CN2CCC1CC2]

The title compound was prepared as described in Example 22 with (3-(3-(1,3-dioxolan-2-yl)propoxy)phenyl)methanol replacing (4-((1,3-dioxolan-2-yl)methyl)phenyl)methanol in Step 2. The additional steps required to make the target compound are described in the preparation of Example 1.

$^1$H NMR (400 MHz, CD$_3$OD): δ 8.56 (s, 1H); 8.38 (d, J=9.9 Hz, 1H); 7.33-7.20 (m, 8H); 7.07-6.85 (m, 7H); 6.70-6.65 (m, 1H); 5.87 (s, 1H); 5.43-5.36 (m, 1H); 5.03 (s, 2H); 4.92 (m, 1H); 4.08-4.02 (m, 2H); 3.51-3.50 (m, 1H); 3.27-3.06 (m, 9H); 2.30-1.60 (m, 9H).

Step 3. (3R)-3-((((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamoyl)oxy)-1-(2-oxo-2-phenylethyl)quinuclidin-1-ium

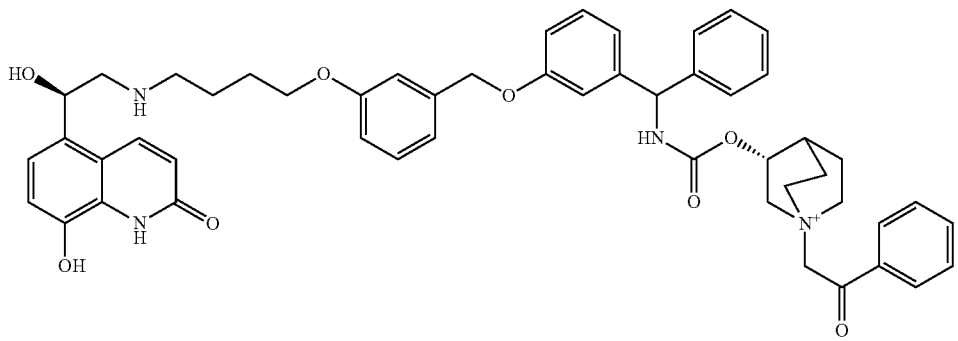 [SMILES: O=C(NC(c1ccccc1)c1cccc(OCc2cccc(OCCCCNC[C@H](O)c3ccc(O)c4[nH]c(=O)ccc34)c2)c1)O[C@H]1C[N+]2(CC(=O)c3ccccc3)CCC1CC2]

The title compound was prepared as described in Example 24 with (R)-quinuclidin-3-yl((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamate replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 42

(3R)-3-(((((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)-carbamoyl)oxy)-1-(2-phenoxyethyl)quinuclidin-1-ium (compound 21B)

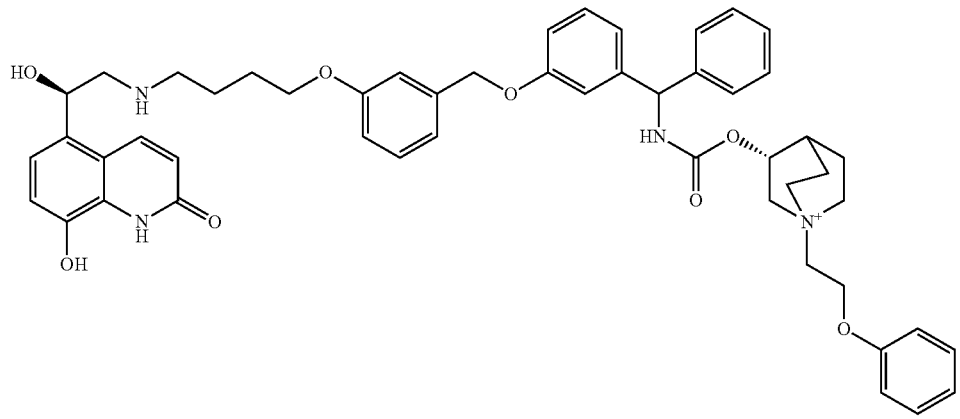 [SMILES: O=C(NC(c1ccccc1)c1cccc(OCc2cccc(OCCCCNC[C@H](O)c3ccc(O)c4[nH]c(=O)ccc34)c2)c1)O[C@H]1C[N+]2(CCOc3ccccc3)CCC1CC2]

The title compound was prepared as in Example 24 with (R)-quinuclidin-3-yl((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamate replacing (R)-quinuclidin-3-yl(3-(6-(((R)-2-hydroxy-2-(8-hydroxy-2-oxo-1,2-dihydroquinolin-5-yl)ethylamino)hexyloxy)phenyl)(phenyl)methylcarbamate and β-bromophenetole replacing 2-bromoacetophenone.

Example 43

(3R)-3-((((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)-carbamoyl)oxy)-1-(2-oxo-2-phenylethyl)quinuclidin-1-ium (compound 22B)

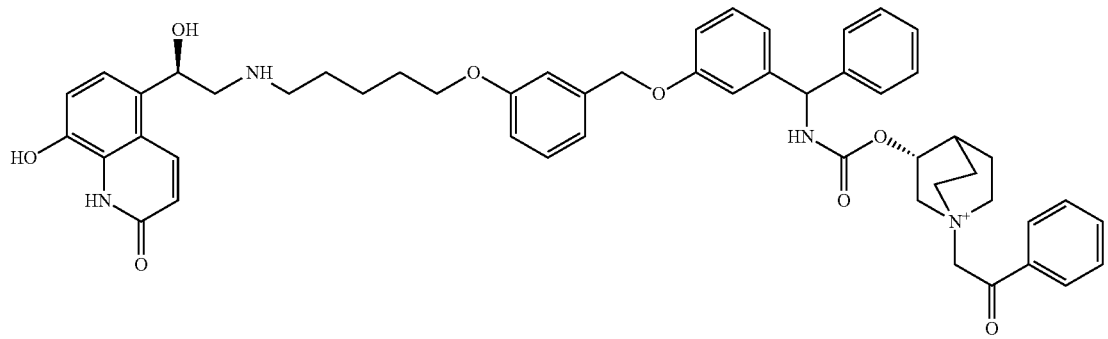 [SMILES: O=C(NC(c1ccccc1)c1cccc(OCc2cccc(OCCCCCNC[C@H](O)c3ccc(O)c4[nH]c(=O)ccc34)c2)c1)O[C@H]1C[N+]2(CC(=O)c3ccccc3)CCC1CC2]

The title compound was prepared as described in Example 22 with (3-(4-(1,3-dioxolan-2-yl)butyloxy)phenyl)methanol replacing (3-(3-(1,3-dioxolan-2-yl)propoxy)phenyl)methanol in Step 2. The additional steps required to make the target compound are described in the preparation of Example 1 and Example 44.

Example 44

(3R)-3-((((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)-carbamoyl)oxy)-1-(2-phenoxyethyl)quinuclidin-1-ium (compound 23B)

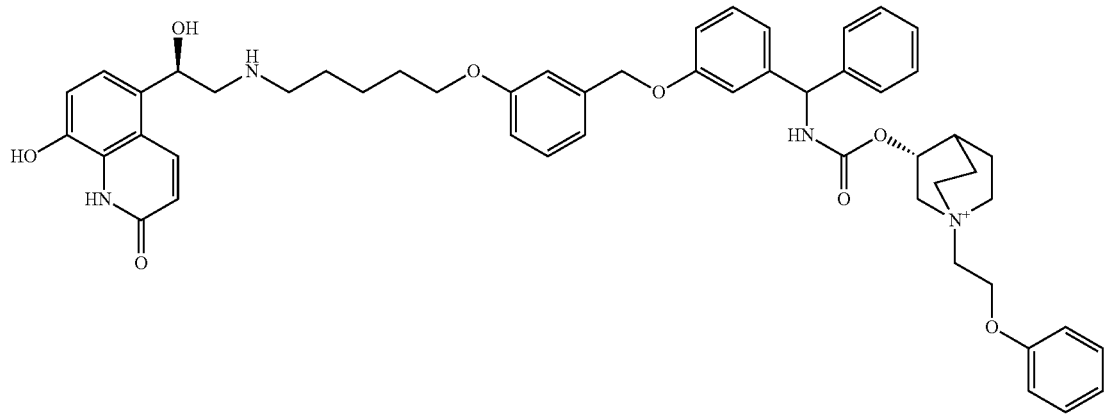 [SMILES: O=C(NC(c1ccccc1)c1cccc(OCc2cccc(OCCCCCNC[C@H](O)c3ccc(O)c4[nH]c(=O)ccc34)c2)c1)O[C@H]1C[N+]2(CCOc3ccccc3)CCC1CC2]

The title compound was prepared as in Example 24 with (R)-quinuclidin-3-yl((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)carbamate replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate and (3-bromophenetole replacing 2-bromoacetophenone.

Example 45

(R)-quinuclidin-3-yl(3-fluorophenyl)(3-(6-((R)-2-hydroxy-2-(8-hydroxy-2-oxo-1,2-dihydroquinolin-5-yl)ethylamino)hexyloxy)phenyl)methylcarbamate (compound 24B)

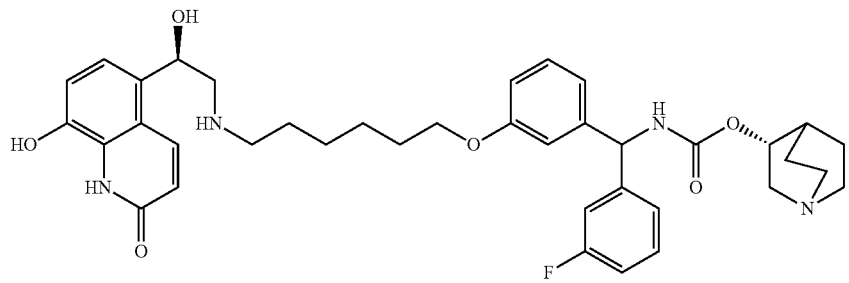 [SMILES: O=C(NC(c1cccc(F)c1)c1cccc(OCCCCCCNC[C@H](O)c2ccc(O)c3[nH]c(=O)ccc23)c1)O[C@H]1CN2CCC1CC2]

Step 1. 3-((5-(1,3-dioxolan-2-yl)pentyl)oxy)benzaldehyde

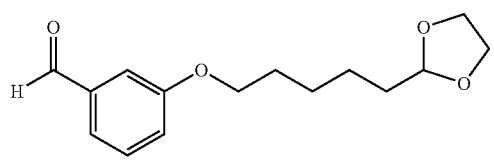 [SMILES: O=Cc1cccc(OCCCCCC2OCCO2)c1]

The title compound was prepared as described in Example 10 Step 1 with 2-(5-bromopentyl)-1,3-dioxolane replacing 2-(8-bromooctyl)-1,3-dioxolane.

$^1$H NMR (400 MHz, CDCl$_3$): δ 9.99-9.92 (m, 1H); 7.47-7.36 (m, 3H); 7.19-7.13 (m, 1H); 4.89-4.83 (m, 1H); 4.04-3.82 (m, 6H); 1.90-1.78 (m, 2H); 1.74-1.65 (m, 2H); 1.58-1.48 (m, 4H).

Step 2. (3-((5-(1,3-dioxolan-2-yl)pentyl)oxy)phenyl)(3-fluorophenyl)methanol

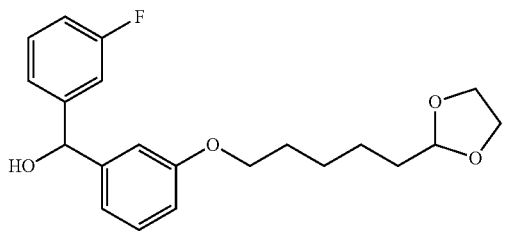 [SMILES: OC(c1cccc(F)c1)c1cccc(OCCCCCC2OCCO2)c1]

The title compound was prepared as described in Example 10 Step 2 with 3-fluorophenylmagnesium bromide and 3-((5-(1,3-dioxolan-2-yl)pentyl)oxy)benzaldehyde replacing 2-thienylmagnesium bromide and 3-(8-(1,3-dioxolan-2-yl)octyloxy)benzaldehyde respectively.

$^1$H NMR (400 MHz, CDCl$_3$): δ 7.32-7.08 (m, 4H); 6.98-6.89 (m, 3H); 6.87-6.77 (m, 1H); 5.79-5.75 (m, 1H); 4.88-4.82 (m, 1H); 4.01-3.78 (m, 6H); 2.35-2.25 (m, 1H); 1.82-1.65 (m, 4H); 1.54-1.44 (m, 4H).

Step 3. (R)-quinuclidin-3-yl(3-fluorophenyl)(3-(6-((R)-2-hydroxy-2-(8-hydroxy-2-oxo-1,2-dihydroquinolin-5-yl)ethylamino)hexyloxy)phenyl)methylcarbamate

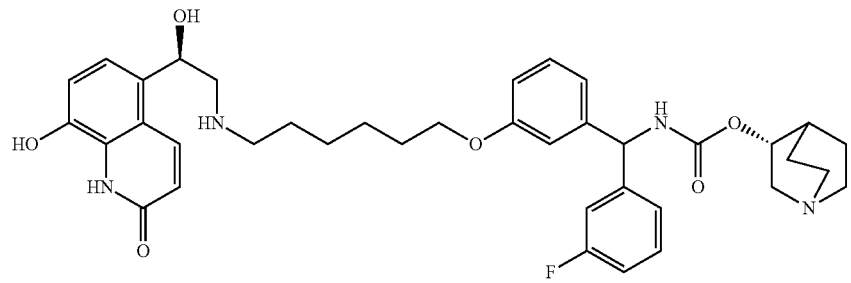 [SMILES: O=C(NC(c1cccc(F)c1)c1cccc(OCCCCCCNC[C@H](O)c2ccc(O)c3[nH]c(=O)ccc23)c1)O[C@H]1CN2CCC1CC2]

The additional steps required to prepare the title compound are described in Example 1 Steps 3 through 7.

Example 46

(3R)-3-((((3-((5-(((R)-2-hydroxy-2-(8-hydroxy-2-oxo-1,2-dihydroquinolin-5-yl)ethyl)amino)pentyl)oxy)phenyl)(phenyl)methyl)carbamoyl)oxy)-1-(4-phenylbutyl)quinuclidin-1-ium (compound 25B)

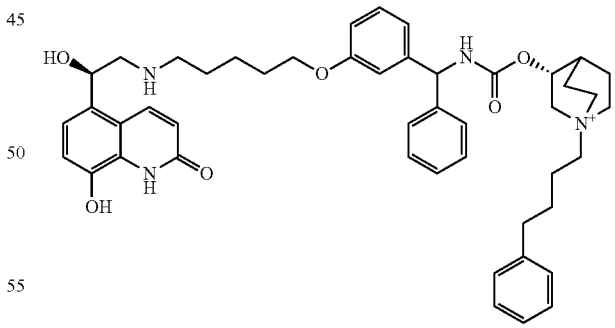

The title compound was prepared as in Example 24 with (R)-quinuclidin-3-yl(3-(5-((R)-2-hydroxy-2-(8-hydroxy-2-oxo-1,2-dihydroquinolin-5-yl)ethylamino)pentyloxy)-phenyl)(phenyl)methylcarbamate (Example 5) replacing (R)-quinuclidin-3-yl(3-(6-((R)-2-hydroxy-2-(8-hydroxy-2-oxo-1,2-dihydroquinolin-5-yl)ethylamino)hexyloxy)phenyl)-(phenyl)methylcarbamate and (4-bromobutyl)benzene replacing 2-bromoacetophenone.

Example 47

(R)-Quinuclidin-3-yl(3-fluorophenyl)(3-(3-(2-((R)-2-hydroxy-2-(8-hydroxy-2-oxo-1,2-dihydroquinolin-5-yl)ethylamino)ethyl)benzyloxy)phenyl)-methylcarbamate (compound 26B)

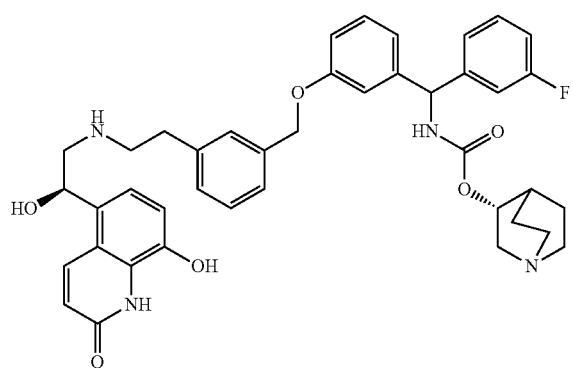 [SMILES: O=C(NC(c1cccc(F)c1)c1cccc(OCc2cccc(CCNC[C@H](O)c3ccc(O)c4[nH]c(=O)ccc34)c2)c1)O[C@H]1CN2CCC1CC2]

Step 1. 3-((3-((1,3-Dioxolan-2-yl)methyl)benzyl)oxy)benzaldehyde

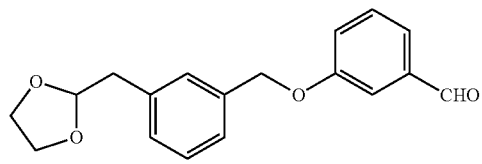 [SMILES: O=Cc1cccc(OCc2cccc(CC3OCCO3)c2)c1]

The title compound was prepared as described in Example 22 with (3-((1,3-dioxolan-2-yl)methyl)phenyl)methanol and 3-hydroxybenzaldehyde replacing (4-((1,3-dioxolan-2-yl)methyl)phenyl)methanol and 3-hydroxybenzophenone, respectively, in Step 2.

Step 2. (3-((3-((1,3-Dioxolan-2-yl)methyl)benzyl)oxy)phenyl)(3-fluorophenyl)methanol

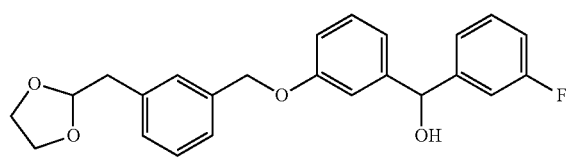 [SMILES: OC(c1cccc(F)c1)c1cccc(OCc2cccc(CC3OCCO3)c2)c1]

The title compound was prepared as described in Example 10 Step 2 with 3-fluorophenylmagnesium bromide and 3-((3-((1,3-dioxolan-2-yl)methyl)benzyl)oxy)-benzaldehyde replacing 2-thienylmagnesium bromide and 3-(8-(1,3-dioxolan-2-yl)octyloxy)benzaldehyde, respectively.

$^1$H NMR (400 MHz, CDCl$_3$): δ 7.34-7.21 (m, 6H); 7.13-7.06 (m, 2H); 7.00 (t, J=2.0 Hz, 1H); 6.97-6.87 (m, 3H); 5.77 (d, J=3.5 Hz, 1H); 5.10-4.99 (m, 3H); 3.94-3.87 (m, 2H); 3.88-3.78 (m, 2H); 2.97 (d, J=4.8 Hz, 2H); 2.35 (d, J=3.5 Hz, 1H).

Step 3. (R)-Quinuclidin-3-yl(3-fluorophenyl)(3-(3-(2-((R)-2-hydroxy-2-(8-hydroxy-2-oxo-1,2-dihydroquinolin-5-yl)ethylamino)ethyl)benzyloxy)phenyl)methylcarbamate (compound 27B)

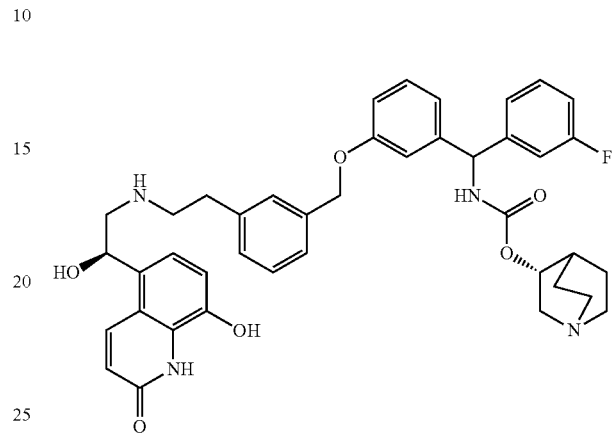

The title compound was prepared using the additional steps described in Example 1 Steps 3 through 7.

Example 48

(3R)-3-((((3-fluorophenyl)(3-((3-(2-(((R)-2-hydroxy-2-(8-hydroxy-2-oxo-1,2-dihydroquinolin-5-yl)ethyl)amino)ethyl)benzyl)oxy)phenyl)methyl)carbamoyl)oxy)-1-(2-oxo-2-phenylethyl)quinuclidin-1-ium (compound 27B)

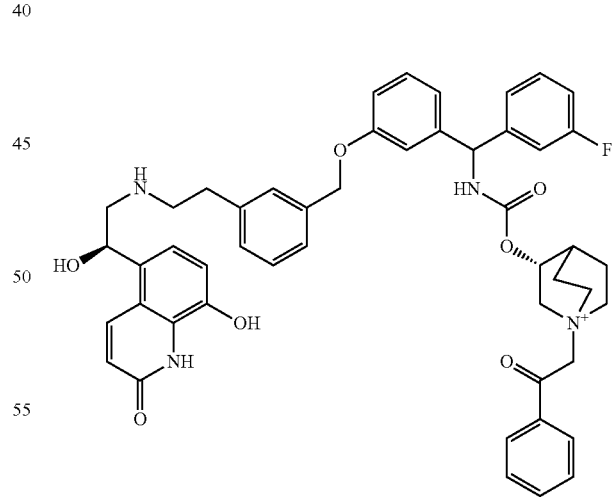

The title compound was prepared as in Example 24 with (R)-quinuclidin-3-yl(3-fluorophenyl)(3-(3-(2-((R)-2-hydroxy-2-(8-hydroxy-2-oxo-1,2-dihydroquinolin-5-yl)ethylamino)ethyl)benzyloxy)phenyl)methylcarbamate replacing (R)-quinuclidin-3-yl (3-(6-((R)-2-hydroxy-2-(8-hydroxy-2-oxo-1,2-dihydroquinolin-5-yl)ethylamino)-hexyloxy)phenyl)(phenyl)methylcarbamate.

Example 49

(3R)-3-(((((3-((4-((((R)-2-hydroxy-2-(8-hydroxy-2-oxo-1,2-dihydroquinolin-5-yl)ethyl)amino)methyl)benzyl)oxy)phenyl)(phenyl)methyl)carbamoyl)oxy)-1-(2-oxo-2-phenylethyl)quinuclidin-1-ium (compound 28B)

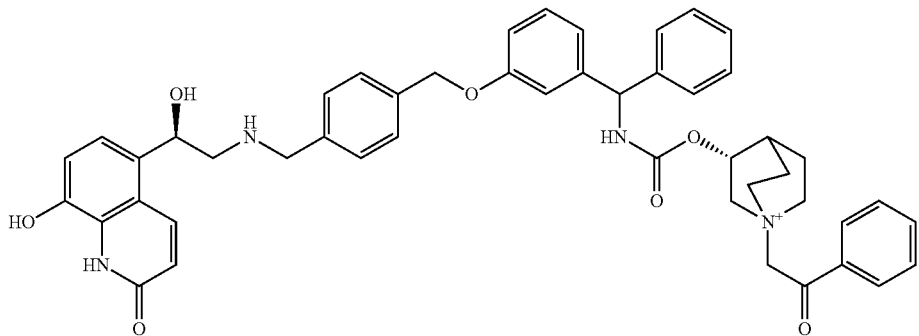 [SMILES: O=C(NC(c1ccccc1)c1cccc(OCc2ccc(CNC[C@H](O)c3ccc(O)c4[nH]c(=O)ccc34)cc2)c1)O[C@H]1C[N+]2(CC(=O)c3ccccc3)CCC1CC2]

Step 1. (4-(1,3-Dioxolan-2-yl)phenyl)methanol

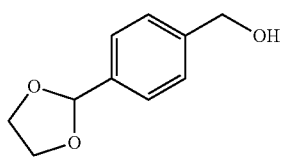 [SMILES: OCc1ccc(C2OCCO2)cc1]

A mixture of terephthaldehyde (5.4 g, 40 mmol), para-toluenesulfonic acid—monohydrate (0.4 g, 2 mmol), and ethylene glycol in toluene (80 mL) was heated at 110° C. for 4 hours. The reaction mixture was allowed to cool and was washed with saturated sodium hydrogen carbonate and dried with anhydrous magnesium sulphate. The filtrate was evaporated at reduced pressure to afford a oil. The oil was dissolved in ethanol (200 mL), and then the reaction mixture cooled to 0° C. Sodium borohydride (5.9 g, 160 mmol) was added portionwise, and the resultant reaction mixture allowed to warm to ambient temperature over 16 hours. The reaction mixture was quenched with saturated sodium hydrogen carbonate and subsequently extracted twice with ethyl acetate. The combined organic extracts were dried with anhydrous magnesium sulphate, and the solvent evaporated at reduced pressure. The crude material was purified by silica gel chromatography eluting with 100% iso-hexane to 50% ethyl acetate in iso-hexane to afford the title compound as a colourless oil (3.4 g, 48%).

$^1$H NMR (400 MHz, CDCl$_3$): δ 7.47 (d, J=8 Hz, 2H); 7.37 (d, J=8 Hz, 2H); 5.81 (s, 1H); 4.69 (d, J=5.6 Hz, 2H); 4.14 (m, 2H); 4.05 (m, 2H); 1.83 (d, J=6 Hz, 1H).

Step 2. (3-((4-(1,3-Dioxolan-2-yl)benzyl)oxy)phenyl)(phenyl)methanone

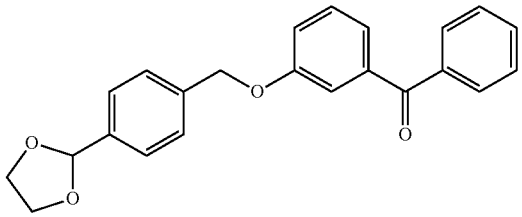 [SMILES: O=C(c1ccccc1)c1cccc(OCc2ccc(C3OCCO3)cc2)c1]

The title compound was prepared as described in Example 22 with (4-(1,3-dioxolan-2-yl)phenyl)methanol replacing (4-((1,3-dioxolan-2-yl)methyl)phenyl)methanol in Step 2.

$^1$H NMR (400 MHz, CDCl$_3$): δ 7.79-7.76 (m, 2H); 7.58 (m, 1H); 7.52-7.35 (m, 9H); 7.20 (m, 1H); 5.83 (s, 1H); 5.13 (s, 2H); 4.15 (m, 2H); 4.06 (m, 2H).

Step 3. (R)-quinuclidin-3-yl((3-((4-((((R)-2-hydroxy-2-(8-hydroxy-2-oxo-1,2-dihydroquinolin-5-yl)ethyl)amino)methyl)benzyl)oxy)phenyl)(phenyl)methyl)carbamate

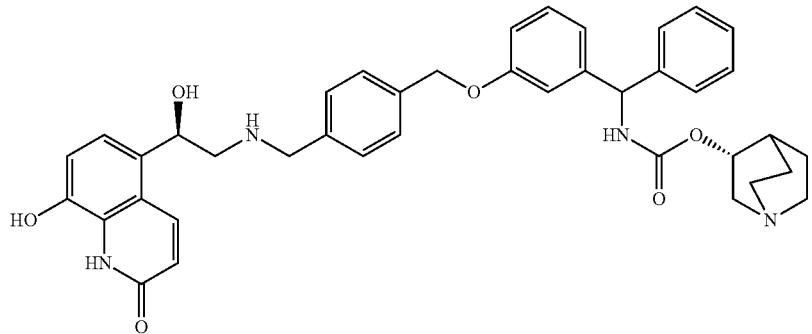 [SMILES: O=C(NC(c1ccccc1)c1cccc(OCc2ccc(CNC[C@H](O)c3ccc(O)c4[nH]c(=O)ccc34)cc2)c1)O[C@H]1CN2CCC1CC2]

The title compound was prepared using the additional steps described in Example 1 Steps 3 through 7.

$^1$H NMR (400 MHz, DMSO-d$_6$): δ 8.37 (m, 1H); 8.31 (s, 2H); 8.16 (m, 1H); 7.44-7.42 (m, 4H); 7.38-7.34 (m, 5H); 7.30-7.26 (m, 2H); 7.13 (d, J=8.4 Hz, 1H); 7.08 (s, 1H); 6.99-6.92 (m, 3H); 6.55 (d, J=10 Hz, 1H); 5.87 (d, J=9.6 Hz, 1H); 5.21 (m, 1H); 5.09 (s, 2H); 4.72 (m, 1H); 3.93 (s, 2H); 3.32 (m, 1H); 2.95-2.73 (m, 6H); 2.06 (s, 1H); 1.92 (s, 1H); 1.74-1.51 (m, 3H).

Step 4. (3R)-3-((3-(4-(((R)-2-hydroxy-2-(8-hydroxy-2-oxo-1,2-dihydroquinolin-5-yl)ethylamino)methyl)benzyloxy)phenyl)(phenyl)methylcarbamoyloxy)-1-(2-oxo-2-phenylethyl)-1-azoniabicyclo[2.2.2]octane

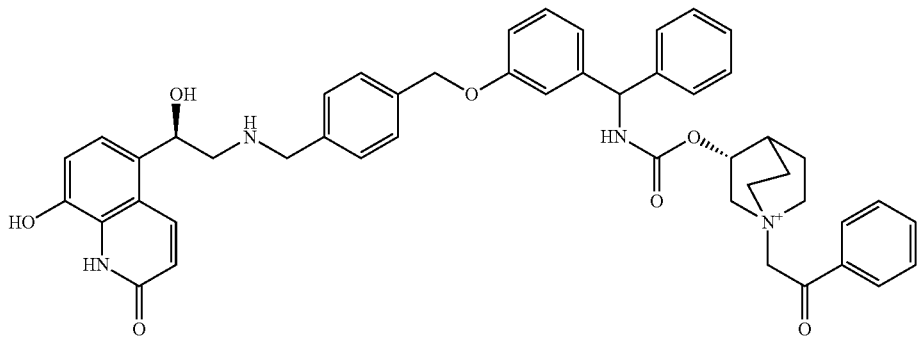 [SMILES: O=C(NC(c1ccccc1)c1cccc(OCc2ccc(CNC[C@H](O)c3ccc(O)c4[nH]c(=O)ccc34)cc2)c1)O[C@H]1C[N+]2(CC(=O)c3ccccc3)CCC1CC2]

The title compound was prepared as in Example 24 with ((R)-quinuclidin-3-yl((3-((4-((((R)-2-hydroxy-2-(8-hydroxy-2-oxo-1,2-dihydroquinolin-5-yl)ethyl)amino)methyl)-benzyl)oxy)phenyl)(phenyl)methyl)carbamate replacing (R)-quinuclidin-3-yl(3-(6-((R)-2-hydroxy-2-(8-hydroxy-2-oxo-1,2-dihydroquinolin-5-yl)ethylamino)hexyloxy)-phenyl)(phenyl)methylcarbamate.

Example 50

(R)-Quinuclidin-3-yl(3-((4'-(2-((R)-2-hydroxy-2-(8-hydroxy-2-oxo-1,2-dihydroquinolin-5-yl)ethylamino)ethyl)biphenyl-3-yl)methoxy)phenyl)(phenyl)-methylcarbamate (compound 29B)

Step 1. 2-(4-Bromobenzyl)-1,3-dioxolane

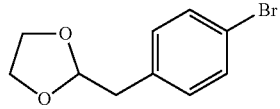

To a cooled (0° C.) solution of 4-bromophenethylalcohol (3.9 g, 19.4 mmol) in DCM (50 mL), was added the Dess-Martin reagent (8.22 g, 19.4 mmol). After 10 minutes, the coolant was removed, and the reaction mixture was stirred at ambient temperature for 2 hours. The reaction mixture was quenched with 10% aqueous potassium carbonate, and the mixture was separated. The aqueous phase was extracted with further DCM (×2), and the combined organic phases were dried with anhydrous magnesium sulphate, and the solvent evaporated at reduced pressure. The crude material was purified by silica gel chromatography eluting with 100% iso-hexane to 50% ethyl acetate in iso-hexane to afford a oil. The oil was dissolved in toluene (35 mL), para-toluenesulfonic acid—monohydrate (0.1 g, 0.52 mmol) and ethylene glycol (5.3 mL, 94.2 mmol) was added, and the mixture heated at reflux under Dean and Stark conditions for 2 hours. The solvent was evaporated at reduced pressure and the residue dissolved in ethyl acetate. The solution was washed with 10% aqueous potassium carbonate, dried with anhydrous magnesium sulfate, and the solvent evaporated at reduced pressure. The crude material was purified by silica gel chromatography eluting with 100% iso-hexane to 50% ethyl acetate in iso-hexane to afford an oil (2.3 g, 49%).

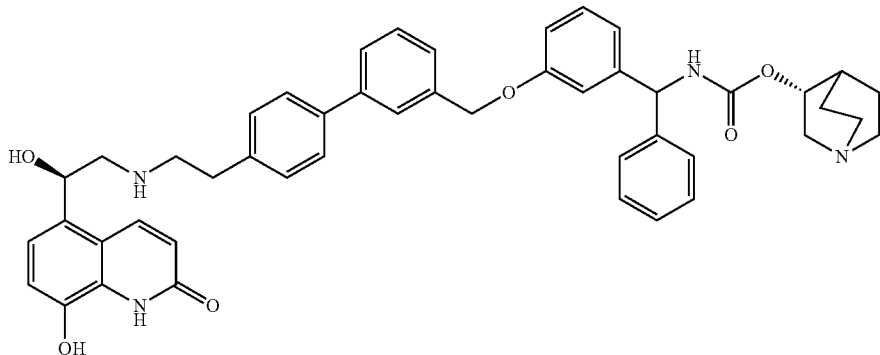 [SMILES: O=C(NC(c1ccccc1)c1cccc(OCc2cccc(-c3ccc(CCNC[C@H](O)c4ccc(O)c5[nH]c(=O)ccc45)cc3)c2)c1)O[C@H]1CN2CCC1CC2]

¹H NMR (400 MHz, CDCl₃): δ 7.52-7.36 (m, 2H); 7.19-7.06 (m, 2H); 5.03 (t, J=4.6 Hz, 1H); 3.95-3.85 (m, 2H); 3.86-3.76 (m, 2H); 2.93-2.86 (m, 2H).

Step 2. (4'-((1,3-Dioxolan-2-yl)methyl)-[1,1'-biphenyl]-3-yl)methanol

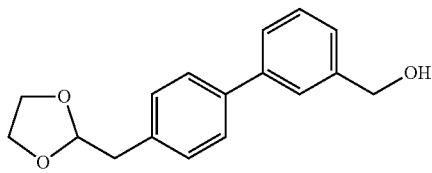 [SMILES: OCc1cccc(-c2ccc(CC3OCCO3)cc2)c1]

A mixture of 2-(4-bromobenzyl)-1,3-dioxolane (2.0 g, 8.2 mmol), 3-formylboronic acid (2.45 g, 16.4 mmol), tetrakis-(triphenylphosphine)palladium (0) (0.763 g, 0.66 mmol), and sodium carbonate (1.74 g, 16.4 mmol) in dioxan/water (15 mL/3 mL) in a microwave vessel was degassed in a stream of nitrogen for 10 minutes. The vessel was sealed and heated in the microwave at 125° C. for 30 minutes. The solvent was decanted off, and the solid residues washed with ethyl acetate. The organic phases were combined, and the solvent evaporated at reduced pressure. The crude material was purified by silica gel chromatography eluting with 100% iso-hexane to 50% ethyl acetate in iso-hexane to afford an oil. The oil was dissolved in methanol (25 mL) and cooled to 0° C. Sodium borohydride (0.393 g, 10.4 mmol) was added portion-wise, and the reaction mixture was stirred at 0° C. for 30 minutes followed by 1 hour at ambient temperature. The reaction mixture was quenched with water and extracted twice with ethyl acetate. The combined organic extracts were dried with anhydrous magnesium sulfate, and the solvent evaporated at reduced pressure. The crude material was purified by silica gel chromatography eluting with 100% iso-hexane to 100% ethyl acetate in iso-hexane to afford the title compound (1.16 g, 52%).

¹H NMR (400 MHz, CDCl₃): δ 7.58-7.45 (m, 4H); 7.44-7.30 (m, 4H); 5.09 (t, J=4.8 Hz, 1H); 4.73 (d, J=5.0 Hz, 2H); 3.99-3.83 (m, 4H); 3.00 (d, J=4.8 Hz, 2H); 2.05-1.98 (m, 1H).

Step 3. tert-butyl((3-((4'-((1,3-dioxolan-2-yl)methyl)-[1,1'-biphenyl]-3-yl)methoxy)phenyl)(phenyl)methyl)carbamate

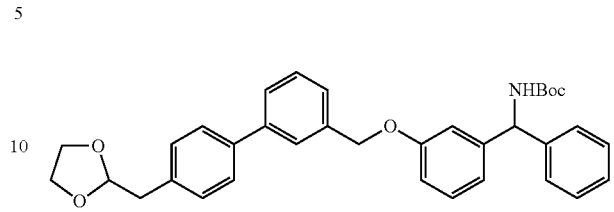

The title compound was prepared as described in Example 22 Step 2 with (4'-((1,3-dioxolan-2-yl)methyl)-[1,1'-biphenyl]-3-yl)methanol and tert-butyl(3-hydroxy-phenyl)(phenyl)methylcarbamate replacing (4-((1,3-dioxolan-2-yl)methyl)phenyl)-methanol and 3-hydroxybenzophenone respectively.

Step 4. (3-((4'-((1,3-dioxolan-2-yl)methyl)-[1,1'-biphenyl]-3-yl)methoxy)phenyl)-(phenyl)methanamine hydrochloride

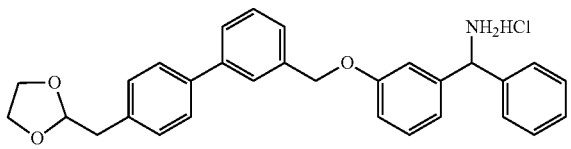

To a solution of tert-butyl((3-((4'-((1,3-dioxolan-2-yl)methyl)-[1,1'-biphenyl]-3-yl)methoxy)phenyl)(phenyl)methyl)carbamate (1.44 g, 2.6 mmol) in methanol (6.5 mL), was added hydrogen chloride in dioxan (6.5 mL). The reaction mixture was stirred at ambient temperature for 16 hours. The solvent was evaporated to afford a mixture of the title compound and the corresponding dimethyl acetal. The material was used in the next step without further purification.

Step 5. (R)-Quinuclidin-3-yl(3-((4'-(2-((R)-2-hydroxy-2-(8-hydroxy-2-oxo-1,2-dihydroquinolin-5-yl)ethylamino)ethyl)biphenyl-3-yl)methoxy)phenyl)(phenyl)-methylcarbamate (compound 29B)

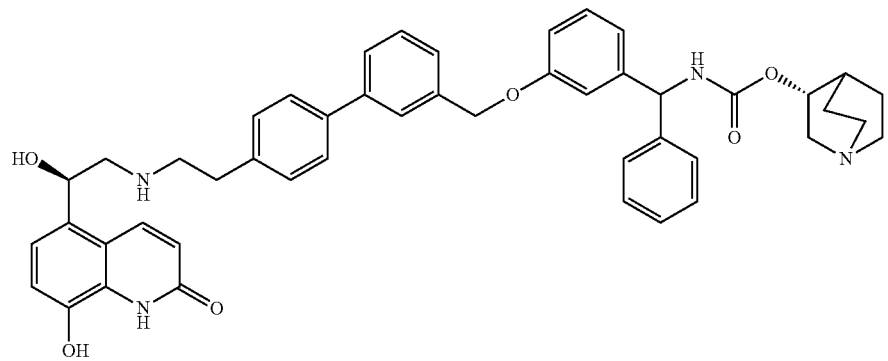 [SMILES: O=C(NC(c1ccccc1)c1cccc(OCc2cccc(-c3ccc(CCNC[C@H](O)c4ccc(O)c5[nH]c(=O)ccc45)cc3)c2)c1)O[C@H]1CN2CCC1CC2]

The title compound was prepared using the additional steps described in Example 1 Steps 3 through 7.
Synthetic scheme for the preparation of ester and amide analogues.
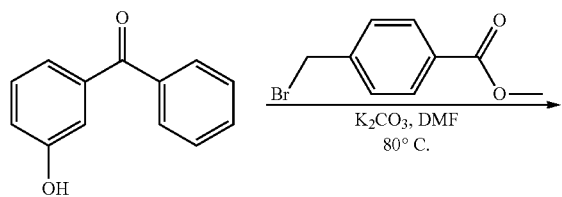
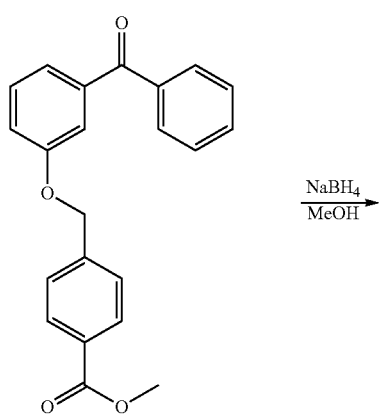
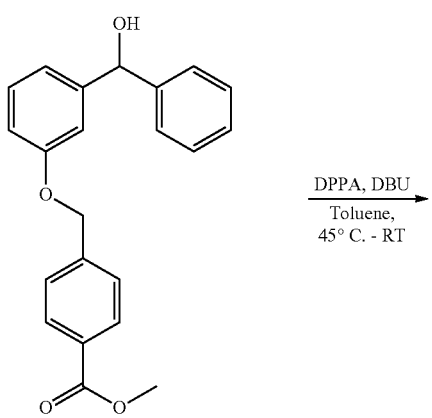
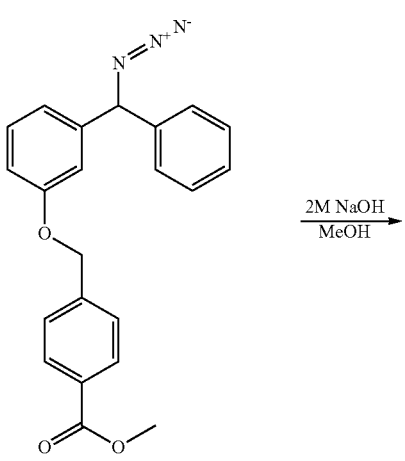
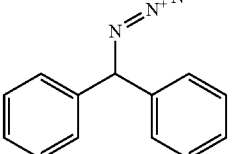
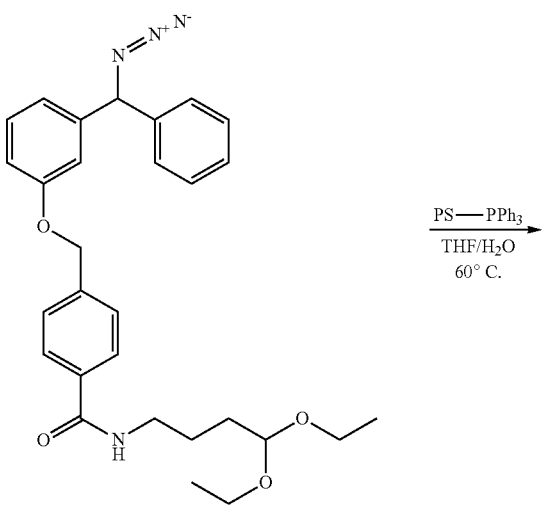
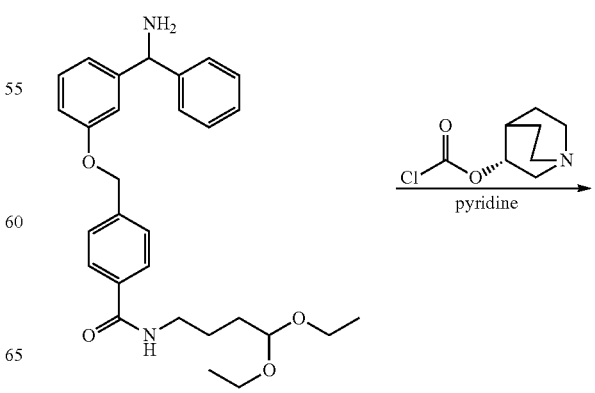

119
-continued

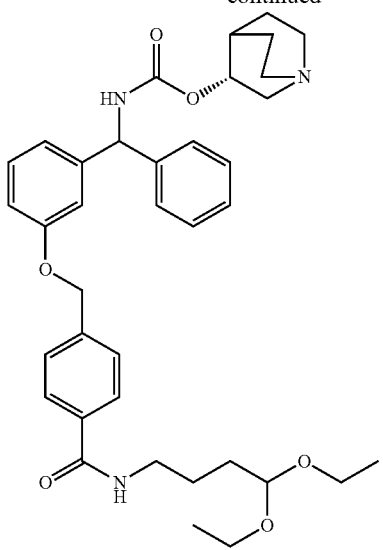

pTSA
Acetone
→

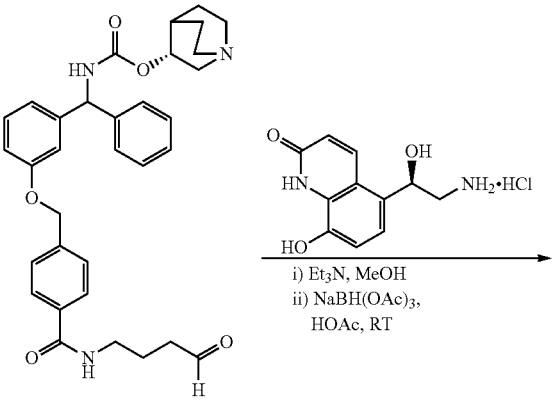

i) Et₃N, MeOH
ii) NaBH(OAc)₃,
HOAc, RT
→

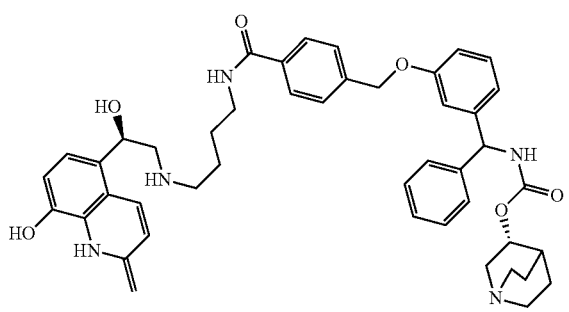

120

Example 51

(R)-quinuclidin-3-yl((3-((4-((4-(((R)-2-hydroxy-2-(8-hydroxy-2-oxo-1,2-dihydroquinolin-5-yl)ethyl)amino)butyl)carbamoyl)benzyl)oxy)phenyl)(phenyl)methyl)carbamate (compound 30B)

Step 1. Methyl 4-((3-benzoylphenoxy)methyl)benzoate

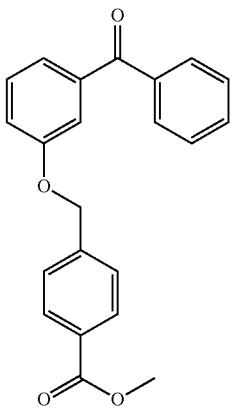 [SMILES: COC(=O)c1ccc(COc2cccc(C(=O)c3ccccc3)c2)cc1]

To a stirred solution of 3-hydroxybenzophenone (1.00 g, 5.04 mmol) in dimethyl formamide (10 mL), was added potassium carbonate (1.05 g, 7.61 mmol), and the mixture was stirred for 10 minutes at room temperature. Methyl 4-bromobenzoate (1.30 g, 6.05 mmol) in dimethyl formamide (5 mL) was added, and the reaction mixture allowed to stir at room temperature for 16 hours. The reaction mixture was diluted with water and extracted with ethyl acetate. The organic extract was washed with brine, dried (MgSO₄), and concentrated under reduced pressure. The crude material was purified by silica gel chromatography eluting with 0-17% ethyl acetate in iso-hexane to afford the title compound (1.64 g, 99%).

$^1$H NMR (400 MHz, CDCl₃): δ 8.07 (d, J=8.4 Hz, 2H); 7.79 (d, J=8.4 Hz, 2H); 7.61-7.57 (m, 1H); 7.52-7.37 (m, 8H); 5.18 (s, 2H); 3.93 (s, 3H).

Step 2. Methyl 4-((3-(azido(phenyl)methyl)phenoxy)methyl)benzoate

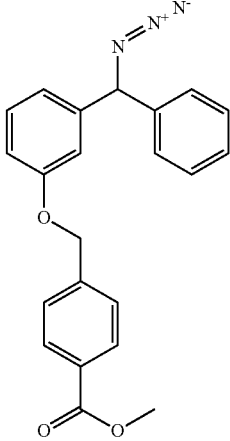

To an ice-cooled suspension of methyl 4-((3-benzoylphenoxy)methyl)benzoate (1.62 g, 4.88 mmol) in methanol (20 mL), was added sodium borohydride (0.27 g, 7.32 mmol). The reaction mixture was allowed to warm to room temperature over 2 hours. The reaction mixture was diluted with water and extracted with ethyl acetate. The organic extracts were washed with brine, dried (MgSO$_4$), and concentrated under reduced pressure to afford an oil. To a solution of the oil in toluene (25 mL), was added diphenylphosphoryl azide (1.26 mL, 5.85 mmol) and 1,8-diazabicyclo[5.4.0]undec-7-ene (881 μL, 5.85 mmol). The reaction mixture was stirred at 100° C. for 3 hours. The reaction mixture was allowed to cool to room temperature, diluted with ethyl acetate and washed with water, brine, dried (magnesium sulphate), filtered and concentrated. The crude material was purified by silica gel chromatography eluting with 0-10% ethyl acetate in iso-hexane to afford the title compound (1.62 g, 92% over 2 steps).

$^1$H NMR (400 MHz, CDCl$_3$): δ 8.05-8.03 (m, 2H); 7.48-7.46 (m, 2H); 7.39-7.25 (m, 6H); 6.93-6.88 (m, 3H); 5.67 (s, 1H); 5.10 (s, 2H); 3.92 (s, 3H).

Step 3. 4-((3-(Azido(phenyl)methyl)phenoxy)methyl)benzoic acid

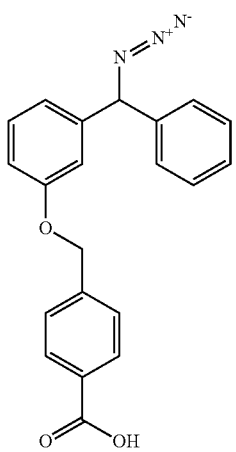

To a stirred suspension of methyl 4-((3-(azido(phenyl)methyl)phenoxy)-methyl)benzoate (1 g, 2.79 mmol) in methanol (25 mL), was added 2M sodium hydroxide (25 mL). The reaction was allowed to stir at room temperature for 3 days. Tetrahydrofuran (10 mL) was added to the reaction mixture, and the mixture was stirred at 50° C. for 4 hours followed by 16 hours at room temperature. The reaction mixture was acidified with 10% hydrochloric acid, extracted with dichloromethane, dried (sodium sulphate), filtered, and concentrated under reduced pressure to give the title compound (1 g, quantitative).

$^1$H NMR (400 MHz, CDCl$_3$): δ 8.10 (d, J=8.09 Hz, 2H); 7.51 (d, J=8.03 Hz, 2H); 7.38-7.27 (m, 6H); 6.95-6.88 (m, 3H); 5.67 (s, 1H); 5.12 (s, 2H).

Step 4. 4-((3-(Azido(phenyl)methyl)phenoxy)methyl)-N-(4,4-diethoxybutyl)benzamide

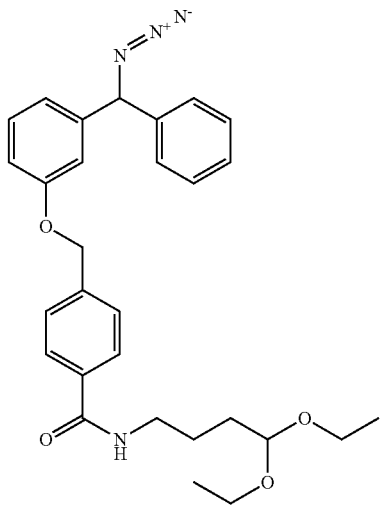

To a stirred solution of 4-((3-(azido(phenyl)methyl)phenoxy)methyl)benzoic acid (0.5 g, 1.39 mmol) in dimethyl formamide (14 mL), was added 1-ethyl-3-(3-dimethyllaminopropyl)carbodiimide hydrochloride (0.29 g, 1.53 mmol), 2-hydroxypyridine-N-oxide (0.16 g, 1.53 mmol), and triethylamine (0.49 mL. 3.48 mmol). The reaction mixture was stirred at room temperature for 10 minutes. 4-Amino-butyraldehyde diethyl ether (0.27 g, 1.67 mmol) was added, and the reaction mixture stirred at room temperature for 16 hours. The reaction mixture was diluted with water and extracted with ethyl acetate. The organic extracts were washed with brine, dried (sodium sulphate), filtered, and concentrated under reduced pressure. The crude material was purified by silica gel chromatography eluting with 0-100% ethyl acetate in iso-hexane to afford the title compound as a colourless oil (0.51 g, 73%).

$^1$H NMR (400 MHz, CDCl$_3$): δ 7.78 (d, J=8.08 Hz, 2H); 7.46 (d, J=7.94 Hz, 2H); 7.40-7.24 (m, 6H); 6.94-6.83 (m, 3H); 6.52 (s, 1H); 5.67 (s, 1H); 5.08 (s, 2H); 4.58-4.48 (m, 1H); 3.72-3.62 (m, 2H); 3.56-3.46 (m, 4H); 1.83-1.69 (m, 4H); 1.21 (t, J=7.04 Hz, 6H).

Step 5. 4-((3-(Amino(phenyl)methyl)phenoxy)methyl)-N-(4,4-diethoxybutyl)benzamide

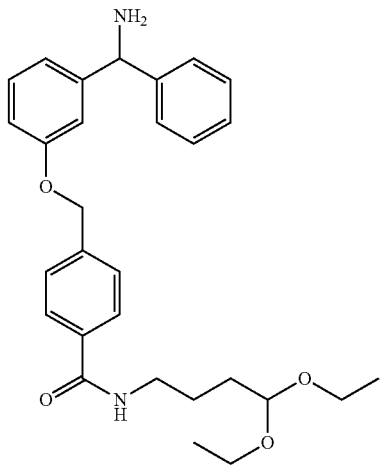 [SMILES: CCOC(CCCNC(=O)c1ccc(COc2cccc(C(N)c3ccccc3)c2)cc1)OCC]

To a solution of 4-((3-(azido(phenyl)methyl)phenoxy)methyl)-N-(4,4-diethoxybutyl)benzamide (0.51 g, 1.03 mmol) in tetrahydrofuran (10 mL), was added polymer supported triphenylphosphine (3 mmol/g, 0.38 g, 1.13 mmol) and water (0.2 mL). The reaction mixture was stirred at 60° C. for 16 hours. The reaction mixture was allowed to cool to room temperature, filtered, the filter-cake washed with dichloromethane and concentrated under reduced pressure to give the title compound (0.41 g, 83%).

$^1$H NMR (400 MHz, CDCl$_3$): δ 7.76 (d, J=8.04 Hz, 2H); 7.48 (d, J=10.02 Hz, 2H); 7.37-7.19 (m, 5H); 7.03 (d, J=2.34 Hz, 1H); 6.98 (d, J=7.60 Hz, 1H); 6.83 (d, J=2.79 Hz, 1H); 6.41 (s, 1H); 5.18 (s, 1H); 5.02 (s, 2H); 4.56-4.50 (m, 1H); 3.67 (dq, J=9.43, 7.05 Hz, 2H); 3.56-3.45 (m, 4H); 1.89-1.80 (m, 2H); 1.73 (s, 2H); 1.21 (t, J=7.05 Hz, 6H).

Step 6. (R)-Quinuclidin-3-yl((3-((4-((4-(((R)-2-hydroxy-2-(8-hydroxy-2-oxo-1,2-dihydroquinolin-5-yl)ethyl)amino)butyl)carbamoyl)benzyl)oxy)phenyl)(phenyl)-methyl)carbamate (compound 30B)

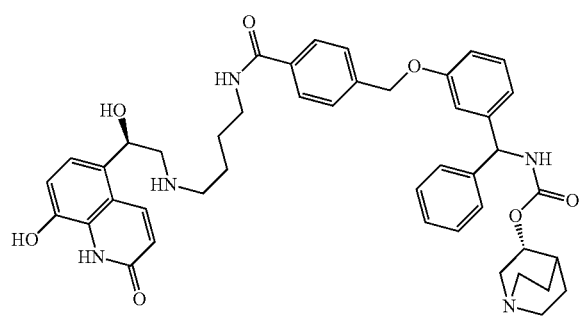 [SMILES: O=C(NC(c1ccccc1)c1cccc(OCc2ccc(C(=O)NCCCCNC[C@H](O)c3ccc(O)c4[nH]c(=O)ccc34)cc2)c1)O[C@H]1CN2CCC1CC2]

The title compound was prepared as described in Example 1 Step 5 through 7 with 4-((3-(amino(phenyl)methyl)phenoxy)methyl)-N-(4,4-diethoxybutyl)benzamide (3-(8-(1,3-dioxolan-2-yl)octyloxy)phenyl)(phenyl)methanamine in Step 5 and the product used in the subsequent steps.

Example 52

(R)-quinuclidin-3-yl(3-(4-(3-(((R)-2-hydroxy-2-(8-hydroxy-2-oxo-1,2-dihydroquinolin-5-yl)ethylamino)propylcarbamoyl)benzyloxy)phenyl)(phenyl)-methylcarbamate (compound 31B)

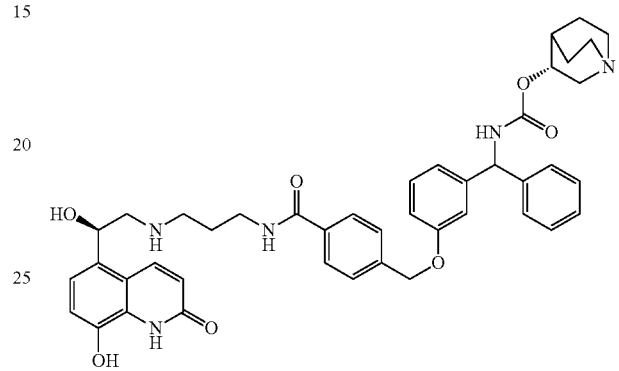

The title compound was prepared as described in Example 51 with 3-amino-propylaldehyde diethyl ether replacing 4-amino-butyraldehyde diethyl ether in Step 4 and the product used in the subsequent steps.

Example 53

(3R)-3-((((3-((4-((3-(((R)-2-hydroxy-2-(8-hydroxy-2-oxo-1,2-dihydroquinolin-5-yl)ethyl)amino)propyl)carbamoyl)benzyl)oxy)phenyl)(phenyl)-methyl)carbamoyl)oxy)-1-(2-oxo-2-phenylethyl)quinuclidin-1-ium (compound 32B)

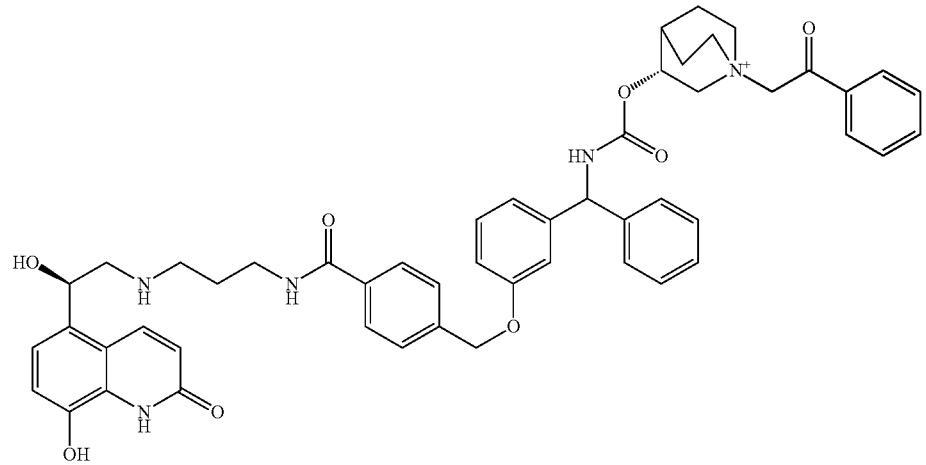 [SMILES: O=C(NC(c1ccccc1)c1cccc(OCc2ccc(C(=O)NCCCNC[C@H](O)c3ccc(O)c4[nH]c(=O)ccc34)cc2)c1)O[C@H]1C[N+]2(CC(=O)c3ccccc3)CCC1CC2]

The title compound was prepared as in Example 24 with (R)-quinuclidin-3-yl(3-(4-(3-(((R)-2-hydroxy-2-(8-hydroxy-2-oxo-1,2-dihydroquinolin-5-yl)ethylamino)-propylcarbamoyl)benzyloxy)phenyl)(phenyl)methylcarbamate (Example 52) replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 54

4-(((R)-2-Hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)-methyl)phenoxy)methyl)benzoate (compound 33B)

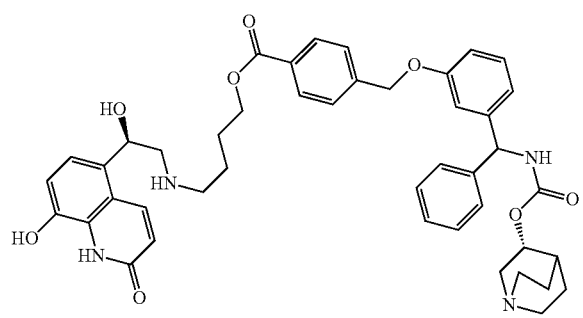 [SMILES: O=C(NC(c1ccccc1)c1cccc(OCc2ccc(C(=O)OCCCCNC[C@H](O)c3ccc(O)c4[nH]c(=O)ccc34)cc2)c1)O[C@H]1CN2CCC1CC2]

Step 1. 3-(1,3-Dioxolan-2-yl)propyl 4-((3-(azido(phenyl)methyl)phenoxy)methyl)-benzoate

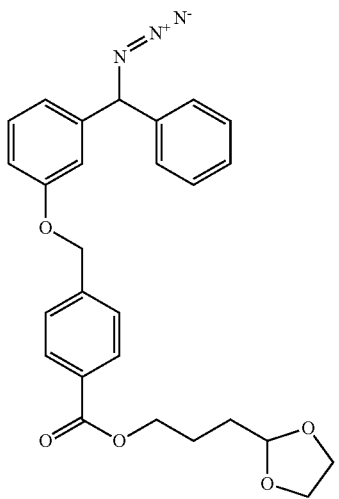

To a stirred solution of 3-chloropropyl-1,3-dioxolane (0.2 g, 1.35 mmol) in dimethyl formamide (14 mL), was added 4-((3-(azido(phenyl)methyl)phenoxy)-methyl)benzoic acid (Example 51 Step 3) (0.5 g, 1.39 mmol) and potassium carbonate (0.38 g, 2.78 mmol). The reaction was allowed to stir at 80° C. for 16 hours. The reaction mixture was cooled to room temperature, diluted with water and extracted with ethyl acetate (×3). The organic extracts were washed with brine, dried (sodium sulphate), filtered, and concentrated under reduced pressure. The crude material was purified by silica gel chromatography eluting with 0-100% ethyl acetate in iso-hexane to afford the title compound (0.63 g, 96%).

$^1$H NMR (400 MHz, CDCl$_3$): δ 7.53-7.43 (m, 2H); 7.39-7.25 (m, 8H); 6.92 (d, J=5.57 Hz, 3H); 5.67 (s, 1H); 5.10 (s, 2H); 4.94 (t, J=4.40 Hz, 1H); 4.40-4.33 (t, J=6.39 Hz, 2H); 4.03-3.93 (m, 2H); 3.93-3.81 (m, 2H); 1.96-1.79 (m, 4H).

Step 2. 4-(((R)-2-Hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)-methyl)phenoxy)methyl)benzoate (compound 33B)

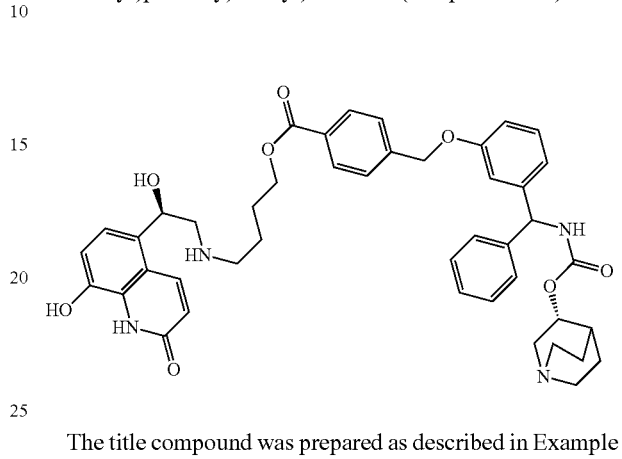

The title compound was prepared as described in Example 54 Steps 5 to 6 with 3-(1,3-dioxolan-2-yl)propyl 4-((3-(azido(phenyl)methyl)phenoxy)methyl)benzoate replacing 4-((3-(azido(phenyl)methyl)phenoxy)methyl)-N-(4,4-diethoxybutyl)benzamide in Step 5 and the product used in subsequent steps.

The following compounds were prepared using the appropriate bromides in Example 55, Step 1:

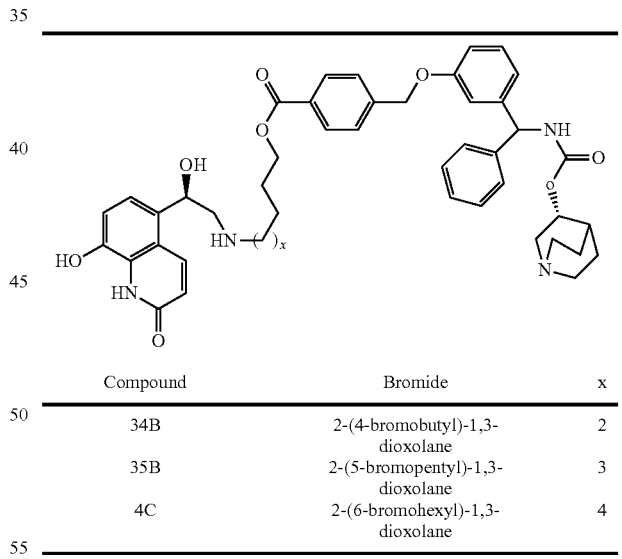

| Compound | Bromide | x |
|---|---|---|
| 34B | 2-(4-bromobutyl)-1,3-dioxolane | 2 |
| 35B | 2-(5-bromopentyl)-1,3-dioxolane | 3 |
| 4C | 2-(6-bromohexyl)-1,3-dioxolane | 4 |

The following compounds were prepared by coupling 4-((3-(azido(phenyl)-methyl)phenoxy)methyl)benzoic acid (Example 51 Step 3) with the appropriate alcohol using the protocol below and the product so formed used in the subsequent steps for the preparation of Example 51.

To a stirred solution of the 4-((3-(azido(phenyl)methyl)phenoxy)methyl)benzoic acid and the appropriate alcohol (2.0 equivalents) in DMF (0.2 M), was added diisopropylethylamine (1.5 equivalents) and HATU (1.2 equivalents). The reaction mixture was heated at 60° C. for 24 hours. The reaction mixture was diluted with ethyl acetate and was washed sequentially with aqueous 1M sodium hydroxide, water and brine. The organic phase was dried over anhydrous magnesium sulfate, filtered, and concentrated under reduced pressure. The crude residue was purified by silica gel column chromatography eluting with 0-50% ethyl acetate in iso-hexane to afford the required compound.
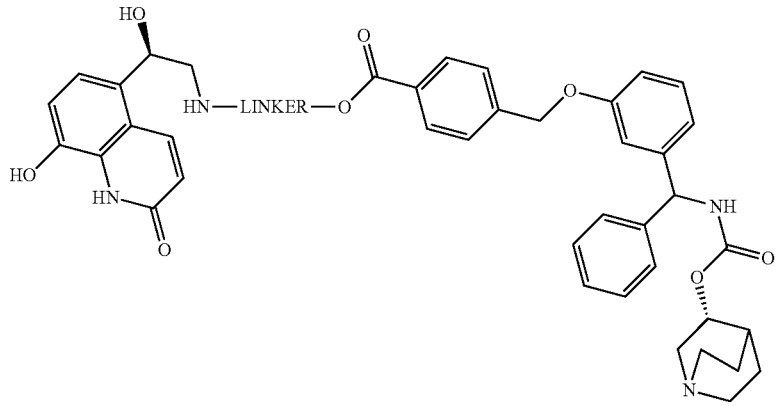

Example 56

(3R)-3-(((((3-((4-(1-((4-(((R)-2-hydroxy-2-(8-hydroxy-2-oxo-1,2-dihydroquinolin-5-yl)ethyl)amino)butoxy)carbonyl)cyclopropyl)benzyl)oxy)-phenyl)(phenyl)methyl)carbamoyl)oxy)-1-(2-oxo-2-phenylethyl)quinuclidin-1-ium (compound 36B)

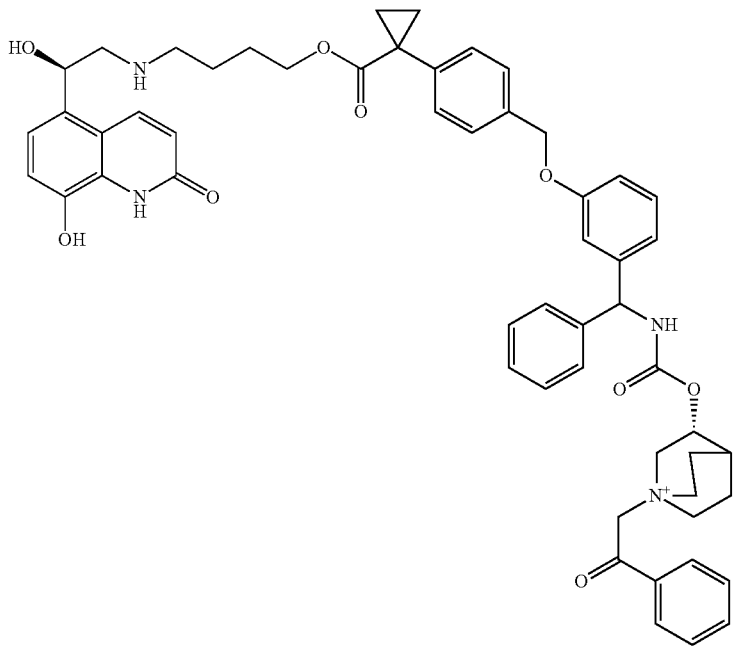 [SMILES: O=C(NC(c1ccccc1)c1cccc(OCc2ccc(C3(C(=O)OCCCCNC[C@H](O)c4ccc(O)c5[nH]c(=O)ccc45)CC3)cc2)c1)O[C@H]1C[N+]2(CC(=O)c3ccccc3)CCC1CC2]

Step 1. Methyl 1-(p-tolyl)cyclopropanecarboxylate

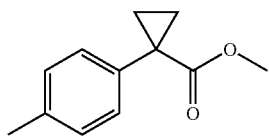

To a stirred solution of 1-(p-tolyl)cyclopropanecarboxylic acid (6 g, 34.05 mmol) in methanol (48 mL), was added para-toluenesulphonic acid monohydrate (0.648 g, 3.405 mmol). The reaction was stirred at 75° C. for 16 hours. The mixture was concentrated under reduced pressure, and the residue partitioned between ethyl acetate and saturated aqueous sodium bicarbonate solution. The organic layer was washed with saturated aqueous sodium bicarbonate solution (×2), brine and dried (magnesium sulfate), filtered, and concentrated under reduced pressure to afford the title compound as an orange oil (6.279 g, 97%). The material was used directly in the next step with no further purification.

$^1$H NMR (400 MHz, CDCl$_3$): δ 7.25-7.21 (m, 2H); 7.14-7.10 (m, 2H); 3.62 (s, 3H); 2.34 (s, 3H); 1.60-1.56 (m, 2H); 1.18-1.14 (m, 2H).

Step 2. Methyl 1-(4-(bromomethyl)phenyl)cyclopropanecarboxylate

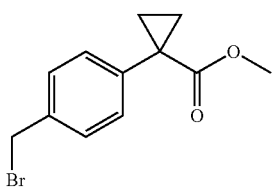

To a stirred solution of methyl 1-(p-tolyl)cyclopropanecarboxylate (3 g, 15.77 mmol) in acetonitrile (42 mL), was added N-bromosuccinimide (2.807 g, 15.77 mmol) followed by benzoyl peroxide (0.164 g, 0.473 mmol). The reaction was stirred at 80° C. for 2 hours 40 minutes and then allowed to cool to room temperature. The reaction mixture was diluted with water and extracted with dichloromethane (×3). The combined organic extracts were washed with brine and dried (magnesium sulfate), filtered and concentrated under reduced pressure to afford a red oil. The crude material was purified by silica gel column chromatography eluting with 0-9% ethyl acetate in iso-hexane to afford the title compound (2.478 g, 58%).

$^1$H NMR (400 MHz, CDCl$_3$): δ 7.36-7.30 (m, 4H); 4.49 (s, 2H); 3.62 (s, 3H); 1.63-1.59 (m, 2H); 1.20-1.16 (m, 2H).

Step 3. Methyl 1-(4-((3-benzoylphenoxy)methyl)phenyl)cyclopropanecarboxylate

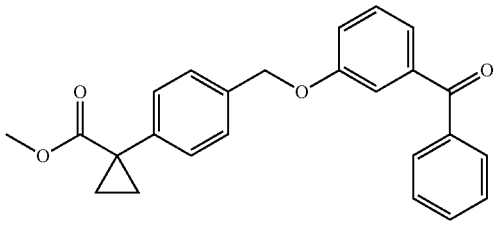 [SMILES: COC(=O)C1(c2ccc(COc3cccc(C(=O)c4ccccc4)c3)cc2)CC1]

Methyl 1-(4-(bromomethyl)phenyl)cyclopropanecarboxylate (2.478 g, 9.207 mmol) was added to a mixture of 3-hydroxybenzophenone (2.19 g, 11.05 mmol) and potassium carbonate (3.054 g, 22.10 mmol) in dimethyl formamide (46 mL). The reaction mixture was stirred at 60° C. for 16 hours. The reaction mixture was diluted with water and extracted with ethyl acetate (×3). The combined organic extracts were washed with 10% aqueous potassium carbonate (×5), 2M NaOH (×5), brine and dried (magnesium sulfate), filtered, and concentrated under reduced pressure to afford the title compound (3.721 g, quantitative yield). The material was used directly in the next step with no further purification.

$^1$H NMR (400 MHz, CDCl$_3$): δ 7.81-7.77 (m, 2H); 7.61-7.56 (m, 1H); 7.50-7.35 (m, 9H); 7.23-7.19 (m, 1H); 5.10 (s, 2H); 3.62 (s, 3H); 1.64-1.59 (m, 2H); 1.22-1.17 (m, 2H).

Step 4. Methyl 1-(4-((3-(hydroxy(phenyl)methyl)phenoxy)methyl)phenyl)-cyclopropanecarboxylate

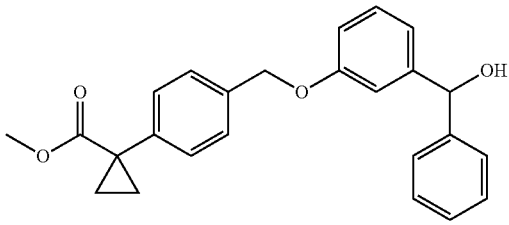 [SMILES: COC(=O)C1(c2ccc(COc3cccc(C(O)c4ccccc4)c3)cc2)CC1]

To a stirred solution of methyl 1-(4-((3-benzoylphenoxy)methyl)phenyl)-cyclopropanecarboxylate (1.85 g, 4.787 mmol) in methanol (22.6 mL) at 0° C. under an atmosphere of nitrogen, was added sodium borohydride (0.181 g, 4.787 mmol) in one portion. The reaction mixture was stirred at 0° C. for 1 hour and then allowed to warm to room temperature. After stirring for 40 minutes, the reaction was cooled to 0° C., and additional sodium borohydride (0.091 g, 2.380 mmol) was added. The reaction mixture was allowed to warm to room temperature and stirred for 30 minutes. The reaction was quenched with water (3.5 mL), filtered to remove insoluble material, and then concentrated under reduced pressure. Water was added to the residue and extracted with ethyl acetate (×2). The combined organic extracts were washed with 10% aqueous potassium carbonate (×2), brine, dried (magnesium sulfate), filtered, and concentrated under reduced pressure to afford the title compound as a red oil (1.824 g, 98%). The material was used directly in the next step with no further purification.

$^1$H NMR (400 MHz, CDCl$_3$): δ 7.40-7.22 (m, 10H); 7.05-7.03 (m, 1H); 6.98 (d, J=7.7 Hz, 1H); 6.87 (dd, J=8.3, 2.6 Hz, 1H); 5.82 (d, J=3.4 Hz, 1H); 5.02 (s, 2H); 3.62 (s, 3H); 2.20 (d, J=3.6 Hz, 1H); 1.63-1.59 (m, 2H); 1.20-1.16 (m, 2H).

Step 5. Methyl 1-(4-((3-(azido(phenyl)methyl)phenoxy)methyl)phenyl)-cyclopropanecarboxylate

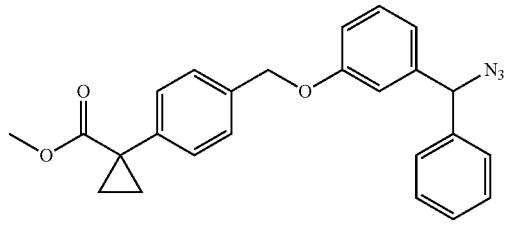 [SMILES: COC(=O)C1(c2ccc(COc3cccc(C(N=[N+]=[N-])c4ccccc4)c3)cc2)CC1]

To a stirred solution of methyl 1-(4-((3-(hydroxy(phenyl)methyl)phenoxy)-methyl)phenyl)cyclopropanecarboxylate (1.824 g, 4.695 mmol) in toluene (21.8 mL) under an atmosphere of nitrogen, was added diphenylphosphoryl azide (1.21 mL, 5.635 mmol) followed by 1,8-diazabicyclo[5.4.0]undec-7-ene (0.84 mL, 5.635 mmol). The reaction mixture was stirred at 100° C. for 3 hours and then allowed to cool to room temperature. The reaction was quenched by addition of saturated aqueous ammonium chloride solution and extracted with ethyl acetate (×3). The combined organic extracts were washed with brine and dried (magnesium sulfate), filtered, and concentrated under reduced pressure to afford a brown oil. The crude material was purified by silica gel chromatography eluting with 0-14% ethyl acetate in iso-hexane to afford the title compound as a colourless oil (1.214 g, 62%).

$^1$H NMR (400 MHz, CDCl$_3$): δ 7.38-7.25 (m, 10H); 6.95-6.89 (m, 3H); 5.67 (s, 1H); 5.01 (s, 2H); 3.62 (s, 3H); 1.63-1.59 (m, 2H); 1.20-1.16 (m, 2H).

Step 6. 1-(4-((3-(Azido(phenyl)methyl)phenoxy)methyl)phenyl)cyclopropanecarboxylic acid

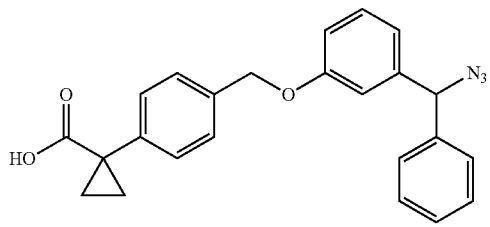 [SMILES: [N-]=[N+]=NC(c1ccccc1)c1cccc(OCc2ccc(C3(C(=O)O)CC3)cc2)c1]

To a stirred solution of methyl 1-(4-((3-(azido(phenyl)methyl)phenoxy)methyl)-phenyl)cyclopropanecarboxylate (0.569 g, 1.375 mmol) in methanol (12.9 mL) and tetrahydrofuran (5.1 mL), was added 2M aqueous sodium hydroxide (12.9 mL). The reaction was stirred at 50° C. for 3 hours 30 minutes and then at room temperature for 16 hours. The reaction mixture was concentrated under reduced pressure, and the pH was adjusted to pH4 using 2M aqueous hydrochloric acid with stirring. The mixture was extracted with dichloromethane (×3), and the combined organic extracts washed with brine, dried (magnesium sulfate), filtered, and concentrated under reduced pressure to afford the title compound (0.552 g, quantitative yield). The material was used directly in the next step with no further purification $^1$H NMR (400 MHz, CDCl$_3$): δ 7.39-7.24 (m, 10H); 6.94-6.88 (m, 3H); 5.67 (s, 1H); 5.00 (s, 2H); 1.69-1.65 (m, 2H); 1.28-1.24 (m, 2H).

Step 7. 4-(((R)-2-hydroxy-2-(8-hydroxy-2-oxo-1,2-dihydroquinolin-5-yl)ethyl)amino)butyl 1-(4-((3-(phenyl((((R)-quinuclidin-3-yloxy)carbonyl)amino)-methyl)phenoxy)methyl)phenyl)cyclopropanecarboxylate

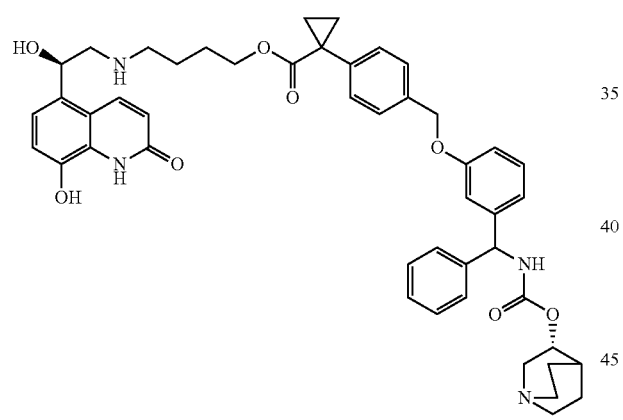

The title compound was prepared as described in Example 54 Step 1 through 2 with 1-(4-((3-(Azido(phenyl)methyl)phenoxy)methyl)phenyl)cyclopropanecarboxylic acid replacing 4-((3-(azido(phenyl)methyl)phenoxy)methyl)benzoic acid in Step 1, and the product used in the subsequent steps.

Step 8. (3R)-3-(((((3-((4-(1-((4-(((R)-2-hydroxy-2-(8-hydroxy-2-oxo-1,2-dihydroquinolin-5-yl)ethyl)amino)butoxy)carbonyl)cyclopropyl)benzyl)oxy)phenyl)(phenyl)methyl)-carbamoyl)oxy)-1-(2-oxo-2-phenylethyl)quinuclidin-1-ium (compound 36B)

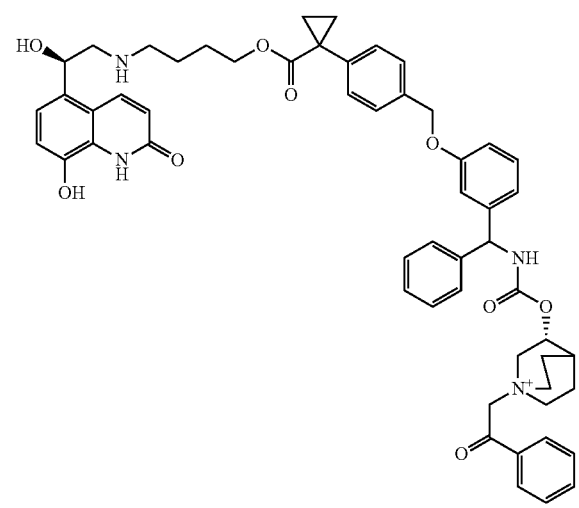 [SMILES: O=C(NC(c1ccccc1)c1cccc(OCc2ccc(C3(C(=O)OCCCCNC[C@H](O)c4ccc(O)c5[nH]c(=O)ccc45)CC3)cc2)c1)O[C@H]1C[N+]2(CC(=O)c3ccccc3)CCC1CC2]

The title compound was prepared as in Example 24 with 4-(((R)-2-hydroxy-2-(8-hydroxy-2-oxo-1,2-dihydroquinolin-5-yl)ethyl)amino)butyl 1-(4-((3-(phenyl((((R)-quinuclidin-3-yloxy)carbonyl)amino)methyl)phenoxy)methyl)phenyl)cyclopropanecarboxylate replacing (R)-quinuclidin-3-yl (3-(6-((R)-2-hydroxy-2-(8-hydroxy-2-oxo-1,2-dihydroquinolin-5-yl)ethylamino)hexyloxy)phenyl)(phenyl)methylcarbamate.

Example 57

(R)-quinuclidin-3-yl((3-(2-(4'-((((R)-2-hydroxy-2-(8-hydroxy-2-oxo-1,2-dihydroquinolin-5-yl)ethyl)amino)methyl)-[1,1'-biphenyl]-4-yl)ethoxy)phenyl)(phenyl)-methyl)carbamate (compound 37B)

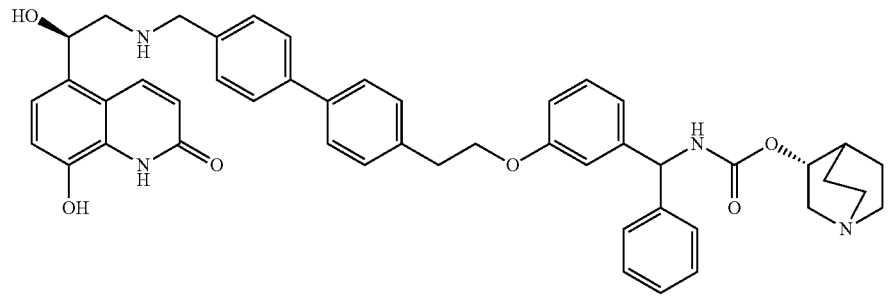 [SMILES: O=C(NC(c1ccccc1)c1cccc(OCCc2ccc(-c3ccc(CNC[C@H](O)c4ccc(O)c5[nH]c(=O)ccc45)cc3)cc2)c1)O[C@H]1CN2CCC1CC2]

Step 1. tert-Butyl((3-(4-bromophenethoxy)phenyl)(phenyl)methyl)carbamate

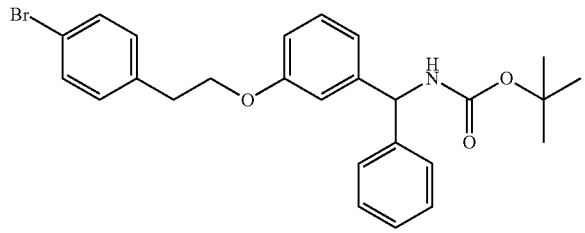 [SMILES: CC(C)(C)OC(=O)NC(c1ccccc1)c1cccc(OCCc2ccc(Br)cc2)c1]

The title compound was prepared as described in Example 22 Step 2 with 4-bromophenethyl alcohol and tert-butyl(3-hydroxyphenyl)(phenyl)methylcarbamate replacing (4-((1,3-dioxolan-2-yl)methyl)phenyl)methanol and 3-hydroxybenzophenone, respectively.

$^1$H NMR (400 MHz, CDCl$_3$): δ 7.44-7.39 (m, 2H); 7.34-7.18 (m, 6H); 7.16-7.11 (m, 2H); 6.84-6.74 (m, 3H); 5.86 (s, 1H); 5.12 (s, 1H); 4.15-4.08 (m, 2H); 3.01 (t, J=6.8 Hz, 2H); 1.43 (s, 9H).

Step 2. (3-(4-bromophenethoxy)phenyl)(phenyl)methanamine hydrochloride

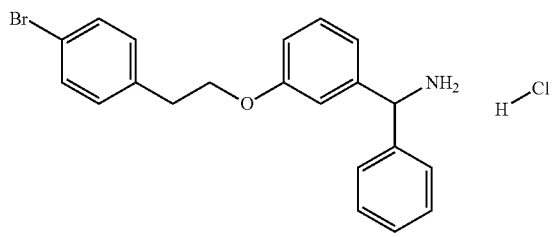 [SMILES: NC(c1ccccc1)c1cccc(OCCc2ccc(Br)cc2)c1 ; Cl]

The title compound was prepared as described in Example 50 Step 4 with tert-butyl((3-(4-bromophenethoxy)phenyl)(phenyl)methyl)carbamate replacing tert-butyl((3-((4'-((1,3-dioxolan-2-yl)methyl)-[1,1'-biphenyl]-3-yl)methoxy)phenyl)(phenyl)-methyl)carbamate.

$^1$H NMR (400 MHz, DMSO-d$_6$): δ 8.95 (s, 3H); 7.53-7.27 (m, 10H); 7.14-7.10 (m, 1H); 7.05-7.00 (m, 1H); 6.96-6.90 (m, 1H); 5.61-5.54 (m, 1H); 4.18 (t, J=6.7 Hz, 2H); 3.02 (t, J=6.7 Hz, 2H).

Step 3. (R)-quinuclidin-3-yl((3-(4-bromophenethoxy)phenyl)(phenyl)methyl)carbamate

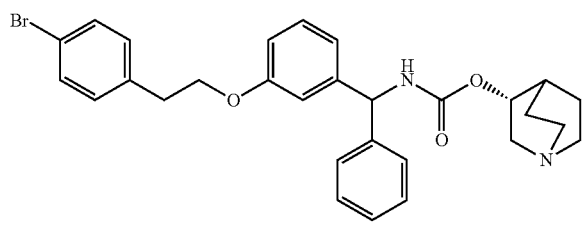 [SMILES: O=C(NC(c1ccccc1)c1cccc(OCCc2ccc(Br)cc2)c1)O[C@H]1CN2CCC1CC2]

The title compound was prepared as described in Example 1 Step 5 with (3-(4-bromophenethoxy)phenyl)(phenyl)methanamine hydrochloride replacing (3-(8-(1,3-dioxolan-2-yl)octyloxy)phenyl)(phenyl)methanamine.

$^1$H NMR (400 MHz, CDCl$_3$): δ 7.45-7.39 (m, 2H); 7.37-7.19 (m, 6H); 7.16-7.10 (m, 2H); 6.87-6.75 (m, 3H); 5.90 (s, 1H); 5.29 (s, 1H); 4.75-4.68 (m, 1H); 4.16-4.07 (m, 2H); 3.26-3.13 (m, 1H); 3.01 (t, J=6.8 Hz, 2H); 2.93-2.62 (m, 5H); 2.02-1.96 (m, 1H); 1.86-1.75 (m, 1H); 1.71-1.44 (m, 2H); 1.42-1.29 (m, 1H).

Step 4; (R)-quinuclidin-3-yl((3-(2-(4'-formyl-[1,1'-biphenyl]-4-yl)ethoxy)phenyl)-(phenyl)methyl)carbamate

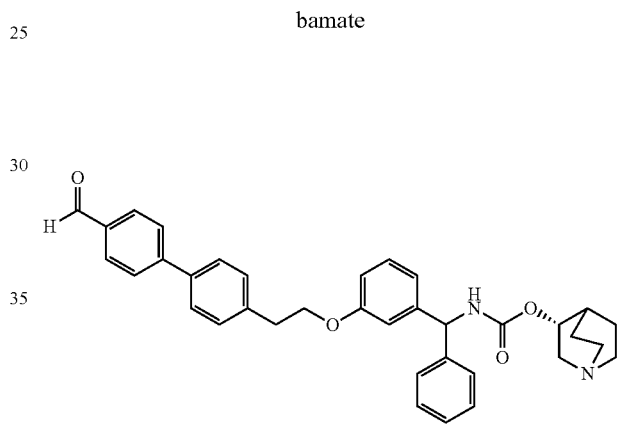

(R)-quinuclidin-3-yl((3-(4-bromophenethoxy)phenyl)(phenyl)methyl)carbamate (0.40 g, 0.747 mmol), 4-formylphenylboronic acid (0.123 g, 0.822 mmol), and sodium carbonate (0.158 g, 1.494 mmol) were combined in toluene (9.94 mL) and water (2.48 mL). The mixture was degassed with nitrogen for 10 minutes. Tetrakis-(triphenylphosphine)palladium(0) (0.087 g, 0.075 mmol) was added, and the mixture heated at 120° C. for 30 minutes in a microwave. The mixture was filtered, and the filtrate partitioned between ethyl acetate and water. The organic layer was dried (sodium sulfate), filtered, and concentrated under reduced pressure to afford a brown oil. The crude material was partially purified using a flash C18 cartridge eluting with 30-60% acetonitrile in water to afford a brown oil (0.174 g). The material was used directly in the next step with no further purification.

Step 5. (R)-quinuclidin-3-yl((3-(2-(4'-((((R)-2-hydroxy-2-(8-hydroxy-2-oxo-1,2-dihydroquinolin-5-yl)ethyl)amino)methyl)-[1,1'-biphenyl]-4-yl)ethoxy)phenyl)(phenyl)-methyl)carbamate

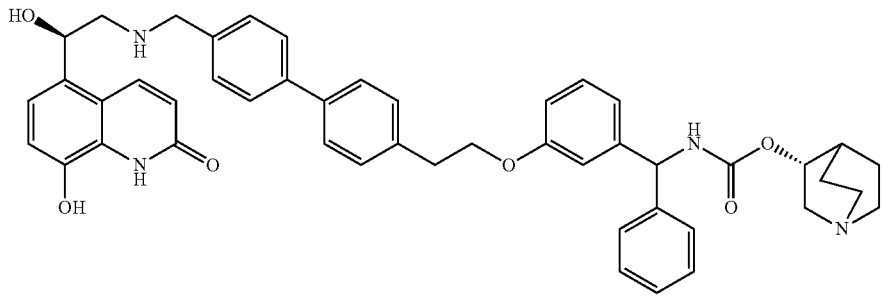 [SMILES: O=C(NC(c1ccccc1)c1cccc(OCCc2ccc(-c3ccc(CNC[C@H](O)c4ccc(O)c5[nH]c(=O)ccc45)cc3)cc2)c1)O[C@H]1CN2CCC1CC2]

The title compound was prepared as described in Example 1 Step 7 with (R)-quinuclidin-3-yl((3-(2-(4'-formyl-[1,1'-biphenyl]-4-yl)ethoxy)phenyl)(phenyl)-methyl)carbamate replacing (R)-quinuclidin-3-yl(3-(9-oxononyloxy)phenyl)(phenyl)-methylcarbamate.

Example 58

(R)-quinuclidin-3-yl(3-(2-(3'-(((R)-2-hydroxy-2-(8-hydroxy-2-oxo-1,2-dihydroquinolin-5-yl)ethylamino)methyl)biphenyl-4-yl)ethoxy)phenyl)(phenyl)-methylcarbamate (compound 38B)

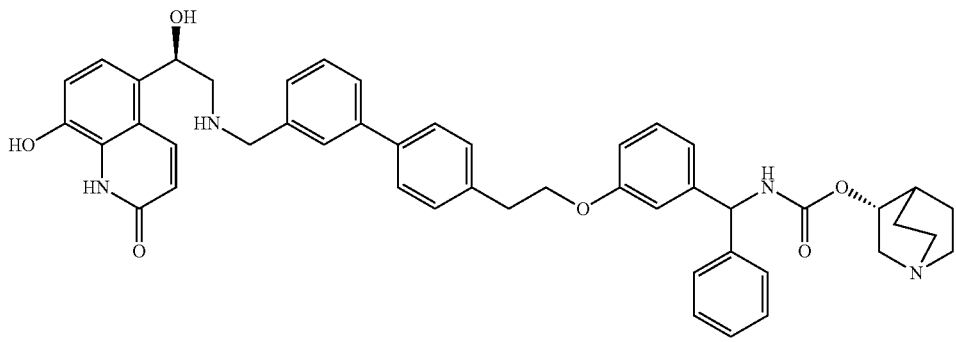 [SMILES: O=C(NC(c1ccccc1)c1cccc(OCCc2ccc(-c3cccc(CNC[C@H](O)c4ccc(O)c5[nH]c(=O)ccc45)c3)cc2)c1)O[C@H]1CN2CCC1CC2]

The title compound was prepared as described in Example 57 with 3-formylboronic acid replacing 4-formylboronic acid in Step 4 and the product used in the subsequent step.

Example 59

6-((R)-2-hydroxy-2-(8-hydroxy-2-oxo-1,2-dihydroquinolin-5-yl)ethylamino)hexyl 2-(3-(phenyl(((R)-quinuclidin-3-yloxy)carbonylamino)-methyl)phenoxy)acetate (compound 39B)

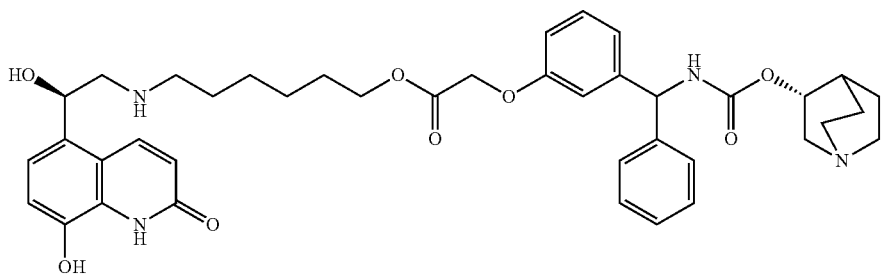 [SMILES: O=C(COc1cccc(C(NC(=O)O[C@H]2CN3CCC2CC3)c2ccccc2)c1)OCCCCCCNC[C@H](O)c1ccc(O)c2[nH]c(=O)ccc12]

Step 1. Methyl 2-(3-(((tert-butoxycarbonyl)amino)(phenyl)methyl)phenoxy)acetate

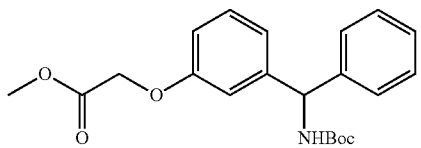 [SMILES: COC(=O)COc1cccc(C(NC(=O)OC(C)(C)C)c2ccccc2)c1]

The title compound was prepared as described in Example 1 Step 1 with tert-butyl (3-hydroxyphenyl)(phenyl)methylcarbamate and methyl bromoacetate replacing 3-hydroxybenzophenone and 2-(8-bromooctyl)-1,3-dioxolane, respectively Step 2. 2-(3-(((tert-Butoxycarbonyl)amino)(phenyl)methyl)phenoxy)acetic acid

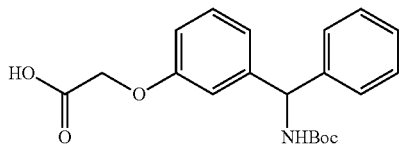 [SMILES: CC(C)(C)OC(=O)NC(c1ccccc1)c1cccc(OCC(=O)O)c1]

The title compound was prepared as described in Example 56 Step 6 with methyl 2-(3-(((tert-butoxycarbonyl)amino)(phenyl)methyl)phenoxy)acetate replacing methyl 1-(4-((3-(azido(phenyl)methyl)phenoxy)methyl)phenyl)cyclopropanecarboxylate.

Step 3; 5-(1,3-Dioxolan-2-yl)pentyl 2-(3-(((tert-butoxycarbonyl)amino)-(phenyl)methyl)phenoxy)acetate

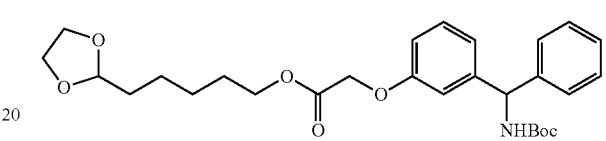

The title compound was prepared as described in Example 54 Step 1 with -(3-(((tert-Butoxycarbonyl)amino)(phenyl)methyl)phenoxy)acetic acid and 2-(5-bromopentyl)-1,3-dioxolane 4-((3-(azido(phenyl)methyl)phenoxy)methyl)benzoic acid and 2-(3-chloropropyl)-1,3-dioxolane respectively.

Step 4. 6-((R)-2-hydroxy-2-(8-hydroxy-2-oxo-1,2-dihydroquinolin-5-yl)ethylamino)hexyl 2-(3-(phenyl(((R)-quinuclidin-3-yloxy)carbonylamino)-methyl)phenoxy)acetate (compound 40B)

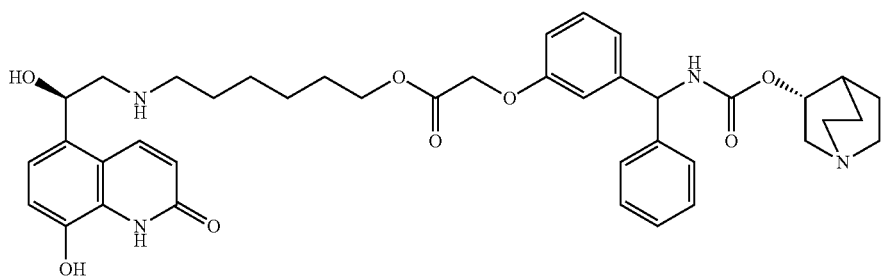 [SMILES: O=C(COc1cccc(C(NC(=O)O[C@H]2CN3CCC2CC3)c2ccccc2)c1)OCCCCCCNC[C@H](O)c1ccc(O)c2[nH]c(=O)ccc12]

The title compound was prepared as described in Example 53 Step 3 and Step 4 with 5-(1,3-dioxolan-2-yl)pentyl 2-(3-(((tert-butoxycarbonyl)amino)(phenyl)-methyl)phenoxy)acetate replacing tert-butyl((3-((4'-((1,3-dioxolan-2-yl)methyl)-[1,1'-biphenyl]-3-yl)methoxy)phenyl)(phenyl)methyl)carbamate in Step 3, and the product used in the subsequent steps.

The following compounds were prepared using the appropriate alkylating agent in Example 59 Step 1 and the appropriate coupling partner replacing 2-(5-bromopentyl)-1,3-dioxolane in Example 59 Step 3:

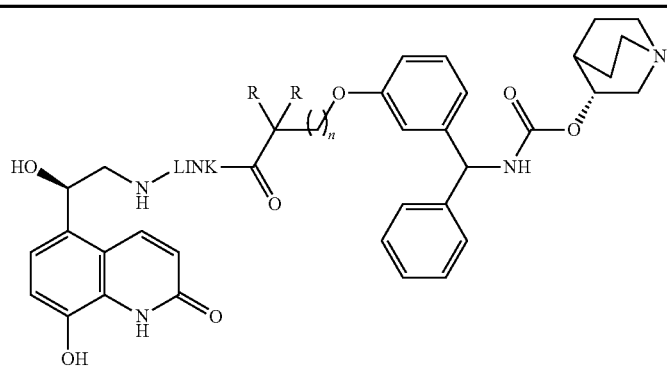
| Compound | LINK | Coupling partner | Alkylating agent | n | R |
|---|---|---|---|---|---|
| 9C | pentyl | | | 0 | H |
| 10C | butyl | | | 0 | H |
| 11C | pentyl | | | 0 | Me |
| 12C | butyl | | | 0 | Me |
| 13C | pentyl | | | 1 | Me |
| 14C | | | | 0 | H |
| 15C | | | | 0 | H |
The coupling partner for Compound 14C was prepared from 1-(tert-butoxycarbonyl)piperidine-4-carboxylic acid and 2-(3-bromopropyl)-1,3-dioxolane using standard alkylation conditions detailed in Example 1 Step 1.

Example 60

(R)-Quinuclidin-3-yl((3-((9-(((R)-2-hydroxy-2-(8-hydroxy-2-oxo-1,2-dihydroquinolin-5-yl)ethyl)amino)nonyl)oxy)-4-methylphenyl)(phenyl)methyl)carbamate (Compound 16C)

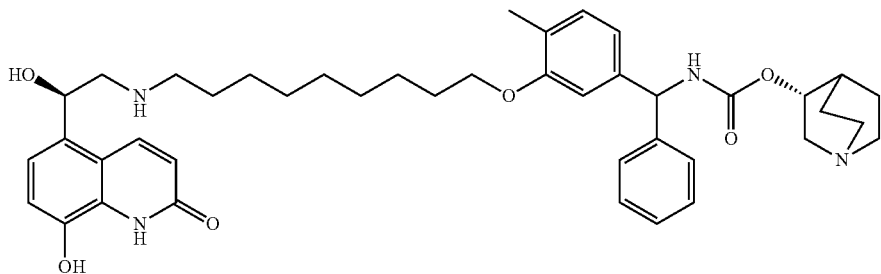 [SMILES: Cc1ccc(C(NC(=O)O[C@H]2CN3CCC2CC3)c2ccccc2)cc1OCCCCCCCCCNC[C@H](O)c1ccc(O)c2[nH]c(=O)ccc12]

The title compound was prepared as described in Example 35.

Example 61

(R)-Quinuclidin-3-yl((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate (Compound 17C)

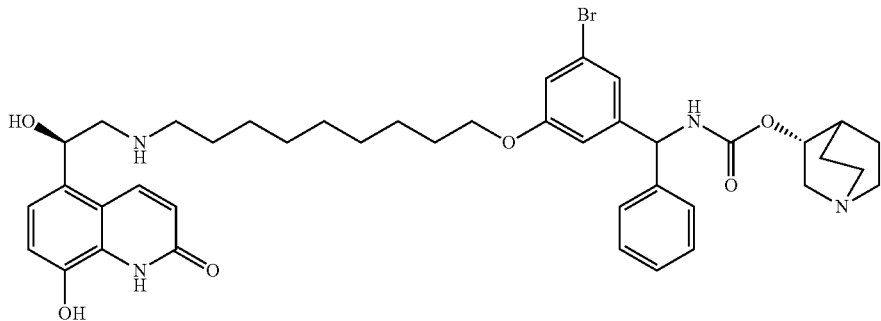 [SMILES: O=C(NC(c1ccccc1)c1cc(Br)cc(OCCCCCCCCCNC[C@H](O)c2ccc(O)c3[nH]c(=O)ccc23)c1)O[C@H]1CN2CCC1CC2]

The title compound was prepared as described in Example 28.

Example 62

(R)-Quinuclidin-3-yl((5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)methyl)-carbamate (Compound 18C)

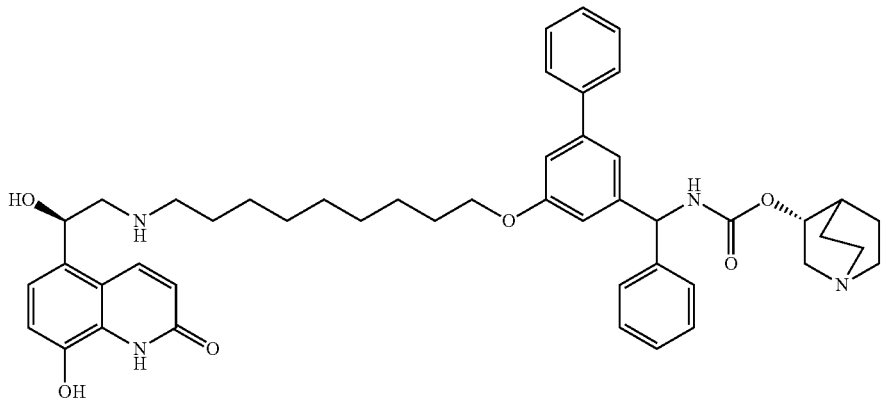 [SMILES: O=C(NC(c1ccccc1)c1cc(OCCCCCCCCCNC[C@H](O)c2ccc(O)c3[nH]c(=O)ccc23)cc(-c2ccccc2)c1)O[C@H]1CN2CCC1CC2]

The title compound was prepared as described in Example 40.

Example 63

(R)-Quinuclidin-3-yl((2-bromo-3-((9-(((R)-2-hydroxy-2-(8-hydroxy-2-oxo-1,2-dihydroquinolin-5-yl)ethyl)amino)nonyl)oxy)phenyl)(phenyl)methyl)carbamate (Compound 19C)

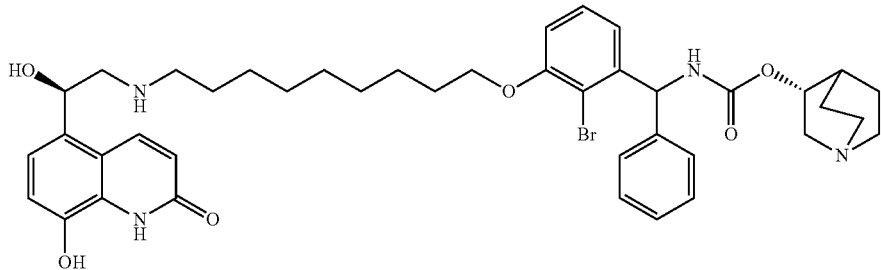 [SMILES: O=C(NC(c1ccccc1)c1cccc(OCCCCCCCCCNC[C@H](O)c2ccc(O)c3[nH]c(=O)ccc23)c1Br)O[C@H]1CN2CCC1CC2]

The title compound was prepared as described in Example 29 with 2-bromo-3-hydroxybenzaldehyde used in Step 1.

Example 64

(R)-Quinuclidin-3-yl((3'-fluoro-5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)-methyl)carbamate (Compound 20C)

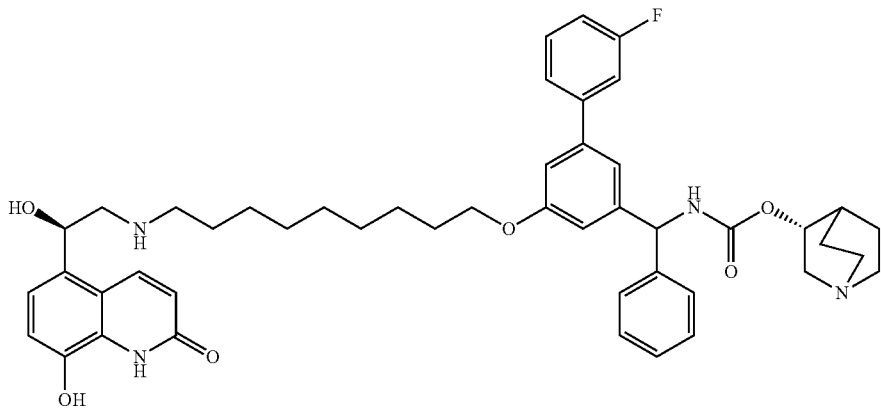 [SMILES: O=C(NC(c1ccccc1)c1cc(OCCCCCCCCCNC[C@H](O)c2ccc(O)c3[nH]c(=O)ccc23)cc(-c2cccc(F)c2)c1)O[C@H]1CN2CCC1CC2]

The title compound was prepared as described in Example 40 with 3-fluorophenylboronic acid replacing phenyl boronic acid in Step 1.

Example 65

(R)-Quinuclidin-3-yl((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamate (Compound 21C)

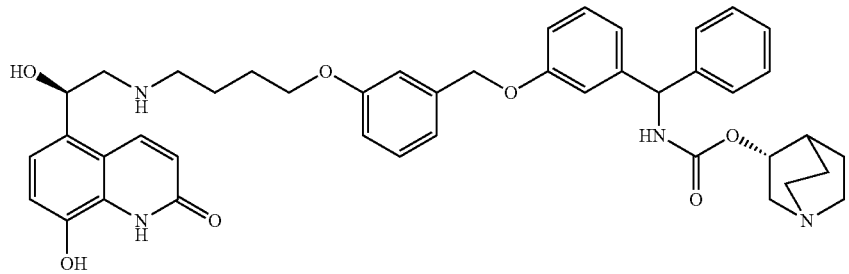 [SMILES: O=C(NC(c1ccccc1)c1cccc(OCc2cccc(OCCCCNC[C@H](O)c3ccc(O)c4[nH]c(=O)ccc34)c2)c1)O[C@H]1CN2CCC1CC2]

The title compound was prepared as described in Example 42 Step 2

Example 66

(R)-Quinuclidin-3-yl((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)-carbamate (Compound 22C)

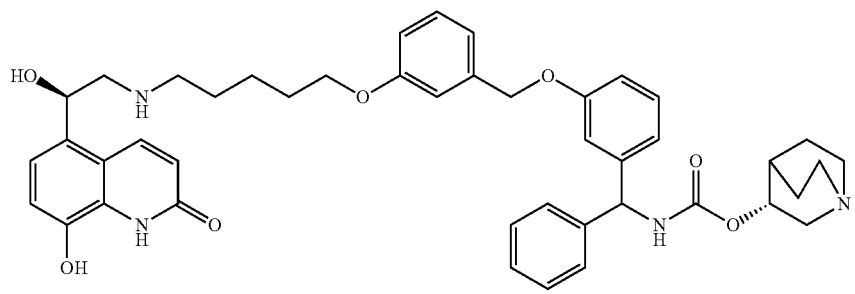 [SMILES: O=C(NC(c1ccccc1)c1cccc(OCc2cccc(OCCCCCNC[C@H](O)c3ccc(O)c4[nH]c(=O)ccc34)c2)c1)O[C@H]1CN2CCC1CC2]

The title compound was prepared as described in Example 44.

Example 67

(3R)-3-((((Cyclohexyl(3-((9-(((R)-2-hydroxy-2-(8-hydroxy-2-oxo-1,2-dihydroquinolin-5-yl)ethyl)amino)nonyl)oxy)phenyl)methyl)carbamoyl)oxy)-1-(2-oxo-2-phenylethyl)quinuclidin-1-ium (Compound 23C)

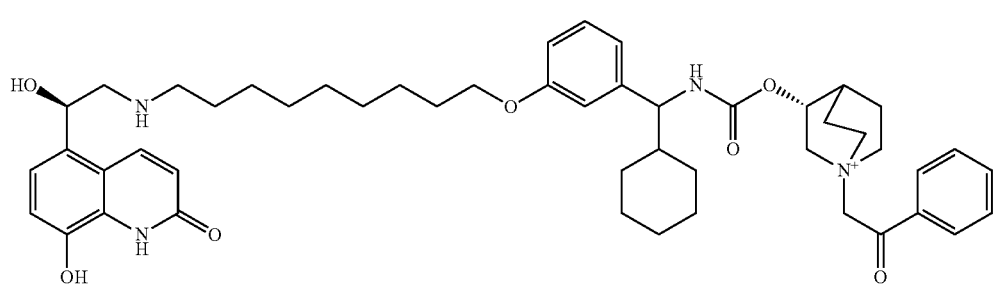 [SMILES: O=C(NC(c1cccc(OCCCCCCCCCNC[C@H](O)c2ccc(O)c3[nH]c(=O)ccc23)c1)C1CCCCC1)O[C@H]1C[N+]2(CC(=O)c3ccccc3)CCC1CC2]

The title compound was prepared as described in Example 24 with Compound 1C replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 68

(3R)-3-((((3-((6-(((R)-2-Hydroxy-2-(8-hydroxy-2-oxo-1,2-dihydroquinolin-5-yl)ethyl)amino)hexyl)oxy)phenyl)(thiophen-2-yl)methyl)carbamoyl)oxy)-1-(2-oxo-2-phenylethyl)quinuclidin-1-ium (Compound 24C)

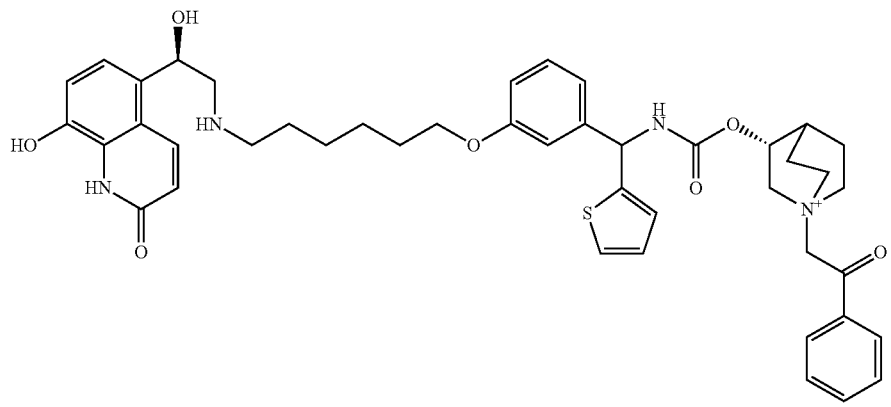 [SMILES: O=C(NC(c1cccc(OCCCCCCNC[C@H](O)c2ccc(O)c3[nH]c(=O)ccc23)c1)c1cccs1)O[C@H]1C[N+]2(CC(=O)c3ccccc3)CCC1CC2]

The title compound was prepared as described in Example 24 with Compound 2C replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 69

(3R)-3-((((3-Fluorophenyl)(3-((6-(((R)-2-hydroxy-2-(8-hydroxy-2-oxo-1,2-dihydroquinolin-5-yl)ethyl)amino)hexyl)oxy)phenyl)methyl)carbamoyl)oxy)-1-(2-oxo-2-phenylethyl)quinuclidin-1-ium (Compound 25C)

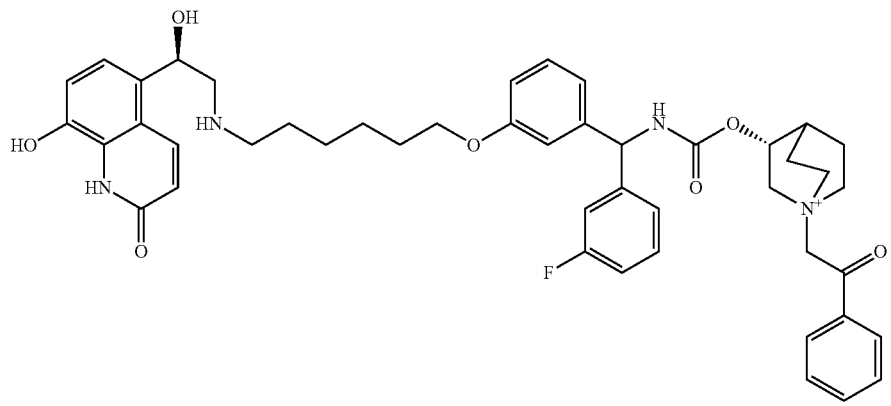 [SMILES: O=C(NC(c1cccc(F)c1)c1cccc(OCCCCCCNC[C@H](O)c2ccc(O)c3[nH]c(=O)ccc23)c1)O[C@H]1C[N+]2(CC(=O)c3ccccc3)CCC1CC2]

The title compound was prepared as described in Example 24 with Compound 24B replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 70

(3R)-3-((((3-((6-(((R)-2-Hydroxy-2-(8-hydroxy-2-oxo-1,2-dihydroquinolin-5-yl)ethyl)amino)hexyl)oxy)phenyl)(thiophen-3-yl)methyl)carbamoyl)oxy)-1-(2-oxo-2-phenylethyl)quinuclidin-1-ium (Compound 26C)

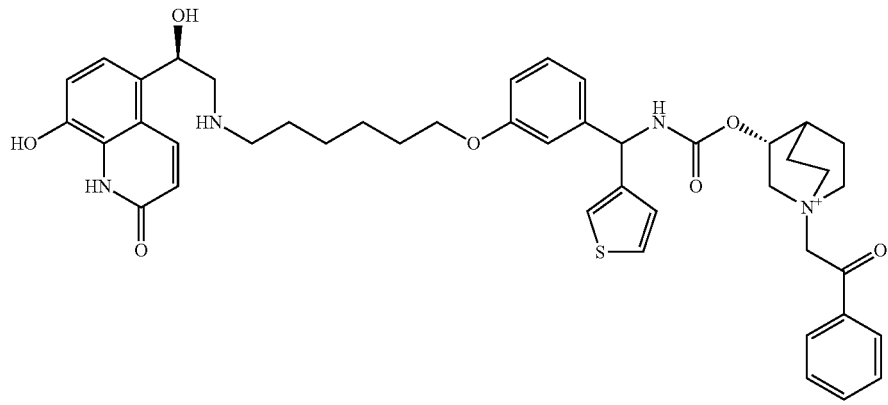 [SMILES: O=C(NC(c1ccsc1)c1cccc(OCCCCCCNC[C@H](O)c2ccc(O)c3[nH]c(=O)ccc23)c1)O[C@H]1C[N+]2(CC(=O)c3ccccc3)CCC1CC2]

The title compound was prepared as described in Example 24 with Compound 3C replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 71

(3R)-3-((((3-((4-((4-(((R)-2-Hydroxy-2-(8-hydroxy-2-oxo-1,2-dihydroquinolin-5-yl)ethyl)amino)butyl)carbamoyl)benzyl)oxy)phenyl)(phenyl)methyl)-carbamoyl)oxy)-1-(2-oxo-2-phenylethyl)quinuclidin-1-ium (Compound 27C)

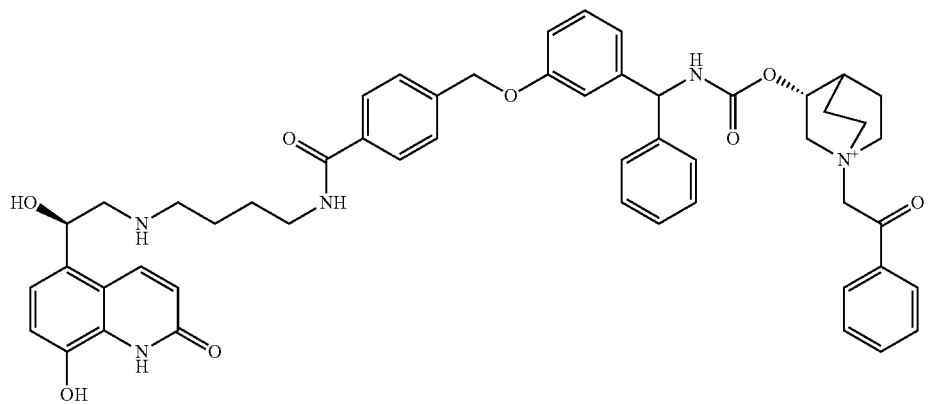 [SMILES: O=C(NC(c1ccccc1)c1cccc(OCc2ccc(C(=O)NCCCCNC[C@H](O)c3ccc(O)c4[nH]c(=O)ccc34)cc2)c1)O[C@H]1C[N+]2(CC(=O)c3ccccc3)CCC1CC2]

The title compound was prepared as described in Example 24 with Compound 31B replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 72

(3R)-3-((((3-((7-(((R)-2-Hydroxy-2-(8-hydroxy-2-oxo-1,2-dihydroquinolin-5-yl)ethyl)amino)heptyl)oxy)phenyl)(phenyl)methyl)carbamoyl)oxy)-1-(2-oxo-2-phenylethyl)quinuclidin-1-ium (Compound 28C)

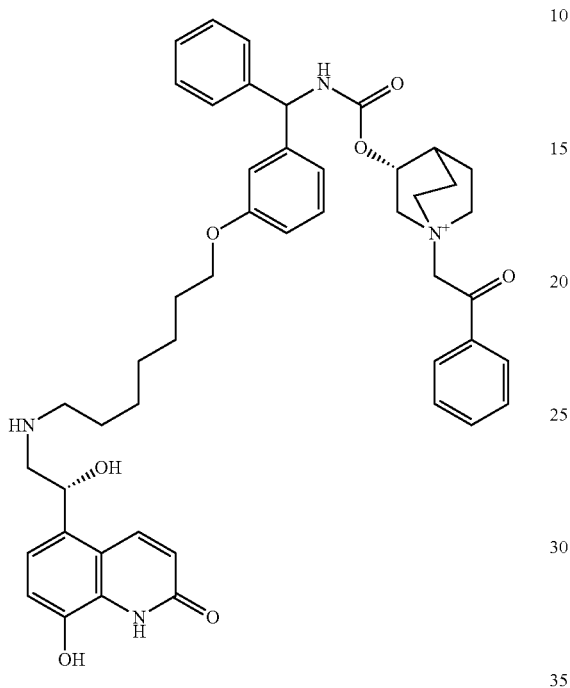

The title compound was prepared as described in Example 24 with Compound 3 replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 73

(3R)-3-((((3-((7-(((R)-2-Hydroxy-2-(8-hydroxy-2-oxo-1,2-dihydroquinolin-5-yl)ethyl)amino)heptyl)oxy)phenyl)(phenyl)methyl)carbamoyl)oxy)-1-(3-phenylpropyl)quinuclidin-1-ium (Compound 29C)

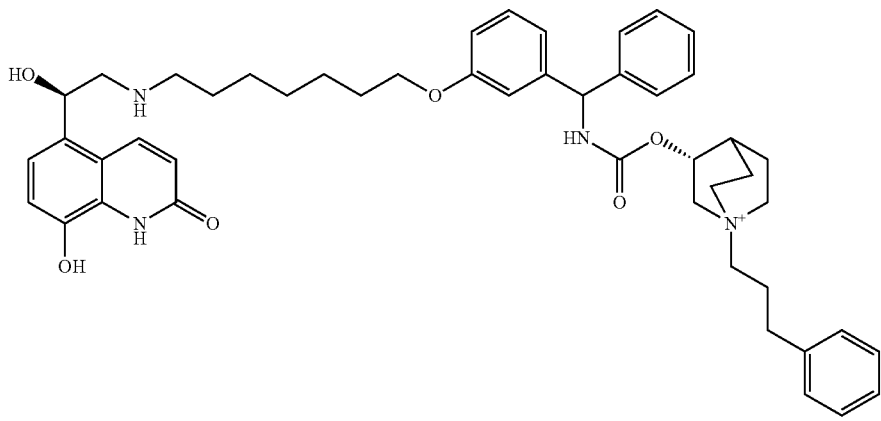 [SMILES: O=C(NC(c1ccccc1)c1cccc(OCCCCCCCNC[C@H](O)c2ccc(O)c3[nH]c(=O)ccc23)c1)O[C@H]1C[N+]2(CCCc3ccccc3)CCC1CC2]

The title compound was prepared as described in Example 24 with Compound 3 replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate, and (3-bromopropyl)benzene replacing bromoacetophenone.

Example 74

(3R)-3-(((((3-((5-(((R)-2-Hydroxy-2-(8-hydroxy-2-oxo-1,2-dihydroquinolin-5-yl)ethyl)amino)pentyl)oxy)phenyl)(phenyl)methylcarbamoyl)oxy)-1-(2-oxo-2-phenylethyl)quinuclidin-1-ium (Compound 30C)

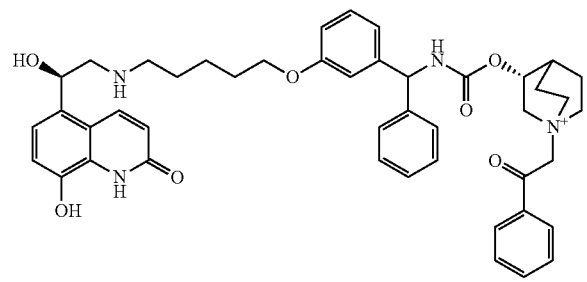 [SMILES: O=C(NC(c1ccccc1)c1cccc(OCCCCCNC[C@H](O)c2ccc(O)c3[nH]c(=O)ccc23)c1)O[C@H]1C[N+]2(CC(=O)c3ccccc3)CCC1CC2]

The title compound was prepared as described in Example 24 with Compound 5 replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Example 75

4-(((R)-2-Hydroxy-2-(8-hydroxy-2-oxo-1,2-dihydroquinolin-5-yl)ethyl)amino)butyl 1-(4-((3-(phenyl((((R)-quinuclidin-3-yloxy)carbonyl)amino)-methyl)phenoxy)methyl)phenyl)cyclopentanecarboxylate (Compound 31C)

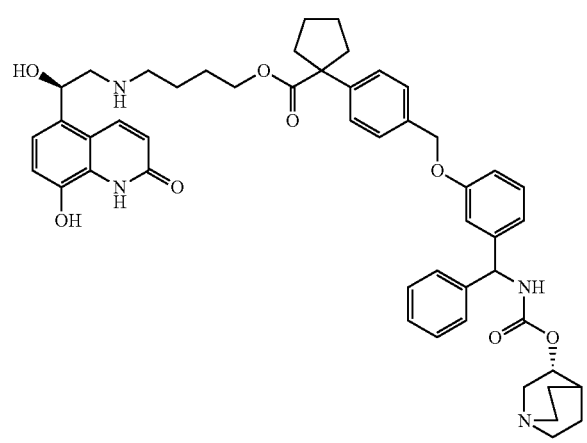 [SMILES: O=C(NC(c1ccccc1)c1cccc(OCc2ccc(C3(C(=O)OCCCCNC[C@H](O)c4ccc(O)c5[nH]c(=O)ccc45)CCCC3)cc2)c1)O[C@H]1CN2CCC1CC2]

The title compound was prepared as described in Example 56 Step 1 through Step 7 with 1-(p-tolyl)cyclopentanecarboxylic acid replacing 1-(p-tolyl)cyclopropanecarboxylic acid in Step 1.

Example 76

4-(((R)-2-Hydroxy-2-(8-hydroxy-2-oxo-1,2-dihydroquinolin-5-yl)ethyl)amino)butyl 1-(4-((3-(phenyl((((R)-quinuclidin-3-yloxy)carbonyl)amino)-methyl)phenoxy)methyl)phenyl)cyclohexanecarboxylate (Compound 32C)

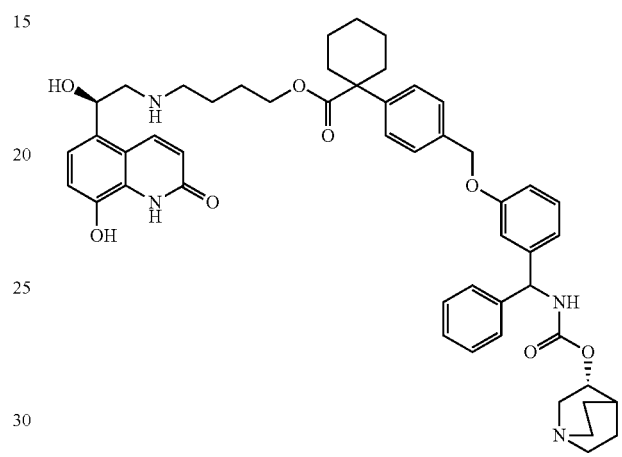

The title compound was prepared as described in Example 56 Step 1 through Step 7 with 1-(p-tolyl)cyclohexanecarboxylic acid replacing 1-(p-tolyl)cyclopropanecarboxylic acid in Step 1.

Example 77

4-(((R)-2-Hydroxy-2-(8-hydroxy-2-oxo-1,2-dihydroquinolin-5-yl)ethyl)amino)butyl 2-methyl-2-(4-((3-(phenyl((((R)-quinuclidin-3-yloxy)carbonyl)amino)methyl)phenoxy)methyl)phenyl)propanoate (Compound 33C)

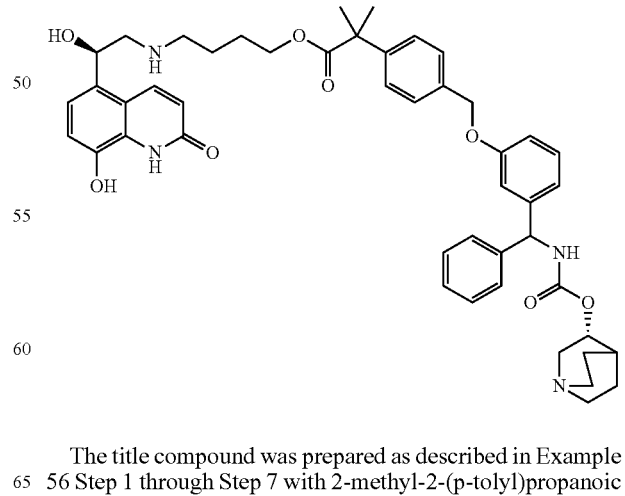

The title compound was prepared as described in Example 56 Step 1 through Step 7 with 2-methyl-2-(p-tolyl)propanoic acid replacing 1-(p-tolyl)cyclopropanecarboxylic acid in Step 1.

Synthesis of Benzoic Acid Derivatives:

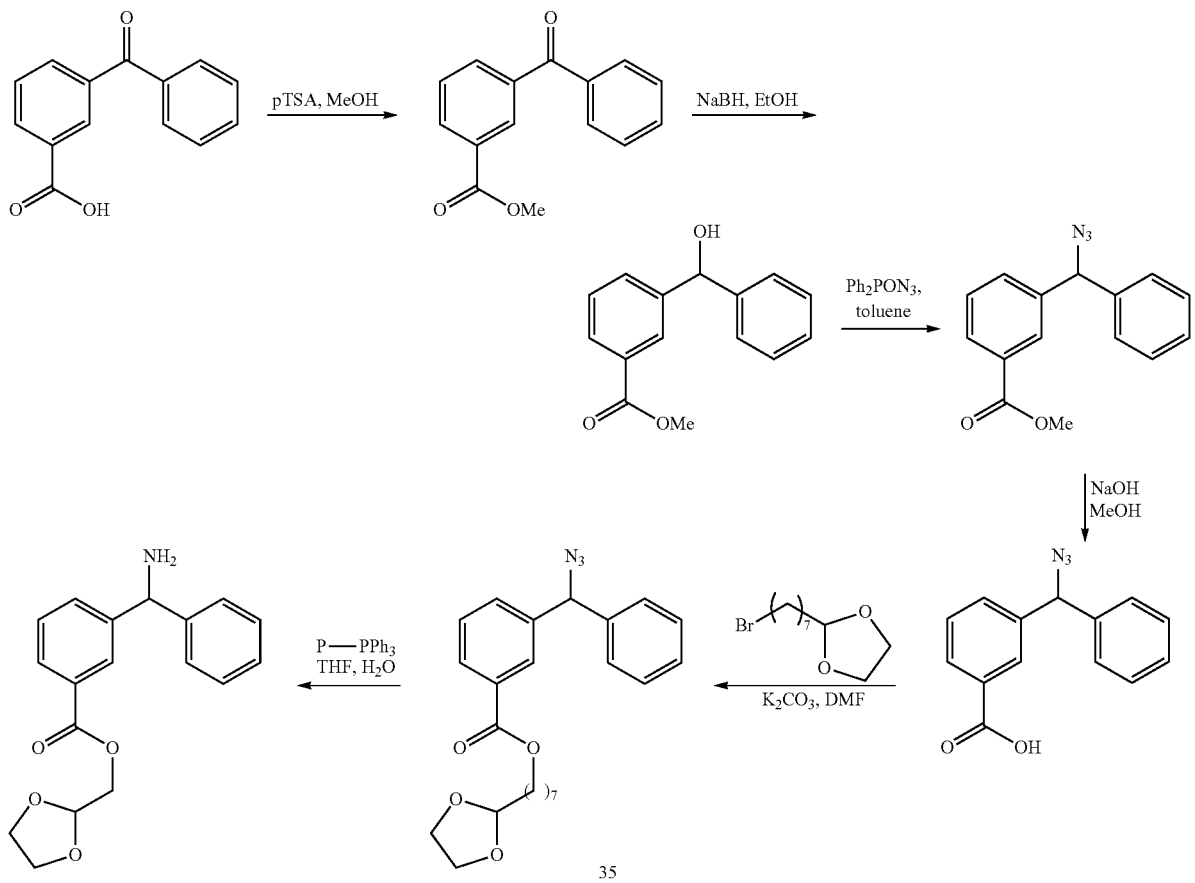

Example 78

8-(((R)-2-hydroxy-2-(8-hydroxy-2-oxo-1,2-dihydro-quinolin-5-yl)ethyl)amino)octyl 3-(phenyl((((R)-quinuclidin-3-yloxy)carbonyl)amino)methyl)-benzoate (Compound 34C)

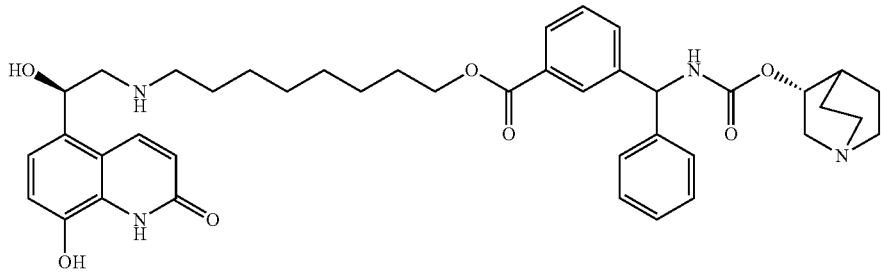 [SMILES: O=C(NC(c1ccccc1)c1cccc(C(=O)OCCCCCCCCNC[C@H](O)c2ccc(O)c3[nH]c(=O)ccc23)c1)O[C@H]1CN2CCC1CC2]

Step 1. Methyl 3-benzoylbenzoate

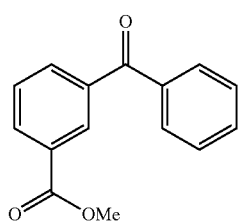 [SMILES: COC(=O)c1cccc(C(=O)c2ccccc2)c1]

A stirred solution of 3-benzoylbenzoic acid (10.0 g, 44.4 mmol) and p-TSA (0.85 g, 4.39 mmol) in methanol (200 mL) was heated at 75° C. for 18 hours. The reaction mixture was allowed to cool, and the solvent evaporated at reduced pressure. The residue was partitioned between ethyl acetate and saturated aqueous sodium hydrogen carbonate. The organic phase was dried with anhydrous sodium sulfate, filtered, and the filtrate was evaporated at reduced pressure to afford the title compound (9.55 g, 90%).

$^1$H NMR (400 MHz, CDCl$_3$): δ 8.44 (s, 1H); 8.27 (m, 1H); 8.01 (m, 1H); 7.86 (m 2H); 7.61 (m, 2H); 7.50 (m, 2H); 3.94 (s, 3H).

Step 2. Methyl 3-(hydroxy(phenyl)methyl)benzoate

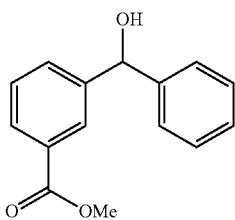 [SMILES: COC(=O)c1cccc(C(O)c2ccccc2)c1]

The title compound was prepared as described in Example 1 Step 2 with methyl 3-benzoylbenzoate replacing (3-(8-(1,3-dioxolan-2-yl)octyloxy)phenyl)(phenyl)methanone.

¹H NMR (400 MHz, CDCl₃): δ 8.07 (s, 1H); 7.90 (m, 2H); 7.58 (m, 1H); 7.40-7.21 (m, 6H); 5.87 (s, 1H); 3.88 (s, 3H); 2.46 (s, 1H).

Step 3. Methyl 3-(azido(phenyl)methyl)benzoate

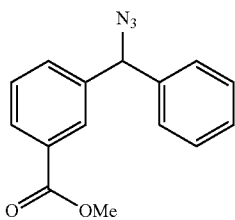 [SMILES: COC(=O)c1cccc(C(N=[N+]=[N-])c2ccccc2)c1]

The title compound was prepared as described in Example 1 Step 3 with methyl 3-(hydroxy(phenyl)methyl)benzoate replacing (3-(8-(1,3-dioxolan-2-yl)octyloxy)phenyl)-(phenyl)methanol.

¹H NMR (400 MHz, CDCl₃): δ 8.09 (s, 1H); 7.99 (m, 1H); 7.50-7.20 (m, 7H); 5.75 (s, 1H); 3.93 (s, 3H).

Step 4; 3-(Azido(phenyl)methyl)benzoic acid

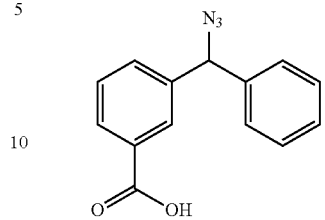

The title compound was prepared as described in Example 56 Step 6 with methyl 3-(azido(phenyl)methyl)benzoate replacing methyl 1-(4-((3-(azido(phenyl)methyl)-phenoxy)methyl)phenyl)cyclopropanecarboxylate.

¹H NMR (400 MHz, CDCl₃): δ 8.15 (s, 1H); 8.00 (m, 1H); 7.56 (m, 1H); 7.47 (m, 1H), 7.40-7.20 (m, 5H); 5.72 (s, 1H).

Step 5. 7-(1,3-Dioxolan-2-yl)heptyl 3-(azido(phenyl)methyl)benzoate

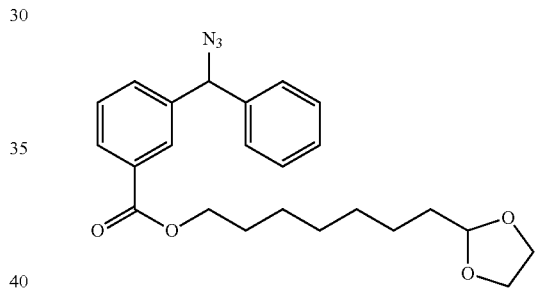

The title compound was prepared as described in Example 54 Step 1 with 3-(7-bromoheptyl)-1,3-dioxolane and 3-(azido(phenyl)methyl)benzoic acid replacing 2-(3-chloropropyl)-1,3-dioxolane and 4-((3-(azido(phenyl)methyl)phenoxy)methyl)benzoic acid, respectively.

Step 6; 8-(((R)-2-hydroxy-2-(8-hydroxy-2-oxo-1,2-dihydroquinolin-5-yl)ethyl)amino)octyl 3-(phenyl ((((R)-quinuclidin-3-yloxy)carbonyl)amino)methyl)-benzoate (Compound 34C)

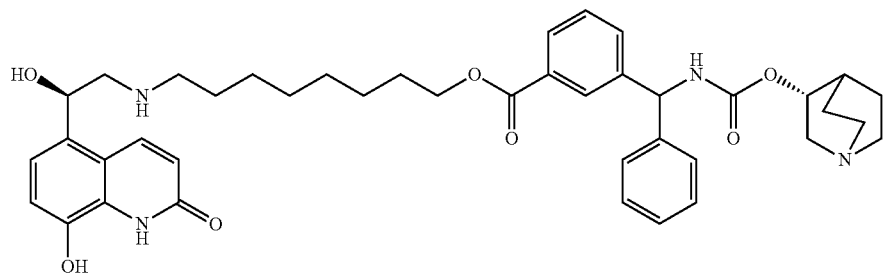 [SMILES: O=C(NC(c1ccccc1)c1cccc(C(=O)OCCCCCCCCNC[C@H](O)c2ccc(O)c3[nH]c(=O)ccc23)c1)O[C@H]1CN2CCC1CC2]

The title compound was prepared as described in Example 54 Step 2.

The following compounds were prepared using the appropriate alkylating agent in Example 78 Step 5 and using the products in the subsequent steps. Alcohol based alkylating agents were coupled using the conditions described in Example 22 Step 2 with the appropriate alcohol replacing (4-((1,3-dioxolan-2-yl)methyl)phenyl)methanol. Amine based alkylating agents were coupled using the conditions described in Example 51 Step 4 with the appropriate amine replacing 4-amino-butyraldehyde diethyl ether.

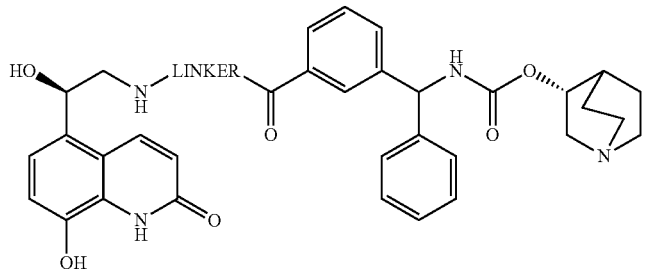

| Compound | Linker | Alkylating agent |
|---|---|---|
| 35C | | |
| 36C | | |
| 37C | | |
| 38C | | |
| 39C | | |
| 40C | | |
| 41C | | |

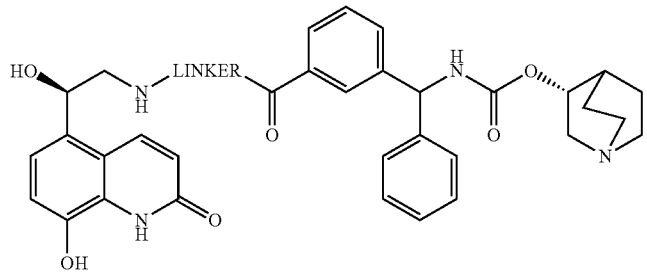

| Compound | Linker | Alkylating agent |
|---|---|---|
| 42C | 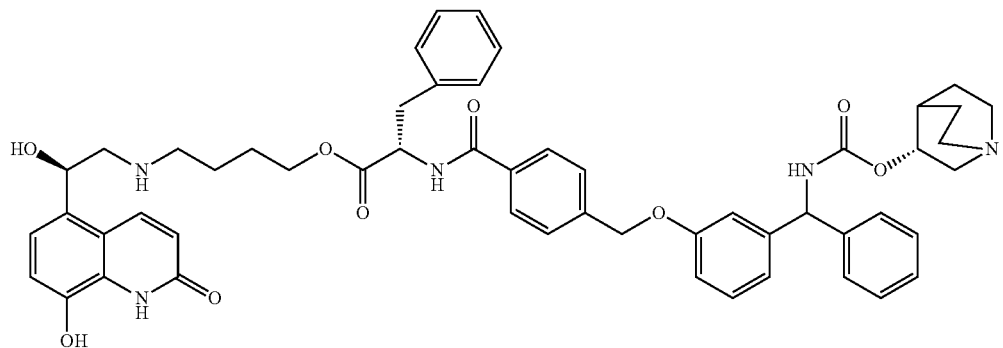 | |

Example 79

(2S)-4-(((R)-2-hydroxy-2-(8-hydroxy-2-oxo-1,2-dihydroquinolin-5-yl)ethyl)amino)butyl 3-phenyl-2-(4-((3-(phenyl((((R)-quinuclidin-3-yloxy)carbonyl)-amino)methyl)phenoxy)methyl)benzamido)propanoate (Compound 43C)

Step 1. Step 1;
N-((3-hydroxyphenyl)(phenyl)methyl)formamide

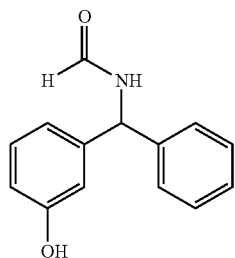 [SMILES: O=CNC(c1ccccc1)c1cccc(O)c1]

3-Hydroxybenzophenone (25 g, 126.1 mmol) in formamide (130 mL, 3.3 mmol) was heated to 180° C. for 18 hours. The reaction was allowed to cool slightly then poured into ice-cooled water and stirred for 30 minutes, filtered, and washed with water. The solid was stirred in water (60 mL) and ethanol (60 mL) and heated to 50° C. for 1 hour, then allowed to cool. The solid was filtered and washed with water to give the title compound (33.94 g, 118%).

$^1$H NMR (400 MHz, CD$_3$OD): δ 7.39-7.28 (m, 5H); 7.21-7.13 (m, 1H); 6.79 (d, J=7.78 Hz, 1H); 6.73-6.68 (m, 2H); 5.45 (s, 1H).

Step 2. 3-(Amino(phenyl)methyl)phenol hydrochloride

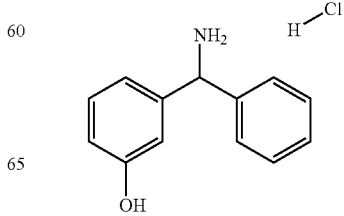

Methanol (125 mL), was cooled to 0° C., and acetyl chloride (17.8 mL) added dropwise to give a 2M solution of methanolic hydrogen chloride. N-((3-hydroxyphenyl)-(phenyl)methyl)formamide was stirred at 40° C. for 1.5 hours with the 2M methanolic hydrogen chloride. The solvent was removed under reduced pressure and the residue re-dissolved in methanol and the solvent removed under reduced pressure. This process was repeated three times to give the title compound (29.09 g, 97.9%).

$^1$H NMR (400 MHz, DMSO-d$_6$): δ 9.76 (s, 1H); 9.07 (s, 3H); 7.59-7.53 (m, 2H); 7.51-7.37 (m, 3H); 7.26 (t, J=7.89 Hz, 1H); 6.99 (d, J=7.75 Hz, 1H); 6.90 (t, J=1.97 Hz, 1H); 6.81 (dd, J=8.10, 2.32 Hz, 1H); 5.58 (d, J=5.82 Hz, 1H).

Step 3.
tert-Butyl(3-hydroxyphenyl)(phenyl)methylcarbamate

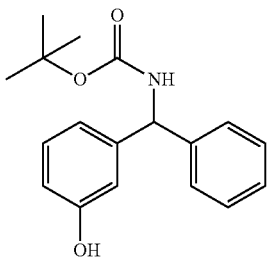 [SMILES: CC(C)(C)OC(=O)NC(c1ccccc1)c1cccc(O)c1]

3-(Amino(phenyl)methyl)phenol hydrochloride (29.09 g, 123.4 mmol) in dichloromethane (450 mL) was cooled to 0° C., and diisopropylethylamine (65.9 mL, 370.2 mmol) and di-tert-butyl dicarbonate (59.2 g, 271.5 mmol) were added slowly. The reaction was stirred at 0° C. for 2 hours then warmed to room temperature over 16 hours. The solvent was removed and compound purified through a silica plug, eluting with 0-20% ethyl acetate in iso-hexane to give a black oil. To this mixture in methanol (300 mL), was added potassium carbonate (51 g, 370.2 mmol), and the mixture was stirred at room temperature for 16 hours. The suspension was filtered, and the filtrate was evaporated at reduced pressure, and the residue re-dissolved in ethyl acetate (370 mL). Silica (73 g) was added, and the suspension was stirred for 30 minutes, filtered, and the filter cake washed with further ethyl acetate. The filtrate was evaporated to dryness. The dark solid residue was dissolved in ethyl acetate (200 mL), charcoal was added, and the suspension was heated under refluxed for 1 hour. The suspension was filtered through celite and solvent removed at reduced pressure. The dark solid was dissolved in dichloromethane and iso-hexane added then solvent evaporated (repeated 3 times) to give the title compound (34.81 g, 92%).

$^1$H NMR (400 MHz, CDCl$_3$): δ 7.36-7.16 (m, 6H); 6.80 (d, J=7.79 Hz, 1H); 6.74-6.69 (m, 2H); 5.83 (s, 1H); 5.15 (s, 1H); 1.53-1.30 (s, 9H).

Step 4. Methyl 4-((3-(((tert-butoxycarbonyl)amino)(phenyl)methyl)phenoxy)-methyl)benzoate

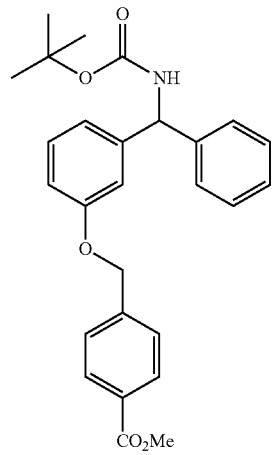 [SMILES: COC(=O)c1ccc(COc2cccc(C(NC(=O)OC(C)(C)C)c3ccccc3)c2)cc1]

A mixture of tert-butyl(3-hydroxyphenyl)(phenyl)methylcarbamate (3.20 g, 10.7 mmol), methyl 4-(bromomethyl)benzoate (2.70 g, 11.8 mmol), and potassium carbonate (2.20 g, 16.1 mmol) in acetonitrile (54 mL) was stirred at room temperature for 16 hours. The reaction mixture was concentrated at reduced pressure, and the residue partitioned between ethyl acetate and water. The aqueous phase was extracted with further ethyl acetate, and the combined organic extracts combined, dried with anhydrous magnesium sulfate, filtered and the solvent evaporated at reduced pressure. The residue was re-crystallised from ethyl acetate and iso-hexane to afford the title compound (3.25 g, 68%).

$^1$H NMR (400 MHz, CDCl$_3$): δ 8.04 (d, J=8.2 Hz, 2H); 7.46 (d, J=8.2 Hz, 2H); 7.34-7.20 (m, 6H); 6.90-6.81 (m, 3H); 5.87 (s, 1H); 5.13 (s, 1H); 5.07 (s, 2H); 3.92 (s, 3H); 1.44 (s, 9H).

Step 5. Methyl 4-((3-(amino(phenyl)methyl)phenoxy)methyl)benzoate hydrochloride

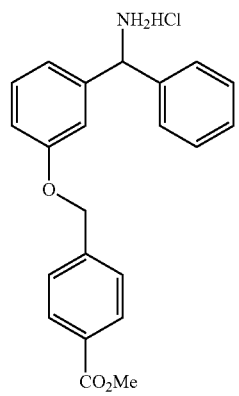

To a solution of methyl 4-((3-(((tert-butoxycarbonyl)amino)(phenyl)methyl)-phenoxy)methyl)benzoate (3.21 g, 7.20 mmol) in methanol (36 mL), was added hydrogen chloride in dioxan (4 M, 9.0 mL, 36 mmol). The reaction mixture was stirred at room temperature for 16 hours. The solvent was removed at reduced pressure to afford the title compound (2.65 g, >95%).

$^1$H NMR (400 MHz, CDCl$_3$): δ 9.21 (s, 2H); 8.03 (d, J=8.1 Hz, 2H); 7.64 (d, J=8.1 Hz, 2H); 7.59 (d, J=7.6 Hz, 2H); 7.49-7.34 (m, 5H); 7.17 (d, J=7.7 Hz, 1H); 7.06 (dd, J=8.3, 2.4 Hz, 1H); 5.64 (s, 1H); 5.28 (s, 2H); 3.91 (s, 3H).

Step 6. Methyl 4-((3-(phenyl((((R)-quinuclidin-3-yloxy)carbonyl)amino)methyl)-phenoxy)methyl)benzoate

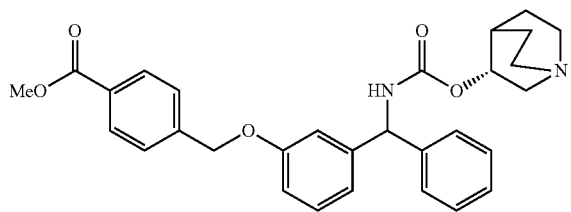 [SMILES: COC(=O)c1ccc(COc2cccc(C(NC(=O)O[C@H]3CN4CCC3CC4)c3ccccc3)c2)cc1]

The title compound was prepared as in Example 1 Step 5 with methyl 4-((3-(amino(phenyl)methyl)phenoxy)methyl)benzoate hydrochloride replacing (3-(8-(1,3-dioxolan-2-yl)octyloxy)phenyl)(phenyl)methanamine.

Step 7. 4-((3-(Phenyl((((R)-quinuclidin-3-yloxy)carbonyl)amino)methyl)phenoxy)-methyl)benzoic acid

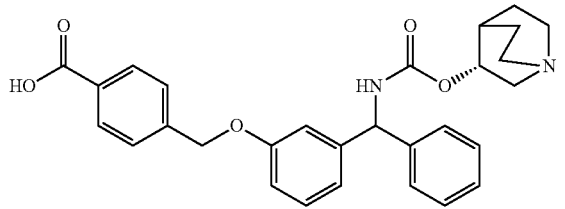 [SMILES: O=C(NC(c1ccccc1)c1cccc(OCc2ccc(C(=O)O)cc2)c1)O[C@H]1CN2CCC1CC2]

To a stirred solution of methyl 4-((3-(phenyl((((R)-quinuclidin-3-yloxy)carbonyl)amino)methyl)phenoxy)methyl)benzoate (2.27 g, 4.50 mmol) in THF (23 mL), was added an aqueous solution of lithium hydroxide (2.0 M, 9.0 ml, 18.0 mmol). The mixture was stirred at room temperature for 16 hours. The pH of the reaction mixture was adjusted to 6 by the addition of 4M aqueous hydrochloric acid. The mixture was then extracted with 10% methanolic ethyl acetate (×2), and the combined organic extracts evaporated at reduced pressure. The residue was then dissolved in ethanol and re-evaporated at reduced pressure to afford the title compound (1.85 g, 84%).

$^1$H NMR (400 MHz, DMSO-d$_6$): δ 8.41 (d, J=9.4 Hz, 1H); 7.99 (d, J=7.9 Hz, 2H); 7.58 (d, J=8.0 Hz, 2H); 7.42-7.26 (m, 6H); 7.09 (s, 1H); 7.02-6.91 (m, 2H); 5.87 (d, J=9 Hz, 1H); 5.21 (s, 2H); 4.76 (s, 1H); 3.98-2.72 (m, 6H); 2.12-1.54 (m, 5H).

Step 8. (S)-3-(1,3-Dioxolan-2-yl)propyl 2-amino-3-phenylpropanoate

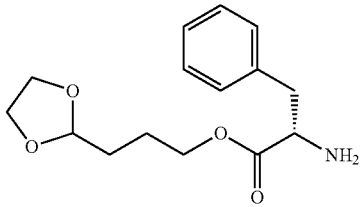 [SMILES: N[C@@H](Cc1ccccc1)C(=O)OCCCC1OCCO1]

The title compound was prepared in two steps. Boc-Phe-OH was reacted with 2-(3-chloropropyl)-1,3-dioxolane according to Example 10 Step 1, and the subsequent product reacted with hydrogen chloride in dioxan according to Example 79 Step 5.

Step 9. 2S)-4-(((R)-2-hydroxy-2-(8-hydroxy-2-oxo-1,2-dihydroquinolin-5-yl)ethyl)-amino)butyl 3-phenyl-2-(4-((3-(phenyl((((R)-quinuclidin-3-yloxy)carbonyl)amino)-methyl)phenoxy)methyl)benzamido)propanoate (Compound 43C)

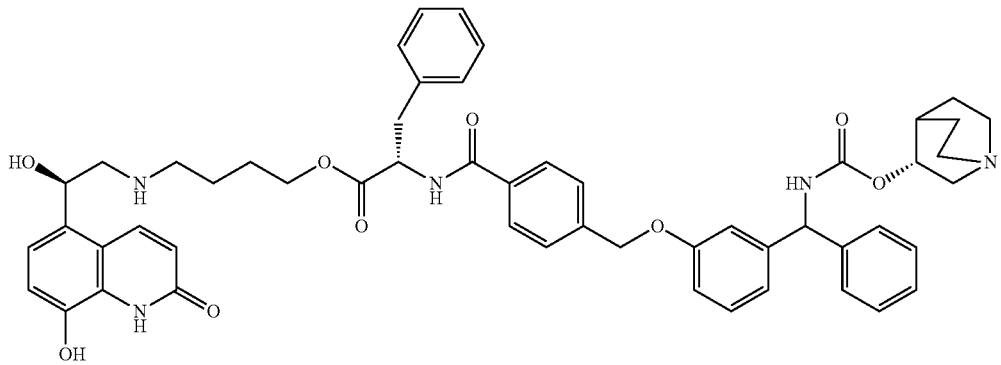 [SMILES: O=C(NC(c1ccccc1)c1cccc(OCc2ccc(C(=O)N[C@@H](Cc3ccccc3)C(=O)OCCCCNC[C@H](O)c3ccc(O)c4[nH]c(=O)ccc34)cc2)c1)O[C@H]1CN2CCC1CC2]

The title compound was prepared in three steps. The product from Example 79 Step 7 was coupled to the product from Example 79 Step 8 using the method described in Example 51 Step 4. The subsequent product was then used in the methods of Example 1 Step 6 followed by Example 1 Step 7.

Example 80

(R)-Quinuclidin-3-yl((3-((3-(4-(2-(((R)-2-hydroxy-2-(8-hydroxy-2-oxo-1,2-dihydroquinolin-5-yl)ethyl)amino)ethyl)phenyl)-1,2,4-oxadiazol-5-yl)methoxy)phenyl)(phenyl)methyl)carbamate (Compound 44C)

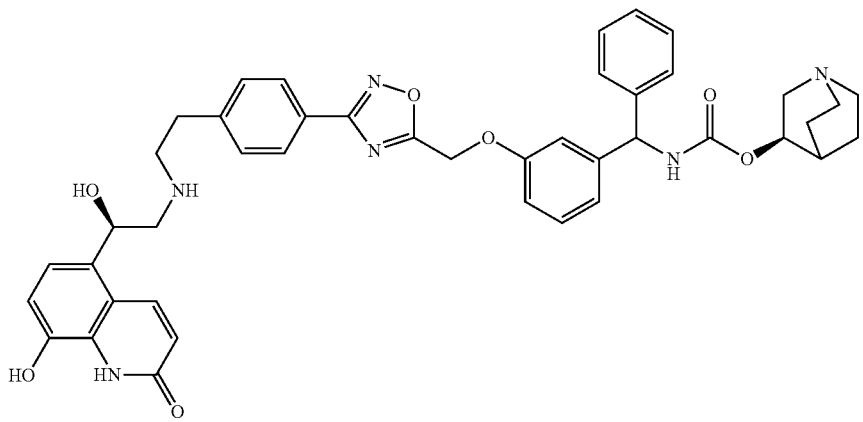 [SMILES: O=C(NC(c1ccccc1)c1cccc(OCc2nc(-c3ccc(CCNC[C@H](O)c4ccc(O)c5[nH]c(=O)ccc45)cc3)no2)c1)O[C@H]1CN2CCC1CC2]

Step 1. 4-((1,3-Dioxolan-2-yl)methyl)benzonitrile

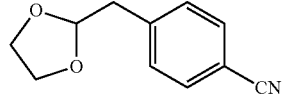 [SMILES: N#Cc1ccc(CC2OCCO2)cc1]

To a stirred solution of 4-(2-hydroxyethyl)benzonitrile (1.09 g, 7.41 mmol) in DCM (20 mL), was added Dess-Martin Periodinane (3.77 g, 8.84 mmol), and the reaction mixture stirred at room temperature for 1 hour. A 1:1 mixture of saturated aqueous sodium hydrogen carbonate and saturated sodium thiosulfate was added, and the bi-phasic mixture stirred for 1 hour. The organic phase was separated, and the aqueous phase extracted with further DCM (×3). The combined organic extracts were dried with anhydrous magnesium sulphate, and the solvent evaporated at reduced pressure. The crude material was dissolved in toluene (40 mL) and ethylene glycol (2.29 g, 37.05 mmol), and p-toluenesulfonic acid (0.14 g, 0.74 mmol) added. The mixture was heated under Dean and Stark conditions for 2 hours. The solvent was evaporated under reduced pressure, and the residue partitioned between saturated aqueous sodium hydrogen carbonate and ethyl acetate. The organic phase was removed, and the aqueous phase was extracted with further ethyl acetate (×3). The combined organic phases were dried with anhydrous magnesium sulphate, and the solvent evaporated at reduced pressure to afford the title compound (1.40 g, 99%).

$^1$H NMR (400 MHz, CDCl$_3$): δ 7.69-7.53 (m, 2H); 7.48-7.34 (m, 2H); 5.08 (t, J=4.5 Hz, 1H); 3.94-3.81 (m, 4H); 3.03 (t, J=4.5 Hz, 2H).

Step 2. 4-((1,3-Dioxolan-2-yl)methyl)-N'-hydroxybenzimidamide

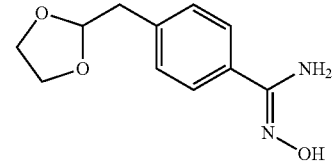 [SMILES: N/C(=N\O)c1ccc(CC2OCCO2)cc1]

To a solution of 4-((1,3-dioxolan-2-yl)methyl)benzonitrile (1.40 g, 7.41 mmol) in ethanol (10 mL), was added 50% aqueous hydroxylamine (5 mL), and the resultant mixture was heated at 80° C. for 16 hours. The solvent was evaporated at reduced pressure, and the residue partitioned between ethyl acetate and brine. The organic phase was removed, and the aqueous phase was extracted with further ethyl acetate (×2). The combined organic extracts were dried with aqueous magnesium sulfate and evaporated at reduced pressure to afford the title compound (1.21 g, 73%).

$^1$H NMR (400 MHz, DMSO-d$_6$): δ 9.57 (s, 1H); 7.62-7.49 (m, 2H); 7.34-7.23 (m, 2H); 5.76 (s, 2H); 5.03-4.90 (m, 1H); 3.95-3.66 (m, 4H); 2.91 (dd, J=16.6, 4.9 Hz, 2H).

171

Step 3. tert-butyl((3-((3-(4-((1,3-Dioxolan-2-yl)methyl)phenyl)-1,2,4-oxadiazol-5-yl)methoxy)phenyl)(phenyl)methyl)carbamate

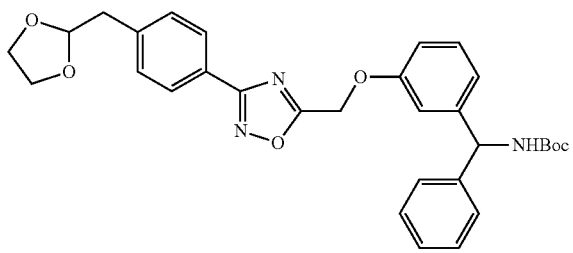 [SMILES: CC(C)(C)OC(=O)NC(c1ccccc1)c1cccc(OCc2nc(-c3ccc(CC4OCCO4)cc3)no2)c1]

To a stirred solution of 4-((1,3-dioxolan-2-yl)methyl)-N'-hydroxybenzimidamide (0.747 g, 3.35 mmol) and 2-(3-(((tert-butoxycarbonyl)amino)(phenyl)methyl)phenoxy)-acetic acid (Example 59 Step 2, 1.0 g, 2.79 mmol)) in acetonitrile (5 mL), was added 1-ethyl-3-(3-dimethylaminopropyl)carbodiimide hydrochloride (0.8 g, 4.18 mmol). The reaction mixture was stirred at ambient temperature for 16 hours. The reaction mixture was diluted with pyridine (1 mL) and heated at 150° C. for 30 minutes in a microwave. The reaction was diluted with saturated brine and extracted with ethyl acetate (×3). The combined organic fractions were dried with magnesium sulphate, and the solvent evaporated at reduced pressure. Material used directly in the next step without further purification (1.01 g, 65%).

$^1$H NMR (400 MHz, CDCl$_3$): δ 8.04-7.96 (m, 2H); 7.45-7.37 (m, 2H); 6.96-6.88 (m, 3H); 5.88 (s, 1H); 5.29 (s, 2H); 5.19-5.07 (m, 2H); 3.98-3.80 (m, 4H); 3.03 (d, J=4.6 Hz, 2H); 1.44 (s, 9H).

172

Step 4. (3-((3-(4-(2,2-dimethoxyethyl)phenyl)-1,2,4-oxadiazol-5-yl)methoxy)phenyl)-(phenyl)methanamine

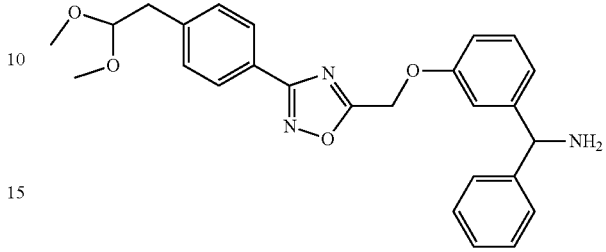

Hydrogen chloride in dioxan (4.0 M, 5 mL, 24 mmol) was added to a solution of tert-butyl((3-((3-(4-((1,3-dioxolan-2-yl)methyl)phenyl)-1,2,4-oxadiazol-5-yl)methoxy)phenyl)(phenyl)methyl)carbamate (1.01 g, 1.85 mmol) in methanol (5 mL), and the resultant solution was stirred at ambient temperature for 2 hours. The solvent was evaporated at reduced pressure, and the residue was loaded onto an SCX-2 cartridge. The cartridge was eluted with methanol (eight column volumes) followed by ammonia/methanol. Fractions containing the product were combined and evaporated at reduced pressure to afford the title compound (0.796 g, 96%).

$^1$H NMR (400 MHz, CDCl$_3$): δ 8.02 (d, J=8.0 Hz, 2H); 7.42-7.15 (m, 8H); 7.12-7.01 (m, 2H); 6.88 (dd, J=8.2, 2.7 Hz, 1H); 5.34-5.27 (m, 2H); 5.19 (s, 1H); 4.60-4.54 (m, 1H); 3.38-3.31 (m, 6H); 2.98 (d, J=5.6 Hz, 2H).

Step 5. (R)-quinuclidin-3-yl((3-((3-(4-(2-(((R)-2-hydroxy-2-(8-hydroxy-2-oxo-1,2-dihydroquinolin-5-yl)ethyl)amino)ethyl)phenyl)-1,2,4-oxadiazol-5-yl)methoxy)phenyl)-(phenyl)methyl)carbamate (Compound 44C)

The title compound was prepared as described in Example 1 Step 5, 6 and 7.

Example 81

(R)-Quinuclidin-3-yl((5-((9-(((R)-2-hydroxy-2-(8-hydroxy-2-oxo-1,2-dihydroquinolin-5-yl)ethyl)amino)nonyl)oxy)pyridin-3-yl)(phenyl)methyl)carbamate (Compound 45C)

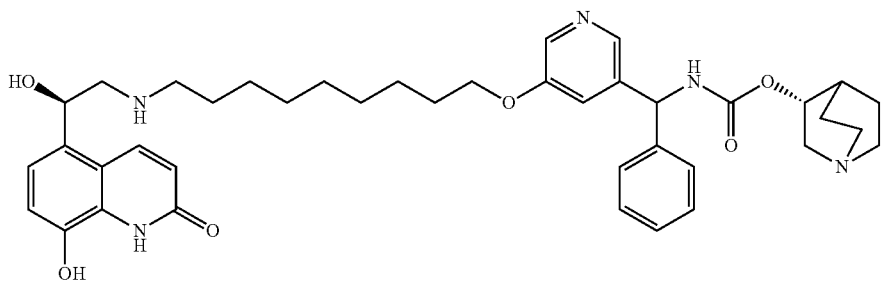 [SMILES: O=C(NC(c1ccccc1)c1cncc(OCCCCCCCCCNC[C@H](O)c2ccc(O)c3[nH]c(=O)ccc23)c1)O[C@H]1CN2CCC1CC2]

The title compound was prepared as described in Example 10 with 5-hydroxy-nicotinaldehyde replacing 3-hydroxybenzaldehyde in Step 1 and phenyl magnesium bromide replacing 2-thienylmagnesium bromide in Step 2.

Example 82

(R)-Quinuclidin-3-yl((3-fluorophenyl)(5-((9-(((R)-2-hydroxy-2-(8-hydroxy-2-oxo-1,2-dihydroquinolin-5-yl)ethyl)amino)nonyl)oxy)pyridin-3-yl)methyl)-carbamate (Compound 46C)

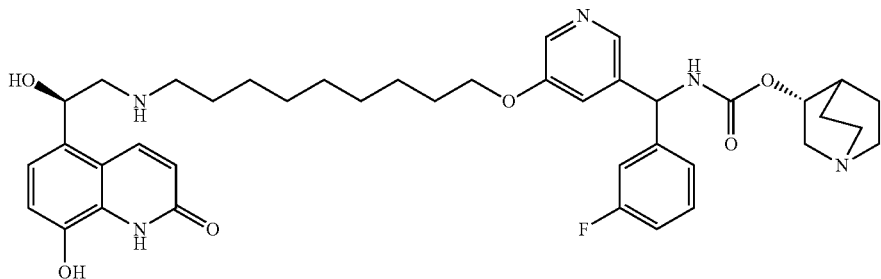 [SMILES: O=C(NC(c1cccc(F)c1)c1cncc(OCCCCCCCCCNC[C@H](O)c2ccc(O)c3[nH]c(=O)ccc23)c1)O[C@H]1CN2CCC1CC2]

The title compound was prepared as described in Example 10 with 5-hydroxy-nicotinaldehyde replacing 3-hydroxybenzaldehyde in Step 1, and 3-fluorophenyl magnesium bromide replacing 2-thienylmagnesium bromide in Step 2.

Synthesis of Single Diastereoisomers

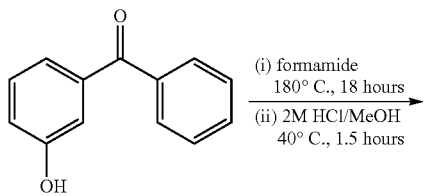

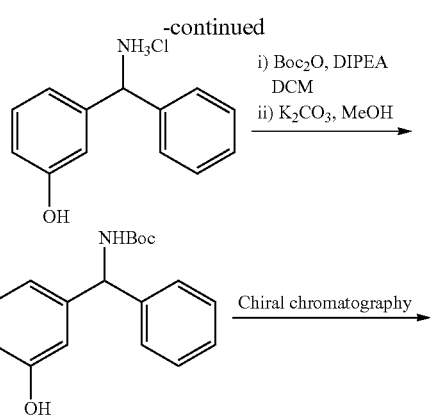

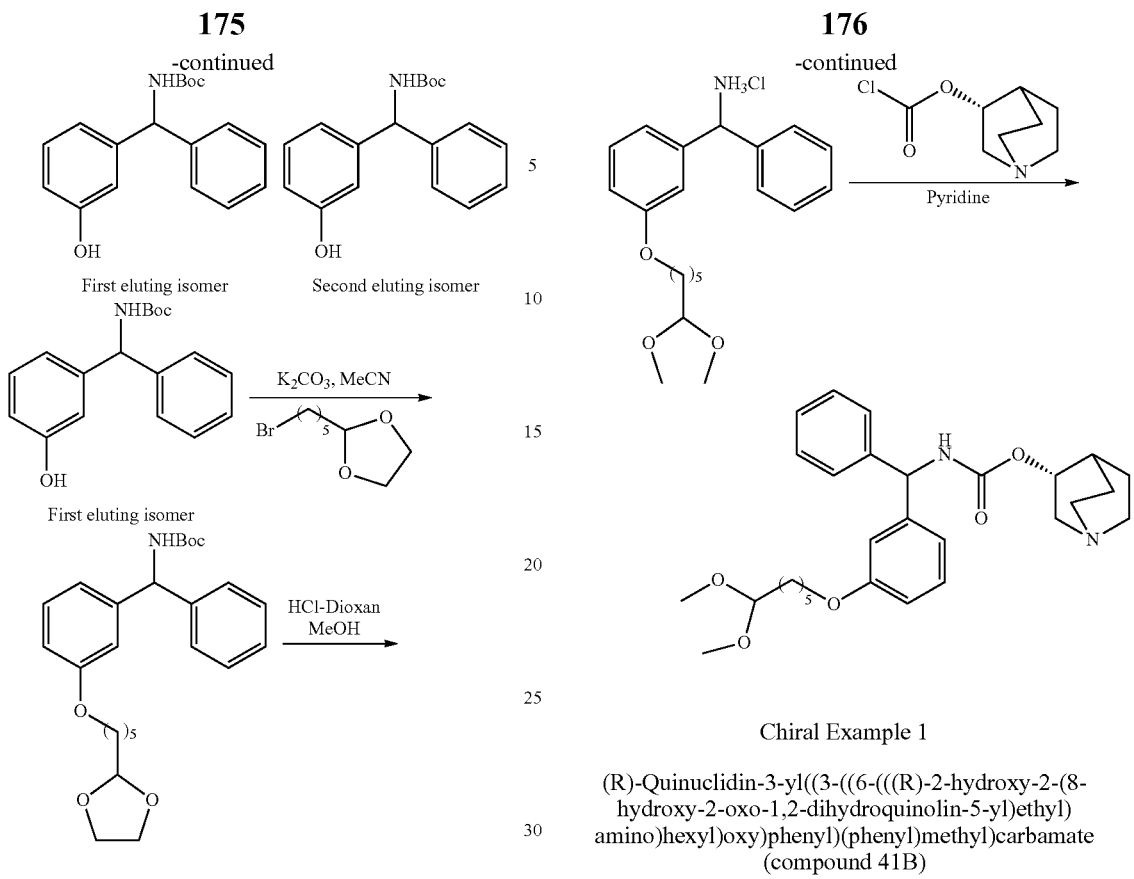
Chiral Example 1
(R)-Quinuclidin-3-yl((3-(((6-(((R)-2-hydroxy-2-(8-hydroxy-2-oxo-1,2-dihydroquinolin-5-yl)ethyl)amino)hexyl)oxy)phenyl)(phenyl)methyl)carbamate (compound 41B)
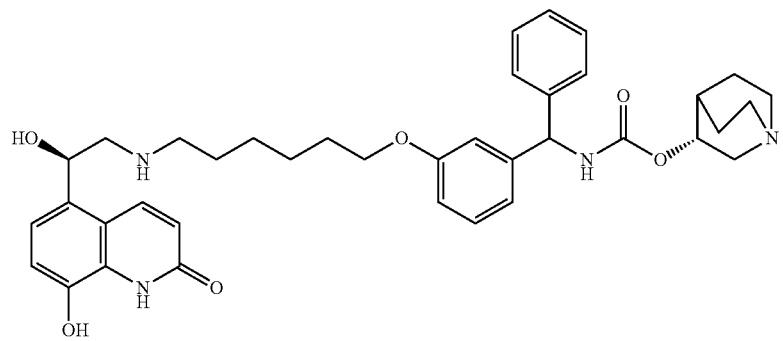 [SMILES: O=C(NC(c1ccccc1)c1cccc(OCCCCCCNC[C@H](O)c2ccc(O)c3[nH]c(=O)ccc23)c1)O[C@H]1CN2CCC1CC2]
Step 1.
N-((3-hydroxyphenyl)(phenyl)methyl)formamide
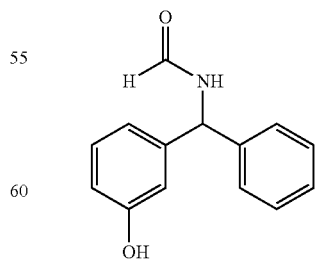
3-Hydroxybenzophenone (25 g, 126.1 mmol) in formamide (130 mL, 3.3 mmol) was heated to 180° C. for 18 hours. The reaction was allowed to cool slightly, then poured into ice-cooled water and stirred for 30 minutes, filtered, and washed with water. The solid was stirred in water (60 mL) and ethanol (60 mL) and heated to 50° C. for 1 hour, then allowed to cool. The solid was filtered and washed with water to give the title compound (33.94 g, 118%).

$^1$H NMR (400 MHz, CH$_{30}$H-d$_4$): δ 7.39-7.28 (m, 5H); 7.21-7.13 (m, 1H); 6.79 (d, J=7.78 Hz, 1H); 6.73-6.68 (m, 2H); 5.45 (s, 1H).

Step 2. 3-(Amino(phenyl)methyl)phenol hydrochloride

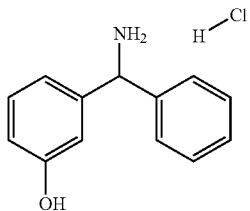

Methanol (125 mL), was cooled to 0° C., and acetyl chloride (17.8 mL) added dropwise to give a 2M solution of methanolic hydrogen chloride. N-((3-hydroxyphenyl)-(phenyl)methyl)formamide was stirred at 40° C. for 1.5 hours with the 2M methanolic hydrogen chloride. The solvent was removed under reduced pressure, and the residue re-dissolved in methanol and the solvent removed under reduced pressure. This process was repeated three times to give the title compound (29.09 g, 97.9%)

$^1$H NMR (400 MHz, DMSO-d$_6$): δ 9.76 (s, 1H); 9.07 (s, 3H); 7.59-7.53 (m, 2H); 7.51-7.37 (m, 3H); 7.26 (t, J=7.89 Hz, 1H); 6.99 (d, J=7.75 Hz, 1H); 6.90 (t, J=1.97 Hz, 1H); 6.81 (dd, J=8.10, 2.32 Hz, 1H); 5.58 (d, J=5.82 Hz, 1H).

Step 2a. Synthesis of enantiomerically pure 3-(Amino(phenyl)methyl)phenol Mandelate (fast eluting enantiomer)

3-(Amino(phenyl)methyl)phenol (878 g, 4.4 mol) was dissolved in 17.5 l of iPrOH and heated to reflux. To the mixture, a solution of R-mandelic acid (737 g, 4.8 mol) in 1760 ml of iPrOH was dropped. The mixture was refluxed for 1 hour and then allowed to cool to 10° C. (overnight). The precipitate was filtered, washed with cold iPrOH, and dried in vacuum oven at 35° C. The collected salt was refluxed in 95% iPrOH for 1 hour, then slowly cooled to 70° C. (beginning of crystallization), and stirred at constant temperature for 5 hours. The mixture was allowed to cool down to 10° C. overnight. The solid was filtered, washed with cold iPrOH, and dried in vacuum oven at 35° C.

Chiral analyses were made for free amine (the salt treated with sodium hydrogen carbonate, extracted with AcOEt and the organic layer concentrated).
Chiralpak IC, 4.6 mm×250 mm—(A) Ethanol+0.1% TEA (B) Hexane+0.1% TEA flow: 1 ml/min (10% A; 90% B) ee>99% retention time 10.58 min $^1$H NMR (600 MHz, d$_6$-DMSO) 4.65 (s, 1H), 5.34 (s, 1H), 6.70 (m, 1H, Ar), 6.82 (m, 1H, Ar), 6.86 (m, 1H, Ar), 7.12 (m, 1H, Ar), 7.18 (m, 1H, Ar), 7.23-7.29 (m, 3H, Ar), 7.33-7.38 (m, 4H, Ar), 7.42 (m, 2H, Ar).

A sample of amine was converted into the corresponding hydrochloride.
$[\alpha]_D^{20}$=−0.019° (c=4.4, MeOH)

A sample of amine was converted into the corresponding BOC derivative as described in following Step 3 and analized by chiral HPLC that confirmed identical retention time of fast eluting enantiomer BOC protected.

Step 2b. Synthesis of enantiomerically pure 3-(Amino(phenyl)methyl)phenol Mandelate (slow eluting enantiomer)

The product was prepared as described in Step 2a using S-mandelic acid. ee>99% retention time 16.37 min A sample of amine was converted into the corresponding hydrochloride.
$[\alpha]_D^{20}$=+0.019° (c=4.4, MeOH)

A sample of amine was converted into the corresponding BOC derivative as described in following Step 3 and analized by chiral HPLC that confirmed identical retention time of slow eluting enantiomer BOC protected.

Step 3. tert-Butyl(3-hydroxyphenyl)(phenyl)methylcarbamate

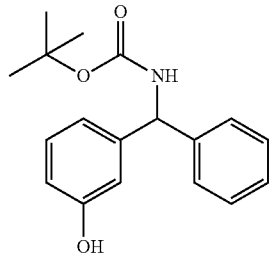 [SMILES: CC(C)(C)OC(=O)NC(c1ccccc1)c1cccc(O)c1]

3-(Amino(phenyl)methyl)phenol hydrochloride (29.09 g, 123.4 mmol) in dichloromethane (450 mL) was cooled to 0° C., and diisopropylethylamine (65.9 mL, 370.2 mmol) and di-tert-butyl dicarbonate (59.2 g, 271.5 mmol) were added slowly. The reaction was stirred at 0° C. for 2 hours and then warmed to room temperature over 16 hours. The solvent was removed, and the compound was purified through a silica plug, eluting with 0-20% ethyl acetate in iso-hexane to give a black oil. To this mixture in methanol (300 mL), was added potassium carbonate (51 g, 370.2 mmol), and the mixture was stirred at room temperature for 16 hours. The suspension was filtered, and the filtrate was evaporated at reduced pressure, and the residue re-dissolved in ethyl acetate (370 mL). Silica (73 g) was added, and the suspension was stirred for 30 minutes, filtered, and the filter cake washed with further ethyl acetate. The filtrate was evaporated to dryness. The dark solid residue was dissolved in ethyl acetate (200 m L), charcoal was added, and the suspension was heated under refluxed for 1 hour. The suspension was filtered through celite, and solvent was removed. The dark solid was dissolved in dichloromethane and iso-hexane added then solvent evaporated (repeated 3 times) to give the title compound (34.81 g, 92%).

$^1$H NMR (400 MHz, CDCl$_3$-d): δ 7.36-7.16 (m, 6H); 6.80 (d, J=7.79 Hz, 1H); 6.74-6.69 (m, 2H); 5.83 (s, 1H); 5.15 (s, 1H); 1.53-1.30 (s, 9H).

Step 4. Resolution of the Racemic Mixture into First and Second Eluting Isomers

The racemic mixture was purified by SFC using a CHIRALPAK®AD 20 μM 250×110 mm column using n-heptane/2-propanol/diethylamine (60/40/0.1) as eluant with a flow rate of 570 ml/min at 25° C. From 54.1 g of crude material, the first eluting enantiomer ($R_t$=4.5 min, 26.7 g, >99.9% e.e.) and second eluting isomer ($R_t$=8.5-8.6 min, 23.9 g, 99.2 e.e.) were separated.

Step 5. tert-Butyl((3-((5-(1,3-dioxolan-2-yl)pentyl)oxy)phenyl)(phenyl)methyl)-carbamate

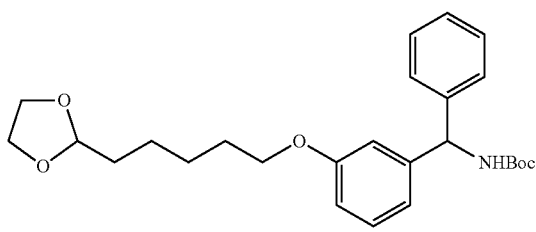 [SMILES: CC(C)(C)OC(=O)NC(c1ccccc1)c1cccc(OCCCCCC2OCCO2)c1]

Potassium carbonate (0.566 g, 4.10 mmol) was added to a solution of tert-butyl (3-hydroxyphenyl)(phenyl)methylcarbamate (derived from the first eluting isomer, 0.614 g, 2.05 mmol) in acetonitrile (6 mL). The reaction mixture was stirred at ambient temperature for 10 minutes, and 2-(5-bromopentyl)-1,3-dioxolane (0.549 g, 2.46 mmol) was added. The reaction mixture was heated at 60° C. for 20 hours. The reaction mixture was allowed to cool and diluted with water and DCM. The mixture was poured through a hydrophobic frit, and the organic phase was evaporated at reduced pressure. The crude material was purified by silica gel chromatography eluting with 100% iso-hexane to 10% ethyl acetate in iso-hexane to afford the title compound as a colourless oil (0.503 g, 56%).

$^1$H NMR (400 MHz, CDCl$_3$): δ 7.34-7.13 (m, 6H); 6.81-6.76 (m, 3H); 5.85 (br s, 1H); 5.10 (br s, 1H); 4.86 (t, J=4.8 Hz, 1H); 3.97-3.83 (m, 6H); 1.78-1.66 (m, 4H); 1.50-1.44 (m, 4H), 1.30 (s, 9H).

Step 6. (3-((6,6-Dimethoxyhexyl)oxy)phenyl)(phenyl)methanamine

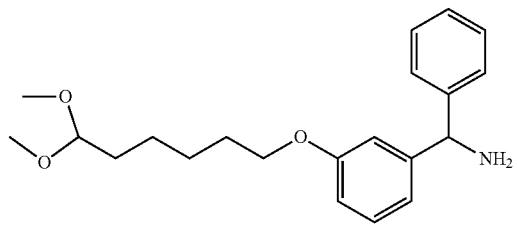 [SMILES: COC(CCCCCOc1cccc(C(N)c2ccccc2)c1)OC]

To a solution of tert-butyl((3-((5-(1,3-dioxolan-2-yl)pentyl)oxy)phenyl)(phenyl)-methyl)carbamate (0.483 g, 1.10 mmol) in methanol (4 mL), was added hydrogen chloride in dioxan (4 M, 4 mL, 16 mmol). The reaction was stirred at ambient temperature for 7 hours. The solvent was evaporated at reduced pressure, and the residue loaded onto an SCX-2 cartridge. The cartridge was eluted with methanol (eight column volumes) followed by ammonia/methanol. Fractions containing the product were combined and evaporated at reduced pressure to afford the title compound as a colourless oil (0.322 g, 85%).

$^1$H NMR (400 MHz, CDCl$_3$): δ 7.38-7.18 (m, 6H); 6.94-6.92 (m, 2H); 6.73-6.73 (m, 1H); 5.17 (s, 1H); 4.38 (t, J=5.6 Hz, 1H); 3.93 (t, J=6.4 Hz, 2H); 3.32 (s, 6H); 1.80-1.73 (m, 4H); 1.65-1.60 (m, 2H); 1.49-1.40 (m, 4H).

Step 7. (R)-quinuclidin-3-yl((3-((6-(((R)-2-hydroxy-2-(8-hydroxy-2-oxo-1,2-dihydroquinolin-5-yl)ethyl)amino)hexyl)oxy)phenyl)(phenyl)methyl)carbamate (compound 41B)

The title compound was prepared using Step 5, 6 and 7 of Example 1.

Chiral Example 2

(R)-Quinuclidin-3-yl((3-((6-(((R)-2-hydroxy-2-(8-hydroxy-2-oxo-1,2-dihydroquinolin-5-yl)ethyl)amino)hexyl)oxy)phenyl)(phenyl)methyl)carbamate (compound 42B)

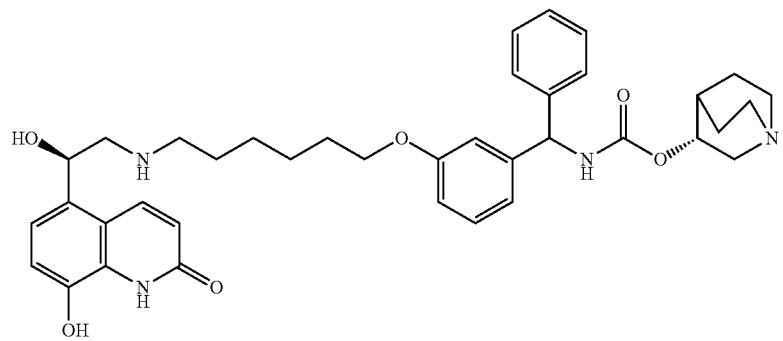 [SMILES: O=C(NC(c1ccccc1)c1cccc(OCCCCCCNC[C@H](O)c2ccc(O)c3[nH]c(=O)ccc23)c1)O[C@H]1CN2CCC1CC2]

The title compound was prepared as in Chiral Example 1 with the second eluting isomer from Step 4 used in Step 5.

Chiral Example 3

(3R)-3-((((3-((6-(((R)-2-Hydroxy-2-(8-hydroxy-2-oxo-1,2-dihydroquinolin-5-yl)ethyl)amino)hexyl)oxy)phenyl)(phenyl)methyl)carbamoyl)oxy)-1-(2-oxo-2-phenylethyl)quinuclidin-1-ium (compound 43B)

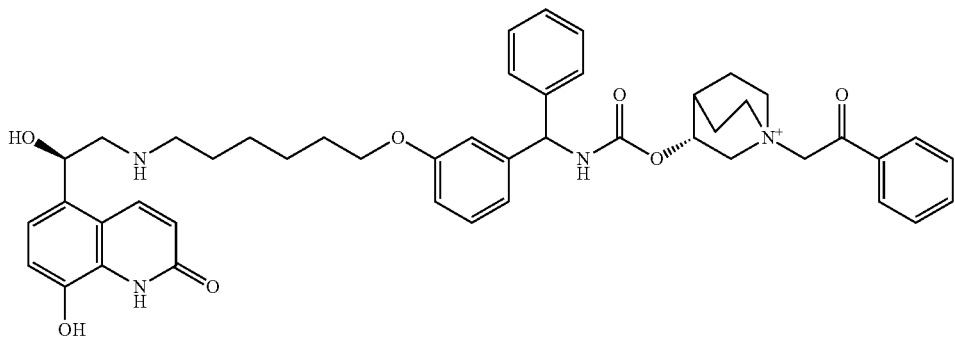 [SMILES: O=C(NC(c1ccccc1)c1cccc(OCCCCCCNC[C@H](O)c2ccc(O)c3[nH]c(=O)ccc23)c1)O[C@H]1C[N+]2(CC(=O)c3ccccc3)CCC1CC2]

The title compound was prepared as in Example 24 with Chiral Example 1 replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Chiral Example 4

(3R)-3-((((3-((6-(((R)-2-Hydroxy-2-(8-hydroxy-2-oxo-1,2-dihydroquinolin-5-yl)ethyl)amino)hexyl)oxy)phenyl)(phenyl)methyl)carbamoyl)oxy)-1-(2-oxo-2-phenylethyl)quinuclidin-1-ium (compound 44B)

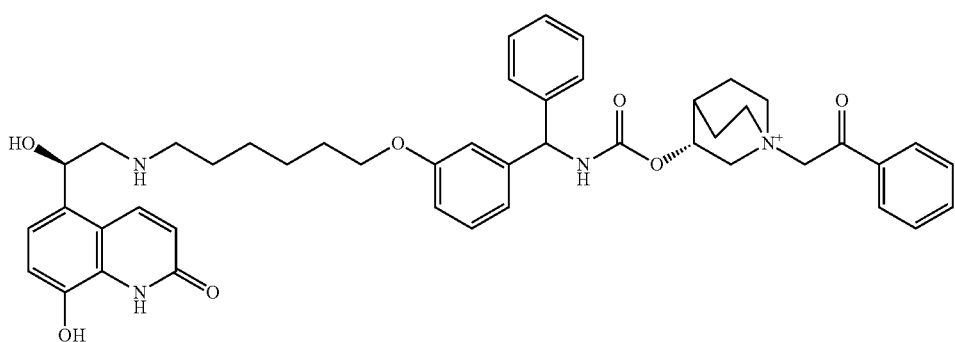 [SMILES: O=C(NC(c1ccccc1)c1cccc(OCCCCCCNC[C@H](O)c2ccc(O)c3[nH]c(=O)ccc23)c1)O[C@H]1C[N+]2(CC(=O)c3ccccc3)CCC1CC2]

The title compound was prepared as in Example 24 with Chiral Example 2 replacing (R)-quinuclidin-3-yl(3-(6-((R)-2-hydroxy-2-(8-hydroxy-2-oxo-1,2-dihydroquinolin-5-yl)ethylamino)hexyloxy)phenyl)(phenyl)methylcarbamate.

Chiral Example 5

4-(((R)-2-Hydroxy-2-(8-hydroxy-2-oxo-1,2-dihydro-quinolin-5-yl)ethyl)amino)butyl 4-((3-(phenyl((((R)-quinuclidin-3-yloxy)carbonyl)amino)-methyl)phenoxy)methyl)benzoate (compound 45B)

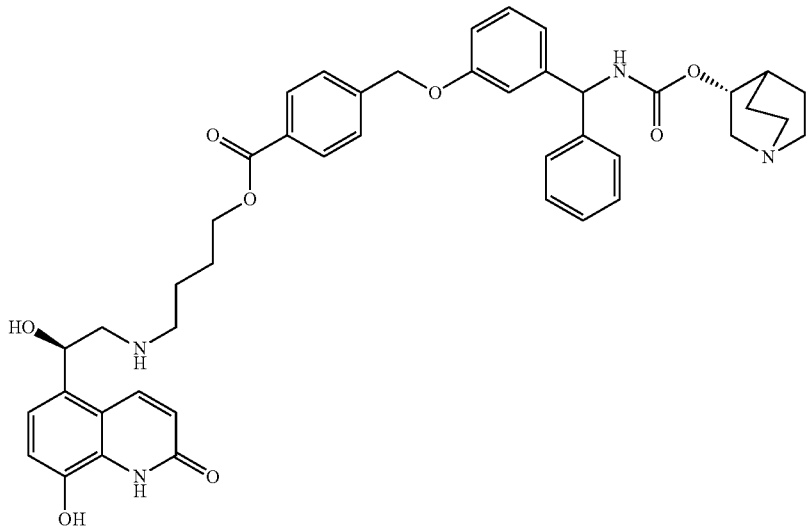 [SMILES: O=C(NC(c1ccccc1)c1cccc(OCc2ccc(C(=O)OCCCCNC[C@H](O)c3ccc(O)c4[nH]c(=O)ccc34)cc2)c1)O[C@H]1CN2CCC1CC2]

Step 1. 3-(1,3-Dioxolan-2-yl)propyl 4-(hydroxymethyl)benzoate

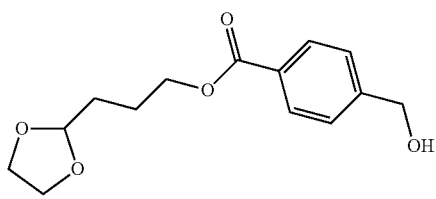 [SMILES: O=C(OCCCC1OCCO1)c1ccc(CO)cc1]

To a stirred solution of 4-hydroxymethylbenzoic acid (3.33 g, 21.9 mmol) in DMF (100 mL), was added potassium carbonate (5.67 g, 41.04 mmol) followed by 2-(3-bromopropyl)-1,3-dioxolane (3.0 g, 19.9 mmol). The resulting mixture was heated at 80° C. for 16 hours. The reaction mixture was diluted with ethyl acetate and washed sequentially with water and twice with brine. The organic phase was dried with anhydrous magnesium sulfate, and filtered, and the filtrate evaporated at reduced pressure. The crude material was purified by silica gel chromatography eluting with 100% iso-hexane to 100% ethyl acetate in iso-hexane to afford the title compound as a colourless oil (2.55 g, 48%).

$^1$H NMR (400 MHz, CDCl$_3$): δ 8.06-7.98 (m, 2H); 7.44 (d, J=8.0 Hz, 2H); 4.96-4.88 (m, 1H); 4.77 (d, J=4.0 Hz, 2H); 4.36 (t, J=6.4 Hz, 2H); 4.02-3.94 (m, 2H); 3.92-3.81 (m, 2H); 1.96-1.80 (m, 4H).

Step 2. 3-(1,3-Dioxolan-2-yl)propyl 4-((3-(((tert-butoxycarbonyl)amino)(phenyl)-methyl)phenoxy)methyl)benzoate

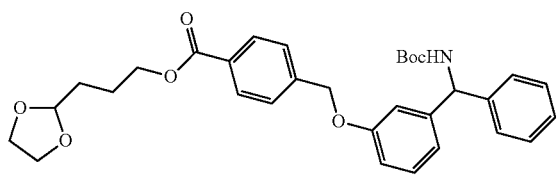 [SMILES: CC(C)(C)OC(=O)NC(c1ccccc1)c1cccc(OCc2ccc(C(=O)OCCCC3OCCO3)cc2)c1]

The title compound was prepared as described in Example 22 Step 2 with 3-(1,3-dioxolan-2-yl)propyl 4-(hydroxymethyl)benzoate and tert-butyl(3-hydroxyphenyl)(phenyl)methylcarbamate (first eluting isomer from Chiral Example 1 Step 4) replacing (4-((1,3-dioxolan-2-yl)methyl)phenyl)methanol and 3-hydroxybenzophenone, respectively.

$^1$H NMR (400 MHz, CDCl$_3$): δ 8.04-8.02 (m, 2H); 7.47-7.45 (m, 2H); 7.33-7.21 (m, 6H); 6.88-6.84 (m, 3H); 5.87 (br s, 1H); 5.15 (br s, 1H); 5.08 (s, 2H); 4.95-4.93 (m, 1H); 4.38-4.35 (m, 2H); 4.10-3.97 (m, 2H); 3.88-3.85 (m, 2H); 1.94-1.90 (m, 2H); 1.86-1.83 (m, 2H), 1.30 (s, 9H).

Step 3. 3-(1,3-Dioxolan-2-yl)propyl 4-((3-(amino(phenyl)methyl)phenoxy)methyl)-benzoate hydrochloride

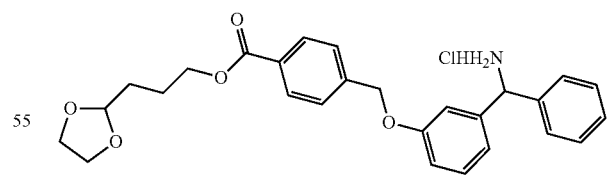

Hydrogen chloride in dioxan (4.0 M, 6 mL, 24 mmol) was added to 3-(1,3-dioxolan-2-yl)propyl 4-((3-(((tert-butoxycarbonyl)amino)(phenyl)methyl)phenoxy)-methyl)benzoate (0.756 g, 1.38 mmol), and the resultant solution was stirred at ambient temperature for 2 hours. The solvent was evaporated at reduced pressure to afford the title compound (0.750 g, 100%).

Step 4. 4-(((R)-2-hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)-phenoxy)methyl)benzoate (compound 45B)

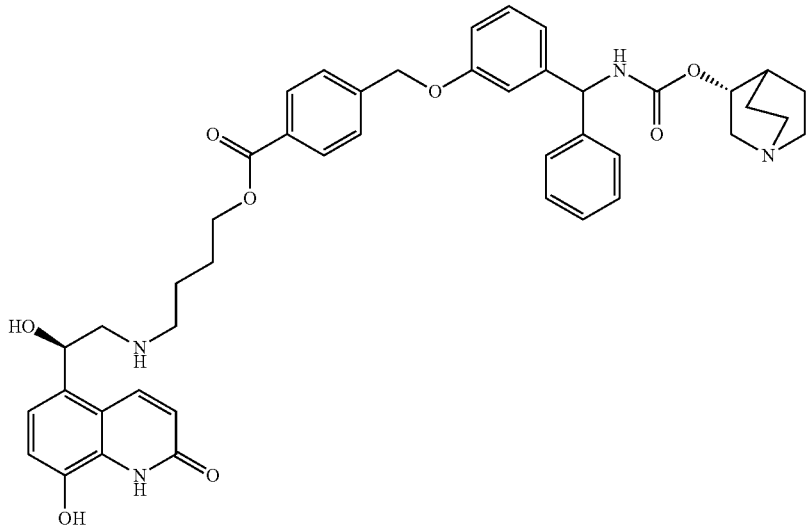 [SMILES: O=C(NC(c1ccccc1)c1cccc(OCc2ccc(C(=O)OCCCCNC[C@H](O)c3ccc(O)c4[nH]c(=O)ccc34)cc2)c1)O[C@H]1CN2CCC1CC2]

The title compound was prepared using Step 5, 6 and 7 of Example 1.

Chiral Example 6

4-(((R)-2-Hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)-phenoxy)methyl)benzoate (compound 46B)

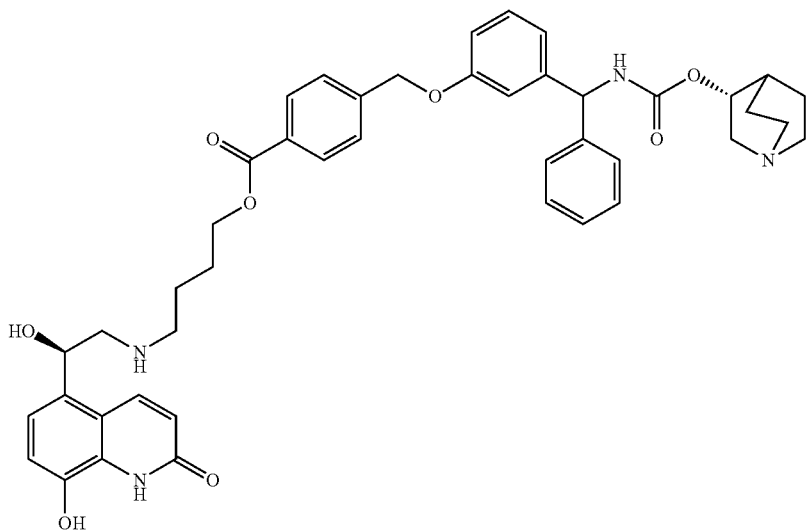 [SMILES: O=C(NC(c1ccccc1)c1cccc(OCc2ccc(C(=O)OCCCCNC[C@H](O)c3ccc(O)c4[nH]c(=O)ccc34)cc2)c1)O[C@H]1CN2CCC1CC2]

The title material was prepared as described in Chiral Example 5 with tert-butyl (3-hydroxyphenyl)(phenyl)methylcarbamate (second eluting isomer from Chiral Example 1 Step 4) replacing tert-butyl(3-hydroxyphenyl)(phenyl)methylcarbamate (first eluting isomer from Chiral Example 1 Step 4) in Step 2.

An alternative method to prepare the key intermediate A in Chiral Example 5 or Chiral Example 6 is detailed below. The example below details the use of the second eluting isomer derived from Chiral Example 1 Step 4.

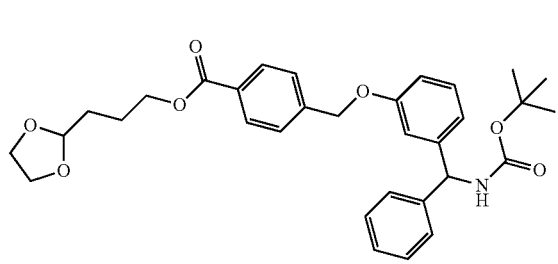

A

Step 1. Methyl 4-((3-(((tert-butoxycarbonyl)amino)(phenyl)methyl)phenoxy)-methyl)benzoate

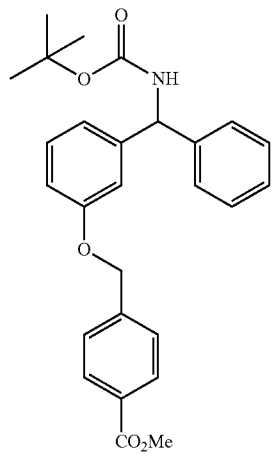 [SMILES: COC(=O)c1ccc(COc2cccc(C(NC(=O)OC(C)(C)C)c3ccccc3)c2)cc1]

The title compound was prepared as described in Example 106 Step 4 with the second eluting isomer from Chiral Example 1 Step 4 replacing tert-butyl(3-hydroxyphenyl)(phenyl)methylcarbamate.

$^1$H NMR (400 MHz, CDCl$_3$): δ 8.04 (d, J=8.2 Hz, 2H); 7.46 (d, J=8.2 Hz, 2H); 7.34-7.20 (m, 6H); 6.90-6.81 (m, 3H); 5.87 (s, 1H); 5.13 (s, 1H); 5.07 (s, 2H); 3.92 (s, 3H); 1.44 (s, 9H).

Step 2. 4-((3-(((tert-Butoxycarbonyl)amino)(phenyl)methyl)phenoxy)methyl)benzoic acid

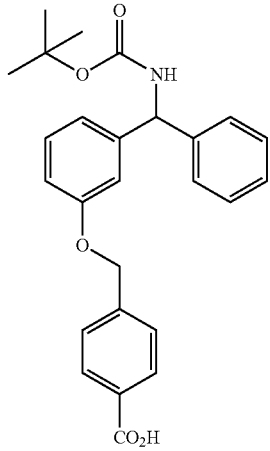 [SMILES: CC(C)(C)OC(=O)NC(c1ccccc1)c1cccc(OCc2ccc(C(=O)O)cc2)c1]

The title compound was prepared as described in Example 81 Step 7 with methyl 4-((3-(((tert-butoxycarbonyl)amino)(phenyl)methyl)phenoxy)methyl)benzoate replacing methyl 4-((3-(phenyl((((R)-quinuclidin-3-yloxy)carbonyl)amino)methyl)phenoxy)-methyl)benzoate.

$^1$H NMR (DMSO-d$_6$): δ 7.94 (3H, m), 7.54 (2H, d, J=7.97 Hz), 7.43 (1H, d, J=7.98 Hz), 7.37-7.15 (5H, m), 7.02 (1H, s), 6.96-6.84 (2H, m), 5.79 (1H, d, J=9.68 Hz), 5.16 (2H, s), 1.39 (9H, s)

Step 3. 3-(1,3-Dioxolan-2-yl)propyl 4-((3-(((tert-butoxycarbonyl)amino)(phenyl)-methyl)phenoxy)methyl)benzoate

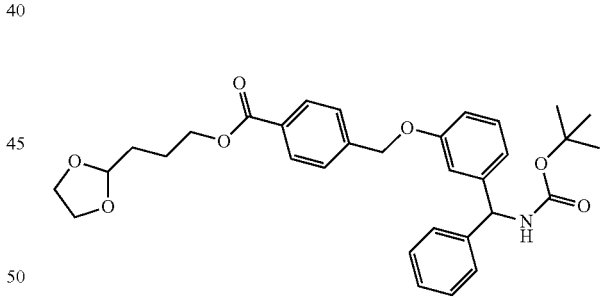

The title compound was prepared from 4-((3-(((tert-butoxycarbonyl)amino)-(phenyl)methyl)phenoxy)methyl)benzoic acid and 2-(3-chloropropyl)-1,3-dioxolane according to the method of Chiral Example 5 Step 1.

$^1$H NMR (400 MHz, CDCl$_3$): δ 8.04-8.02 (m, 2H); 7.47-7.45 (m, 2H); 7.33-7.21 (m, 6H); 6.88-6.84 (m, 3H); 5.87 (br s, 1H); 5.15 (br s, 1H); 5.08 (s, 2H); 4.95-4.93 (m, 1H); 4.38-4.35 (m, 2H); 4.10-3.97 (m, 2H); 3.88-3.85 (m, 2H); 1.94-1.90 (m, 2H); 1.86-1.83 (m, 2H), 1.30 (s, 9H).

The following compounds were made using this alternative synthesis starting from the second eluting isomer of tert-butyl (3-hydroxyphenyl)(phenyl)methylcarbamate using the appropriate alkylating agent in Step 1.

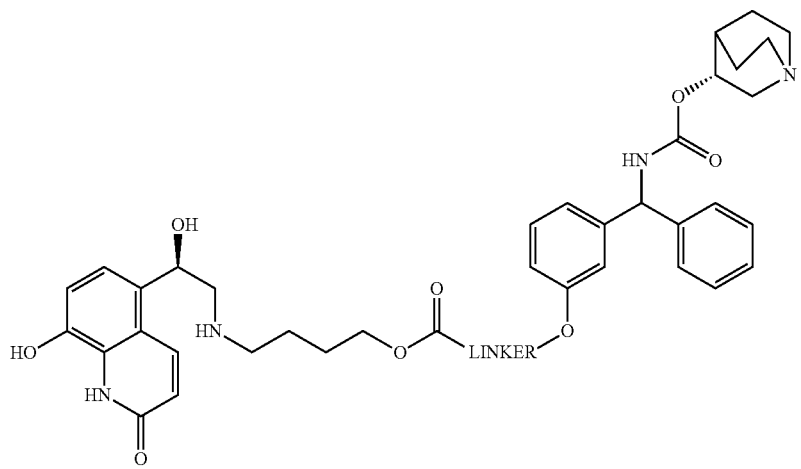
| Compound | LINKER | Appropriate alkylating agent |
|---|---|---|
| 47C | 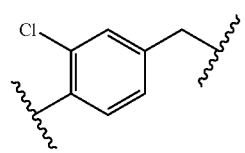 [SMILES: *Cc1ccc(*)c(Cl)c1] | 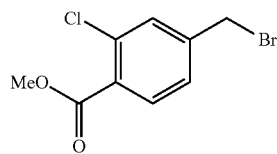 [SMILES: COC(=O)c1ccc(CBr)cc1Cl] |
| 48C | 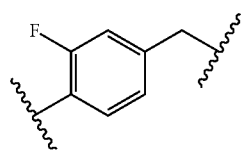 [SMILES: *Cc1ccc(*)c(F)c1] |  |
| 49C | 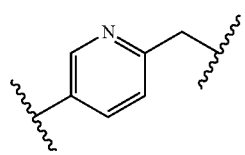 [SMILES: *Cc1ccc(*)cn1] | 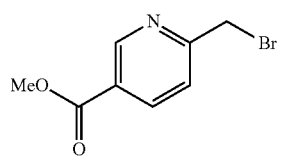 [SMILES: COC(=O)c1ccc(CBr)nc1] |
| 50C | 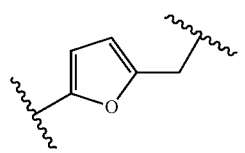 [SMILES: *Cc1ccc(*)o1] | 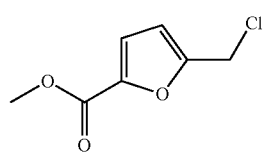 |
| 51C | 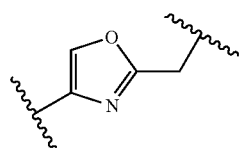 [SMILES: *Cc1nc(*)co1] | 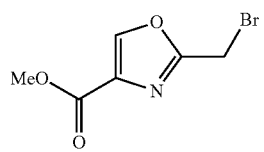 [SMILES: COC(=O)c1coc(CBr)n1] |
| 52C | 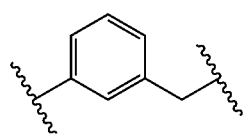 [SMILES: *Cc1cccc(*)c1] | 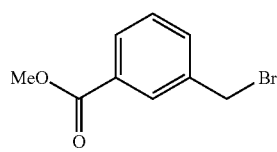 [SMILES: COC(=O)c1cccc(CBr)c1] |

Chiral Example 7

5-(((R)-2-Hydroxy-2-(8-hydroxy-2-oxo-1,2-dihydroquinolin-5-yl)ethyl)amino)pentyl 2-(3-(phenyl((((R)-quinuclidin-3-yloxy)carbonyl)amino)-methyl)phenoxy)acetate (Compound 53C)

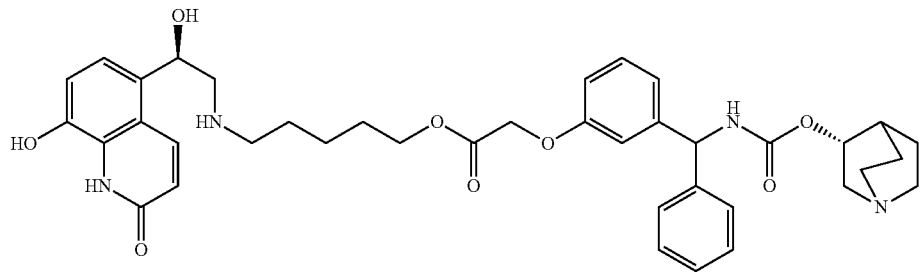 [SMILES: O=C(COc1cccc(C(NC(=O)O[C@H]2CN3CCC2CC3)c2ccccc2)c1)OCCCCCNC[C@H](O)c1ccc(O)c2[nH]c(=O)ccc12]

The title compound was prepared as described in Compound 9C but starting from the second eluting isomer from Chiral Example 1 Step 4.

Chiral Example 8

5-(((R)-2-Hydroxy-2-(8-hydroxy-2-oxo-1,2-dihydroquinolin-5-yl)ethyl)amino)pentyl 2-(3-(phenyl((((R)-quinuclidin-3-yloxy)carbonyl)amino)methyl)-phenoxy)acetate (Compound 54C)

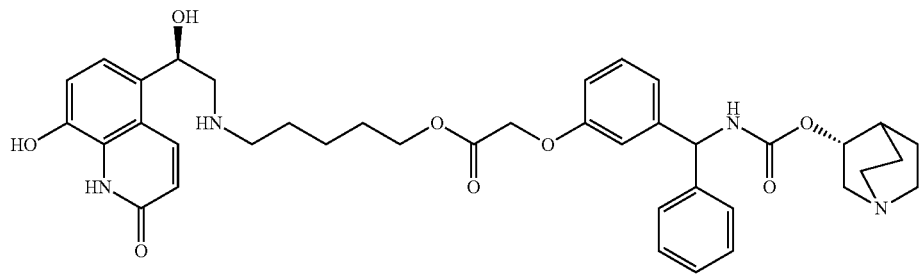 [SMILES: O=C(COc1cccc(C(NC(=O)O[C@H]2CN3CCC2CC3)c2ccccc2)c1)OCCCCCNC[C@H](O)c1ccc(O)c2[nH]c(=O)ccc12]

The title compound was prepared as described for Compound 9C but starting from the first eluting isomer from Chiral Example 1 Step 4.

Chiral Example 9

6-(((R)-2-Hydroxy-2-(8-hydroxy-2-oxo-1,2-dihydroquinolin-5-yl)ethyl)amino)hexyl 2-(3-(phenyl((((R)-quinuclidin-3-yloxy)carbonyl)amino)-methyl)phenoxy)acetate (Compound 55C)

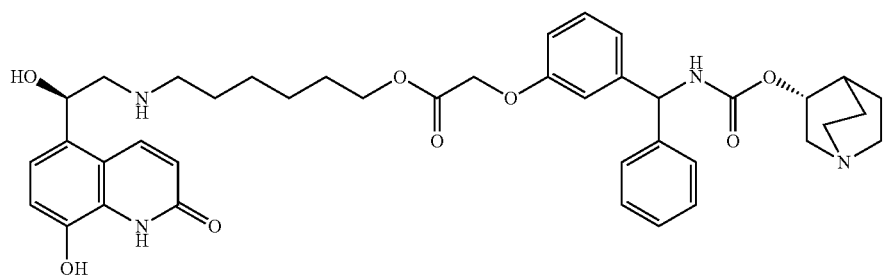 [SMILES: O=C(COc1cccc(C(NC(=O)O[C@H]2CN3CCC2CC3)c2ccccc2)c1)OCCCCCCNC[C@H](O)c1ccc(O)c2[nH]c(=O)ccc12]

The title compound was prepared as described in Example 59 but starting from the second eluting isomer from Chiral Example 1 Step 4.

Chiral Example 10

6-(((R)-2-Hydroxy-2-(8-hydroxy-2-oxo-1,2-dihydro-quinolin-5-yl)ethyl)amino)hexyl 2-(3-(phenyl((((R)-quinuclidin-3-yloxy)carbonyl)amino)methyl)-phenoxy)acetate (Compound 56C)

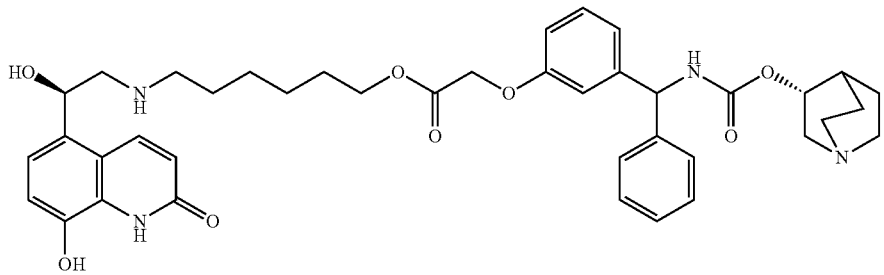 [SMILES: O=C(COc1cccc(C(NC(=O)O[C@H]2CN3CCC2CC3)c2ccccc2)c1)OCCCCCCNC[C@H](O)c1ccc(O)c2[nH]c(=O)ccc12]

The title compound was prepared as described in Example 59 but starting from the first eluting isomer from Chiral Example 1 Step 4.

Chiral Example 11

(R)-Quinuclidin-3-yl((3-((4-((3-(((R)-2-hydroxy-2-(8-hydroxy-2-oxo-1,2-dihydroquinolin-5-yl)ethyl)amino)propyl)carbamoyl)benzyl)oxy)phenyl)-(phenyl)methyl)carbamate (Compound 57C)

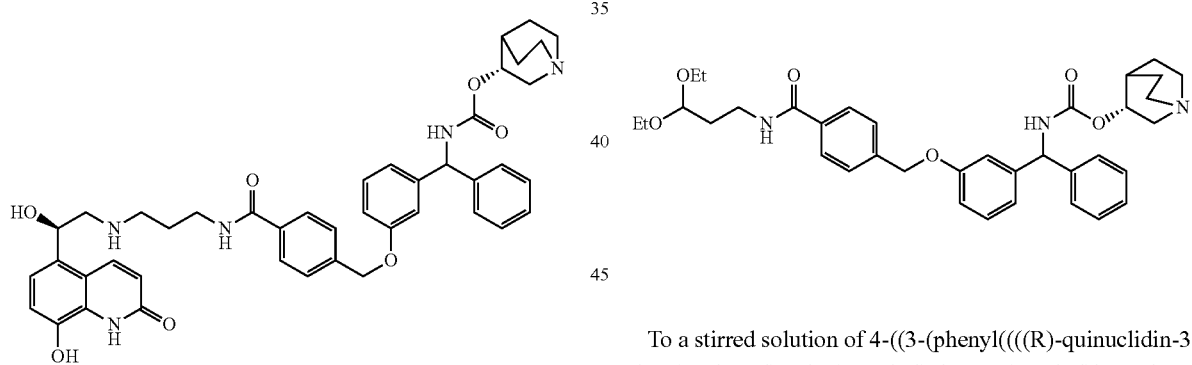

Step 1. 4-((3-(Phenyl((((R)-quinuclidin-3-yloxy)carbonyl)amino)methyl)phenoxy)-methyl)benzoic acid

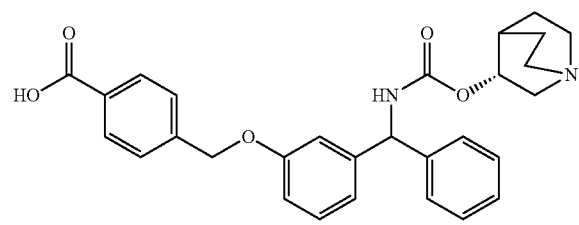 [SMILES: O=C(NC(c1ccccc1)c1cccc(OCc2ccc(C(=O)O)cc2)c1)O[C@H]1CN2CCC1CC2]

The title compound was prepared as described in Example 79 Steps 4-7 with the second eluting isomer from Chiral Example 1 Step 4 replacing the racemic tert-butyl(3-hydroxyphenyl)(phenyl)methylcarbamate in Step 4.

Step 2; (R)-Quinuclidin-3-yl((3-((4-((3,3-diethoxypropyl)carbamoyl)benzyl)oxy)-phenyl)(phenyl)methyl)carbamate To a stirred solution of 4-((3-(phenyl((((R)-quinuclidin-3-yloxy)carbonyl)amino)-methyl)phenoxy)methyl)benzoic acid (0.300 g, 0.57 mmol) in DMF (2.5 mL), was added HATU (0.262 g, 0.69 mmol) and diisopropylethylamine (0.250 mL, 1.43 mmol), and the reaction mixture was stirred at room temperature for 30 minutes. 1-Amino-3,3-diethoxypropane (0.139 mL, 0.86 mmol) was added, and the reaction mixture was stirred at room temperature for 18 hours. The reaction mixture was diluted with ethyl acetate and washed sequentially with saturated sodium hydrogen carbonate and brine (×2). The organic phase was dried wih anhydrous sodium sulfate, and filtered, and the solvent was evaporated at reduced pressure. The crude material was purified by silica gel chromatography eluting with 100% iso-hexane to 100% ethyl acetate in iso-hexane to afford the title compound (0.347 g, 99%), which was used directly in the next step.

Step 3. (R)-quinuclidin-3-yl((3-((4-((3-(((R)-2-hydroxy-2-(8-hydroxy-2-oxo-1,2-dihydroquinolin-5-yl)ethyl)amino)propyl)carbamoyl)benzyl)oxy)phenyl)(phenyl)-methyl)carbamate

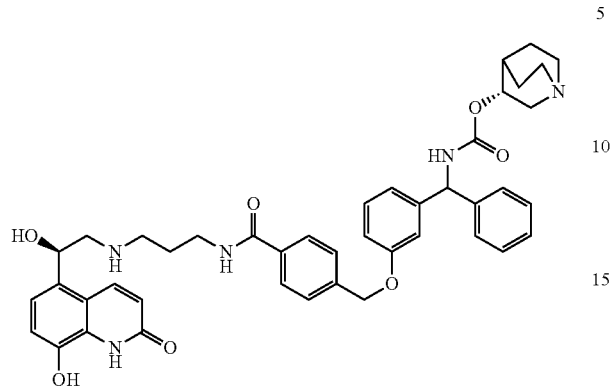

The title compound was prepared as described in Example 1 Step 6 and Step 7.

The following compounds were prepared in the same fashion as Chiral Example 11 using the appropriate amine in Step 2.

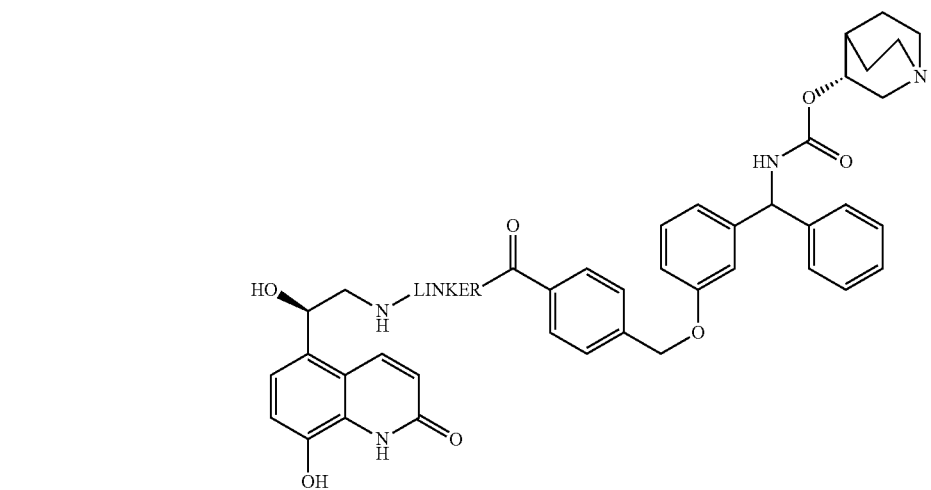

| Compound No | Linker | Appropriate amine |
|---|---|---|
| 58C | 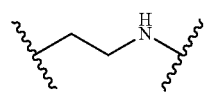 [SMILES: *CCN*] | 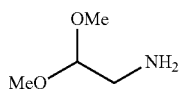 |
| 59C | 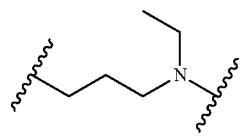 [SMILES: *CCCN(*)CC] | 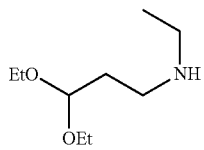 |
| 60C | 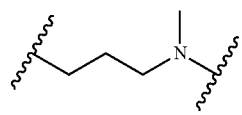 [SMILES: *CCCN(*)C] | 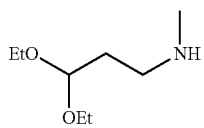 |

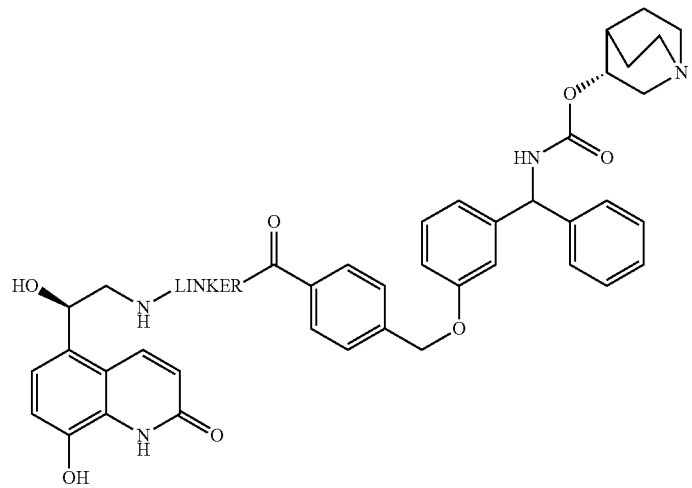

The amines for Compounds 59C, 60C, 61C, 65C, and 66C were prepared as detailed below (exemplified for the amine for Compound 60C).

N-Benzylmethylamine (1 equivalent), 2-(2-bromoethyl)-1,3-dioxalane (1.5 equivalents), and potassium carbonate (1.5 equivalents) in acetonitrile (0.4 M) were heated at 80° C. for 24 hours. The reaction mixture was diluted with ethyl acetate and washed sequentially with water and saturated aqueous brine. The organic phase was dried with anhydrous magnesium sulfate and filtered, and the solvent was evaporated at reduced pressure. The residue was purified by chromatography on an SCX-2 cartridge. The material was subjected to the procedure described in the synthesis of (R)-5-(2-amino-1-(tert-butyldimethylsilyloxy)ethyl)-8-hydroxyquinolin-2(1H)-one.

The amine for Compound 62C was prepared by alkylating trans-4-(((tert-butoxycarbonyl)amino)methyl)cyclohexanecarboxylic acid with 2-(3-chloropropyl)-1,3-dioxolane according to the protocol in Example 54 Step 1 followed by removal of the protecting group according to the protocol in Example 81 Step 5.

The amine for Compound 63C was prepared by coupling (S)-3-((tert-butoxycarbonyl)amino)-4-methoxy-4-oxobutanoic acid and 2,2-dimethoxy-N-methylethanamine according to the protocol in Chiral Example 11 Step 2 followed by removal of the protecting group according to the protocol in Example 81 Step 5.

The following compounds were prepared in a similar fashion to Chiral Example 11 but using the appropriate alcohol (heated at 60° C.) in Step 2.

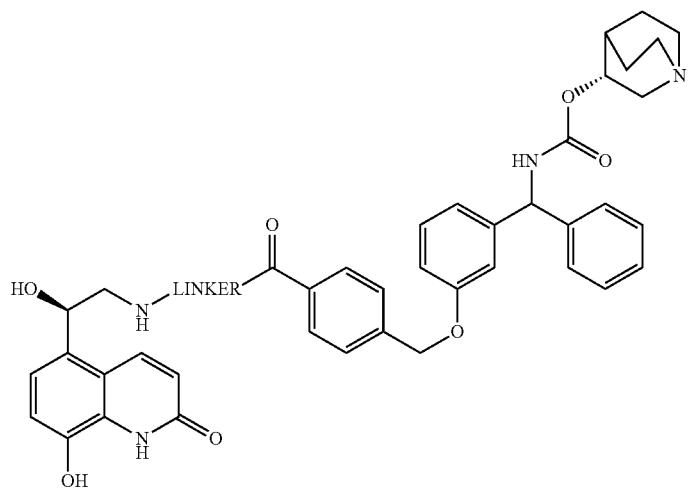

| Compound No | Linker | Appropriate alcohol |
|---|---|---|
| 67C | | |
| 68C | | |
| 69C | | |
| 70C | | |
| 71C | | |

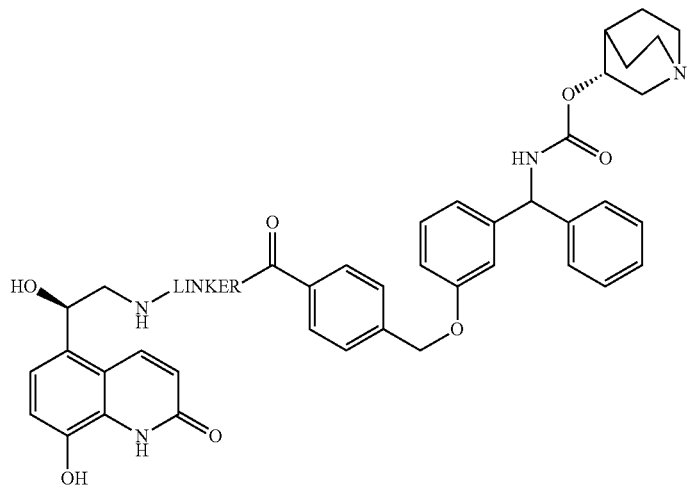

| Compound No | Linker | Appropriate alcohol |
|---|---|---|
| 72C | 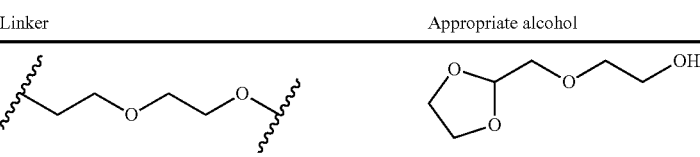 | |
| 73C | 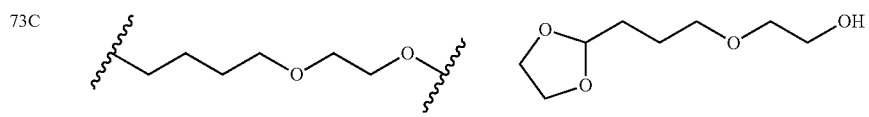 | |
| 74C | 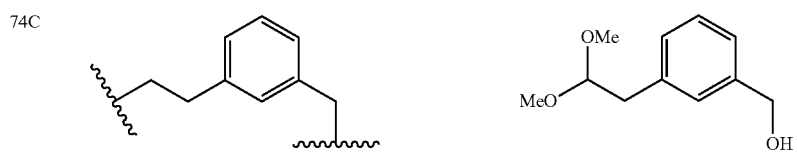 | |

The alcohol required to prepare Compound 67C was prepared as described in Faming Zhuanli Shenqing Gongkai Shuomingshu, 101153000, 2 Apr. 2008, which is incorporated herein by reference in its entirety.

The alcohol required to prepare Compound 68C and 69C was prepared from the requisite amine and hydroxyacetic acid.

The alcohol required to prepare Compound 70C and 71C was prepared from the requisite alcohol and hydroxyacetic acid.

The alcohol required to prepare Compound 72C and 73C was prepared from ethylene glycol and the requisite bromide.

Chiral Example 12

3-(3-(Phenyl((((R)-quinuclidin-3-yloxy)carbonyl)amino)methyl)-phenoxy)propyl 4-(2-(((R)-2-hydroxy-2-(8-hydroxy-2-oxo-1,2-dihydroquinolin-5-yl)ethyl)amino)ethyl)benzoate (Compound 75C)

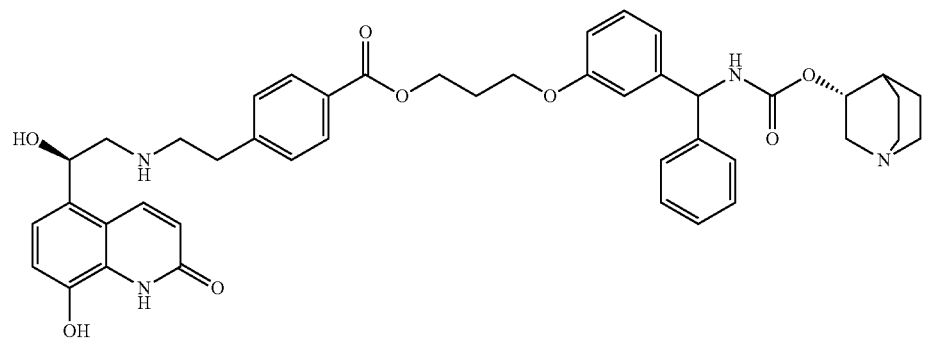 [SMILES: O=C(NC(c1ccccc1)c1cccc(OCCCOC(=O)c2ccc(CCNC[C@H](O)c3ccc(O)c4[nH]c(=O)ccc34)cc2)c1)O[C@H]1CN2CCC1CC2]

Step 1. 3-(3-(((tert-Butoxycarbonyl)amino)(phenyl)methyl)phenoxy)propyl benzoate

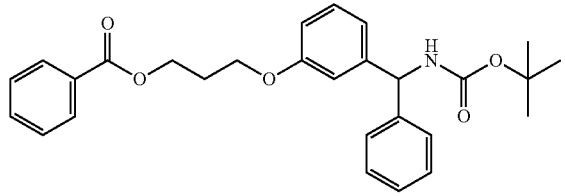 [SMILES: CC(C)(C)OC(=O)NC(c1ccccc1)c1cccc(OCCCOC(=O)c2ccccc2)c1]

The title compound was prepared as described in Example 22 Step 3 with 3-hydroxypropyl benzoate (prepared as outlined in Organic & Biomolecular Chemistry, 8(24), 5505-5510; 2010, which is incorporated herein by reference in its entirety) and tert-butyl((3-hydroxyphenyl)(phenyl)methyl)carbamate (derived from the second eluting isomer Chiral Example 1 Step 4) replacing (4-((1,3-dioxolan-2-yl)methyl)phenyl)methanol and 3-hydroxybenzophenone respectively.

$^1$H NMR (400 MHz, CDCl$_3$): δ 8.03 (d, J=7.7 Hz, 2H); 7.60-7.52 (m, 1H); 7.48-7.40 (m, 2H); 7.35-7.19 (m, 6H); 6.85-6.76 (m, 3H); 5.86 (s, 1H); 5.13 (s, 1H); 4.54-4.47 (m, 2H); 4.16-4.05 (m, 2H); 2.29-2.19 (m, 2H); 1.43 (s, 9H).

Step 2. 3-(3-(Amino(phenyl)methyl)phenoxy)propyl benzoate hydrochloride

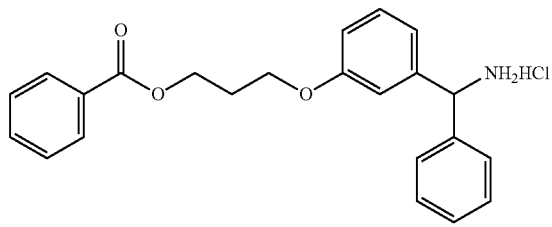

Hydrogen chloride in dioxane (4 M, 3.30 mL, 13.2 mmol) was added to 3-(3-(((tert-tutoxycarbonyl)amino)(phenyl)methyl)phenoxy)propyl benzoate (0.359 g, 0.78 mmol), and the resultant mixture was stirred at room temperature for 2 hours. The solvent was evaporated at reduced pressure to afford the title compound (0.271 g, 88%).

$^1$H NMR (400 MHz, DMSO-d$_6$): δ 8.95 (s, 3H); 7.98 (d, J=7.7 Hz, 2H); 7.71-7.63 (m, 1H); 7.52 (dd, J=15.3, 7.6 Hz, 4H); 7.46-7.29 (m, 4H); 7.17 (s, 1H); 7.05 (d, J=7.7 Hz, 1H); 6.96 (d, J=8.3 Hz, 1H); 5.60 (s, 1H); 4.47-4.40 (m, 2H); 4.18-4.11 (m, 2H); 2.24-2.16 (m, 2H).

Step 3. 3-(3-(Phenyl((((R)-quinuclidin-3-yloxy)carbonyl)amino)methyl)phenoxy)propyl

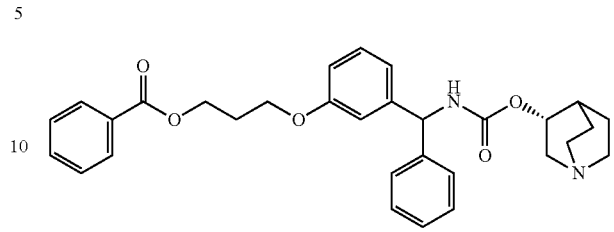

The title compound was prepared as described in Example 1 Step 5 with 3-(3-(amino(phenyl)methyl)phenoxy)propyl benzoate hydrochloride replacing (3-(8-(1,3-dioxolan-2-yl)octyloxy)phenyl)(phenyl)methanamine.

$^1$H NMR (400 MHz, CDCl$_3$): δ 8.05-8.00 (m, 2H); 7.60-7.53 (m, 1H); 7.48-7.40 (m, 2H); 7.37-7.29 (m, 2H); 7.28-7.18 (m, 4H); 6.88-6.78 (m, 3H); 5.91 (s, 1H); 5.31 (s, 1H); 4.72 (s, 1H); 4.54-4.47 (m, 2H); 4.16-4.06 (m, 2H); 3.20 (s, 1H); 2.93-2.63 (s, 4H); 2.28-2.19 (m, 2H); 2.03-1.48 (br, 6H).

Step 4. (R)-Quinuclidin-3-yl((3-(3-hydroxypropoxy)phenyl)(phenyl)methyl)carbamate

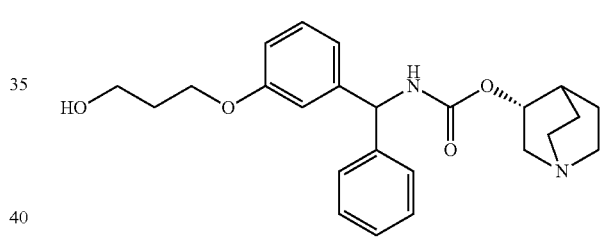

To a stirred solution of 3-(3-(phenyl((((R)-quinuclidin-3-yloxy)carbonyl)amino)-methyl)phenoxy)propyl benzoate (0.370 g, 0.72 mmol) in methanol (3.6 mL), was added a solution of lithium hydroxide monohydrate (0.060 g, 1.44 mmol) in water (1.2 mL). The reaction mixture was stirred at room temperature for 1 hour. Further lithium hydroxide monohydrate (0.060 g, 1.44 mmol) was added, and the reaction stirred at room temperature for a further 16 hours. The reaction mixture was heated at 40° C. for 3.5 hours and allowed to cool. The solvent was evaporate at reduced pressure, and the residue partitioned between ethyl acetate and water. The aqueous phase was further extracted with ethyl acetate (×2). The combined organic extracts were washed with 10% aqueous potassium carbonate (×2), saturated brine, and dried with anhydrous sodium sulfate. The mixture was filtered and the solvent evaporated at reduced pressure to afford the title compound (0.275 g, 93%).

$^1$H NMR (400 MHz, CDCl$_3$): δ 7.38-7.20 (m, 6H); 6.83 (t, J=8.5 Hz, 3H); 5.91 (s, 1H); 5.30 (s, 1H); 4.72 (s, 1H); 4.16-4.06 (m, 2H); 3.83 (t, J=5.8 Hz, 2H); 3.19 (s, 1H); 2.94-2.62 (m, 4H); 2.04-1.96 (m, 2H); 1.90-1.32 m, 7H).

Step 5. 3-(3-(Phenyl((((R)-quinuclidin-3-yloxy)carbonyl)amino)methyl)phenoxy)propyl 4-((1,3-dioxolan-2-yl)methyl)benzoate

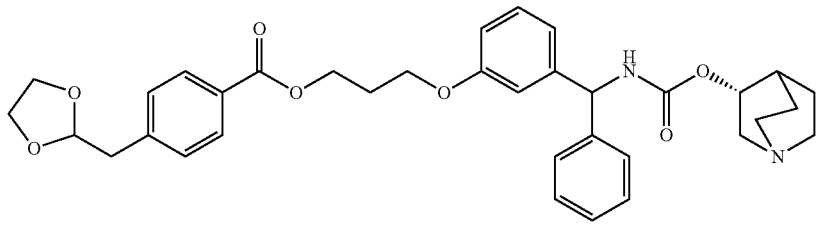 [SMILES: O=C(NC(c1ccccc1)c1cccc(OCCCOC(=O)c2ccc(CC3OCCO3)cc2)c1)O[C@H]1CN2CCC1CC2]

The title compound was prepared as described in Chiral Example 11 Step 2 with (R)-quinuclidin-3-yl((3-(3-hydroxypropoxy)phenyl)(phenyl)methyl)carbamate and 4-(1,3-dioxolan-2-ylmethyl)-benzoic acid replacing 4-((3-(phenyl ((((R)-quinuclidin-3-yloxy)carbonyl)amino)methyl) phenoxy)methyl)benzoic acid and 1-amino-3,3-diethoxypropane, respectively.

Step 6. 3-(3-(Phenyl((((R)-quinuclidin-3-yloxy)carbonyl)amino)methyl)phenoxy)propyl 4-(2-(((R)-2-hydroxy-2-(8-hydroxy-2-oxo-1,2-dihydroquinolin-5-yl)ethyl)amino)ethyl)benzoate (Compound 75C)

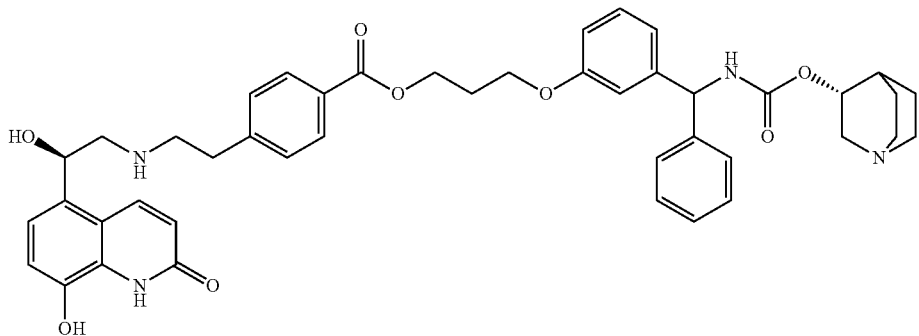 [SMILES: O=C(NC(c1ccccc1)c1cccc(OCCCOC(=O)c2ccc(CCNC[C@H](O)c3ccc(O)c4[nH]c(=O)ccc34)cc2)c1)O[C@H]1CN2CCC1CC2]

The title compound was prepared as described in Example 1 Step 6 and 7.

Chiral Example 13

4-(((R)-2-Hydroxy-2-(8-hydroxy-2-oxo-1,2-dihydroquinolin-5-yl)ethyl)amino)butyl 4-(2-(3-(phenyl ((((R)-quinuclidin-3-yloxy)carbonyl)amino)-methyl) phenoxy)ethyl)benzoate (Compound 76C)

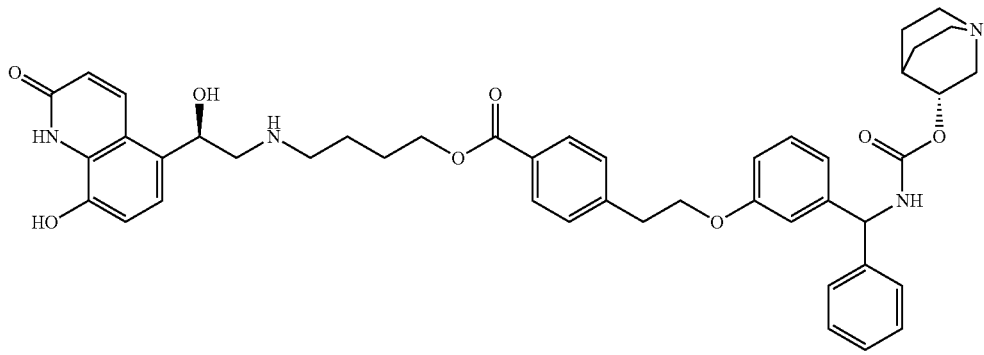 [SMILES: O=C(NC(c1ccccc1)c1cccc(OCCc2ccc(C(=O)OCCCCNC[C@H](O)c3ccc(O)c4[nH]c(=O)ccc34)cc2)c1)O[C@H]1CN2CCC1CC2]

The title compound was prepared as in Chiral Example 5 with 4-(2-hydroxyethyl)benzoic acid replacing 4-hydroxymethylbenzoic acid and using tert-butyl (3-hydroxyphenyl)(phenyl)methylcarbamate (second eluting isomer from Chiral Example 1 Step 4) in Step 1.

Chiral Example 14

4-(((R)-2-hydroxy-2-(8-hydroxy-2-oxo-1,2-dihydroquinolin-5-yl)ethyl)amino)butyl 4-(5-((3-(phenyl ((((R)-quinuclidin-3-yloxy)carbonyl)amino)-methyl)phenoxy)methyl)-1,2,4-oxadiazol-3-yl)benzoate (Compound 77C)

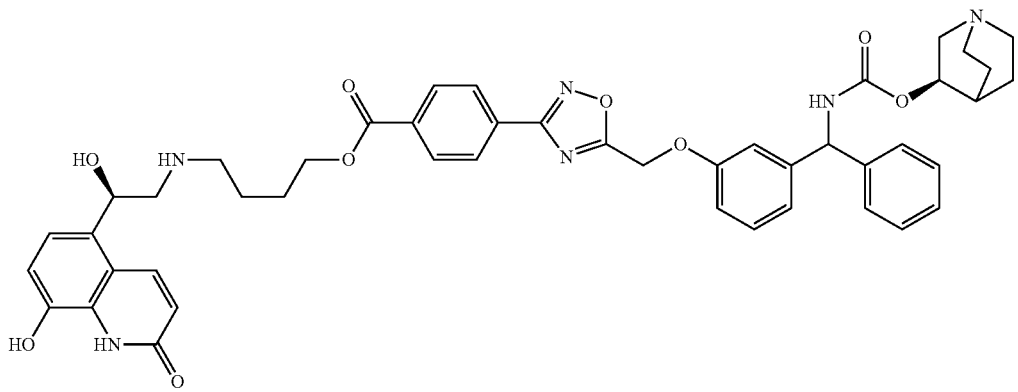 [SMILES: O=C(NC(c1ccccc1)c1cccc(OCc2nc(-c3ccc(C(=O)OCCCCNC[C@H](O)c4ccc(O)c5[nH]c(=O)ccc45)cc3)no2)c1)O[C@H]1CN2CCC1CC2]

Step 1. 3-(1,3-Dioxolan-2-yl)propyl 4-cyanobenzoate

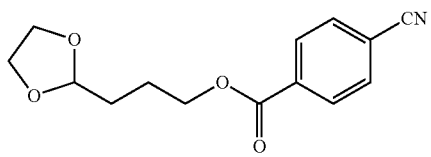 [SMILES: N#Cc1ccc(C(=O)OCCCC2OCCO2)cc1]

The title compound was prepared as described in Chiral Example 4 Step 1 with 4-cyanobenzoic acid replacing 4-hydroxymethylbenzoic acid.

$^1$H NMR (400 MHz, CDCl$_3$): δ 8.16-8.12 (m, 2H); 7.77-7.73 (m, 2H); 4.97-4.89 (m, 1H); 4.44-4.36 (m, 2H); 4.04-3.83 (m, 4H); 1.97-1.88 (m, 2H); 1.86-1.79 (m, 2H).

Step 2. 3-(1,3-Dioxolan-2-yl)propyl 4-(N'-hydroxycarbamimidoyl)benzoate

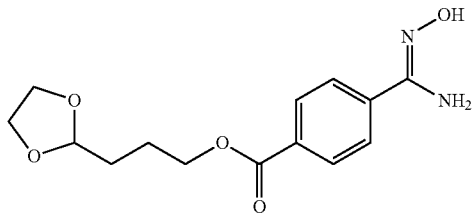 [SMILES: N/C(=N\O)c1ccc(C(=O)OCCCC2OCCO2)cc1]

To a solution of 3-(1,3-dioxolan-2-yl)propyl 4-cyanobenzoate (1.00 g, 4.38 mmol) in ethanol (5 mL), was added hydroxylamine (50% aqueous solution, 5 mL), and the mixture heated at 80° C. for 4 hours. The reaction was diluted with saturated brine and extracted with ethyl acetate (×3). The combined organic fractions were dried with magnesium sulphate, and the solvent evaporated at reduced pressure. The material was used directly in the next step without further purification.

Step 3. Methyl 2-(3-((((tert-butoxycarbonyl)amino)(phenyl)methyl)phenoxy)acetate

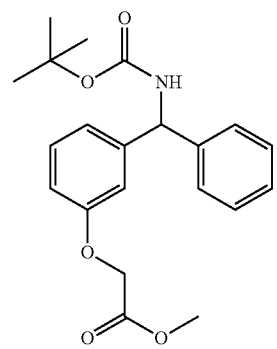 [SMILES: COC(=O)COc1cccc(C(NC(=O)OC(C)(C)C)c2ccccc2)c1]

The title compound was prepared as described in Example 79 Step 4 with the second eluting isomer from Chiral Example 1 Step 4 replacing tert-butyl(3-hydroxyphenyl)(phenyl)methylcarbamate.

Step 4. 2-(3-(((tert-Butoxycarbonyl)amino)(phenyl)methyl)phenoxy)acetic acid

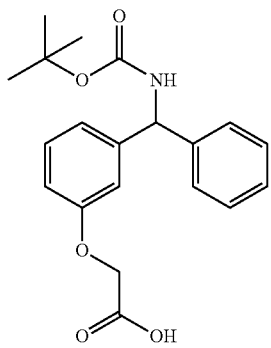 [SMILES: CC(C)(C)OC(=O)NC(c1ccccc1)c1cccc(OCC(=O)O)c1]

The title compound was prepared as described in Example 79 Step 7 with methyl 2-(3-(((tert-butoxycarbonyl)amino)(phenyl)methyl)phenoxy)acetate acid replacing methyl 4-((3-(phenyl((((R)-quinuclidin-3-yloxy)carbonyl)amino)methyl)phenoxy)-methyl)benzoate.

Step 5. 3-(1,3-Dioxolan-2-yl)propyl 4-(5-((3-(((tert-butoxycarbonyl)amino)(phenyl)-methyl)phenoxy)methyl)-1,2,4-oxadiazol-3-yl)benzoate

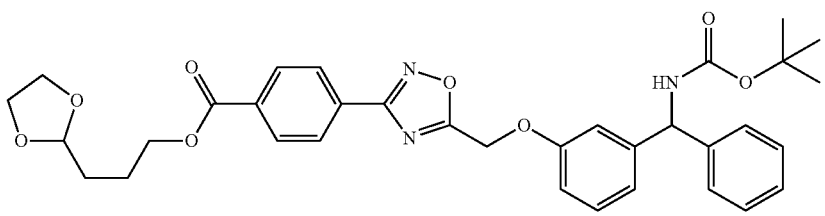 [SMILES: CC(C)(C)OC(=O)NC(c1ccccc1)c1cccc(OCc2nc(-c3ccc(C(=O)OCCCC4OCCO4)cc3)no2)c1]

To a solution of 2-(3-(((tert-butoxycarbonyl)amino)(phenyl)methyl)phenoxy)-acetic acid (0.087 g. 0.34 mmol) and 3-(1,3-dioxolan-2-yl)propyl 4-(N'-hydroxy-carbamimidoyl)benzoate (0.10 g, 0.28 mmol) in acetonitrile (1 mL), was added 1-ethyl-3-(3-dimethylaminopropyl)carbodiimide hydrochloride (0.087 g, 0.42 mmol). The reaction mixture was stirred at ambient temperature for 16 hours. The reaction mixture was diluted with pyridine and heated at 150° C. for 30 minutes in a microwave. The reaction was diluted with saturated brine and extracted with ethyl acetate (×3). The combined organic fractions were dried with magnesium sulfate, and the solvent evaporated at reduced pressure. The material was used directly in the next step without further purification (0.142 g, 87%).

$^1$H NMR (400 MHz, CDCl$_3$): δ 8.16 (s, 4H); 7.40-7.33 (m, 6H); 7.00-6.88 (m, 3H); 5.35-5.26 (m, 2H); 4.97-4.92 (m, 1H); 4.45-4.35 (m, 2H); 4.04-3.93 (m, 2H); 3.93-3.83 (m, 2H); 2.01-1.81 (m, 4H); 1.43 (s, 9H).

Step 6. 3-(1,3-dioxolan-2-yl)propyl 4-(5-((3-(amino(phenyl)methyl)phenoxy)methyl)-1,2,4-oxadiazol-3-yl)benzoate hydrochloride

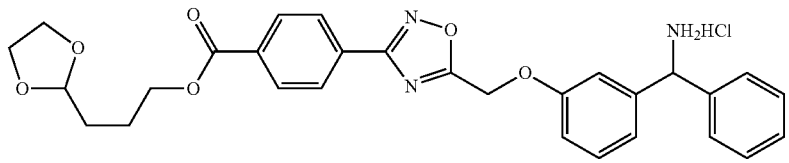

Hydrogen chloride in dioxan (4.0 M, 5 mL, 24 mmol) was added to 3-(1,3-dioxolan-2-yl)propyl 4-(5-((3-(((tert-butoxycarbonyl)amino)(phenyl)methyl)-phenoxy)methyl)-1,2,4-oxadiazol-3-yl)benzoate (0.237 g, 0.41 mmol), and the resultant solution was stirred at ambient temperature for 2 hours. The solvent was evaporated at reduced pressure to afford the title compound (0.212 g, 100%).

$^1$H NMR (400 MHz, DMSO-d$_6$): δ 9.05 (s, 3H); 8.18-8.07 (m, 4H); 7.50 (d, J=7.6 Hz, 2H); 7.42-7.30 (m, 5H); 7.15 (d, J=7.8 Hz, 1H); 7.10 (dd, J=8.3, 2.6 Hz, 1H); 5.71-5.53 (m, 3H); 4.86-4.81 (m, 1H); 4.35-4.27 (m, 2H); 3.91-3.81 (m, 2H); 3.79-3.73 (m, 2H); 1.86-1.68 (m, 4H).

Step 7. 4-(((R)-2-hydroxy-2-(8-hydroxy-2-oxo-1,2-dihydroquinolin-5-yl)ethyl)amino)butyl 4-(5-((3-(phenyl((((R)-quinuclidin-3-yloxy)carbonyl)amino)-methyl)phenoxy)methyl)-1,2,4-oxadiazol-3-yl)benzoate (Compound 77C)

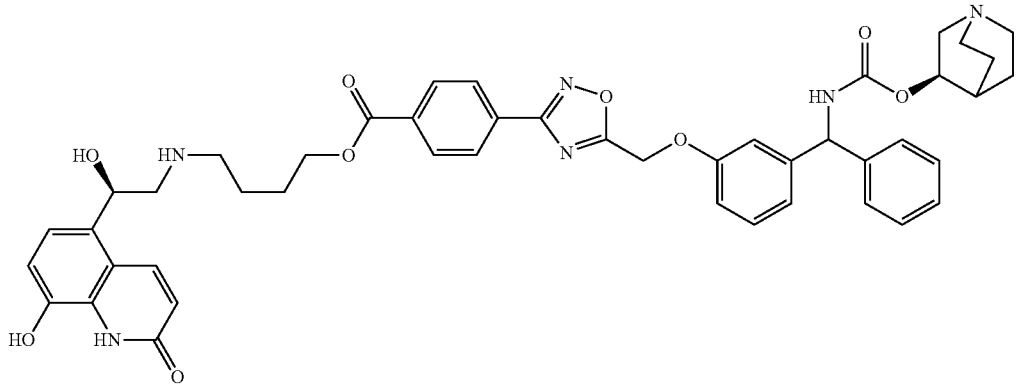 [SMILES: O=C(NC(c1ccccc1)c1cccc(OCc2nc(-c3ccc(C(=O)OCCCCNC[C@H](O)c4ccc(O)c5[nH]c(=O)ccc45)cc3)no2)c1)O[C@H]1CN2CCC1CC2]

The title compound was prepared using Step 5, 6 and 7 of Example 1.

Chiral Example 15

4-(((R)-2-Hydroxy-2-(8-hydroxy-2-oxo-1,2-dihydroquinolin-5-yl)ethyl)amino)butyl 4-((4-((3-(phenyl((((R)-quinuclidin-3-yloxy)carbonyl)amino)-methyl)phenoxy)methyl)piperidin-1-yl)methyl)benzoate (Compound 78C)

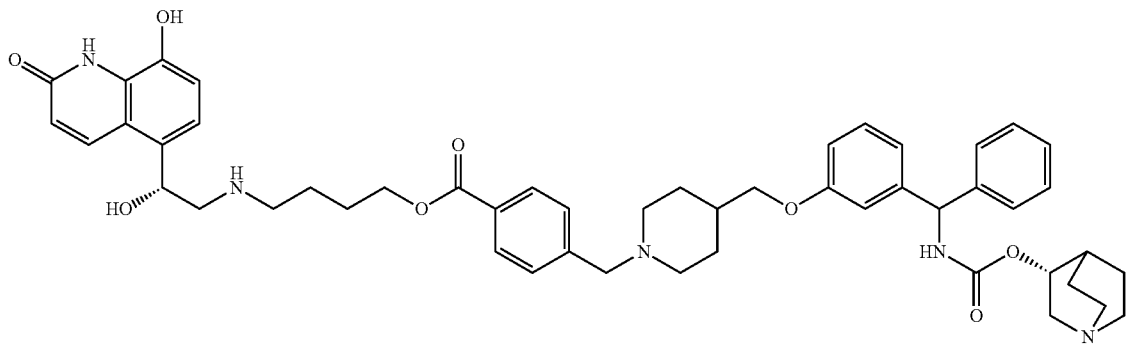 [SMILES: O=C(NC(c1ccccc1)c1cccc(OCC2CCN(Cc3ccc(C(=O)OCCCCNC[C@H](O)c4ccc(O)c5[nH]c(=O)ccc45)cc3)CC2)c1)O[C@H]1CN2CCC1CC2]

Step 1. Benzyl 4-((3-(((tert-butoxycarbonyl)amino)(phenyl)methyl)phenoxy)methyl)-piperidine-1-carboxylate

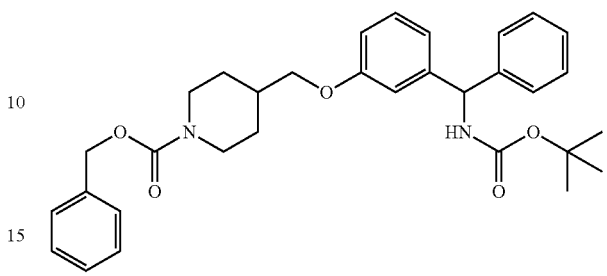

To a stirred solution of tert-butyl(3-hydroxyphenyl)(phenyl)methylcarbamate. (the second eluting isomer from Chiral Example 1 Step 4, 1.00 g, 3.34 mmol) in DMF (15 mL), was added potassium carbonate (0.554 g, 4.01 mmol). The reaction mixture was stirred for 10 minutes, and benzyl 4-((tosyloxy)methyl)piperidine-1-carboxylate (prepared according to Bioorganic & Medicinal Chemistry Letters, 20(1), 380-382; 2010, which is incorporated herein by reference in its entirety, 1.48 g, 3.67 mmol) added. The reaction mixture was heated at 60° C. for 2 days followed by 80° C. for 5 days. The reaction mixture was diluted with ethyl acetate and washed with water and saturated brine (×2). The organic phase was dried with anhydrous magnesium sulfate, and the solvent evaporated at reduced pressure. The crude material was purified by silica gel chromatography eluting with 100% isohexane to 50% ethyl acetate in iso-hexane to afford the title compound (1.12 g, 63%).

¹H NMR (400 MHz, CDCl₃): δ 7.40-7.18 (m, 11H); 6.82 (d, J=7.7 Hz, 1H); 6.79-6.73 (m, 2H); 5.86 (s, 1H); 5.13 (s, 3H); 4.23 (s, 2H); 3.76 (d, J=6.3 Hz, 2H); 2.81 (m, 2H); 1.99-1.89 (m, 1H); 1.82 (d, J=13.1 Hz, 2H); 1.44 (s, 9H); 1.33-1.22 (m, 2H).

Step 2. tert-Butyl(phenyl(3-(piperidin-4-ylmethoxy)phenyl)methyl)carbamate

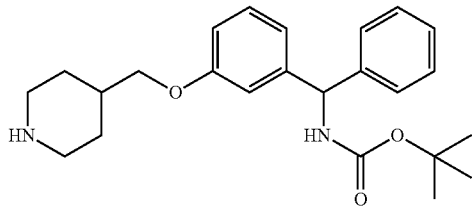 [SMILES: CC(C)(C)OC(=O)NC(c1ccccc1)c1cccc(OCC2CCNCC2)c1]

To a stirred solution of benzyl 4-((3-(((tert-butoxycarbonyl)amino)(phenyl)-methyl)phenoxy)methyl)piperidine-1-carboxylate (1.12 g, 2.11 mmol) in ethanol (10 mL), was added 10% palladium on charcoal (0.22 g) and 1-methyl1,4-cyclohexadiene (1.18 mL, 10.55 mmol). The reaction mixture was heated to 80° C. for 7 hours. The reaction mixture was filtered through a pad of celite, and the filter-pad washed with further ethanol. The filtrate was evaporated at reduced pressure to afford the title compound (0.716 g, 85%).

¹H NMR (400 MHz, CDCl₃): δ 7.38-7.17 (m, 6H); 6.82-6.73 (m, 3H); 5.86 (s, 1H); 5.15 (s, 1H); 3.78-3.68 (m, 2H); 3.13 (d, J=12.3 Hz, 2H); 2.65 (td, J=12.1, 2.5 Hz, 2H); 1.96-1.78 (m, 5H); 1.33-1.18 (m, 9H) (no exchangeable observed)

Step 3. 3-(1,3-Dioxolan-2-yl)propyl 4-((4-((3-(((tert-butoxycarbonyl)amino)(phenyl)-methyl)phenoxy)methyl)piperidin-1-yl)methyl)benzoate

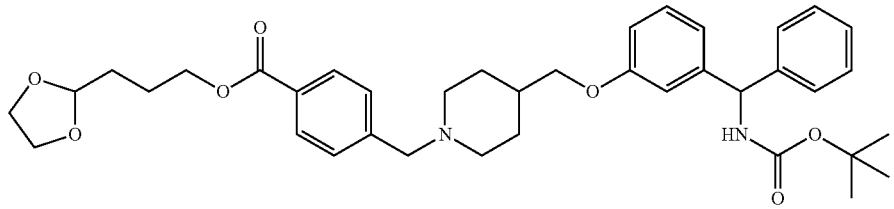 [SMILES: CC(C)(C)OC(=O)NC(c1ccccc1)c1cccc(OCC2CCN(Cc3ccc(C(=O)OCCCC4OCCO4)cc3)CC2)c1]

To a stirred solution of tert-butyl(phenyl(3-(piperidin-4-ylmethoxy)phenyl)-methyl)carbamate (0.335 g, 0.84 mmol) and 3-(1,3-dioxolan-2-yl)propyl 4-formylbenzoate (0.706 g, 2.67 mmol) in DCM (5 mL), was added sodium triacetoxyborohydride (0.213 g, 1.01 mmol). The reaction mixture was stirred at room temperature for 18 hours. The reaction mixture was diluted with DCM and washed with water, saturated aqueous sodium hydrogen carbonate, and brine. The organic phase was dried with anhydrous magnesium sulfate, and the solvent evaporated at reduced pressure. The residue was triturated with iso-hexane/diethyl ether (3:1) to afford the title compound (0.286 g, 0.44 mmol).

¹H NMR (400 MHz, CDCl₃): δ 7.98 (d, J=8.0 Hz, 2H); 7.39 (d, J=8.0 Hz, 2H); 7.35-7.16 (m, 6H); 6.83-6.73 (m, 3H); 5.86 (s, 1H); 5.13 (s, 1H); 4.96-4.91 (m, 1H); 4.40-4.32 (m, 2H); 4.00-3.95 (m, 2H); 3.90-3.84 (m, 2H); 3.76 (d, J=5.8 Hz, 2H); 3.55 (s, 2H); 2.89 (d, J=11.1 Hz, 2H); 2.05-1.97 (m, 2H); 1.97-1.77 (m, 7H); 1.63-1.19 (m, 11H).

Step 4. 4-(((R)-2-Hydroxy-2-(8-hydroxy-2-oxo-1,2-dihydroquinolin-5-yl)ethyl)amino)-butyl 4-((4-((3-(phenyl((((R)-quinuclidin-3-yloxy)carbonyl)amino)methyl)phenoxy)-methyl)piperidin-1-yl)methyl)benzoate (Compound 78C)

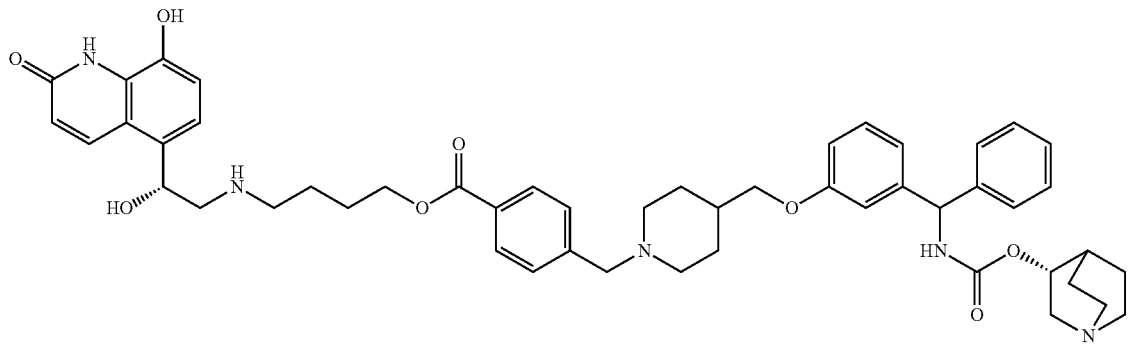 [SMILES: O=C(NC(c1ccccc1)c1cccc(OCC2CCN(Cc3ccc(C(=O)OCCCCNC[C@H](O)c4ccc(O)c5[nH]c(=O)ccc45)cc3)CC2)c1)O[C@H]1CN2CCC1CC2]

The title compound was prepared as described in Chiral Example 5 Step 3 and 4.

The following compounds were prepared as described above using the first eluting isomer of tert-butyl(3-hydroxyphenyl)(phenyl)methylcarbamate (Chiral Example 1 Step 4).

Chiral Example 16

2-(4-(((R)-2-Hydroxy-2-(8-hydroxy-2-oxo-1,2-dihydroquinolin-5-yl)ethyl)amino)butoxy)ethyl 4-((3-(phenyl((((R)-quinuclidin-3-yloxy)carbonyl)amino)methyl)phenoxy)methyl)benzoate (Compound 79C)

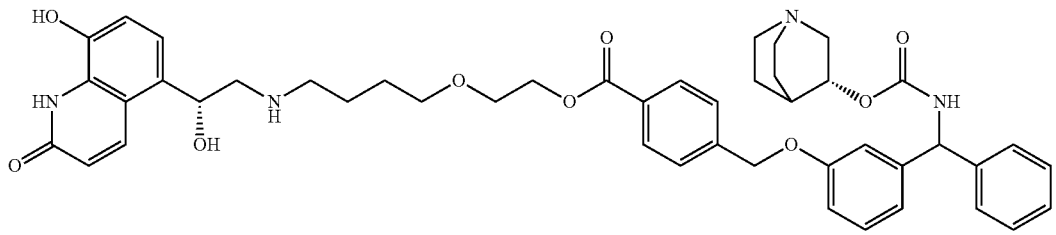 [SMILES: O=C(NC(c1ccccc1)c1cccc(OCc2ccc(C(=O)OCCOCCCCNC[C@H](O)c3ccc(O)c4[nH]c(=O)ccc34)cc2)c1)O[C@H]1CN2CCC1CC2]

The title compound was prepared as described for Compound 73C using the first eluting isomer of tert-butyl(3-hydroxyphenyl)(phenyl)methylcarbamate.

Chiral Example 17

4-(2-(((R)-2-Hydroxy-2-(8-hydroxy-2-oxo-1,2-dihydroquinolin-5-yl)ethyl)amino)ethyl)benzyl 4-((3-(phenyl((((R)-quinuclidin-3-yloxy)carbonyl)amino)methyl)phenoxy)methyl)benzoate (Compound 80C)

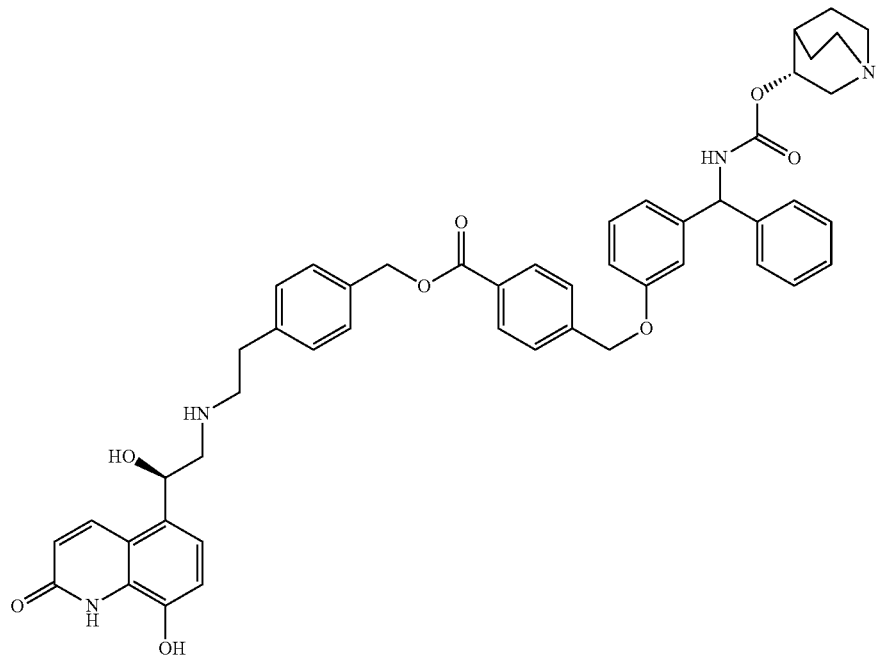 [SMILES: O=C(NC(c1ccccc1)c1cccc(OCc2ccc(C(=O)OCc3ccc(CCNC[C@H](O)c4ccc(O)c5[nH]c(=O)ccc45)cc3)cc2)c1)O[C@H]1CN2CCC1CC2]

The title compound was prepared as described for Compound 8C using the first eluting isomer of tert-butyl(3-hydroxyphenyl)(phenyl)methylcarbamate.

Chiral Example 18

2-(2-(((R)-2-Hydroxy-2-(8-hydroxy-2-oxo-1,2-dihydroquinolin-5-yl)ethyl)amino)ethoxy)ethyl 4-((3-(phenyl((((R)-quinuclidin-3-yloxy)carbonyl)amino)-methyl)phenoxy)methyl)benzoate (Compound 81C)

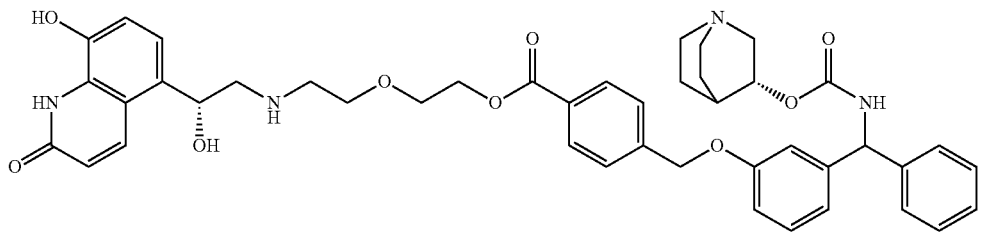 [SMILES: O=C(NC(c1ccccc1)c1cccc(OCc2ccc(C(=O)OCCOCCNC[C@H](O)c3ccc(O)c4[nH]c(=O)ccc34)cc2)c1)O[C@H]1CN2CCC1CC2]

The title compound was prepared as described for Compound 72C using the first eluting isomer of tert-butyl(3-hydroxyphenyl)(phenyl)methylcarbamate.

Chiral Example 19

4-(((R)-2-Hydroxy-2-(8-hydroxy-2-oxo-1,2-dihydroquinolin-5-yl)ethyl)amino)butyl 2-chloro-4-((3-(phenyl((((R)-quinuclidin-3-yloxy)carbonyl)amino)-methyl)phenoxy)methyl)benzoate (Compound 82C)

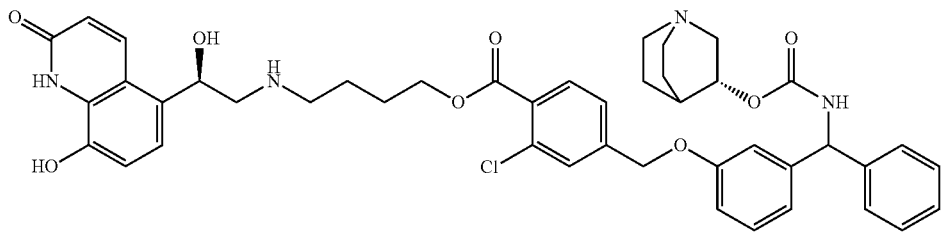 [SMILES: O=C(NC(c1ccccc1)c1cccc(OCc2ccc(C(=O)OCCCCNC[C@H](O)c3ccc(O)c4[nH]c(=O)ccc34)c(Cl)c2)c1)O[C@H]1CN2CCC1CC2]

The title compound was prepared as described for Compound 47C using the first eluting isomer of tert-butyl(3-hydroxyphenyl)(phenyl)methylcarbamate.

Chiral Example 20

4-(((R)-2-Hydroxy-2-(8-hydroxy-2-oxo-1,2-dihydroquinolin-5-yl)ethyl)amino)butyl 2-fluoro-4-((3-(phenyl((((R)-quinuclidin-3-yloxy)carbonyl)amino)-methyl)phenoxy)methyl)benzoate (Compound 83C)

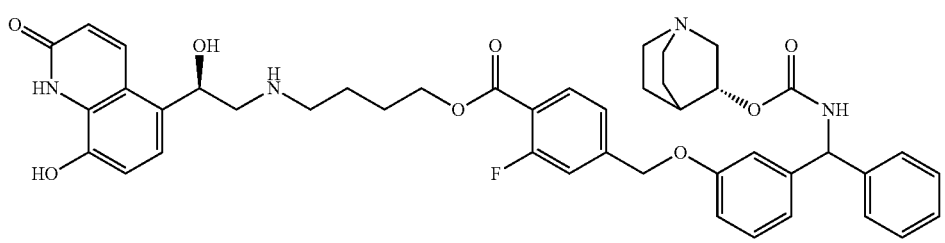 [SMILES: O=C(NC(c1ccccc1)c1cccc(OCc2ccc(C(=O)OCCCCNC[C@H](O)c3ccc(O)c4[nH]c(=O)ccc34)c(F)c2)c1)O[C@H]1CN2CCC1CC2]

The title compound was prepared as described for Compound 48C using the first eluting isomer of tert-butyl(3-hydroxyphenyl)(phenyl)methylcarbamate.

Properties of certain compounds according to the present invention are shown in the following table

| Compound | LCMS/HPLC method | NMR data at 400 MHz | Salt |
|---|---|---|---|
| 1 | B | (CD$_3$OD): δ 8.54 (s, 2 H); 8.37 (d, J = 9.88 Hz, 1 H); 7.36-7.18 (m, 7 H); 7.02 (d, J = 8.16 Hz, 1 H); 6.83-6.77 (m, 2 H); 6.68 (d, J = 9.88 Hz, 1 H); 5.86 (s, 1 H); 5.37 (dd, J = 7.81, 5.61 Hz, 1 H); 3.93 (t, J = 6.36 Hz, 2 H); 3.43 (d, J = 11.82 Hz, 1 H); 3.23-3.04 (m, 3 H); 3.06-2.93 (m, 7 H); 2.19 (s, 1 H); 2.09 (s, 1 H); 1.88 (s, 1 H); 1.78-1.66 (m, 8 H); 1.46 (s, 3 H); 1.38 (s, 9 H) | diformate |
| 2 | B | (CD$_3$OD): δ 8.56 (s, 2 H); 8.45-8.36 (m, 1 H); 7.38-7.20 (m, 7 H); 7.05 (d, J = 8.16 Hz, 1 H); 6.89-6.78 (m, 3 H); 6.70 (d, J = 9.84 Hz, 1 H); 5.88 (s, 1 H); 5.45-5.36 (m, 1 H); 4.90 (m, 1H, obscured by solvent); 3.95 (t, J = 6.34 Hz, 2 H); 3.59 (m, 1 H), 3.3-2.99 (m, 9 H), 2.30 (s, 1 H); 2.16 (s, 1 H); 2.03-1.69 (m, 7 H); 1.58-1.39 (m, 8 H) | diformate |
| 3 | B | (CD$_3$OD): δ 8.56 (s, 2 H); 8.40 (d, 1 H); 7.37-7.20 (m, 7 H); 7.04 (d, J = 8.16 Hz, 1 H); 6.89-6.78 (m, 3 H); 6.72 (d, 1 H); 5.88 (s, 1 H); 5.39 (t, J = 6.73 Hz, 1 H); 4.90 (m, 1H, obscured by solvent); 3.96 (t, J = 6.30 Hz, 2 H); 3.51 (m, 1 H); 3.22-2.98 (m, 9 H); 2.25 (s, 1 H); 2.13 (s, 1 H); 1.99-1.64 (m, 7 H); 1.59-1.41 (m, 6 H) | diformate |
| 4 | B | (CD$_3$OD): δ 8.54 (s, 2H); 8.40 (d, J = 9.6 Hz, 1H); 7.36-7.23 (m, 7H), 7.05 (d, J = 8 Hz, 1H), 6.88-6.82 (m, 3H), 6.76 (d, J = 9.6 Hz, 1H), 5.88 (br s, 1H), 5.41-5.38 (m, 1H), 4.88 (m, 1H), 3.99-3.96 (m, 2H), 3.58 (m, 1H), 3.27-3.06 (m, 9H), 2.29 (br s, 1H), 2.17 (m, 1H), 1.98-1.73 (m, 6H), 1.60-1.45 (m, 5H) | diformate |
| 5 | B | (DMSO-d$_6$): δ 8.32 (s, 2H), 8.27-8.25 (m, 1H), 8.21 (d, J = 10 Hz, 1H), 7.33-7.29 (m, 4H), 7.24-7.20 (m, 2H), 7.12 (d, J = 8.4 Hz, 1H), 6.98-6.90 (m, 3H), 6.80 (d, J = 8.0 Hz, 1H), 6.55 (d, J = 10 Hz, 1H), 5.82 (d, J = 8.8 Hz, 1H), 5.24-5.21 (m, 1H), 4.59 (br s, 1H), 3.94-3.91 (m, 2H), 3.13 (m, 1H), 2.91-2.33 (m, 8H), 1.93-1.39 (m, 12H) | diformate |
| 6 | B | (CD$_3$OD): δ 8.53 (s, 1 H), 8.38 (d, J = 9.87 Hz, 1 H), 7.45-7.21 (m, 12 H), 7.05 (d, J = 8.17 Hz, 1 H), 6.81 (s, 3 H), 6.70 (d, J = 9.84 Hz, 1 H), 5.86 (s, 1 H), 5.40 (t, J = 6.76 Hz, 1 H), 4.72 (s, 1 H), 3.95 (s, 2 H), 3.78 (s, 1 H), 3.26-3.20 (m, 2 H), 3.07 (t, J = 7.98 Hz, 2 H), 2.94 (s, 1 H), 2.60 (s, 2 H), 1.99 (s, 4 H), 1.84-1.71 (m, 6 H), 1.54-1.30 (s, 10 H). | formate |
| 7 | B | (DMSO-d$_6$): δ 8.32 (s, 1 H); 8.20 (t, J = 9.75 Hz, 2 H); 7.35-7.26 (m, 4 H); 7.25-7.16 (m, 2 H); 7.11 (d, J = 8.17 Hz, 1 H); 6.96 (d, J = 8.14 Hz, 1 H); 6.93-6.85 (m, 2 H); 6.77 (dd, J = 8.21, 2.42 Hz, 1 H); 6.53 (d, J = 9.86 Hz, 1 H); 5.81 (d, J = 9.40 Hz, 1 H); 5.21 (dd, J = 8.51, 4.13 Hz, 1 H); 4.51 (m, 1 H); 3.91 (t, J = 6.48 Hz, 2 H); 2.94-2.85 (m, 2 H); 2.79-2.72 (m, 2 H); 2.61 (s, 2 H); 2.24-1.97 (m, 5 H); 1.81 (s, 2 H); 1.72-1.62 (m, 2 H); 1.61-1.45 (m, 4 H); 1.44-1.14 (m, 10H) | formate |
| 8 | A | (DMSO-d$_6$): δ 8.35 (s, 1 H); 8.19 (d, J = 9.86 Hz, 2 H); 7.37-7.15 (m, 10 H); 7.10 (d, J = 8.15 Hz, 1 H); 6.96 (d, J = 8.13 Hz, 1 H); 6.92-6.83 (m, 2 H); 6.77 (dd, J = 8.20, 2.50 Hz, 1 H); 6.52 (d, J = 9.84 Hz, 1 H); 5.79 (d, J = 9.39 Hz, 1 H); 5.18 (m, 1 H); 4.81 (m, 1 H); 3.91 (t, J = 6.50 Hz, 2 H); 3.54 (s, 2 H); 3.15 (d, J = 5.01 Hz, 2 H); 2.84 (m, 1 H); 2.73-2.65 (m, 1 H); 1.95 (s, 2 H); 1.79 (s, 2 H); 1.71-1.52 (m, 7 H); 1.49-1.21 (m, 13 H). | formate |
| 9 | B | (CD$_3$OD): δ 8.55 (s, 2 H); 8.36 (d, J = 9.84 Hz, 1 H); 7.34-7.21 (m, 6 H); 7.14 (s, 3 H); 7.01 (d, J = 8.24 Hz, 1 H); 6.85 (d, J = 8.24 Hz, 2 H); 6.67 (d, J = 9.82 Hz, 1 H); 5.84 (s, 1 H); 5.39-5.32 (m, 1 H); 3.93 (t, J = 3.20 Hz, 2 H); 3.46-3.29 (m, 1 H); 3.19-3.14 (m, 2 H); 3.11-2.87 (m, 8 H); 2.17 (s, 1 H); 2.07 (s, 1 H); 1.86 (s, 1 H); 1.77-1.66 (m, 7 H); 1.47 (s, 3 H); 1.38 (s, 9 H). | formate |
| 10 | A | (CD$_3$OD): δ 8.39 (d, J = 9.83 Hz, 1 H); 7.34-7.17 (m, 3 H); 6.97-6.92 (m, 4 H); 6.90-6.80 (m, 2 H); 6.65 (d, J = 9.79 Hz, 1 H); 6.07 (s, 1 H); 5.25 (dd, J = 9.11, 3.86 Hz, 1 H); 4.74 (d, J = 7.36 Hz, 1 H); 3.97 (t, J = 6.39 Hz, 2 H); 3.28-3.14 (m, 1 H); 3.03-2.63 (m, 9 H); 2.12-1.88 (m, 2 H); 1.84-1.70 (m, 3 H); 1.67-1.4 (m, 14 H) | none |
| 11 | B | (DMSO-d$_6$): δ 8.34 (s, 1 H); 8.28 (d, J = 9.65 Hz, 1 H); 8.18 (d, J = 9.93 Hz, 1 H); 7.62 (t, J = 8.73 Hz, 4 H); 7.49-7.39 (m, 4 H); 7.35 (t, J = 7.35 Hz, 1 H); 7.23 (t, J = 7.90 Hz, 1 H); 7.10 (d, J = 8.16 Hz, 1 H); 6.95 (d, J = 8.34 Hz, 3 H); 6.79 (d, J = 8.37 Hz, 1 H); 6.52 (d, J = 9.86 Hz, 1 H); 5.86 (d, J = 9.33 Hz, 1 H); 5.17 (t, J = 6.14 Hz, 1 H); 4.59 (s, 1 H); 3.93 (t, J = 6.49 Hz, 2 H); 3.16-3.05 (m, 1 H); 2.86-2.81 (m, 2 H); 2.81-2.37 (m, 6 H); 1.92 (s, 1 H); 1.81 (s, 1 H); 1.74-1.11 (m, 18 H) | formate |
| 12 | A | (DMSO-d$_6$): δ 8.35 (s, 2 H); 8.19 (d, J = 9.93 Hz, 1 H); 7.89-7.83 (m, 4 H); 7.54-7.45 (m, 3 H); 7.22 (t, J = 7.90 Hz, 1 H); 7.11 (d, J = 8.18 Hz, 1 H); 6.97 (d, J = 8.27 Hz, 3 H); 6.79 (d, J = 8.34 Hz, 1 H); 6.53 (d, J = 9.86 Hz, 1 H); 5.98 (s, 1 H); 5.22 (dd, J = 8.73, 4.00 Hz, 1 H); 4.61 (s, 1 H); 3.91 (t, J = 6.46 Hz, 2 H); 3.12 (m, 1 H); 2.94-2.81 (m, 2 H); 2.81-2.54 (m, 4 H); 1.93 (s, 1 H); 1.81 (s, 1 H); 1.73-1.1 (m, 20 H) | formate |

| Compound | LCMS/HPLC method | NMR data at 400 MHz | Salt |
|---|---|---|---|
| 13 | A | (DMSO-d$_6$): δ 8.29 (d, J = 9.64 Hz, 1 H); 8.17 (d, J = 9.92 Hz, 1 H); 7.72-7.59 (m, 3 H); 7.52 (dd, J = 7.65, 1.84 Hz, 1 H); 7.48-7.31 (m, 5 H); 7.21 (t, J = 7.87 Hz, 1 H); 7.07 (d, J = 8.15 Hz, 1 H); 6.99-6.88 (m, 3 H); 6.77 (d, J = 8.21 Hz, 1 H); 6.50 (d, J = 9.86 Hz, 1 H); 5.89 (d, J = 9.31 Hz, 1 H); 5.03 (dd, J = 7.83, 4.59 Hz, 1 H); 4.57 (s, 1 H); 3.92 (t, J = 6.46 Hz, 2 H); 3.08 (s, 1 H); 2.78-2.54 (m, 6 H); 1.90 (s, 1 H); 1.80 (s, 1 H); 1.72-1.61 (m, 2 H); 1.57 (s, 1 H); 1.51-1.19 (m, 17 H) | none |
| 14 | A | (DMSO-d$_6$): δ 8.51-8.48 (m, 1 H); 8.32 (s, 2 H); 8.19 (d, J = 9.9 Hz, 1 H); 8.10 (d, J = 9.1 Hz, 1 H); 7.80-7.73 (m, 1 H); 7.47 (d, J = 7.9 Hz, 1 H); 7.29-7.23 (m, 1 H); 7.19 (t, J = 7.9 Hz, 1 H); 7.10 (d, J = 8.2 Hz, 1 H); 6.99-6.87 (m, 3 H); 6.78 (d, J = 8.4 Hz, 1 H); 6.52 (d, J = 9.9 Hz, 1 H); 5.85 (d, J = 9.1 Hz, 1 H); 5.17 (t, J = 6.1 Hz, 1 H); 4.57 (m, 1 H); 3.91 (t, J = 6.8 Hz, 2 H); 3.16-3.04 (m, 1 H); 2.86-2.81 (m, 2 H); 2.79-2.38 (m, 4 H); 1.94-1.86 (m, 1 H); 1.86-1.73 (m, 1 H); 1.72-1.14 (m, 20 H) | diformate |
| 15 | B | (DMSO-d$_6$): δ 8.34-8.25 (m, 2 H); 8.18 (d, J = 9.9 Hz, 1 H); 7.23 (t, J = 7.9 Hz, 1 H); 7.16-7.06 (m, 4 H); 6.97-6.88 (m, 3 H); 6.81 (d, J = 8.3 Hz, 1 H); 6.52 (d, J = 9.9 Hz, 1 H); 5.86 (d, J = 9.2 Hz, 1 H); 5.15 (t, J = 6.3 Hz, 1 H); 4.62-4.55 (m, 1 H); 3.93 (t, J = 6.5 Hz, 2 H); 3.15-3.05 (m, 1 H); 2.83 (d, J = 6.3 Hz, 2 H); 2.80-2.44 (m, 4 H); 1.95-1.21 (m, 22 H). | formate |
| 16 | B | (DMSO-d$_6$): δ 8.32-8.24 (m, 2 H); 8.18 (d, J = 9.9 Hz, 1 H); 7.41-7.33 (m, 2 H); 7.23 (t, J = 7.9 Hz, 1 H); 7.09 (d, J = 8.2 Hz, 1 H); 6.97-6.87 (m, 3 H); 6.81 (d, J = 8.3 Hz, 1 H); 6.52 (d, J = 9.9 Hz, 1 H); 5.85 (d, J = 9.0 Hz, 1 H); 5.14 (t, J = 6.3 Hz, 1 H); 4.61-4.55 (m, 1 H); 3.92 (t, J = 6.5 Hz, 2 H); 3.14-3.05 (m, 1 H); 2.81 (d, J = 6.3 Hz, 2 H); 2.79-2.45 (m, 4 H); 1.93-1.21 (m, 22 H). | formate |
| 17 | B | (DMSO-d$_6$): δ 8.22-8.06 (m, 2 H); 7.22-7.13 (m, 5 H); 7.04 (d, J = 8.14 Hz, 1 H); 6.87 (d, J = 8.11 Hz, 1 H); 6.80 (d, J = 7.85 Hz, 3 H); 6.48 (d, J = 9.85 Hz, 1 H); 5.97 (d, J = 8.81 Hz, 1 H); 4.99 (dd, J = 7.96, 4.44 Hz, 1 H); 4.54 (d, J = 7.42 Hz, 1 H); 3.93-3.86 (m, 2 H); 3.10-2.99 (m, 1 H); 2.74-2.60 (m, 6 H); 2.27 (d, J = 6.69 Hz, 3 H); 1.88 (s, 1 H); 1.77 (d, J = 13.00 Hz, 1 H); 1.73-1.61 (m, 2 H); 1.56 (s, 2 H); 1.31 (d, J = 46.22 Hz, 16 H). | none |
| 18 | A | (DMSO-d$_6$): δ 8.17 (d, J = 9.87 Hz, 2 H); 7.23-7.10 (m, 4 H); 7.08-7.00 (m, 2 H); 6.92-6.85 (m, 3 H); 6.77 (d, J = 8.40 Hz, 1 H); 6.49 (d, J = 9.86 Hz, 1 H); 5.75 (d, J = 9.21 Hz, 1 H); 5.00 (dd, J = 7.96, 4.49 Hz, 1 H); 4.55 (s, 1 H); 3.94-3.87 (m, 2 H); 3.07 (t, J = 10.34 Hz, 1 H); 2.74-2.60 (m, 6 H); 2.26 (s, 3 H); 1.88 (s, 1 H); 1.78 (s, 1 H); 1.73-1.61 (m, 2 H); 1.56 (s, 1 H); 1.31 (d, J = 46.94 Hz, 17 H) | none |
| 19 | A | (DMSO-d$_6$): δ 8.21-8.10 (m, 2 H); 7.23-7.15 (m, 3 H); 7.11 (d, J = 7.79 Hz, 2 H); 7.05 (d, J = 8.15 Hz, 1 H); 6.92-6.84 (m, 3 H); 6.77 (d, J = 8.32 Hz, 1 H); 6.49 (d, J = 9.86 Hz, 1 H); 5.76 (d, J = 9.15 Hz, 1 H); 5.00 (d, J = 7.91, 4.48 Hz, 1 H); 4.55 (s, 1 H); 3.94-3.87 (m, 2 H); 3.06 (s, 1 H); 2.73-2.60 (m, 6 H); 2.25 (s, 3 H); 1.88 (s, 1 H); 1.78 (s, 1 H); 1.73-1.61 (m, 2 H); 1.56 (s, 1 H); 1.57-1.14 (m, 17 H). | none |
| 20 | B | (DMSO-d$_6$): δ 8.31 (s, 2 H); 8.27-8.15 (m, 2 H); 7.41-7.31 (m, 2 H); 7.24-7.07 (m, 4 H); 6.98-6.84 (m, 3 H); 6.81-6.75 (m, 1 H); 6.53 (d, J = 9.9 Hz, 1 H); 5.82 (d, J = 9.3 Hz, 1 H); 5.22-5.16 (m, 1 H); 4.62-4.54 (m, 1 H); 3.91 (t, J = 6.5 Hz, 2 H); 3.15-3.06 (m, 1 H); 2.92-2.81 (m, 2 H); 2.80-2.45 (m, 4 H); 1.94-1.20 (m, 22 H). | diformate |
| 1B | A | (DMSO-d$_6$): δ 8.25 (d, J = 9.8 Hz, 1 H); 8.17 (d, J = 9.9 Hz, 1 H); 7.40-7.32 (m, 1 H); 7.25-7.15 (m, 3 H); 7.09-7.02 (m, 2 H); 6.96-6.87 (m, 3 H); 6.82-6.77 (m, 1 H); 6.49 (d, J = 9.9 Hz, 1 H); 5.84 (d, J = 9.0 Hz, 1 H); 5.00 (dd, J = 7.9, 4.5 Hz, 1 H); 4.60-4.53 (m, 1 H); 3.92 (t, J = 6.5 Hz, 2 H); 3.12-3.02 (m, 1 H); 2.77-2.53 (m, 6H); 1.92-1.20 (m, 22 H) | none |
| 2B | B | (DMSO-d$_6$): δ 8.33-8.26 (m, 3 H); 8.18 (d, J = 9.9 Hz, 1 H); 7.42 (s, 1 H); 7.38-7.27 (m, 3 H); 7.22 (t, J = 8.0 Hz, 1 H); 7.10 (d, J = 8.2 Hz, 1 H); 6.98-6.87 (m, 3 H); 6.82-6.77 (m, 1 H); 6.53 (d, J = 9.9 Hz, 1 H); 5.84 (d, J = 9.2 Hz, 1 H); 5.18 (dd, J = 8.0, 4.6 Hz, 1 H); 4.62-4.55 (m, 1 H); 3.92 (t, J = 6.6 Hz, 2 H); 3.16-3.06 (m, 1 H); 2.90-2.83 (m, 2 H); 2.80-2.52 (m, 6 H); 1.94-1.22 (m, 20 H). | diformate |
| 1C | C | (DMSO-d$_6$ @105° C.): δ 8.21-8.10 (m, 3 H); 7.19-7.11 (m, 1 H); 7.06 (d, J = 8.2 Hz, 1 H); 6.97-6.89 (m, 2 H); 6.86-6.77 (m, 2 H); 6.74 (d, J = 8.2 Hz, 1 H); 6.46 (d, J = 9.9 Hz, 1 H); 5.04-4.96 (m, 1 H); 4.55-4.47 (m, 1 H); 4.28-4.18 (m, 1 H); 3.99-3.89 (m, 2 H); 3.07-2.97 (m, 1 H); 2.81-2.50 (m, 8 H); 1.88-0.79 (m, 31 H). | diformate |
| 2C | C | (DMSO-d6): δ 8.38 (d, J = 9.86 Hz, 1 H); 8.31 (s, 1 H); 8.19 (d, J = 9.93 Hz, 1 H); 7.41-7.38 (m, 1 H); 7.29-7.20 (m, 1 H); 7.11 (d, J = 8.16 Hz, 1 H); 7.02-6.89 (m, 4 H); 6.87-6.79 (m, 2 H); 6.53 (d, J = 9.85 Hz, 1 H); 6.00 (d, J = 8.88 Hz, 1 H); 5.19 (dd, J = 8.24, 4.47 Hz, 1 H); 4.60 (s, 1 H); 3.97-3.90 (m, 2 H); 3.12 (d, J = 13.06 Hz, 1 H); 2.87 (d, J = 8.12 Hz, 2 H); 2.80-2.49 (m, 6 H); 1.99-1.86 (m, 1 H); 1.8-1.3 (m, 13 H). | formate |
| 3C | B | (DMSO-d6): δ 8.30 (s, 2 H); 8.26-8.15 (m, 2 H); 7.46 (dd, J = 5.00, 2.93 Hz, 1 H); 7.30 (s, 1 H); 7.26-7.18 (m, 1 H); 7.12 (d, J = 8.17 Hz, 1 H); 7.07-7.03 (m, 1 H); 6.94 (dd, J = 19.65, 8.17 Hz, 3 H); 6.79 (d, J = 8.29 Hz, 1 H); 6.54 (d, J = 9.85 Hz, 1 H); 5.86 (d, J = 8.02 Hz, 1 H); 5.23 (dd, J = 8.83, 3.83 Hz, 1 H); 4.60 (s, 1 H); 3.96-3.90 (m, 2 H); 3.14 (s, 1 H); 2.99-2.83 (m, 2 H); 2.87-2.44 (m, 6 H); 1.92 (s, 1 H); 1.80 (s, 1 H); 1.72-1.31 (m, 12 H). | diformate |

-continued

| Compound | LCMS/HPLC method | NMR data at 400 MHz | Salt |
|---|---|---|---|
| 21 | A | (DMSO-$d_6$): δ 8.20 (br s, 1H), 7.34-7.18 (m, 6H), 6.92-6.88 (m, 2H), 6.79 (d, J = 8.4 Hz, 1H), 6.68 (d, J = 8.4 Hz, 1H), 5.80 (br s, 1H), 4.57-4.55 (m, 1H), 3.93-3.90 (m, 2H), 3.10-3.05 (m, 1H), 2.72-2.68 (m, 3H), 2.60-2.50 (m, 8H), 1.88 (s, 1H), 1.71-1.67 (m, 2H), 1.64 (br s, 1H), 1.57-1.25 (m, 15H) | none |
| 22 | A | (DMSO-$d_6$): δ 8.29-8.21 (m, 2 H); 8.18 (d, J = 9.9 Hz, 1 H); 7.37-7.27 (m, 6 H); 7.26-7.18 (m, 4 H); 7.09 (d, J = 8.2 Hz, 1 H); 7.01 (s, 1 H); 6.97-6.84 (m, 3 H); 6.52 (d, J = 9.9 Hz, 1 H); 5.82 (d, J = 9.3 Hz, 1 H); 5.12 (t, J = 6.3 Hz, 1 H); 5.02 (s, 2 H); 4.63-4.56 (m, 1 H); 3.19-3.09 (m, 1 H); 2.97-2.52 (m, 11 H); 1.96-1.74 (m, 2 H); 1.67-1.30 (m, 3 H). | formate |
| 23 | B | (DMSO-$d_6$): δ 8.30-8.21 (m, 3 H); 8.17 (d, J = 9.9 Hz, 1 H); 7.35-7.13 (m, 8 H); 7.08 (d, J = 8.0 Hz, 2 H); 6.94 (d, J = 8.1 Hz, 1 H); 6.51 (d, J = 9.9 Hz, 1 H); 5.82 (d, J = 9.3 Hz, 1 H); 5.13 (t, J = 6.3 Hz, 1 H); 4.63-4.55 (m, 1 H); 3.18-3.09 (m, 1 H); 2.95-2.52 (m, 11 H); 1.96-1.75 (m, 2 H); 1.65-1.28 (m, 3 H). | diformate |
| 24 | A | (DMSO-$d_6$): δ 8.60 (br d, J = 8.8 Hz, 1H), 8.48 (s, 1H), 8.18-8.16 (m, 1H), 7.99-7.97 (m, 2H), 7.75-7.74 (m, 1H), 7.63-7.58 (m, 2H), 7.37-7.32 (m, 4H), 7.27-7.21 (m, 2H), 7.06-7.04 (m, 1H), 6.96-6.89 (m, 3H), 6.82-6.80 (m, 1H), 6.49-6.47 (m, 1H), 5.85 (br d, J = 8.8 Hz, 1H), 5.20 (br s, 2H), 5.04 (br m, 2H), 4.08 (m, 1H), 3.92 (t, J = 6 Hz, 2H), 3.75-3.69 (m, 3H), 3.44 (m, 2H), 2.72-2.67 (m, 2H), 2.56-2.51 (m, 2H), 2.34-2.33 (m, 1H), 2.20 (m, 1H), 2.09-1.98 (m, 3H), 1.69-1.66 (m, 2H), 1.44-1.30 (m, 6H) | formate |
| 3B | A | (DMSO-$d_6$): δ 8.30-8.22 (m, 2 H); 8.18 (d, J = 9.9 Hz, 1 H); 7.38-7.14 (m, 10 H); 7.10-7.00 (m, 2 H); 6.97-6.86 (m, 3 H); 6.51 (d, J = 9.9 Hz, 1 H); 5.82 (d, J = 8.8 Hz, 1 H); 5.10 (t, J = 6.3 Hz, 1 H); 5.02 (s, 2 H); 4.62-4.54 (m, 1 H); 3.17-3.07 (m, 1 H); 2.95-2.52 (m, 11 H); 1.95-1.74 (m, 2 H); 1.66-1.28 (m, 3 H). | formate |
| 4B | B | (DMSO-$d_6$): δ 8.58 (dd, J = 9.2, 4.7 Hz, 1 H); 8.40 (s, 2 H); 8.17 (dd, J = 9.9, 1.7 Hz, 1 H); 7.97 (t, J = 7.5 Hz, 2 H); 7.75 (q, J = 6.8 Hz, 1 H); 7.60 (q, J = 8.0 Hz, 2 H); 7.40-7.16 (m, 10 H); 7.07-7.00 (m, 2 H); 6.97-6.87 (m, 3 H); 6.49 (dd, J = 9.9, 1.8 Hz, 1 H); 5.87-5.82 (m, 1 H); 5.22-5.14 (m, 2 H); 5.07-4.99 (m, 4 H); 4.13-4.04 (m, 1 H); 3.79-3.53 (m, 5 H); 2.85-2.66 (m, 6 H); 2.38-2.31 (m, 1 H); 2.24-2.13 (m, 1 H); 2.10-1.91 (m, 3 H). | diformate |
| 5B | A | (DMSO-$d_6$): δ 8.61 (d, J = 9.2 Hz, 1 H); 8.42 (s, 2 H); 8.18 (d, J = 9.9 Hz, 1 H); 8.02-7.94 (m, 2 H); 7.79-7.71 (m, 1 H); 7.65-7.57 (m, 2 H); 7.44 (d, J = 10.5 Hz, 1 H); 7.40-7.29 (m, 3 H); 7.28-7.21 (m, 1 H); 7.06 (d, J = 8.1 Hz, 1 H); 6.99-6.89 (m, 3 H); 6.83 (d, J = 8.3 Hz, 1 H); 6.49 (d, J = 9.8 Hz, 1 H); 5.87 (d, J = 8.4 Hz, 1 H); 5.24-5.13 (m, 2 H); 5.11-5.00 (m, 2 H); 4.14-4.02 (m, 1 H); 3.93 (t, J = 7.1 Hz, 2 H); 3.80-3.65 (m, 4 H); 2.79-2.66 (m, 2 H); 2.65-2.54 (m, 2 H); 2.39-2.31 (m, 1 H); 2.24-2.12 (m, 1 H); 2.11-1.91 (m, 3 H); 1.73-1.62 (m, 2 H); 1.48-1.18 (m, 13 H). | diformate |
| 6B | A | (DMSO-d6): δ 8.59 (d, J = 8.87 Hz, 1 H); 8.43 (s, 2 H); 8.18 (d, J = 9.89 Hz, 1 H); 7.98 (d, J = 7.80 Hz, 2 H); 7.79-7.71 (m, 1 H); 7.65-7.57 (m, 2 H); 7.39-7.33 (m, 4 H); 7.27 (dd, J = 8.36, 5.16 Hz, 1 H); 7.15 (d, J = 10.12 Hz, 1 H); 7.09-7.01 (m, 2 H); 7.01-6.91 (m, 2 H); 6.49 (dd, J = 9.85, 1.23 Hz, 1 H); 5.86 (d, J = 8.44 Hz, 1 H); 5.19 (s, 2 H); 5.04 (d, J = 7.00 Hz, 2 H); 4.14-4.04 (m, 1 H); 3.98-3.91 (m, 2 H); 3.7-3.5 (m, 4 H); 2.74-2.64 (m, 2 H); 2.56 (d, J = 10.06 Hz, 2 H); 2.38-2.31 (m, 2 H); 2.19 (d, J = 17.51 Hz, 1 H); 2.09-1.92 (m, 3 H); 1.66 (d, J = 8.03 Hz, 2 H); 1.32 (d, J = 52.59 Hz, 12 H). | diformate |
| 7B | B | (DMSO-d6): δ 8.32 (s, 1 H); 8.27 (d, J = 9.28 Hz, 1 H); 8.18 (d, J = 9.93 Hz, 1 H); 7.35-7.21 (m, 6 H); 7.15-7.03 (m, 3 H); 6.95 (d, J = 8.13 Hz, 1 H); 6.53 (d, J = 9.86 Hz, 1 H); 6.23 (d, J = 8.86 Hz, 1 H); 5.18 (dd, J = 8.02, 4.59 Hz, 1 H); 4.56 (s, 1 H); 4.06-3.99 (m, 2 H); 3.14-3.03 (m, 1 H); 2.86 (d, J = 7.36 Hz, 2 H); 2.79-2.53 (m, 6 H); 1.94-1.85 (m, 1 H); 1.79-1.68 (m, 3 H); 1.76-1.13 (m, 16 H). | formate |
| 8B | A | (DMSO-d6): δ 8.32 (s, 1 H); 8.22-8.11 (m, 2 H); 7.35-7.24 (m, 5 H); 7.16-7.07 (m, 2 H); 7.06-6.96 (m, 1 H); 6.95 (d, J = 8.13 Hz, 1 H); 6.53 (d, J = 9.86 Hz, 1 H); 6.23 (d, J = 8.18 Hz, 1 H); 5.20-5.14 (m, 1 H); 4.59 (s, 1 H); 4.02-3.95 (m, 2 H); 3.14-3.04 (m, 1 H); 2.88-2.83 (m, 2 H); 2.78-2.53 (m, 6 H); 1.99-1.77 (m, 2 H); 1.72-1.63 (m, 2 H); 1.73-1.12 (m, 16 H). | formate |
| 9B | A | (DMSO-$d_6$): δ 8.34-8.24 (m, 3 H); 8.18 (d, J = 9.9 Hz, 1 H); 7.51-7.43 (m, 1 H); 7.37-7.19 (m, 5 H); 7.18-7.07 (m, 2 H); 6.96 (d, J = 8.1 Hz, 1 H); 6.83 (dd, J = 8.8, 2.9 Hz, 1 H); 6.53 (d, J = 9.9 Hz, 1 H); 6.16-6.07 (m, 1 H); 5.20 (dd, J = 8.4, 4.3 Hz, 1 H); 4.63-4.54 (m, 1 H); 3.94 (t, J = 6.5 Hz, 2 H); 3.19-3.04 (m, 1 H); 2.93-2.82 (m, 2 H); 2.81-2.53 (m, 6 H); 1.97-1.86 (m, 1 H); 1.85-1.08 (m, 19 H). | diformate |
| 10B | B | (DMSO-d6): δ 8.59 (dd, J = 8.88, 3.56 Hz, 1 H); 8.43 (s, 2 H); 8.18 (d, J = 9.92 Hz, 1 H); 8.01-7.94 (m, 2 H); 7.79-7.72 (m, 1 H); 7.61 (q, J = 6.64 Hz, 2 H); 7.39-7.21 (m, 6 H); 7.15-7.02 (m, 3 H); 6.95 (d, J = 8.10 Hz, 1 H); 6.49 (d, J = 9.83 Hz, 1 H); 6.28-6.20 (m, 1 H); 5.20 (d, J = 7.19 Hz, 2 H); 5.07-5.00 (m, 2 H); 4.09-4.00 (m, 3 H); 3.80-3.56 (m, 4 H); 2.72 (d, J = 7.37 Hz, 2 H); 2.6 (m, 2 H); 2.34 (m, 2 H); 2.2-1.9 (m, 4 H); 1.72 (d, J = 8.43 Hz, 2 H); 1.27 (t, J = 51.58 Hz, 12 H). | diformate |

| Compound | LCMS/ HPLC method | NMR data at 400 MHz | Salt |
|---|---|---|---|
| 11B | A | (DMSO-d6): δ 8.54-8.45 (m, 1 H); 8.42 (s, 2 H); 8.17 (d, J = 9.92 Hz, 1 H); 8.01-7.90 (m, 2 H); 7.75 (dd, J = 14.66, 7.33 Hz, 1 H); 7.67-7.56 (m, 2 H); 7.41-7.27 (m, 5 H); 7.19-7.10 (m, 1 H); 7.08-6.99 (m, 2 H); 6.95 (t, J = 7.26 Hz, 1 H); 6.49 (d, J = 9.84 Hz, 1 H); 6.25 (dd, J = 14.03, 8.15 Hz, 1 H); 5.19 (d, J = 12.14 Hz, 2 H); 5.05 (s, 2 H); 4.09 (dd, J = 13.40, 8.00 Hz, 1 H); 4.03-3.96 (m, 2 H); 3.83-3.50 (m, 4 H); 2.74-2.66 (m, 2 H); 2.6 (m, 2 H); 2.39-2.22 (m, 3 H); 2.11-1.91 (m, 3 H); 1.69 (d, J = 7.79 Hz, 2 H); 1.32 (d, J = 55.24 Hz, 12 H). | diformate |
| 12B | B | (DMSO-d$_6$): δ 8.67-8.58 (m, 1 H); 8.43 (s, 2 H); 8.18 (d, J = 9.9 Hz, 1 H); 8.02-7.93 (m, 2 H); 7.75 (q, J = 7.1 Hz, 1 H); 7.61 (q, J = 7.8 Hz, 2 H); 7.50 (d, J = 8.7 Hz, 1 H); 7.40-7.22 (m, 5 H); 7.14 (dd, J = 19.7, 3.0 Hz, 1 H); 7.06 (d, J = 8.2 Hz, 1 H); 6.95 (d, J = 8.1 Hz, 1 H); 6.85 (dd, J = 8.8, 2.9 Hz, 1 H); 6.49 (d, J = 9.8 Hz, 1 H); 6.21-6.11 (m, 1 H); 5.20 (d, J = 8.9 Hz, 1 H); 5.10-5.00 (m, 2 H); 4.14-4.04 (m, 1 H); 4.01-3.89 (m, 2 H); 3.81-3.51 (m, 5 H); 2.78-2.66 (m, 2 H); 2.63-2.53 (m, 2 H); 2.40-2.30 (m, 1 H); 2.23-1.90 (m, 4 H); 1.74-1.64 (m, 2 H); 1.47-1.17 (m, 12 H). | diformate |
| 13B | A | (DMSO-d6): δ 8.51 (d, J = 9.58 Hz, 1 H); 8.43 (s, 2 H); 8.17 (d, J = 9.96 Hz, 1 H); 8.01-7.95 (m, 2 H); 7.80-7.72 (m, 1 H); 7.64-7.57 (m, 2 H); 7.36-7.30 (m, 4 H); 7.26-7.21 (m, 1 H); 7.08-7.04 (m, 2 H); 6.94 (d, J = 8.15 Hz, 2 H); 6.85-6.79 (m, 1 H); 6.49 (d, J = 9.86 Hz, 1 H); 5.81 (d, J = 8.39 Hz, 1 H); 5.19 (s, 2 H); 5.06-5.01 (m, 2 H); 4.08 (s, 1 H); 3.93 (d, J = 8.29 Hz, 2 H); 3.81-3.53 (m, 4 H); 2.72-2.65 (m, 2 H); 2.6-2.5 (m, 2 H); 2.34 (t, J = 3.03 Hz, 2 H); 2.20-1.95 (m, 7 H); 1.74-1.66 (m, 2 H); 1.33 (d, J = 57.30 Hz, 12 H). | diformate |
| 14B | B | (CD$_3$OD): δ 8.45 (s, 2H), 8.40 (d, J = 10 Hz, 1H); 7.36-7.27 (m, 6H); 7.06 (d, J = 8.4 Hz, 1H); 6.93 (d, J = 8 Hz, 1H); 6.86-6.83 (m, 2H); 6.72 (d, J = 9.6 Hz, 1H); 5.85 (br s, 1H); 5.42 (t, J = 6.8 Hz, 1H); 5.01-4.99 (m, 1H); 3.93 (t, J = 6.4 Hz, 2H); 3.83 (s, 3H); 3.70 (m, 1H), 3.27-3.15 (m, 6H); 3.10-3.06 (m, 2H); 2.37 (br s, 1H); 2.24 (br s, 1H); 2.05 (m, 1H); 1.95-1.86 (m, 2H); 1.77-1.72 (m, 4H); 1.47-1.39 (m, 11H) | diformate |
| 15B | B | (DMSO-d6): δ 8.32 (s, 1 H); 8.18 (m, 2 H); 7.35-7.27 (m, 4 H); 7.26-7.20 (m, 1 H); 7.10 (d, J = 8.16 Hz, 1 H); 6.99-6.91 (m, 1 H); 6.56-6.50 (m, 3 H); 6.34 (s, 1 H); 5.76 (d, J = 8.94 Hz, 1 H); 5.18 (dd, J = 8.05, 4.61 Hz, 1 H); 4.58 (s, 1 H); 3.93-3.87 (m, 2 H); 3.70 (d, J = 1.68 Hz, 3 H); 3.11 (d, J = 12.65 Hz, 1 H); 2.89-2.82 (m, 2 H); 2.74-2.5 (m, 6 H); 1.91 (s, 1 H); 1.81 (s, 1 H); 1.75-1.42 (m, 6 H); 1.67-0.96 (m, 12 H). | formate |
| 16B | A | (CD3OD): δ 8.57 (s, 2 H); 8.39 (d, J = 9.8 Hz, 1 H); 8.01 (d, J = 7.8 Hz, 2 H); 7.78-7.70 (m, 1 H); 7.62-7.55 (m, 2 H); 7.38-7.26 (m, 6 H); 7.03 (d, J = 8.2 Hz, 1 H); 6.93 (d, J = 8.2 Hz, 1 H); 6.90-6.81 (m, 2 H); 6.69 (dd, J = 9.8, 1.3 Hz, 1 H); 5.87 (s, 1 H); 5.41-5.34 (m, 1 H); 5.14 (s, 1 H); 4.23-4.13 (m, 1 H): 3.95-3.70 (m, 10 H); 3.20-3.14 (m, 2 H); 3.04-2.97 (m, 2 H); 2.50 (s, 1 H); 2.45-2.34 (m, 1 H); 2.27-2.17 (m, 1 H); 2.15-2.03 (m, 2 H); 1.77-1.69 (m, 5 H); 1.47-1.39 (s, 11 H) | diformate |
| 17B | B | (DMSO-d6): δ 8.55-8.48 (m, 1 H); 8.41 (s, 2 H); 8.18 (d, J = 9.92 Hz, 1 H); 8.01-7.95 (m, 2 H); 7.79-7.71 (m, 1 H); 7.64-7.57 (m, 2 H); 7.38-7.29 (m, 4 H); 7.27-7.22 (m, 1 H); 7.07 (d, J = 8.15 Hz, 1 H); 6.96 (d, J = 8.11 Hz, 1 H); 6.57-6.46 (m, 3 H); 6.37 (s, 1 H); 5.78 (d, J = 8.97 Hz, 1 H); 5.20 (s, 2 H); 5.13-5.06 (m, 1 H); 5.03 (s, 1 H); 4.14-4.03 (m, 1 H); 3.94-3.87 (m, 2 H); 3.71 (d, J = 2.10 Hz, 5 H); 3.60 (s, 2 H); 2.75 (d, J = 6.24 Hz, 2 H); 2.59 (d, J = 10.43 Hz, 2 H); 2.35 (d, J = 6.09 Hz, 1 H); 2.25-1.92 (m, 4 H); 1.71-1.62 (m, 2 H); 1.54-1.16 (m, 13 H). | diformate |
| 18B | B | (DMSO-d6): δ 8.65-8.58 (m, 1 H); 8.42 (s, 2 H); 8.18 (d, J = 9.89 Hz, 1 H); 7.97 (dd, J = 12.34, 7.73 Hz, 2 H); 7.77-7.70 (m, 1 H); 7.68-7.56 (m, 4 H); 7.48-7.29 (m, 7 H); 7.26 (d, J = 9.96 Hz, 2 H); 7.06 (d, J = 7.09 Hz, 2 H); 6.99 (s, 1 H); 6.94 (d, J = 8.20 Hz, 1 H); 6.52-6.48 (m, 1 H); 5.92 (d, J = 8.66 Hz, 1 H); 5.19 (d, J = 7.20 Hz, 2 H); 5.05 (d, J = 6.31 Hz, 2 H); 4.11-3.98 (m, 3 H); 3.82-3.53 (m, 6 H); 2.74-2.66 (m, 2 H); 2.39-2.31 (m, 2 H); 2.22-1.89 (m, 4 H); 1.75-1.67 (m, 2 H); 1.33 (d, J = 56.95 Hz, 12 H). | diformate |
| 19B | B | (CD3OD): δ 8.57 (s, 2 H); 8.38 (d, J = 9.86 Hz, 1 H); 7.39-7.25 (m, 8 H); 7.17 (s, 1 H); 7.11-6.99 (m, 3 H); 6.76 (s, 1 H); 6.68 (dd, J = 9.83, 6.22 Hz, 1 H); 5.91 (s, 1 H); 5.35 (dd, J = 8.74, 4.54 Hz, 1 H); 4.81 (s, 1 H); 4.03-3.96 (m, 2 H); 3.18-3.07 (m, 2 H); 3.02-2.82 (m, 7 H); 2.09 (d, J = 36.56 Hz, 2 H); 1.90-1.62 (m, 6 H); 1.64-1.23 (m, 12 H). | diformate |
| 20B | B | (CD3OD): δ 8.56 (s, 1 H); 8.39 (d, J = 10 Hz, 1 H); 8.02-7.98 (m, 2 H); 7.73 (m, 1 H); 7.61-7.55 (m, 2 H); 7.36-7.24 (m, 8 H); 7.04-6.87 (m, 7 H); 6.69 (d, J = 12 Hz, 1 H); 5.90 (s, 1 H); 5.39 (m, 1 H); 5.14-4.90 (m, 6 H); 4.26-3.71 (m, 8 H); 3.18-3.11 (m, 4 H); 2.50-1.90 (m, 8 H) | formate |
| 21B | A | (DMSO-d$_6$): δ 8.57 (m, 1 H); 8.45 (s, 2 H); 8.24 (d, J = 12 Hz, 1 H); 7.38-7.23 (m, 10 H); 7.13-6.92 (m, 12 H); 6.54 (d, J = 8 Hz, 1 H); 5.89 (d, J = 8 Hz, 1 H); 5.16 (m, 1 H); 5.08 (s, 2 H); 4.98 (m, 1 H); 4.47 (m, 2 H); 4.08-4.00 (m, 3 H); 3.76-3.40 (m, 5 H); 2.84 (m, 2 H); 2.75 (m, 2 H); 2.36 (m, 1 H); 2.19 (m, 1 H); 2.03-1.93 (m, 3 H); 1.77 (m, 2 H); 1.66 (m, 2 H) | diformate |

| Compound | LCMS/HPLC method | NMR data at 400 MHz | Salt |
|---|---|---|---|
| 22B | B | (CD3OD): δ 8.56 (s, 1 H); 8.39 (d, J = 10 Hz, 1 H); 8.02-7.98 (m, 2 H); 7.73 (m, 1 H); 7.61-7.57 (m, 2 H); 7.36-7.23 (m, 8 H); 7.05-6.85 (m, 7 H); 6.69 (d, J = 10 Hz, 1 H); 5.90 (s, 1 H); 5.40 (t, J = 5.6 Hz, 1 H); 5.18-4.90 (m, 6 H); 4.18 (m, 1 H); 4.04-3.99 (m, 2 H); 3.85-3.60 (m, 5 H); 3.21-3.09 (m, 2 H); 3.10-3.06 (m, 2 H); 2.68-2.00 (m, 5 H); 1.85-1.79 (m, 3 H); 1.62-1.61 (m, 2 H) | formate |
| 23B | B | (DMSO-$d_6$): δ 8.58 (m, 1 H); 8.47 (s, 2 H); 8.24 (d, J = 12 Hz, 1 H); 7.38-7.23 (m, 10 H); 7.13-6.92 (m, 12 H); 6.53 (d, J = 12 Hz, 1 H); 5.89 (d, J = 8 Hz, 1 H); 5.16 (m, 1 H); 5.08 (s, 2 H); 4.98 (m, 1 H); 4.47 (m, 2 H); 4.08-3.97 (m, 3 H); 3.93-3.37 (m, 5 H); 2.83 (m, 2 H); 2.71 (m, 2 H); 2.34 (m, 1 H); 2.19 (m, 1 H); 2.03-1.85 (m, 3 H); 1.76 (m, 2 H); 1.53-1.47 (m, 4 H) | diformate |
| 24B | A | (DMSO-d6): δ 8.29 (s, 3 H); 8.19 (d, J = 9.92 Hz, 1 H); 7.39-7.32 (m, 1 H); 7.21 (d, J = 9.99 Hz, 3 H); 7.15-7.02 (m, 2 H); 6.94 (dd, J = 19.08, 8.27 Hz, 3 H); 6.80 (d, J = 8.28 Hz, 1 H); 6.54 (d, J = 9.85 Hz, 1 H); 5.85 (d, J = 8.92 Hz, 1 H); 5.24 (dd, J = 8.95, 3.71 Hz, 1 H); 4.61 (s, 1 H); 3.96-3.89 (m, 2 H); 3.20-3.10 (m, 1 H); 3.0-2.9 (m, 2H); 2.85-2.5 (m, 6 H); 1.93 (s, 1 H); 1.81 (s, 1 H); 1.72-1.32 (m, 12 H). | diformate |
| 25B | A | (CD$_3$OD): δ 8.55 (s, 2 H); 8.38 (d, J = 10 Hz, 1 H); 7.37-7.18 (m, 13 H); 7.04-6.76 (m, 3 H); 6.69 (m, 1 H); 5.88 (s, 1 H); 5.40-5.36 (m, 1 H); 5.11-4.97 (m, 1 H); 4.00-3.95 (m, 2 H); 3.88-3.77 (m, 1 H); 3.22-3.01 (m, 9 H); 2.78-2.65 (m, 2 H); 2.42 (br s, 1 H); 2.31 (br s, 1 H); 2.19-1.88 (m, 3 H); 1.87-1.58 (m, 12 H). | diformate |
| 26B | B | (DMSO-$d_6$): δ 8.34-8.21 (m, 2 H); 8.17 (d, J = 9.9 Hz, 1 H); 7.40-7.13 (m, 9 H); 7.11-7.00 (m, 3 H); 6.98-6.86 (m, 3 H); 6.50 (d, J = 9.9 Hz, 1 H); 5.85 (d, J = 8.7 Hz, 1 H); 5.10 (t, J = 6.3 Hz, 1 H); 5.02 (s, 2 H); 4.67-4.51 (m, 1 H); 3.17-3.07 (m, 1 H); 2.95-2.53 (m, 8 H); 1.98-1.84 (m, 1 H); 1.81-1.74 (m, 2 H); 1.73-1.20 (m, 4 H). | formate |
| 27B | A | (DMSO-d6): δ 8.62 (d, J = 9.36 Hz, 1 H); 8.39 (s, 2 H); 8.17 (dd, J = 9.92, 2.70 Hz, 1 H); 8.00-7.90 (m, 2 H); 7.74 (q, J = 6.56 Hz, 1 H); 7.65-7.50 (m, 3 H); 7.37 (q, J = 7.36 Hz, 1 H); 7.30-7.12 (m, 7 H); 7.11-7.00 (m, 3 H); 6.98-6.87 (m, 3 H); 6.48 (dd, J = 9.87, 2.28 Hz, 1 H); 5.88 (d, J = 7.77 Hz, 1 H); 5.19 (s, 2 H); 5.03 (s, 4 H); 4.11-3.98 (m, 1 H); 3.65 (d, J = 55.36 Hz, 3 H); 2.85-2.66 (m, 2 H); 2.39-2.26 (m, 5 H); 2.33-2.03 (m, 1 H); 2.07-1.87 (m, 4 H). | diformate |
| 28B | A | (DMSO-$d_6$): δ 8.40 (m, 1 H); 8.18 (s, 2 H); 7.92 (dd, J = 12.0, 8.0 Hz, 1 H); 7.82-7.77 (m, 2 H); 7.57 (m, 1 H); 7.46-7.39 (m, 2 H); 7.20-7.15 (m, 7 H); 7.09-7.03 (m, 2 H); 6.89-6.85 (m, 2 H); 6.77-6.72 (m, 3 H); 6.29 (dd, J = 12.0, 8.0 Hz, 1H); 5.67 (d, J = 8.0 Hz, 1 H); 5.02 (s, 2 H); 4.87 (m, 4 H); 3.92 (m, 1 H); 3.68-3.52 (m, 6 H); 3.42 (m, 1 H); 2.49 (m, 2 H); 2.17 (m, 1 H); 2.00 (m, 1 H); 1.89-1.53 (m, 4 H) | diformate |
| 29B | B | (DMSO-$d_6$): δ 8.30 (s, 2 H); 8.30-8.15 (m, 2 H); 7.70 (s, 1 H); 7.63-7.54 (m, 3 H); 7.50-7.37 (m, 2 H); 7.32-7.17 (m, 8 H); 7.12-7.04 (m, 2 H); 6.98-6.88 (m, 3 H); 6.52 (d, J = 9.9 Hz, 1 H); 5.83 (d, J = 9.2 Hz, 1 H); 5.21-5.05 (m, 3 H); 4.59 (s, 1 H); 3.15-3.10 (m, 1 H); 2.97-2.53 (m, 11 H); 1.92 (s, 1 H); 1.80 (s, 1 H); 1.72-1.24 (m, 3 H). | diformate |
| 30B | B | (DMSO-d6): δ 8.54-8.46 (m, 1 H); 8.31-8.21 (m, 2 H); 8.18 (d, J = 9.94 Hz, 1 H); 7.84 (d, J = 8.04 Hz, 2 H); 7.50 (d, J = 7.91 Hz, 2 H); 7.34-7.27 (m, 4 H); 7.26-7.19 (m, 2 H); 7.10 (d, J = 8.17 Hz, 1 H); 7.04 (s, 1 H); 6.98-6.85 (m, 3 H); 6.53 (d, J = 9.86 Hz, 1 H); 5.82 (d, J = 8.54 Hz, 1 H); 5.20 (d, J = 8.25, 4.32 Hz, 1 H); 5.13 (s, 2 H); 4.59 (s, 1 H); 3.27 (m, 2 H); 3.12 (s, 1 H); 2.93-2.63 (m, 6 H); 1.86 (d, J = 46.19 Hz, 2 H); 1.70-1.22 (m, 10 H). | formate |
| 31B | B | (DMSO-d6): δ 8.62 (s, 1 H); 8.33-8.21 (m, 3 H); 8.19 (d, J = 9.93 Hz, 1 H); 7.85 (d, J = 7.99 Hz, 2 H); 7.50 (d, J = 7.90 Hz, 2 H); 7.35-7.19 (m, 6 H); 7.11 (d, J = 8.16 Hz, 1 H); 7.04 (s, 1 H); 6.99-6.85 (m, 3 H); 6.52 (d, J = 9.86 Hz, 1 H); 5.82 (d, J = 8.75 Hz, 1 H); 5.21 (dd, J = 8.34, 4.26 Hz, 1 H); 5.13 (s, 2 H); 4.60 (s, 1 H); 3.32 (t, J = 6.31 Hz, 2 H); 2.95-2.75 (m, 5 H); 2.67 (s, 3 H); 2.57 (d, J = 16.50 Hz, 1 H); 1.94 (s, 1 H); 1.81 (t, J = 7.70 Hz, 3 H); 1.61 (s, 2 H); 1.51 (s, 2 H). | diformate |
| 32B | A | (DMSO-$d_6$): δ 8.59-8.52 (m, 2 H); 8.40 (s, 2 H); 8.18 (m, 1 H); 7.97 (t, J = 8.2 Hz, 2 H); 7.84 (dd, J = 8.0, 2.1 Hz, 2 H); 7.77-7.71 (m, 1 H); 7.60 (q, J = 8.0 Hz, 2 H); 7.50 (d, J = 7.9 Hz, 2 H); 7.36-7.30 (m, 4 H); 7.28-7.21 (m, 2 H); 7.06 (t, J = 8.4 Hz, 2 H); 6.99-6.88 (m, 3 H); 6.49 (m, 1 H); 5.84 (d, J = 9.0 Hz, 1 H); 5.24-4.96 (m, 6 H); 4.15-4.03 (m, 1 H); 3.80-3.28 (m, 6 H); 2.75-2.63 (m, 4 H); 2.34 (s, 1 H); 2.23-1.89 (m, 5 H); 1.74-1.63 (m, 2 H) | diformate |
| 33B | B | (DMSO-$d_6$): δ 8.33-8.18 (m, 2 H); 8.18 (d, J = 9.93 Hz, 1 H); 8.00-7.92 (m, 2 H); 7.57 (d, J = 7.95 Hz, 2 H); 7.35-7.21 (m, 6 H); 7.10 (d, J = 8.16 Hz, 1 H); 7.04 (s, 1 H); 6.95 (d, J = 8.04 Hz, 2 H); 6.89 (d, J = 8.33 Hz, 1 H); 6.52 (d, J = 9.86 Hz, 1 H); 5.82 (d, J = 8.71 Hz, 1 H); 5.18 (s, 3 H); 4.59 (s, 1 H); 4.32-4.25 (m, 2 H); 3.18-3.08 (m, 1 H); 2.91-2.56 (m, 6 H); 1.92 (s, 1 H); 1.95-1.39 (m, 11 H). | formate |
| 34B | A | (DMSO-$d_6$): δ 8.28 (s, 1 H); 8.24 (d, J = 9.6 Hz, 1 H); 8.19 (d, J = 10 Hz, 1 H); 7.96 (d, J = 8.0 Hz, 2 H); 7.57 (d, J = 7.9 Hz, 2 H); 7.31-7.22 (m, 6 H); 7.10-6.87 (m, 5 H); 6.53 (d, J = 10 Hz, 1 H); 5.83 (d, J = 8.8 Hz, 1 H); 5.18-5.11 (m, 3 H); 4.56 (br s, 1 H); 3.13-3.08 (m, 1 H); 2.85-2.61 (m, 8 H); 1.94-1.86 (m, 1 H); 1.79-1.66 (m, 3 H), 1.63-1.24 (m, 10 H) | formate |

| Compound | LCMS/HPLC method | NMR data at 400 MHz | Salt |
|---|---|---|---|
| 35B | B | (DMSO-d$_6$): 8.31 (s, 1 H); 8.26-8.14 (m, 2H); 7.96 (d, J = 8 Hz, 2 H); 7.56 (d, J = 8 Hz, 2 H); 7.34-7.20 (m, 6 H); 7.13-7.00 (m, 2 H); 6.97-6.87 (m, 3 H); 6.53 (d, J = 9.6 Hz, 1 H); 5.82 (d, J = 8.96 Hz, 1 H); 5.23-5.08 (m, 3 H); 4.57 (s, 1 H); 4.28 (t, J = 6.44 Hz, 2 H); 3.16-3.03 (m, 1 H); 2.83-2.49 (m, 8 H); 1.94-1.26 (m, 14 H) | formate |
| 4C | B | (DMSO-d6): δ 8.29 (s, 2 H); 8.28-8.13 (m, 2 H); 7.96 (d, J = 7.9 Hz, 2 H); 7.57 (d, J = 7.9 Hz, 2 H); 7.34-7.19 (m, 6 H); 7.10 (d, J = 8.1 Hz, 1 H); 6.92 (m, 3 H); 6.53 (d, J = 9.8 Hz, 1 H); 5.82 (d, J = 9.1 Hz, 1 H); 7.03 (s, 1 H); 5.17 (s, 3 H); 4.57 (s, 1 H); 4.28 (t, J = 6.4 Hz, 2 H); 3.15-3.05 (m, 1 H); 2.85 (d, J = 6.4 Hz, 2 H); 2.73 (s, 5 H); 1.90 (s, 1 H); 1.85-1.66 (m, 3 H); 1.51 (s, 4 H); 1.40 (s, 3 H); 1.32 (s, 6 H). | diformate |
| 5C | B | (DMSO-d6): δ 8.22 (s, 2 H); 8.12 (d, J = 9.9 Hz, 1 H); 7.99 (d, J = 7.9 Hz, 2 H); 7.57 (d, J = 7.9 Hz, 2 H); 7.45-7.33 (m, 4 H); 7.33-7.18 (m, 6 H); 7.10-6.99 (m, 2 H); 6.96-6.85 (m, 3 H); 6.47 (d, J = 9.8 Hz, 1 H); 5.81 (d, J = 9.0 Hz, 1 H); 5.33 (s, 2 H); 5.18 (s, 2 H); 5.08 (dd, J = 7.6, 4.2 Hz, 1 H); 4.58 (s, 1 H); 3.79 (s, 2 H); 3.42 (s, 7 H); 3.13 (s, 2 H); 2.78-2.62 (m, 3 H); 1.92 (s, 1 H). | diformate |
| 6C | A | (DMSO-d$_6$): δ 8.38 (s, 2 H); 8.28-8.16 (m, 2 H); 8.13 (d, J = 7.9 Hz, 2 H); 7.65 (d, J = 7.9 Hz, 2 H); 7.36-6.86 (m, 15 H); 6.52 (d, J = 10 Hz, 1 H); 5.87-5.78 (m, 1 H); 5.23 (s, 2 H); 5.05 (m, 1 H); 4.57 (br s, 1 H); 3.14-3.04 (m, 1 H); 2.91-2.63 (m, 11 H); 1.90 (br s, 1 H); 1.77 (br s, 1 H); 1.58 (br s, 1 H); 1.47 (br s, 1 H); 1.32 (br s, 1 H). | diformate |
| 7C | A | (DMSO-d$_6$): δ 8.32-8.19 (m, 2 H); 8.21-8.10 (m, 2 H); 8.02 (d, J = 8.0 Hz, 2 H); 7.58 (d, J = 7.9 Hz, 2 H); 7.37-7.16 (m, 6 H); 7.10 (d, J = 8.2 Hz, 1 H); 7.05 (s, 1 H); 6.92 (dd, J = 23.2, 8.0 Hz, 3 H); 6.53 (d, J = 9.9 Hz, 1 H); 5.82 (d, J = 9.1 Hz, 1 H); 5.22-5.14 (m, 3 H); 4.70 (s, 2 H); 4.58 (s, 1 H); 3.17 (s, 1 H); 3.12 (d, J = 7.1 Hz, 3 H); 2.85 (d, J = 6.3 Hz, 2 H); 2.75 (s, 4 H); 2.65 (d, J = 20.1 Hz, 2 H); 1.92 (s, 1 H); 1.48 (s, 6 H); 1.35 (s, 2 H). | formate |
| 8C | B | (DMSO-d$_6$): δ 8.27 (s, 2 H); 8.25-8.15 (m, 2 H); 7.99 (d, J = 8.0 Hz, 2 H); 7.57 (d, J = 8.0 Hz, 2 H); 7.38 (d, J = 7.9 Hz, 2 H); 7.34-7.18 (m, 8 H); 7.09-7.00 (m, 2 H); 6.96-6.85 (m, 3 H); 6.52 (d, J = 10 Hz, 1 H); 5.82 (d, J = 9.2 Hz, 1 H); 5.32 (s, 2 H); 5.18 (s, 2 H); 5.07 (m, 1 H); 4.60-4.53 (m, 1 H); 3.15-3.05 (m, 1 H); 2.89-2.70 (m, 9 H); 1.89 (br s, 2 H); 1.78 (br s, 2 H); 1.59 (br s, 1 H); 1.46 (br s, 1 H); 1.31 (br s, 1 H) | formate |
| 36B | B | (DMSO-d$_6$): δ 8.58 (d, J = 8.9 Hz, 1 H); 8.37 (s, 2 H); 8.18 (d, J = 9.9 Hz, 1 H); 7.97 (t, J = 6.6 Hz, 2 H); 7.78-7.71 (m, 1 H); 7.60 (q, J = 7.4 Hz, 2 H); 7.40-7.21 (m, 10 H); 7.10-6.99 (m, 2 H); 6.99-6.86 (m, 3 H); 6.50 (dd, J = 9.8, 1.6 Hz, 1 H); 5.85 (d, J = 8.3 Hz, 1 H); 5.22-5.14 (m, 2 H); 5.09 (t, J = 6.2 Hz, 1 H); 5.07-4.97 (m, 3 H); 4.13-4.04 (m, 1 H); 4.01-3.94 (m, 1 H); 3.78-3.53 (m, 6 H); 2.72 (d, J = 6.1 Hz, 2 H); 2.62-2.53 (m, 1 H); 2.37-2.31 (m, 1 H); 2.24-2.13 (m, 1 H); 2.09-1.90 (m, 3 H); 1.55-1.33 (m, 6 H); 1.20-1.12 (m, 2 H). | diformate |
| 37B | B | (DMSO-d$_6$ @105° C.): δ 8.21-8.14 (m, 3 H); 7.63-7.52 (m, 5 H); 7.41-7.18 (m, 10 H); 7.10 (d, J = 8.1 Hz, 1 H); 6.98-6.81 (m, 4 H); 6.46 (d, J = 9.9 Hz, 1 H); 5.83 (d, J = 8.8 Hz, 1 H); 5.09 (dd, J = 7.6, 4.8 Hz, 1 H); 4.64-4.58 (m, 1 H); 4.24 (td, J = 6.7, 2.0 Hz, 2 H); 3.82 (s, 2 H); 3.13-3.03 (m, 3 H); 2.90-2.77 (m, 1 H); 2.76-2.58 (m, 4 H); 2.57-2.52 (m, 2 H); 1.94-1.88 (m, 1 H); 1.82-1.70 (m, 1 H); 1.66-1.56 (m, 1 H); 1.54-1.43 (m, 1 H); 1.36-1.24 (m, 1 H). | diformate |
| 38B | A | (DMSO-d$_6$): δ 8.29-8.20 (m, 2 H); 8.12 (d, J = 9.9 Hz, 1 H); 7.65-7.49 (m, 4 H); 7.44-7.18 (m, 10 H); 7.08 (d, J = 8.2 Hz, 1 H); 6.99-6.80 (m, 4 H); 6.42 (d, J = 9.9 Hz, 1 H); 5.85-5.78 (m, 1 H); 5.11 (dd, J = 7.7, 4.5 Hz, 1 H); 4.63-4.56 (m, 1 H); 4.22-4.14 (m, 2 H); 3.86 (s, 2 H); 3.18-3.02 (m, 3 H); 2.81-2.53 (m, 5 H); 2.52-2.45 (m, 2 H); 1.95-1.73 (m, 2 H); 1.66-1.27 (m, 3 H). | formate |
| 39B | B | (DMSO-d$_6$): δ 8.35 (s, 2 H); 8.26 (d, J = 9.9 Hz, 1 H); 8.20 (d, J = 9.9 Hz, 1 H); 7.35-7.27 (m, 4 H); 7.26-7.18 (m, 2 H); 7.11 (d, J = 8.2 Hz, 1 H); 6.99-6.92 (m, 4 H); 6.80-6.73 (m, 1 H); 6.53 (d, J = 9.9 Hz, 1 H); 5.82 (d, J = 9.5 Hz, 1 H); 5.24-5.18 (m, 1 H); 4.75 (d, J = 1.9 Hz, 2 H); 4.74-4.44 (m, 1 H); 4.08 (t, J = 6.6 Hz, 2 H); 3.19-3.08 (m, 1 H); 2.93-2.80 (m, 2 H); 2.81-2.60 (m, 6 H); 1.99-1.84 (m, 1 H); 1.91-1.70 (m, 1 H); 1.69-1.48 (m, 6 H); 1.48-1.24 (m, 1 H); 1.53-0.98 (m, 4 H) | diformate |
| 40B | A | (DMSO-d$_6$): δ 8.11 (s, 3 H); 8.02 (d, J = 9.9 Hz, 1 H); 7.22-7.05 (m, 4 H); 7.08-7.01 (m, 2 H); 6.95 (d, J = 8.2 Hz, 1 H); 6.81 (d, J = 8.2 Hz, 1 H); 6.76-6.69 (m, 2 H); 6.62 (d, J = 8.3 Hz, 1 H); 6.38 (d, J = 9.8 Hz, 1 H); 5.63 (s, 1 H); 5.11 (d, J = 9.2 Hz, 1 H); 4.45 (s, 1 H); 3.75 (t, J = 6.4 Hz, 2 H); 3.06-2.96 (m, 1 H); 2.85-2.39 (m, 9 H); 1.79 (s, 1 H); 1.66 (s, 1 H); 1.56-1.11 (m, 11 H) | diformate |
| 41B | B | (DMSO-d6): δ 8.30 (s, 1 H); 8.24 (d, J = 10.10 Hz, 1 H); 8.19 (d, J = 9.93 Hz, 1 H); 7.37-7.17 (m, 6 H); 7.11 (d, J = 8.17 Hz, 1 H); 7.00-6.86 (m, 3 H); 6.78 (dd, J = 8.26, 2.44 Hz, 1 H); 6.56-6.48 (m, 1 H); 5.81 (d, J = 8.52 Hz, 1 H); 5.20 (dd, J = 8.28, 4.46 Hz, 1 H); 4.58 (s, 1 H); 3.95-3.88 (m, 2 H); 3.18-3.06 (m, 1 H); 2.86-2.55 (m, 8 H); 1.91 (s, 1 H); 1.80 (s, 1 H); 1.74-1.32 (m, 12 H). | formate |

-continued

| Compound | LCMS/HPLC method | NMR data at 400 MHz | Salt |
|---|---|---|---|
| 42B | A | (DMSO-d6): δ 8.55 (d, J = 9.19 Hz, 1 H); 8.40 (s, 2 H); 8.19 (d, J = 9.91 Hz, 1 H); 7.98 (d, J = 7.80 Hz, 2 H); 7.76 (t, J = 7.40 Hz, 1 H); 7.61 (t, J = 7.67 Hz, 2 H); 7.40-7.30 (m, 4 H); 7.29-7.19 (m, 2 H); 7.07 (d, J = 8.17 Hz, 1 H); 6.99-6.86 (m, 3 H); 6.81 (d, J = 8.37 Hz, 1 H); 6.50 (d, J = 9.84 Hz, 1 H); 5.84 (d, J = 8.86 Hz, 1 H); 5.20 (s, 2 H); 5.09 (s, 1 H); 5.03 (s, 1 H); 4.14-4.03 (m, 1 H); 3.96-3.88 (m, 2 H); 3.82-3.55 (m, 6 H); 2.75 (s, 2 H); 2.64-2.57 (m, 2 H); 2.34 (d, J = 6.23 Hz, 1 H); 2.18 (s, 1 H); 2.13-1.88 (m, 3 H); 1.67 (d, J = 8.37 Hz, 2 H); 1.51-1.21 (m, 5 H). | diformate |
| 43B | A | (CD$_3$OD): δ 8.57 (s, 2 H); 8.39 (d, J = 10 Hz, 1H); 8.02 (d, J = 9.6 Hz, 2 H); 7.75-7.70 (m, 1 H); 7.61-7.55 (m, 2 H); 7.40-7.24 (m, 7 H); 7.03 (d, J = 8.2 Hz, 1 H); 6.94-6.80 (m, 3 H); 6.70 (d, J = 9.6 Hz, 1 H); 5.90 (s, 1 H); 5.40-5.36 (m, 1 H); 5.15 (br s, 1 H); 4.92 (s, 2 H); 4.22-4.15 (m, 1 H); 4.00-3.66 (m, 8 H); 3.19-3.12 (m, 2 H); 3.01 (t, J = 8 Hz, 2 H); 2.51 (s, 2 H); 2.45-2.33 (m, 1 H); 2.26-2.17 (m, 1 H); 2.15-2.00 (m, 1 H); 1.84-1.69 (m, 4 H); 1.58-1.42 (m, 4 H) | diformate |
| 44B | C | (DMSO-d6): δ 8.34-8.22 (m, 3 H); 8.20 (d, J = 10 Hz, 1 H); 7.98 (d, J = 8.4 Hz, 2H); 7.58 (d, J = 8.4 Hz, 2 H); 7.38-7.20 (m, 6 H); 7.15-6.83 (m, 5 H); 6.54 (d, J = 9.6 Hz, 1 H); 5.82 (br s, 1 H); 5.24-5.13 (m, 3 H); 4.61-4.59 (m, 1 H); 4.31 (t, J = 6 Hz, 2 H); 3.21-3.09 (m, 1 H); 2.95-2.42 (m, 8 H); 1.95 (s, 1 H); 1.89-.29 (m, 9 H) | diformate |
| 45B | B | (DMSO-d6): δ 8.29 (s, 1 H); 8.24 (d, J = 9.71 Hz, 1 H); 8.18 (d, J = 9.94 Hz, 1 H); 7.97 (d, J = 8.07 Hz, 2 H); 7.57 (d, J = 8.01 Hz, 2 H); 7.32-7.18 (m, 6 H); 7.09 (d, J = 8.16 Hz, 1 H); 7.04 (s, 1 H); 6.94 (d, J = 8.01 Hz, 1 H); 6.89 (dd, J = 8.27, 2.55 Hz, 1 H); 6.51 (d, J = 9.86 Hz, 1 H); 5.82 (d, J = 9.09 Hz, 1 H); 5.20-5.12 (m, 3 H); 4.58 (s, 1 H); 4.29 (t, J = 6.28 Hz, 2 H); 3.10 (d, J = 10.66 Hz, 1 H); 2.87-2.52 (m, 8 H); 2.06-1.30 (m, 10 H). | formate |
| 9C | A | (DMSO-d$_6$): δ 8.33 (s, 2 H); 8.27 (d, J = 9.9 Hz, 1 H); 8.19 (d, J = 9.9 Hz, 1 H); 7.35-7.27 (m, 4 H); 7.27-7.19 (m, 2 H); 7.11 (d, J = 8.2 Hz, 1 H); 6.99-6.92 (m, 3 H); 6.79-6.74 (m, 1 H); 6.53 (d, J = 9.9 Hz, 1 H); 5.82 (d, J = 9.3 Hz, 1 H); 5.25-5.19 (m, 1 H); 4.75 (d, J = 2.0 Hz, 2 H); 4.80-4.37 (m, 1 H); 4.08 (t, J = 6.7 Hz, 2 H); 3.20-3.08 (m, 1 H); 2.92-2.84 (m, 2 H); 2.79-2.70 (m, 4 H); 2.70-2.59 (m, 3 H); 1.99-1.86 (m, 1 H); 1.90-1.73 (m, 1 H); 1.62-1.47 (m, 6 H); 1.43-1.20 (m, 3 H). | diformate |
| 10C | B | (DMSO-d$_6$): δ 8.34 (s, 2 H); 8.29 (d, J = 10.0 Hz, 1 H); 8.19 (d, J = 9.9 Hz, 1 H); 7.35-7.27 (m, 4 H); 7.25-7.17 (m, 2 H); 7.10 (d, J = 8.2 Hz, 1 H); 6.99-6.92 (m, 3 H); 6.81-6.74 (m, 1 H); 6.52 (d, J = 9.9 Hz, 1 H); 5.82 (d, J = 9.6 Hz, 1 H); 5.22-5.16 (m, 1 H); 4.75 (s, 2 H); 4.67-4.53 (m, 1 H); 4.13-4.06 (m, 2 H); 3.21-3.04 (m, 1 H); 2.87-2.80 (m, 2 H); 2.79-2.46 (m, 7 H); 2.04-1.80 (m, 1 H); 1.95-1.68 (m, 1 H); 1.63-1.48 (m, 6 H); 1.63-1.12 (m, 1 H). | diformate |
| 11C | B | (DMSO-d6): δ 8.32-8.21 (m, 1 H); 8.24 (s, 2 H); 8.17 (d, J = 9.9 Hz, 1 H); 7.33-7.29 (m, 4 H); 7.27-7.17 (m, 2 H); 7.11 (d, J = 8.2 Hz, 1 H); 6.99-6.91 (m, 2 H); 6.72 (s, 1 H); 6.61 (d, J = 8.2 Hz, 1 H); 6.54 (d, J = 9.9 Hz, 1 H); 5.79 (d, J = 9.0 Hz, 1 H); 5.21-5.15 (m, 1 H); 4.62-4.54 (m, 1 H); 4.00 (t, J = 6.4 Hz, 2 H); 3.22-3.02 (m, 1 H); 2.88-2.83 (m, 2 H); 2.80-2.71 (m, 2 H); 2.70-2.67 (m, 4 H); 1.93-1.88 (m, 1 H); 1.81-1.80 (m, 1 H); 1.59-1.58 (m, 1 H); 1.65-1.35 (m, 12 H); 1.43-1.31 (m, 1 H); 1.24-1.14 (m, 2 H) | diformate |
| 12C | B | (DMSO-d$_6$): δ 8.31 (s, 2 H); 8.41-8.12 (m, 1 H); 8.17 (d, J = 9.9 Hz, 1 H); 7.41-7.21 (m, 4 H); 7.30-7.17 (m, 1 H); 7.18 (t, J = 8.1 Hz, 1 H); 7.09 (d, J = 8.2 Hz, 1 H); 6.95 (d, J = 8.3 Hz, 1 H); 6.99-6.83 (m, 1 H); 6.72 (s, 1 H); 6.61 (d, J = 8.1 Hz, 1 H); 6.51 (d, J = 9.8 Hz, 1 H); 5.79 (d, J = 9.0 Hz, 1 H); 5.23-5.06 (m, 1 H); 4.72-4.45 (m, 1 H); 4.01 (t, J = 6.4 Hz, 2 H); 3.25-2.98 (m, 1 H); 2.81-2.72 (m, 4 H); 2.83-2.46 (m, 4 H); 2.67-2.45 (m, 1 H); 2.01-1.80 (m, 1 H); 1.94-1.67 (m, 1 H); 1.85-1.14 (m, 11 H); 1.57-1.13 (m, 1 H). | diformate |
| 13C | C | (CD$_3$OD): δ 8.57 (s, 2 H); 8.37 (d, J = 9.8 Hz, 1 H); 7.34-7.20 (m, 7 H); 7.04 (d, J = 8.1 Hz, 1 H); 6.86 (s, 1 H); 6.82 (d, J = 8.1 Hz, 2 H); 6.69 (d, J = 9.8 Hz, 1 H); 5.83 (d, J = 7.2 Hz, 1 H); 5.38-5.32 (m, 1 H); 4.90-4.74 (m, 1 H); 4.24-3.99 (m, 2 H); 4.11-3.84 (m, 2 H); 3.41-3.36 (m, 1 H); 3.10-3.03 (m, 3 H); 3.04-2.87 (m, 3 H); 2.92-2.58 (m, 2 H); 2.26-2.06 (m, 1 H); 2.25-1.90 (m, 1 H); 2.06-1.68 (m, 1 H); 1.79-1.67 (m, 1 H); 1.67-1.59 (m, 6 H); 1.69-0.95 (m, 8 H). | diformate |
| 14C | A | (DMSO-d$_6$): δ 8.36 (s, 2 H); 8.28 (d, J = 9.9 Hz, 1 H); 8.20 (d, J = 9.9 Hz, 1 H); 7.35-7.27 (m, 4 H); 7.26-7.20 (m, 2 H); 7.11 (d, J = 8.2 Hz, 1 H); 6.97 (d, J = 8.1 Hz, 1 H); 7.00-6.85 (m, 2 H); 6.81-6.70 (m, 1 H); 6.53 (d, J = 9.8 Hz, 1 H); 5.81 (d, J = 9.2 Hz, 1 H); 5.26 (dd, J = 8.9, 3.8 Hz, 1 H); 4.77 (s, 2 H); 4.74-4.52 (m, 1 H); 4.15 (d, J = 12.9 Hz, 1 H); 4.19-3.91 (m, 2 H); 3.77 (d, J = 13.3 Hz, 1 H); 3.24-3.05 (m, 2 H); 2.97-2.88 (m, 2 H); 2.86-2.53 (m, 8 H); 2.09-1.85 (m, 1 H); 2.04-1.65 (m, 3 H); 1.93-1.23 (m, 8 H); 1.58-1.24 (m, 2 H). | diformate |
| 15C | C | (DMSO-d6): δ 8.31 (s, 2 H); 8.38-8.14 (m, 1 H); 8.18 (d, J = 9.9 Hz, 1 H); 7.34-7.15 (m, 9 H); 7.08 (d, J = 8.4 Hz, 1 H); 6.99-6.91 (m, 4 H); 6.82-6.75 (m, 1 H); 6.51 (d, J = 9.8 Hz, 1 H); 5.86-5.78 (m, 1 H); 5.28-4.95 (m, 3 H); 4.88-4.74 (m, 2 H); 4.70-4.49 (m, 1 H); 3.18-3.06 (m, 1 H); 2.98-2.57 (m, 11 H); 2.01-1.80 (m, 1 H); 1.97-1.64 (m, 1 H); 1.76-1.44 (m, 1 H); 1.60-1.36 (m, 1 H); 1.56-1.16 (m, 1 H). | diformate |

-continued

| Compound | LCMS/HPLC method | NMR data at 400 MHz | Salt |
|---|---|---|---|
| 16C | A | (DMSO-d6): δ 8.31 (s, 1 H); 8.24-8.14 (m, 2 H); 7.34-7.26 (m, 4 H); 7.23-7.18 (m, 1 H); 7.10 (d, J = 8.16 Hz, 1 H); 7.04 (d, J = 7.67 Hz, 1 H); 6.95 (d, J = 8.10 Hz, 2 H); 6.82-6.76 (m, 1 H); 6.53 (d, J = 9.86 Hz, 1 H); 5.79 (d, J = 9.14 Hz, 1 H); 5.20-5.14 (m, 1 H); 4.58 (s, 1 H); 3.94-3.88 (m, 2 H); 3.17-3.05 (m, 1 H); 2.86-2.81 (m, 2 H); 2.8-2.6 (m, 6 H); 2.09 (s, 3 H); 1.91 (s, 1 H); 1.80 (s, 1 H); 1.75-1.64 (m, 2 H); 1.76-1.12 (m, 16 H). | formate |
| 17C | A | (DMSO-d6): δ 8.32 (s, 1 H); 8.28 (d, J = 8.85 Hz, 1 H); 8.18 (d, J = 9.93 Hz, 1 H); 7.36-7.30 (m, 4 H); 7.27-7.22 (m, 1 H); 7.15-7.06 (m, 2 H); 6.98 (d, J = 15.67 Hz, 3 H); 6.53 (d, J = 9.86 Hz, 1 H); 5.82 (d, J = 9.15 Hz, 1 H); 5.18 (dd, J = 7.97, 4.67 Hz, 1 H); 4.58 (s, 1 H); 3.97-3.91 (m, 2 H); 3.16-3.05 (m, 1 H); 2.88-2.83 (m, 2 H); 2.80-2.53 (m, 7 H); 1.91 (s, 1 H); 1.80 (s, 1 H); 1.95-1.11 (m, 18 H). | formate |
| 18C | B | (DMSO-d6): δ 8.31 (s, 2 H); 8.18 (d, J = 9.92 Hz, 1 H); 7.66-7.62 (m, 2 H); 7.48-7.28 (m, 7 H); 7.27-7.19 (m, 2 H); 7.10 (d, J = 8.17 Hz, 1 H); 7.04 (s, 1 H); 6.95 (d, J = 7.85 Hz, 2 H); 6.53 (d, J = 9.86 Hz, 1 H); 5.89 (d, J = 8.99 Hz, 1 H); 5.20-5.14 (m, 1 H); 4.59 (s, 1 H); 4.09-3.93 (m, 2 H); 3.12 (d, J = 13.08 Hz, 1 H); 2.87-2.82 (m, 2 H); 2.79-2.57 (m, 6 H); 1.92 (s, 1 H); 1.81 (s, 1 H); 1.75-1.67 (m, 2 H); 1.75-1.12 (m, 16 H). | formate |
| 19C | A | (DMSO-d6 @105° C.): δ 8.23-8.13 (m, 3 H); 7.60-7.49 (m, 1 H); 7.35-7.20 (m, 6 H); 7.15-7.05 (m, 2 H); 7.02-6.92 (m, 2 H); 6.51-6.45 (m, 1 H); 6.33-6.26 (m, 1 H); 5.06-5.00 (m, 1 H); 4.63-4.56 (m, 1 H); 4.10-4.01 (m, 2 H); 3.11-3.01 (m, 1 H); 2.84-2.52 (m, 8 H); 1.92-1.84 (m, 1 H); 1.82-1.54 (m, 4 H); 1.53-1.19 (m, 15 H). | diformate |
| 20C | C | (DMSO-d6): δ 8.28 (s, 2 H); 8.18 (d, J = 9.88 Hz, 1 H); 7.54-7.44 (m, 3 H); 7.39 (s, 2 H); 7.36-7.28 (m, 3 H); 7.24-7.15 (m, 2 H); 7.10 (d, J = 7.01 Hz, 2 H); 7.00 (s, 1 H); 6.95 (d, J = 8.23 Hz, 1 H); 6.53 (d, J = 9.86 Hz, 1 H); 5.89 (d, J = 8.77 Hz, 1 H); 5.16 (d, J = 7.81 Hz, 1 H); 4.59 (s, 1 H); 4.08-3.96 (m, 2 H); 3.11 (s, 1 H); 2.94-2.76 (m, 2 H); 2.7-2.3 (m, 6 H); 1.92 (s, 1 H); 1.81 s, 1 H); 1.75-1.66 (m, 2 H); 1.75-1.13 (m, 16 H). | formate |
| 21C | C | (CD3OD): δ 8.56 (s, 1 H); 8.38 (d, J = 9.9 Hz, 1 H); 7.33-7.20 (m, 8 H); 7.07-6.85 (m, 7 H); 6.70-6.65 (m, 1 H); 5.87 (s, 1 H); 5.43-5.36 (m, 1 H); 5.03 (s, 2 H); 4.92 (m, 1H - obscured by water); 4.08-4.02 (m, 2 H); 3.51-3.50 (m, 1 H); 3.27-3.06 (m, 9 H); 2.30-1.60 (m, 9 H). | formate |
| 22C | A | (CD3OD): δ 8.56 (s, 1 H); 8.38 (d, J = 9.9 Hz, 1 H); 7.33-7.20 (m, 8 H); 7.07-6.85 (m, 7 H); 6.70-6.65 (m, 1 H); 5.87 (s, 1 H); 5.43-5.36 (m, 1 H); 5.03 (s, 2 H); 4.92 (m, 1H - obscured by water); 4.08-4.02 (m, 2 H); 3.51-3.50 (m, 1 H); 3.27-3.06 (m, 9 H); 2.30-1.60 (m, 11 H). | formate |
| 23C | C | (DMSO-d6): δ 8.43 (s, 2 H); 8.19 (d, J = 9.9 Hz, 1 H); 8.03-7.88 (m, 3 H); 7.80-7.69 (m, 1 H); 7.68-7.55 (m, 2 H); 7.20 (t, J = 7.9 Hz, 1 H); 7.06 (d, J = 8.2 Hz, 1 H); 6.96 (d, J = 8.1 Hz, 1 H); 6.92-6.75 (m, 3 H); 6.49 (dd, J = 9.8, 1.3 Hz, 1 H); 5.25-5.06 (m, 3 H); 5.01-4.91 (m, 1 H); 4.26-4.00 (m, 2 H); 3.94 (t, J = 6.8 Hz, 2 H); 3.84-3.50 (m, 5 H); 2.76 (d, J = 6.3 Hz, 2 H); 2.66-2.52 (m, 2 H); 2.38-1.78 (m, 6 H); 1.77-0.77 (m, 24 H). | diformate |
| 24C | B | (DMSO-d6): δ 8.75-8.66 (m, 1 H); 8.39 (s, 2 H); 8.19 (dd, J = 9.92, 1.99 Hz, 1 H); 8.02-7.93 (m, 2 H); 7.77-7.70 (m, 1 H); 7.61 (dd, J = 15.40, 7.70 Hz, 2 H); 7.44-7.41 (m, 1 H); 7.30-7.24 (m, 1 H); 7.10-6.92 (m, 5 H); 6.89-6.81 (m, 2 H); 6.50 (dd, J = 9.85, 1.91 Hz, 1 H); 6.06-6.01 (m, 1 H); 5.20 (d, J = 10.80 Hz, 2 H); 5.16-5.10 (m, 1 H); 5.05 (s, 1 H); 4.14-4.06 (m, 1 H); 3.98-3.90 (m, 2 H); 3.72 (d, J = 14.98 Hz, 3 H); 3.61 (d, J = 12.36 Hz, 2 H); 2.81-2.75 (m, 2 H); 2.70-2.60 (m, 2 H); 2.44-2.29 (m, 1 H); 2.21-1.91 (m, 4 H); 1.73-1.64 (m, 2 H); 1.55-1.28 (m, 6 H). | diformate |
| 25C | A | (DMSO-d6): δ 8.59 (d, J = 9.31 Hz, 1 H); 8.38 (s, 2 H); 8.18 (dd, J = 9.94, 2.25 Hz, 1 H); 7.98 (dd, J = 7.77, 3.44 Hz, 2 H); 7.78-7.71 (m, 1 H); 7.64-7.57 (m, 2 H); 7.38 (d, J = 8.14 Hz, 1 H); 7.28-7.17 (m, 3 H); 7.11-7.05 (m, 2 H); 6.95 (d, J = 8.55 Hz, 3 H); 6.83 (d, J = 8.19 Hz, 1 H); 6.50 (dd, J = 9.85, 1.97 Hz, 1 H); 5.88 (d, J = 8.38 Hz, 1 H); 5.19 (s, 2 H); 5.06 (d, J = 17.58 Hz, 2 H); 4.08 (s, 1 H); 3.96-3.89 (m, 2 H); 3.81-3.51 (d, J = 15.32 Hz, 4 H); 2.76-2.71 (m, 2 H); 2.58 (d, J = 16.78 Hz, 2 H); 2.38-2.32 (m, 2 H); 2.10-1.94 (m, 4 H); 1.67 (d, J = 7.71 Hz, 2 H); 1.48-1.25 (m, 6 H). | diformate |
| 26C | C | (DMSO-d6): δ 8.54 (d, J = 9.47 Hz, 1 H); 8.40 (s, 2 H); 8.21-8.15 (m, 1 H); 8.02-7.94 (m, 2 H); 7.75 (dd, J = 13.60, 6.80 Hz, 1 H); 7.61 (dd, J = 14.38, 7.19 Hz, 2 H); 7.51-7.47 (m, 1 H); 7.36-7.29 (m, 1 H); 7.27-7.19 (m, 1 H); 7.09-7.02 (m, 2 H); 6.98-6.89 (m, 3 H); 6.82 (d, J = 8.31 Hz, 1 H); 6.50 (dd, J = 9.84, 2.05 Hz, 1 H); 5.89 (d, J = 8.63 Hz, 1 H); 5.20 (s, 2 H); 5.10 (s, 1 H); 5.03 (s, 1 H); 4.14-4.04 (m, 1 H); 3.96-3.89 (m, 2 H); 3.88-3.46 (m, 4 H); 2.77-2.72 (m, 2 H); 2.69-2.52 (m, 2 H); 2.34 (t, J = 3.91 Hz, 1 H); 2.17 (s, 1 H); 2.08-1.93 (m, 4 H); 1.68 (d, J = 8.24 Hz, 2 H); 1.51-1.26 (m, 6 H). | diformate |
| 27C | A | (DMSO-d6): δ 8.60-8.54 (m, 1 H); 8.50 (s, 1 H); 8.42 (s, 2 H); 8.17 (d, J = 9.87 Hz, 1 H); 8.01-7.92 (m, 2 H); 7.86-7.82 (m, 1 H); 7.75 (d, J = 7.15 Hz, 1 H); 7.65-7.56 (m, 2 H); 7.49 (d, J = 7.88 Hz, 2 H); 7.37-7.31 (m, 4 H); 7.29-7.23 (m, 2 H); 7.08-7.01 (m, 2 H); 6.99-6.89 (m, 3 H); 6.49 (dd, J = 9.83, 1.19 Hz, 1 H); 5.85 (d, J = 8.77 Hz, 1 H); 5.17 (d, J = 21.19 Hz, 4 H); 5.04 (d, J = 8.06 Hz, 2 H); 4.08 (s, 1 H); 3.79-3.55 (m, 4 H); 3.26 (s, 2 H); 2.73 (d, J = 7.03 Hz, 1 H); 2.69-2.52 (m, 3 H); 2.35 (d, J = 6.54 Hz, 1 H); 2.21-1.89 (m, 5 H); 1.51 (d, J = 22.95 Hz, 4 H). | diformate |

| Compound | LCMS/ HPLC method | NMR data at 400 MHz | Salt |
| --- | --- | --- | --- |
| 28C | B | (CD₃OD): δ 8.56 (s, 2 H); 8.38 (dd, J = 9.9, 3.5 Hz, 1 H); 8.03-7.98 (m, 2 H); 7.77-7.69 (m, 1 H); 7.62-7.54 (m, 2 H); 7.36-7.21 (m, 7 H); 7.04 (d, J = 8.2 Hz, 1 H); 6.95-6.79 (m, 3 H); 6.69 (dd, J = 9.8, 3.3 Hz, 1 H); 5.90 (s, 1 H); 5.43-5.36 (m, 1 H); 5.14 (s, 1 H); 4.25-4.14 (m, 1 H); 4.00-3.97 (m, 2 H); 3.85-3.70 (m, 5 H); 3.34 (m, 2 H); 3.22-3.19 (m, 2 H); 3.10-3.05 (m, 2 H); 2.50 (s, 1 H); 2.45-2.33 (m, 1 H); 2.27-2.02 (m, 3 H); 1.82 (s, 4 H); 1.59 (s, 6 H). | diformate |
| 29C | A | (CD₃OD): δ 8.56 (s, 2 H); 8.39 (d, J = 9.9 Hz, 1 H); 7.35-7.20 (m, 12 H); 7.04 (d, J = 8.2 Hz, 1 H); 6.90-6.77 (m, 3 H); 6.70 (d, J = 9.8 Hz, 1 H); 5.88 (s, 1 H); 5.39 (t, J = 6.7 Hz, 1 H); 5.04 (s, 1 H); 3.94 (t, J = 6.3 Hz, 2 H); 3.89-3.77 (m, 1 H); 3.55-3.18 (m, 6 H); 3.08-2.97 (m, 4 H); 2.69 (t, J = 7.1 Hz, 2 H); 2.41 (s, 1 H); 2.35-2.24 (m, 1H); 2.16-1.87 (m, 4 H); 1.81-1.68 n (m, 4 H); 1.56-1.39 (m, 6 H) | diformate |
| 30C | C | (CD₃OD): δ 8.56 (s, 2 H); 8.38 (dd, J = 9.9, 3.5 Hz, 1 H); 8.03-7.98 (m, 2 H); 7.77-7.69 (m, 1 H); 7.62-7.54 (m, 2 H); 7.36-7.21 (m, 7 H); 7.04 (d, J = 8.2 Hz, 1 H); 6.95-6.79 (m, 3 H); 6.69 (dd, J = 9.8, 3.3 Hz, 1 H); 5.90 (s, 1 H); 5.43-5.36 (m, 1 H); 5.14 (s, 1 H); 4.25-4.14 (m, 1 H); 4.00-3.97 (m, 2 H); 3.85-3.70 (m, 5 H); 3.34 (m, 2 H); 3.22-3.19 (m, 2 H); 3.10-3.05 (m, 2 H); 2.50 (s, 1 H); 2.45-2.33 (m, 1 H); 2.27-2.02 (m, 3 H); 1.82 (s, 4 H); 1.59 (s, 2 H). | diformate |
| 31C | B | (DMSO-d₆): δ 8.32-8.21 (m, 3 H); 8.18 (d, J = 9.9 Hz, 1 H); 7.39-7.19 (m, 10 H); 7.09 (d, J = 8.2 Hz, 1 H); 7.01 (s, 1 H); 6.97-6.89 (m, 2 H); 6.88-6.82 (m, 1 H); 6.52 (d, J = 9.9 Hz, 1 H); 5.82 (d, J = 9.0 Hz, 1 H); 5.13 (t, J = 6.3 Hz, 1 H); 5.00 (s, 2 H); 4.62-4.55 (m, 1 H); 3.97 (t, J = 6.2 Hz, 2 H); 3.16-3.07 (m, 1 H); 2.81-2.52 (m, 9 H); 1.95-1.27 (m, 17 H). | diformate |
| 32C | B | (DMSO-d₆): δ 8.32-8.22 (m, 3 H); 8.18 (d, J = 9.9 Hz, 1 H); 7.42-7.18 (m, 10 H); 7.10 (d, J = 8.2 Hz, 1 H); 7.03-6.89 (m, 3 H); 6.88-6.82 (m, 1 H); 6.53 (d, J = 9.9 Hz, 1 H); 5.82 (d, J = 9.1 Hz, 1 H); 5.18 (dd, J = 8.0, 4.5 Hz, 1 H); 5.00 (s, 2 H); 4.64-4.57 (m, 1 H); 4.02 (t, J = 6.2 Hz, 2 H); 3.20-3.09 (m, 1 H); 2.88-2.52 (m, 7 H); 2.40-2.30 (m, 2 H); 1.97-1.76 (m, 2 H); 1.73-1.16 (m, 17 H) | diformate |
| 33C | B | (DMSO-d₆): δ 8.33-8.23 (m, 3 H); 8.17 (d, J = 9.9 Hz, 1 H); 7.42-7.19 (m, 10 H); 7.10 (d, J = 8.2 Hz, 1 H); 7.01 (s, 1 H); 6.99-6.89 (m, 2 H); 6.88-6.83 (m, 1 H); 6.53 (d, J = 9.9 Hz, 1 H); 5.82 (d, J = 9.2 Hz, 1 H); 5.19 (dd, J = 8.2, 4.5 Hz, 1 H); 5.01 (s, 2 H); 4.64-4.56 (m, 1 H); 4.03 (t, J = 6.1 Hz, 2 H); 3.20-3.09 (m, 1 H); 2.89-2.52 (m, 9 H); 1.97-1.76 (m, 2 H); 1.67-1.28 (m, 13 H). | diformate |
| 34C | A | (DMSO-d6): δ 8.39 (d, J = 9.32 Hz, 1 H); 8.30 (s, 2 H); 8.18 (d, J = 9.94 Hz, 1 H); 7.93 (s, 1 H); 7.83 (d, J = 7.72 Hz, 1 H); 7.65-7.53 (m, 1 H); 7.51-7.44 (m, 1 H); 7.35-7.30 (m, 4 H); 7.26 (d, J = 5.91 Hz, 1 H); 7.11 (d, J = 8.18 Hz, 1 H); 6.96 (d, J = 8.13 Hz, 1 H); 6.53 (d, J = 9.86 Hz, 1 H); 5.94 (d, J = 8.55 Hz, 1 H); 5.21 (dd, J = 8.61, 4.05 Hz, 1 H); 4.60 (s, 1 H); 4.28-4.21 (m, 2 H); 3.12 (s, 1 H); 2.96-2.85 (m, 2 H); 2.80-2.57 (m, 7 H); 1.92 (s, 1 H); 1.81 (s, 1 H); 1.86-1.39 (m, 5 H); 1.32 (d, J = 29.30 Hz, 10 H). | diformate |
| 35C | A | (DMSO-d6): δ 8.39 (d, J = 9.08 Hz, 1 H); 8.32 (s, 2 H); 8.18 (d, J = 9.91 Hz, 1 H); 7.93 (s, 1 H); 7.83 (d, J = 7.65 Hz, 1 H); 7.58 (s, 1 H); 7.52-7.44 (m, 1 H); 7.34 (d, J = 4.53 Hz, 4 H); 7.26 (d, J = 6.13 Hz, 1 H); 7.11 (d, J = 8.14 Hz, 1 H); 6.99-6.91 (m, 1 H); 6.56-6.47 (m, 1 H); 5.94 (d, J = 7.51 Hz, 1 H); 5.24-5.18 (m, 1 H); 4.59 (s, 1 H); 4.29-4.21 (m, 2 H); 3.12 (d, J = 12.48 Hz, 1 H); 2.88 (d, J = 9.45 Hz, 2 H); 2.69 (d, J = 52.79 Hz, 6 H); 1.92 (s, 1 H); 1.81 (s, 1 H); 1.72-1.08 (m, 18 H). | diformate |
| 36C | A | (DMSO-d6): δ 8.38 (d, J = 9.05 Hz, 1 H); 8.30 (d, J = 4.26 Hz, 2 H); 8.18 (d, J = 9.90 Hz, 1 H); 7.93 (s, 1 H); 7.83 (d, J = 7.68 Hz, 1 H); 7.58 (s, 1 H); 7.48 (t, J = 7.67 Hz, 1 H); 7.34 (d, J = 4.51 Hz, 4 H); 7.26 (d, J = 5.85 Hz, 1 H); 7.10 (d, J = 8.16 Hz, 1 H); 6.95 (d, J = 8.11 Hz, 1 H); 6.52 (d, J = 9.85 Hz, 1 H); 5.94 (d, J = 8.11 Hz, 1 H); 5.17 (s, 1 H); 4.58 (s, 1 H); 4.25 (t, J = 6.47 Hz, 2 H); 3.10 (s, 1 H); 2.91-2.52 (m, 8 H); 1.97-1.72 (m, 2 H); 1.73-1.65 (m, 2 H); 1.74-1.20 (m, 12 H). | diformate |
| 37C | A | (DMSO d6): δ 8.30 (s, 1 H); 8.27-8.20 (m, 1 H); 8.17-8.11 (m, 3 H); 7.65 (d, J = 7.9 Hz, 2 H); 7.41 (d, J = 8.0 Hz, 2 H); 7.36-7.15 (m, 8 H); 7.12-7.04 (m, 2 H); 6.98-6.87 (m, 3 H); 6.49 (d, J = 9.8 Hz, 1 H); 5.83 (d, J = 9.2 Hz, 1 H); 5.23 (s, 2 H); 5.08 (dd, J = 7.8, 4.3 Hz, 1 H); 4.57 (s, 1 H); 3.79 (s, 2 H); 3.10 (s, 2 H); 2.76-2.63 (m, 6 H); 1.90 (s, 1 H); 1.80 (s, 1 H); 1.58 (s, 1 H); 1.47 (s, 1 H); 1.33 (s, 1 H). | diformate |
| 38C | A | (DMSO-d6): δ 8.39 (d, J = 8.88 Hz, 1 H); 8.29 (s, 2 H); 8.18 (d, J = 9.91 Hz, 1 H); 7.93 (s, 1 H); 7.84 (d, J = 7.67 Hz, 1 H); 7.59 (d, J = 7.47 Hz, 1 H); 7.52-7.44 (m, 1 H); 7.34 (d, J = 4.53 Hz, 4 H); 7.26 (d, J = 5.97 Hz, 1 H); 7.10 (d, J = 8.16 Hz, 1 H); 6.95 (d, J = 8.13 Hz, 1 H); 6.52 (d, J = 9.86 Hz, 1 H); 5.94 (d, J = 8.37 Hz, 1 H); 5.19-5.12 (m, 1 H); 4.58 (s, 1 H); 4.30-4.22 (m, 2 H); 3.10 (s, 1 H); 2.84 (d, J = 6.23 Hz, 2 H); 2.79-2.58 (m, 6 H); 1.91 (s, 1 H); 1.80 (s, 1 H); 1.76-1.64 (m, 2 H); 1.62-1.32 (m, 8 H). | diformate |
| 39C | B | (DMSO-d6): δ 8.53 (s, 1 H); 8.39 (d, J = 9.67 Hz, 1 H); 8.28 (s, 2 H); 8.18 (d, J = 9.93 Hz, 1 H); 7.99 (s, 1 H); 7.87 (dd, J = 14.46, 7.77 Hz, 3 H); 7.65-7.58 (m, 1 H); 7.55-7.47 (m, 3 H); 7.34 (d, J = 4.80 Hz, 4 H); 7.28-7.23 (m, 1 H); 7.11 (d, J = 8.18 Hz, 1 H); 6.96 (d, J = 8.12 Hz, 1 H); 6.53 (d, J = 9.86 Hz, 1 H); 5.96 (d, J = 7.79 Hz, 1 H); 5.40 (s, 2 H); 5.21 (dd, J = 8.54, 4.15 Hz, 1 H); 4.59 (s, 1 H); 3.33-3.21 (m, 2 H); 3.12 (s, 1 H); 2.90-2.52 (m, 8 H); 1.85 (d, J = 49.16 Hz, 2 H); 1.71-1.21 (m, 8 H). | diformate |

| Compound | LCMS/ HPLC method | NMR data at 400 MHz | Salt |
|---|---|---|---|
| 40C | B | (CD3OD): δ 8.52 (s, 2 H); 8.38 (d, J = 9.94 Hz, 1 H); 8.00 (d, J = 11.22 Hz, 2 H); 7.88 (d, J = 7.98 Hz, 2 H); 7.64 (d, J = 7.97 Hz, 2 H); 7.59-7.45 (m, 2 H); 7.33 (dd, J = 24.56, 7.68 Hz, 6 H); 7.04 (d, J = 8.21 Hz, 1 H); 6.70 (d, J = 9.84 Hz, 1 H); 6.00 (s, 1 H); 5.45 (s, 2 H); 5.42-5.35 (m, 1 H); 4.60 (s, 1 H); 3.53 (m, 1 H); 3.23-3.16 (m, 9 H); 2.97-2.89 (m, 2 H); 2.23-1.48 (m, 9 H). | diformate |
| 41C | B | (DMSO-d6): δ 8.40 (d, J = 8.99 Hz, 1 H); 8.27 (s, 2 H); 8.18 (d, J = 9.90 Hz, 1 H); 7.97 (s, 1 H); 7.86 (d, J = 7.68 Hz, 1 H); 7.67-7.52 (m, 1 H); 7.53-7.44 (m, 1 H); 7.38-7.31 (m, 6 H); 7.29-7.21 (m, 3 H); 7.15-7.05 (m, 1 H); 6.94 (d, J = 8.13 Hz, 1 H); 6.52 (d, J = 9.86 Hz, 1 H); 5.95 (d, J = 8.61 Hz, 1 H); 5.31 (s, 2 H); 5.17-5.10 (m, 1 H); 4.60 (s, 1 H); 3.14 (s, 1 H); 3.00-2.54 (m, 11 H); 1.93 (s, 1 H); 1.80 (s, 1 H); 1.60 (s, 1 H); 1.50 (s, 1 H); 1.36 (s, 1 H). | diformate |
| 42C | C | (DMSO-d6): δ 9.20-9.06 (m, 1 H); 8.32 (s, 2 H); 8.18 (d, J = 9.91 Hz, 1 H); 7.93 (d, J = 8.61 Hz, 3 H); 7.78 (d, J = 7.53 Hz, 1 H); 7.52-7.39 (m, 4 H); 7.34 (d, J = 5.28 Hz, 4 H); 7.25 (s, 1 H); 7.09 (d, J = 8.18 Hz, 1 H); 6.95 (d, J = 8.13 Hz, 1 H); 6.51 (d, J = 9.84 Hz, 1 H); 5.91 (d, J = 8.42 Hz, 1 H); 5.19-5.12 (m, 1 H); 4.61-4.50 (m, 3 H); 4.30-4.24 (m, 2 H); 3.21-3.02 (m, 1 H); 2.88-2.49 (m, 8 H); 1.91 (s, 1 H); 1.92-1.27 (m, 9 H). | diformate |
| 43C | A | (CD$_3$OD): δ 8.54 (s, 2 H); 8.35 (d, J = 9.8 Hz, 1 H); 7.72 (d, J = 8.1 Hz, 2 H); 7.44 (d, J = 8.0 Hz, 2 H); 7.32-7.21 (m, 11 H); 7.03 (d, J = 8.2 Hz, 1 H); 6.91 (m, 4 H); 6.66 (dd, J = 9.8, 1.1 Hz, 1 H); 5.88 (s, 1 H); 5.39-5.34 (m, 1 H); 5.11 (s, 2 H); 4.78-4.73 (m, 1 H); 4.32-4.26 (m, 1 H); 4.14-4.09 (m, 1 H); 3.56 (m, 1 H); 3.30-3.03 (m, 11 H); 1.89-1.64 (m, 10 H). | diformate |
| 44C | B | (DMSO-d6): δ 8.36 (s, 2 H); 8.27 (d, J = 9.3 Hz, 1 H); 8.18 (d, J = 9.9 Hz, 1 H); 7.98-7.89 (m, 2 H); 7.47-7.38 (m, 2 H); 7.35-7.22 (m, 5 H); 7.21-7.16 (m, 1 H); 7.13-6.91 (m, 5 H); 6.50 (d, J = 9.9 Hz, 1 H); 5.84 (d, J = 9.4 Hz, 1 H); 5.56 (s, 2 H); 5.13-5.07 (m, 1 H); 4.59 (d, J = 7.5 Hz, 1 H); 3.11 (d, J = 10.6 Hz, 1 H); 2.96-2.78 (m, 6 H); 2.73-2.44 (m, 5 H); 1.91 (s, 1 H); 1.79 (s, 1 H); 1.59 (s, 1 H); 1.48 (s, 1 H); 1.34 (s, 1 H). | diformate |
| 45C | B | (DMSO-d6): δ 8.49-8.14 (m, 3 H); 8.20-8.13 (m, 3 H); 7.38-7.30 (m, 5 H); 7.29-7.22 (m, 1 H); 7.11 (d, J = 8.2 Hz, 1 H); 6.96 (d, J = 8.1 Hz, 1 H); 6.57-6.49 (m, 1 H); 5.92 (d, J = 9.1 Hz, 1 H); 5.21 (dd, J = 8.5, 4.2 Hz, 1 H); 4.60 (s, 1 H); 4.04-3.96 (m, 2 H); 3.18-3.07 (m, 1 H); 2.91-2.48 (m, 8 H); 1.92 (s, 1 H); 1.75-1.64 (m, 2 H); 1.52 (s, 4 H); 1.38 (d, J = 10.7 Hz, 4 H); 1.27 (s, 9 H). | diformate |
| 46C | A | (DMSO-d$_6$): δ 8.53-8.16 (m, 4H); 7.42-7.36 (m, 2 H); 7.24-7.22 (m, 2 H); 7.11-7.04 (m, 2 H); 6.91-6.89 (m, 2 H); 6.50 (d, J = 9.6 Hz, 1 H); 5.95 (s, 1 H); 5.02-4.99 (dd, J = 7.9, 4.5 Hz, 1 H); 4.60-4.53 (m, 1 H); 3.92 (t, J = 6.5 Hz, 2 H); 3.12-3.02 (m, 1 H); 2.77-2.53 (m, 6H); 1.92-1.20 (m, 21 H). | diformate |
| 47C | A | (DMSO-d6): δ 8.26 (s, 2 H); 8.20 (d, J = 9.51 Hz, 1 H); 8.13 (d, J = 9.93 Hz, 1 H); 7.76 (d, J = 7.99 Hz, 1 H); 7.57 (s, 1 H); 7.43 (d, J = 8.10 Hz, 1 H); 7.27-7.13 (m, 6 H); 7.04 (d, J = 8.17 Hz, 1 H); 6.98 (s, 1 H); 6.90 (d, J = 8.08 Hz, 2 H); 6.83 (dd, J = 8.27, 2.48 Hz, 1 H); 6.45 (d, J = 9.86 Hz, 1 H); 5.76 (d, J = 9.32 Hz, 1 H); 5.21-5.02 (m, 3 H); 4.53 (m, 1 H); 4.24 (t, J = 6.14 Hz, 2 H); 3.12-3.02 (m, 1 H); 2.88-2.49 (m, 9 H); 1.85 (m, 1 H); 1.80-1.20 (m, 8 H). | diformate |
| 48C | C | (DMSO-d6): δ 8.32 (s, 2 H); 8.23 (d, J = 9.88 Hz, 1 H); 8.18 (d, J = 9.92 Hz, 1 H); 7.89 (t, J = 7.85 Hz, 1 H); 7.39-7.17 (m, 8 H); 7.13-6.98 (m, 2 H); 6.97-6.85 (m, 3 H); 6.50 (d, J = 9.85 Hz, 1 H); 5.82 (d, J = 9.01 Hz, 1 H); 5.18 (s, 2 H); 5.11 (t, J = 6.33 Hz, 1 H); 4.57 (s, 1 H); 4.29 (t, J = 6.33 Hz, 2 H); 3.09 (s, 1 H); 2.78 (d, J = 6.45 Hz, 2 H); 2.72 (s, 6 H); 1.90 (s, 1 H); 1.80-1.68 (m, 3 H); 1.73-1.40 (m, 6 H). | diformate |
| 49C | C | (DMSO-d$_6$); δ 9.09-9.05 (m, 1 H); 8.36-8.23 (m, 4 H); 8.18 (d, J = 9.94 Hz, 1 H); 7.63 (d, J = 8.19 Hz, 1 H); 7.32-7.18 (m, 6 H); 7.18-6.98 (m, 2 H); 6.98-6.88 (m, 3 H); 6.55-6.47 (m, 1 H); 5.82 (d, J = 9.28 Hz, 1 H); 5.37-5.19 (m, 2 H); 5.20 (dd, J = 8.41, 4.37 Hz, 1 H); 4.59 (s, 1 H); 4.36-4.30 (m, 2 H); 3.19-3.08 (m, 1 H); 2.92-2.55 (m, 8 H); 2.01-1.84 (m, 1 H); 1.95-1.39 (m, 9 H). | diformate |
| 50C | B | (DMSO-d$_6$): δ 8.39-8.12 (m, 3 H); 8.18 (d, J = 9.94 Hz, 1 H); 7.33-7.19 (m, 7 H); 7.15-7.07 (m, 1 H); 7.04 (s, 1 H,); 6.99-6.89 (m, 3 H); 6.76 (d, J = 3.48 Hz, 1 H); 6.52 (d, J = 9.86 Hz, 1 H); 5.83 (d, J = 9.2 Hz, 1 H); 5.23-5.11 (m, 3 H); 4.60 (s, 1 H); 4.28-4.21 (m, 2 H); 3.14 (dd, J = 14.7, 8.6 Hz, 1 H); 2.88-2.75 (m, 5 H); 2.72-2.48 (m, 7 H); 1.92 (d, J = 5.8 Hz, 1 H); 1.72 (t, J = 6.7 Hz, 3 H); 1.62 (d, J = 10.3 Hz, 3 H); 1.56-1.29 (m, 3 H).. | diformate |
| 51C | C | (DMSO-d6): δ 8.91-8.83 (m, 1 H); 8.37-8.12 (m, 3 H); 8.17 (d, J = 9.9 Hz, 1 H); 7.32-7.17 (m, 6 H); 7.10 (d, J = 8.1 Hz, 1 H); 7.05-6.87 (m, 4 H); 6.52 (d, J = 9.8 Hz, 1 H); 5.82 (d, J = 9.3 Hz, 1 H); 5.27 (s, 2 H); 5.18 (t, J = 5.9 Hz, 1 H); 4.59 (s, 1 H); 4.26 (t, J = 6.2 Hz, 2 H); 3.18-3.09 (m, 1 H); 2.86 (d, J = 7.2 Hz, 2 H); 2.79 (s, 5 H); 2.68-2.66 (m, 1 H); 1.92 (s, 1 H); 1.75-1.56 (m, 5 H); 1.50 (s, 2 H); 1.36 (s, 2 H). | diformate |
| 52C | A | (DMSO-d$_6$): δ 8.31-8.22 (m, 3 H); 8.17 (d, J = 9.9 Hz, 1 H); 8.03 (s, 1 H); 7.92 (d, J = 7.8 Hz, 1 H); 7.71 (d, J = 7.7 Hz, 1 H); 7.54 (t, J = 7.7 Hz, 1 H); 7.36-7.18 (m, 6 H); 7.12-7.02 (m, 2 H); 6.98-6.87 (m, 3 H); 6.52 (d, J = 9.9 Hz, 1 H); 5.82 (d, J = 9.3 Hz, 1 H); 5.21-5.13 (m, 3 H); 4.63-4.56 (m, 1 H); 4.30 (t, J = 6.2 Hz, 2 H); 3.18-3.08 (m, 1 H); 2.91-2.52 (m, 9 H); 1.95-1.89 (m, 1 H); 1.86-1.30 (m, 8 H). | diformate |

| Compound | LCMS/HPLC method | NMR data at 400 MHz | Salt |
|---|---|---|---|
| 53C | A | (DMSO-d6): δ 8.30-8.24 (m, 3 H); 8.18 (d, J = 9.9 Hz, 1 H); 7.31-7.28 (m, 4 H); 7.26-7.20 (m, 2 H); 7.14-7.07 (m, 1 H); 6.96-6.94 (m, 3 H); 6.79-6.76 (m, 1 H); 6.54-6.51 (m, 1 H); 5.82-5.79 (m, 1 H); 5.19-5.16 (m, 1 H); 4.75 (s, 2 H); 4.60-4.56 (m, 1 H); 4.10-4.06 (m, 2 H); 3.11-3.09 (m, 1 H); 2.86-2.50 (m, 8 H); 1.92-1.88 (m, 1 H); 1.80-1.75 (m, 1 H); 1.58-1.48 (m, 7 H); 1.34-1.26 (m, 3 H). | diformate |
| 54C | A | (DMSO-d6): δ 8.30-8.24 (m, 3 H); 8.18 (d, J = 9.9 Hz, 1 H); 7.32-7.28 (m, 4 H); 7.24-7.20 (m, 2 H); 7.11-7.09 (m, 1 H); 6.96-6.93 (m, 3 H); 6.78-6.76 (m, 1 H); 6.53-6.51 (m, 1 H); 5.82-5.80 (m, 1 H); 5.17-5.14 (m, 1 H); 4.75 (s, 2 H); 4.59-4.55 (m, 1 H); 4.09-4.06 (m, 2 H); 3.15-3.08 (m, 1 H); 2.83-2.50 (m, 8 H); 1.91-1.87 (m, 1 H); 1.81-1.75 (m, 1 H); 1.58-1.47 (m, 7 H); 1.33-1.25 (m, 3 H). | diformate |
| 55C | C | (DMSO-d6): δ 8.32-8.27 (m, 3 H); 8.20 (d, J = 9.9 Hz, 1 H); 7.32-7.26 (m, 4 H); 7.25-7.20 (m, 2 H); 7.13-7.10 (m, 1 H); 6.98-6.94 (m, 3 H); 6.79-6.76 (m, 1 H); 6.55-6.52 (m, 1 H); 5.83-5.80 (m, 1 H); 5.29-5.26 (m, 1 H); 4.75 (s, 2 H); 4.63-4.59 (m, 1 H); 4.09-4.06 (m, 2 H); 3.20-3.15 (m, 1 H); 2.98-2.50 (m, 8 H); 1.98-1.87 (m, 1 H); 1.92-1.69 (m, 1 H); 1.76-1.28 (m, 5 H); 1.48-1.26 (m, 2 H); 1.45-1.09 (m, 4 H). | diformate |
| 56C | A | (DMSO-d6): δ 8.35-8.20 (m, 3 H); 8.19 (d, J = 9.9 Hz, 1 H); 7.34-7.27 (m, 4 H); 7.26-7.19 (m, 2 H); 7.14-7.07 (m, 1 H); 7.00-6.90 (m, 3 H); 6.80-6.73 (m, 1 H); 6.56-6.50 (m, 1 H); 5.86-5.78 (m, 1 H); 5.24-5.19 (m, 1 H); 4.75 (s, 2 H); 4.68-4.52 (m, 1 H); 4.11-4.04 (m, 2 H); 3.23-3.03 (m, 1 H); 2.95-2.82 (m, 2 H); 2.91-2.61 (m, 4 H); 2.73-2.50 (m, 3 H); 1.98-1.87 (m, 1 H); 1.92-1.69 (m, 1 H); 1.76-1.28 (m, 5 H); 1.48-1.26 (m, 2 H); 1.45-1.09 (m, 4 H). | diformate |
| 57C | A | (DMSO-d$_6$): δ 8.57 (t, J = 5.5 Hz, 1 H); 8.32 (s, 2 H); 8.27-8.15 (m, 2 H); 7.84 (d, J = 8.0 Hz, 2 H); 7.50 (d, J = 8.0 Hz, 2 H); 7.35-7.19 (m, 6 H); 7.11-7.02 (m, 2 H); 6.96-6.86 (m, 3 H); 6.50 (d, J = 9.9 Hz, 1 H); 5.84-5.79 (m, 1 H); 5.16-5.09 (m, 3 H); 4.60-4.54 (m, 1 H); 3.36-3.28 (m, 2 H); 3.15-3.05 (m, 1 H); 2.83-2.52 (m, 9 H); 1.94-1.68 (m, 4 H); 1.65-1.26 (m, 3 H). | diformate |
| 58C | A | (DMSO-d$_6$): δ 8.45 (t, J = 5.6 Hz, 1 H); 8.32 (s, 2 H); 8.27-8.16 (m, 2 H); 7.83 (d, J = 8.1 Hz, 2 H); 7.50 (d, J = 8.0 Hz, 2 H); 7.36-7.19 (m, 6 H); 7.12-7.03 (m, 2 H); 6.96-6.86 (m, 3 H); 6.48 (d, J = 9.9 Hz, 1 H); 5.82 (d, J = 9.2 Hz, 1 H); 5.14 (s, 2 H); 5.04 (t, J = 6.2 Hz, 1 H); 4.61-4.53 (m, 1 H); 3.40-3.32 (m, 2 H); 3.14-3.04 (m, 1 H); 2.83-2.52 (m, 9 H); 1.93-1.73 (m, 2 H); 1.65-1.26 (m, 3 H). | formate |
| 59C | A | (DMSO-d$_6$ 85° C.): δ 8.22-8.11 (m, 2 H); 7.76-7.65 (m, 1 H); 7.48-7.38 (m, 2 H); 7.36-7.15 (m, 8 H); 7.10-6.82 (m, 5 H); 6.51-6.40 (m, 1 H); 5.85-5.75 (m, 1 H); 5.13-4.94 (m, 3 H); 4.64-4.52 (m, 1 H); 3.40-3.22 (m, 4 H); 3.14-3.00 (m, 1 H); 2.82-2.43 (m, 9 H); 1.94-1.83 (m, 1 H); 1.81-1.55 (m, 4 H); 1.53-1.40 (m, 1 H); 1.36-1.23 (m, 1 H); 1.12-1.00 (m, 3 H). | formate |
| 60C | B | (DMSO-d6 85° C.): δ 8.22-8.15 (m, 3 H); 7.73 (s, 1 H); 7.46 (d, J = 7.85 Hz, 2 H); 7.37-7.27 (m, 6 H); 7.26-7.19 (m, 2 H); 7.08 (d, J = 8.12 Hz, 2 H); 7.03 (s, 1 H); 6.95 (d, J = 7.74 Hz, 2 H); 6.48 (d, J = 9.88 Hz, 1 H); 5.83 (d, J = 7.98 Hz, 1 H); 5.11 (s, 2 H); 5.05-4.99 (m, 1 H); 4.63-4.58 (m, 1 H); 3.39 (s, 2 H); 3.09 (dd, J = 14.46, 8.25 Hz, 1 H); 2.91 (s, 3 H); 2.81-2.49 (m, 9 H); 1.93-1.89 (m, 1 H); 1.73-1.55 (m, 4 H); 1.52-1.45 (m, 1 H); 1.31 (d, J = 11.44 Hz, 1 H). | diformate |
| 61C | C | (DMSO-d6 85° C.): δ 8.25-8.15 (m, 3 H); 7.73 (s, 1 H); 7.46 (d, J = 7.85 Hz, 2 H); 7.33-7.20 (m, 7 H); 7.09 (d, J = 8.12 Hz, 1 H); 7.03 (m, 1 H); 6.97-6.87 (m, 3 H); 6.50 (d, J = 3.46 Hz, 1 H); 5.83 (d, J = 8.55 Hz, 1 H); 5.11 (s, 2 H); 5.07-5.03 (m, 1 H); 4.63-4.58 (m, 1 H); 4.00 (s, 1 H); 3.27 (t, J = 7.50 Hz, 2 H); 3.09 (dd, J = 14.43, 8.27 Hz, 1 H); 2.80-2.5 (m, 9 H); 1.93-1.89 (m, 1 H); 1.78-1.68 (m, 3 H); 1.66-1.56 (m, 1 H); 1.53-1.44 (m, 1 H); 1.32 (q, J = 9.86 Hz, 1 H); 1.15 (d, J = 6.72 Hz, 6 H). | diformate |
| 62C | A | (DMSO-d$_6$): δ 8.46 (t, J = 5.7 Hz, 1 H); 8.29 (s, 2 H); 8.24 (d, J = 9.3 Hz, 1 H); 8.18 (d, J = 9.9 Hz, 1 H); 7.84 (d, J = 7.9 Hz, 2 H); 7.50 (d, J = 7.9 Hz, 2 H); 7.36-7.27 (m, 4 H); 7.27-7.18 (m, 2 H); 7.09 (d, J = 8.1 Hz, 1 H); 7.04 (s, 1 H); 6.98-6.85 (m, 3 H); 6.52 (d, J = 9.9 Hz, 1 H); 5.81 (d, J = 8.9 Hz, 1 H); 5.18-5.10 (m, 3 H); 4.62-4.54 (m, 1 H); 4.00 (t, J = 6.0 Hz, 2 H); 3.17-3.06 (m, 3 H); 2.86-2.53 (m, 9 H); 2.29-2.19 (m, 1 H); 1.96-1.86 (m, 3 H); 1.85-1.72 (m, 3 H); 1.66-1.20 (m, 10 H); 1.05-0.90 (m, 2 H). | diformate |
| 63C | A | (DMSO-d$_6$): 10.80-10.00 (br s, 1 H); 8.70 (t, J = 6.32 Hz, 1 H); 8.27 (s, 2 H); 8.19 (d, J = 9.92 Hz, 1 H); 7.84 (t, J = 6.84 Hz, 2 H), 7.51 (d, J = 7.83 Hz, 2 H); 7.31 (s, 4 H); 7.23 (t, J = 7.47 Hz, 2 H); 7.11-7.02 (m, 2 H); 6.96-6.85 (m, 3 H); 6.50 (dd, J = 9.80, 3.32 Hz, 1 H); 5.81 (s, 1 H); 5.14 (s, 2 H); 5.07 (d, J = 10.80 Hz, 1 H); 4.90 (t, J = 6.69 Hz, 1 H); 4.60 (s, 1 H); 3.63 (d, J = 2.45 Hz, 3 H); 3.50-3.32 (m, 3 H); 3.15 (s, 1 H); 2.98 (s, 3 H); 2.90 (d, J = 6.19 Hz, 1 H), 2.77 (m, 7 H); 2.68 (s, 3 H); 1.94 (s, 1 H); 1.81 (s, 1 H); 1.61 (s, 1 H); 1.51 (s, 1 H); 1.37 (s, 1 H). | diformate |
| 64C | C | (DMSO-d$_6$): δ 8.30-8.21 (m, 3 H); 8.19 (d, J = 9.9 Hz, 1 H); 7.97 (d, J = 7.9 Hz, 2 H); 7.57 (d, J = 7.9 Hz, 2 H); 7.30 (s, 4 H); 7.28-7.19 (m, 2 H); 7.10 (d, J = 8.1 Hz, 1 H); 7.03 (s, 1 H); 6.92 (dd, J = 24.4, 8.0 Hz, 3 H); 6.53 (d, J = 9.9 Hz, 1 H); 5.82 (d, J = 9.1 Hz, 1 H); 5.20-5.11 (m, 3 H); 4.59 (s, 1 H); 4.12 (d, J = 6.2 Hz, 2 H); 3.13 (m, 1 H); 2.88-2.55 (m, 8 H); 1.96-1.32 (m, 12 H); 1.14-0.88 (m, 4 H) | diformate |

| Compound | LCMS/HPLC method | NMR data at 400 MHz | Salt |
|---|---|---|---|
| 65C | B | (DMSO-d$_6$): δ 8.30 (s, 1 H); 8.27-8.20 (m, 1 H); 8.17-8.11 (m, 3 H); 7.65 (d, J = 7.9 Hz, 2 H); 7.41 (d, J = 8.0 Hz, 2 H); 7.36-7.15 (m, 8 H); 7.12-7.04 (m, 2 H); 6.98-6.87 (m, 3 H); 6.49 (d, J = 9.8 Hz, 1 H); 5.83 (d, J = 9.2 Hz, 1 H); 5.23 (s, 2 H); 5.08 (dd, J = 7.8, 4.3 Hz, 1 H); 4.57 (s, 1 H); 3.79 (s, 2 H); 3.10 (s, 2 H); 2.76-2.63 (m, 6 H); 1.90 (s, 1 H); 1.80 (s, 1 H); 1.58 (s, 1 H); 1.47 (s, 1 H); 1.33 (s, 1 H). | diformate |
| 66C | C | (DMSO-d$_6$): δ 8.32-8.20 (m, 2 H); 8.17 (d, J = 10.0 Hz, 2 H); 8.02 (d, J = 7.9 Hz, 2 H); 7.58 (d, J = 7.9 Hz, 2 H); 7.31 (s, 4 H); 7.24 (t, J = 7.8 Hz, 2 H); 7.12-7.01 (m, 2 H); 6.98-6.85 (m, 3 H); 6.51 (d, J = 9.8 Hz, 1 H); 5.82 (d, J = 8.9 Hz, 1 H); 5.19 (s, 2 H); 5.11 (t, J = 6.2 Hz, 1 H); 4.70 (s, 2 H); 4.58 (s, 1 H); 3.16-3.09 (m, 4 H); 2.79 (d, J = 6.5 Hz, 2 H); 2.74-2.65 (m, 4 H); 1.91 (s, 1 H); 1.80 (s, 1 H); 1.64 (t, J = 11.6 Hz, 5 H); 1.48 (s, 1 H); 1.34 (s, 1 H). | diformate |
| 67C | A | (DMSO-d6): δ 8.30-8.16 (m, 3 H); 8.19 (d, J = 10.0 Hz, 1 H); 8.00 (d, J = 8.0 Hz, 2 H); 7.59 (d, J = 8.0 Hz, 2 H); 7.31 (s, 4 H); 7.28-7.19 (m, 2 H); 7.09 (d, J = 8.1 Hz, 1 H); 7.04 (s, 1 H); 6.97-6.86 (m, 3 H); 6.53 (d, J = 10.0 Hz, 1 H); 5.81 (m, 1 H); 5.19 (s, 2 H); 5.11 (t, J = 5.2 Hz, 1 H); 4.93 (s, 2 H); 4.58 (s, 1 H); 4.14 (t, J = 6.3 Hz, 2 H); 3.16-3.04 (m, 1 H); 2.86-2.62 (m, 8 H); 1.90 (s, 1 H); 1.79 (s, 1 H); 1.69-1.41 (m, 7 H); 1.34 (s, 1 H). | diformate |
| 68C | A | (DMSO-d$_6$): δ 8.30-8.16 (m, 3 H); 8.00 (d, J = 8.1 Hz, 2 H); 7.60 (d, J = 8.0 Hz, 2 H); 7.31-7.18 (m, 6 H); 7.12 (d, J = 8.2 Hz, 1 H); 7.03 (s, 1 H); 6.96 (t, J = 6.8 Hz, 2 H); 6.89 (dd, J = 8.2, 2.5 Hz, 1 H); 6.55 (d, J = 9.9 Hz, 1 H); 5.82 (d, J = 9.2 Hz, 1 H); 5.25 (dd, J = 8.9, 3.9 Hz, 1 H); 5.19 (s, 2 H); 4.94 (s, 2 H); 4.60 (s, 1 H); 4.14 (t, J = 6.4 Hz, 2 H); 3.16 (m, 1 H); 2.98-2.89 (m, 2 H); 2.85-2.59 (m, 7 H); 1.94 (s, 1 H); 1.81 (s, 1 H); 1.65-1.55 (m, 6 H); 1.40-1.30 (m, 4 H). | formate |
| 69C | C | (DMSO-d$_6$): δ 8.32-8.20 (m, 3 H); 8.17 (d, J = 9.9 Hz, 1 H); 7.96 (d, J = 8.1 Hz, 2 H); 7.56 (d, J = 8.0 Hz, 2 H); 7.32-7.18 (m, 6 H); 7.08-7.01 (m, 2 H); 6.97-6.84 (m, 3 H); 6.49 (d, J = 9.9 Hz, 1 H); 5.82 (d, J = 9.3 Hz, 1 H); 5.17 (s, 2 H); 5.09-5.02 (m, 1 H); 4.58 (s, 1 H); 4.42-4.37 (m, 2 H); 3.76-3.71 (m, 2 H); 3.61-3.55 (m, 2 H); 3.11 (t, J = 10.6 Hz, 1 H); 2.82-2.50 (m, 9 H); 1.91 (s, 1 H); 1.80 (s, 1 H); 1.59 (s, 1 H); 1.48 (s, 1 H); 1.35 (s, 1 H) | diformate |
| 70C | C | (DMSO-d$_6$): δ 8.31-8.19 (m, 2 H); 8.16 (d, J = 9.9 Hz, 1 H); 7.96 (d, J = 8.1 Hz, 2 H); 7.56 (d, J = 8.0 Hz, 2 H); 7.31-7.18 (m, 6 H); 7.08 (d, J = 8.2 Hz, 1 H); 7.03 (s, 1 H); 6.97-6.90 (m, 2 H); 6.88 (dd, J = 8.3, 2.5 Hz, 1 H); 6.52 (d, J = 9.9 Hz, 1 H); 5.82 (d, J = 9.1 Hz, 1 H); 5.18-5.09 (m, 3 H); 4.57 (s, 1 H); 4.42-4.37 (m, 2 H); 3.72-3.67 (m, 2 H); 3.46 (s, 2 H); 3.21-3.02 (m, 1 H); 2.81-2.50 (m, 10 H); 1.90 (s, 1 H); 1.79 (s, 1 H); 1.53 (s, 5 H); 1.34 (s, 1 H). | formate |
| 71C | A | (DMSO-d$_6$): δ 8.30-8.16 (m, 3 H); 8.00 (d, J = 8.1 Hz, 2 H); 7.60 (d, J = 8.0 Hz, 2 H); 7.31-7.18 (m, 6 H); 7.12 (d, J = 8.2 Hz, 1 H); 7.03 (s, 1 H); 6.96 (t, J = 6.8 Hz, 2 H); 6.89 (dd, J = 8.2, 2.5 Hz, 1 H); 6.55 (d, J = 9.9 Hz, 1 H); 5.82 (d, J = 9.2 Hz, 1 H); 5.25 (dd, J = 8.9, 3.9 Hz, 1 H); 5.19 (s, 2 H); 4.94 (s, 2 H); 4.60 (s, 1 H); 4.14 (t, J = 6.4 Hz, 2 H); 3.16 (m, 1 H); 2.98-2.89 (m, 2 H); 2.85-2.59 (m, 7 H); 1.94 (s, 1 H); 1.81 (s, 1 H); 1.65-1.55 (m, 6 H); 1.40-1.30 (m, 4 H). | formate |
| 72C | C | (DMSO-d$_6$): δ 8.32-8.20 (m, 3 H); 8.17 (d, J = 9.9 Hz, 1 H); 7.96 (d, J = 8.1 Hz, 2 H); 7.56 (d, J = 8.0 Hz, 2 H); 7.32-7.18 (m, 6 H); 7.08-7.01 (m, 2 H); 6.97-6.84 (m, 3 H); 6.49 (d, J = 9.9 Hz, 1 H); 5.82 (d, J = 9.3 Hz, 1 H); 5.17 (s, 2 H); 5.09-5.02 (m, 1 H); 4.58 (s, 1 H); 4.42-4.37 (m, 2 H); 3.76-3.71 (m, 2 H); 3.61-3.55 (m, 2 H); 3.11 (t, J = 10.6 Hz, 1 H); 2.82-2.50 (m, 9 H); 1.91 (s, 1 H); 1.80 (s, 1 H); 1.59 (s, 1 H); 1.48 (s, 1 H); 1.35 (s, 1 H) | diformate |
| 73C | C | (DMSO-d$_6$): δ 8.31-8.19 (m, 2 H); 8.16 (d, J = 9.9 Hz, 1 H); 7.96 (d, J = 8.1 Hz, 2 H); 7.56 (d, J = 8.0 Hz, 2 H); 7.31-7.18 (m, 6 H); 7.08 (d, J = 8.2 Hz, 1 H); 7.03 (s, 1 H); 6.97-6.90 (m, 2 H); 6.88 (dd, J = 8.3, 2.5 Hz, 1 H); 6.52 (d, J = 9.9 Hz, 1 H); 5.82 (d, J = 9.1 Hz, 1 H); 5.18-5.09 (m, 3 H); 4.57 (s, 1 H); 4.42-4.37 (m, 2 H); 3.72-3.67 (m, 2 H); 3.46 (s, 2 H); 3.21-3.02 (m, 1 H); 2.81-2.50 (m, 10 H); 1.90 (s, 1 H); 1.79 (s, 1 H); 1.53 (s, 5 H); 1.34 (s, 1 H). | formate |
| 74C | C | (DMSO-d6): δ 8.29 (s, 1 H); 8.22 (d, J = 9.8 Hz, 1 H); 8.17 (d, J = 9.9 Hz, 1 H); 7.99 (d, J = 8.0 Hz, 2 H); 7.57 (d, J = 8.0 Hz, 2 H); 7.34-7.18 (m, 9 H); 7.09-7.01 (m, 2 H); 6.96-6.84 (m, 3 H); 6.49 (d, J = 9.9 Hz, 1 H); 5.81 (d, J = 9.3 Hz, 1 H); 5.33 (s, 2 H); 5.17 (s, 2 H); 5.05 (dd, J = 7.7, 4.7 Hz, 1 H); 4.56 (s, 1 H); 3.10 (m, 1 H); 2.89-2.70 (m, 10 H); 1.89 (br s, 2 H); 1.78 (br s, 2 H); 1.59 (br s, 1 H); 1.46 (br s, 1 H); 1.31 (br s, 1 H) | formate |
| 75C | B | (DMSO-d$_6$): δ 8.40 (s, 1 H); 8.22 (d, J = 9.3 Hz, 1 H); 8.16 (d, J = 9.9 Hz, 1 H); 7.87 (d, J = 8.1 Hz, 2 H); 7.37-7.26 (m, 6 H); 7.26-7.18 (m, 2 H); 7.05 (d, J = 8.2 Hz, 1 H); 6.98-6.89 (m, 3 H); 6.82 (dd, J = 8.2, 2.4 Hz, 1 H); 6.49 (d, J = 9.9 Hz, 1 H); 5.84-5.77 (m, 1 H); 5.01 (dd, J = 7.9, 4.5 Hz, 1 H); 4.59-4.52 (m, 1 H); 4.40 (t, J = 6.2 Hz, 2 H); 4.10 (t, J = 6.2 Hz, 2 H); 3.12-3.02 (m, 1 H); 2.86-2.53 (m, 8 H); 2.20-2.11 (m, 2 H); 1.92-1.72 (m, 5 H); 1.63-1.22 (m, 3 H). | formate |
| 76C | A | (DMSO-d$_6$): δ 8.31 (s, 2 H); 8.28-8.14 (m, 2 H); 7.91 (d, J = 7.89 Hz, 2 H); 7.46 (d, J = 7.91 Hz, 2 H); 7.31 (d, J = 4.81 Hz, 4 H); 7.26-7.17 (m, 2 H); 7.10 (d, J = 8.15 Hz, 1 H); 6.98-6.87 (m, 3 H); 6.81 (d, J = 8.23 Hz, 1 H); 6.52 (d, J = 9.83 Hz, 1 H); 5.81 (d, J = 9.13 Hz, 1 H); 5.21-5.15 (m, 1 H); 4.59 (s, 2 H); 4.30-4.23 (m, 2 H); 4.19 (t, J = 6.64 Hz, 2 H); 3.13-3.07 (m, 3 H); 2.95-2.51 (m, 7 H); 1.92 (s, 1 H); 1.94-1.32 (m, 9 H). | diformate |

| Compound | LCMS/HPLC method | NMR data at 400 MHz | Salt |
|---|---|---|---|
| 77C | C | (DMSO-d6): δ 8.41-8.12 (m, 3 H); 8.20-8.13 (m, 5 H); 7.35-7.23 (m, 5 H); 7.23-7.15 (m, 1 H); 7.13-7.05 (m, 2 H); 7.05-6.91 (m, 3 H); 6.51 (d, J = 9.9 Hz, 1 H); 5.88-5.80 (m, 1 H); 5.60 (s, 2 H); 5.18-5.11 (m, 1 H); 4.63-4.49 (m, 1 H); 4.36-4.29 (m, 2 H); 3.15-3.05 (m, 1 H); 2.86-2.71 (m, 7 H); 2.69-2.49 (m, 2 H); 1.97-1.82 (m, 1 H); 1.81-1.72 (m, 3 H); 1.69-1.60 (m, 3 H); 1.60-1.33 (m, 1 H); 1.47-1.20 (m, 1 H). | diformate |
| 78C | C | (CD$_3$OD): δ 8.57 (s, 2 H); 8.38 (d, J = 9.9 Hz, 1 H); 8.01 (d, J = 8.0 Hz, 2 H); 7.48 (d, J = 8.0 Hz, 2 H); 7.35-7.19 (m, 7 H); 7.03 (d, J = 8.2 Hz, 1 H); 6.89-6.79 (m, 3 H); 6.67 (d, J = 9.8 Hz, 1 H); 5.88 (s, 1 H); 5.39 (t, J = 6.7 Hz, 1 H); 4.89 (br s, 1 H); 4.51-4.28 (m, 2 H); 3.80 (d, J = 5.5 Hz, 2 H); 3.65 (s, 2 H); 3.46 (m, 1 H); 3.18 (d, J = 6.7 Hz, 2 H); 3.24-2.98 (m, 3 H); 3.09-2.89 (m, 5 H); 2.28-2.13 (m, 1 H); 2.19-2.07 (m, 3 H); 1.98-1.82 (m, 5 H); 1.91-1.75 (m, 5 H); 1.88-1.45 (m, 1 H); 1.51-1.37 (m, 2 H) | diformate |
| 79C | A | (DMSO-d6): δ 8.31 (s, 2 H); 8.23 (d, J = 8.1 Hz, 1 H); 8.17 (d, J = 9.9 Hz, 1 H); 7.95 (d, J = 8.1 Hz, 2 H); 7.55 (d, J = 8.1 Hz, 2 H); 7.34-7.19 (m, 6 H); 7.08 (d, J = 8.2 Hz, 1 H); 7.02 (s, 1 H); 6.96-6.84 (m, 3 H); 6.51 (d, J = 9.9 Hz, 1 H); 5.81 (d, J = 9.2 Hz, 1 H); 5.17-5.08 (m, 3 H); 4.57 (s, 1 H); 4.42-4.37 (m, 2 H); 3.70 (t, J = 4.6 Hz, 2 H); 3.46 (s, 2 H); 3.10 (m, 2 H); 2.79 (d, J = 6.3 Hz, 2 H); 2.75-2.63 (m, 8 H); 1.84 (d, J = 44.6 Hz, 2 H); 1.53 (s, 5 H). | diformate |
| 80C | A | (DMSO-d6): δ 8.32 (s, 1 H); 8.25-8.12 (m, 2 H); 7.98 (d, J = 8.1 Hz, 2 H); 7.57 (d, J = 8.1 Hz, 2 H); 7.38-7.15 (m, 11 H); 7.09-6.98 (m, 2 H); 6.94-6.84 (m, 3 H); 6.50 (d, J = 9.9 Hz, 1 H); 5.81 (d, J = 9.4 Hz, 1 H); 5.32 (s, 2 H); 5.18 (s, 2 H); 5.03 (dd, J = 7.9, 4.6 Hz, 1 H); 4.55 (s, 1 H); 3.04 (m, 1 H); 2.83-2.65 (m, 10 H); 1.94-1.83 (m, 1 H); 1.77 (s, 1 H); 1.56 (d, J = 11.1 Hz, 1 H); 1.45 (s, 1 H); 1.30 (s, 1 H) | formate |
| 81C | C | (CD$_3$OD): δ 8.55 (s, 1 H); 8.33 (d, J = 9.9 Hz, 1 H); 7.95 (d, J = 8.1 Hz, 2 H); 7.46 (d, J = 8.0 Hz, 2 H); 7.35-7.18 (m, 8 H); 7.02-6.88 (m, 4 H); 6.64 (d, J = 9.8 Hz, 1 H); 5.88 (s, 1 H); 5.32 (dd, J = 9.0, 4.3 Hz, 1 H); 5.14 (s, 2 H); 4.80 (m, 1 H); 4.53-4.49 (m, 2 H); 3.91-3.86 (m, 2 H); 3.86-3.80 (m, 2 H); 3.22-3.08 (m, 6 H); 3.01 (s, 3 H); 2.16 (d, J = 44.3 Hz, 2 H); 1.97-1.63 (m, 3 H). | formate |
| 82C | C | (DMSO-d$_6$): δ 8.28 (s, 1 H); 8.23 (d, J = 9.8 Hz, 1 H); 8.17 (d, J = 9.9 Hz, 1 H); 7.81 (d, J = 8.0 Hz, 1 H); 7.62 (s, 1 H); 7.48 (d, J = 8.1 Hz, 1 H); 7.32-7.19 (m, 6 H); 7.09 (d, J = 8.2 Hz, 1 H); 7.03 (s, 1 H); 6.96-6.84 (m, 3 H); 6.51 (d, J = 9.9 Hz, 1 H); 5.82 (d, J = 9.2 Hz, 1 H); 5.18-5.06 (m, 3 H); 4.57 (s, 1 H); 4.29 (t, J = 6.3 Hz, 2 H); 3.10 (s, 2 H); 2.79 (d, J = 6.5 Hz, 2 H); 2.73 (t, J = 7.9 Hz, 4 H); 1.90 (s, 1 H); 1.76 (t, J = 10.9 Hz, 3 H); 1.66-1.57 (m, 4 H); 1.47 (s, 2 H); 1.33 (s, 1 H). | formate |
| 83C | C | (CD$_3$OD): δ 8.55 (s, 2 H); 8.37 (d, J = 9.9 Hz, 1 H); 7.93 (t, J = 7.7 Hz, 1 H); 7.36-7.22 (m, 9 H); 7.03 (d, J = 8.2 Hz, 1 H); 6.95-6.86 (m, 3 H); 6.68 (d, J = 9.8 Hz, 1 H); 5.89 (s, 1 H); 5.40-5.34 (m, 1 H); 5.16 (s, 2 H); 4.95-4.79 (m, 1 H under solvent peak); 4.42 (s, 2 H); 3.56-3.42 (m, 1 H); 3.27-3.01 (m, 9 H); 2.24 (s, 1 H); 2.12 (s, 1 H); 1.94 (s, 7 H). | diformate |

Legend
* NMR
s = singlet
d = doublet
t = triplet
q = quartet
dd = doublet of doublets
m = multiplet
br = broad Biological Characterization.

Example 83

M3 Receptor Radioligand Binding Assay

Human M3 receptor membranes (15 ug/well) from Perkin Elmer were incubated with 0.52 nM Scopolamine Methyl Chloride, [N-methyl-3H] with or without test compounds, or a saturating concentration of Atropine (5 μM) for the determination of non-specific binding. The assay was carried out in 96-well polypropylene plates in a volume of 250 ul. The assay buffer used was 50 mM Tris-HCl, 154 mM NaCl (pH 7.4). The final assay concentration of DMSO was 0.5% (v/v). The plates were sealed and incubated for 2 hours at room temperature on an orbital shaker (slow speed). Membranes were harvested onto 96-well unifilter GF/C filter plates pre-treated with 0.5% polyetyleneimine (v/v), using a filter manifold, washed four times with 200 ul of assay buffer. The plates were dried before addition of 50 μl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the tested compounds are less than 10 nM.

Example 84

β2 Adrenoceptor Radioligand Binding Assay

Human $β_2$ adrenoceptor membranes (7.5 ug/well) from Perkin Elmer were incubated with 0.3 nM 125-I Cyanopindolol with or without test compounds, or a saturating concentration of s-propranolol (2 μM) for the determination of non-specific binding. The assay was carried out in 96-well polypropylene plates in a volume of 200 ul. The assay buffer used was 25 mM HEPES, 0.5% BSA (w/v), 1 mM EDTA, 0.02% ascorbic acid (v/v), (pH 7.4). The final assay concentration of DMSO was 0.5% (v/v). The plates were sealed and incubated for 1 hour at room temperature on an orbital shaker (slow speed). Membranes were harvested onto 96-well unifilter GF/C filter plates pre-treated with 0.5% polyetyleneimine (v/v), using a filter manifold, washed six times with 200 ul of wash buffer containing 10 mM HEPES and 500 mM NaCl. The plates were dried before addition of 50 μl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the tested compounds are less than 5 nM.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

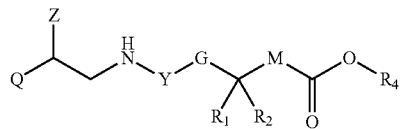

(I)

wherein:
Q is a group of formula Q1, Q3:

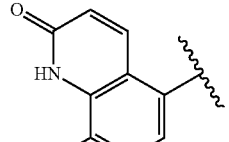

Q1

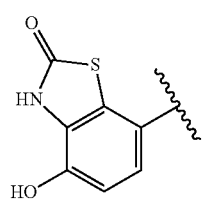

Q3

Z is H or OH;
Y is Y' or Y1:

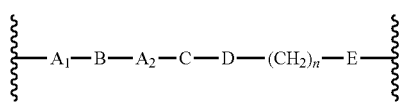

Y'

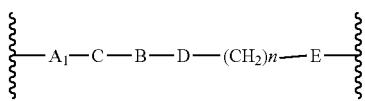

Y1 wherein
A1 and A2 are independently absent or are selected from the group consisting of $(C_1-C_{12})$alkylene, $(C_3-C_8)$cycloalkylene, and $(C_3-C_8)$heterocycloalkylene optionally substituted by one or more substituents selected from the group consisting of $(C_1-C_6)$alkyl, $(C_1-C_6)$arylalkyl, and $(C_1-C_6)$hetero aryl alkyl;

B is absent or is selected from the group consisting of $(C_3-C_8)$cycloalkylene, $(C_3-C_8)$heterocycloalkylene, arylene, and heteroarylene or is a group of formula B1

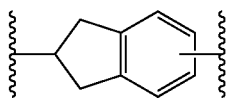

B1 optionally substituted by one or more groups selected from a halogen, nitrile, $(C_1-C_6)$alkyl, $(C_1-C_6)$alkoxy, and $(C_1-C_6)$arylalkyl;

C is absent or is selected from the group consisting of —O—, —CO—, —OC(O)—, —C(OO)—, —S—, —S(O)—, —S(O)$_2$—, —N(R$_7$)—, —N(CO)R$_7$—, —N(CO)NHR$_7$—, —N(SO$_2$)R$_7$— or is one of the following groups C1-C18

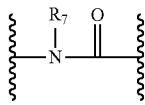

C1

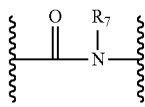

C2

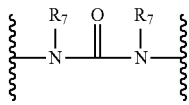

C3

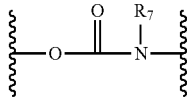

C4

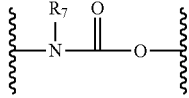

C5

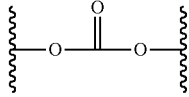

C6

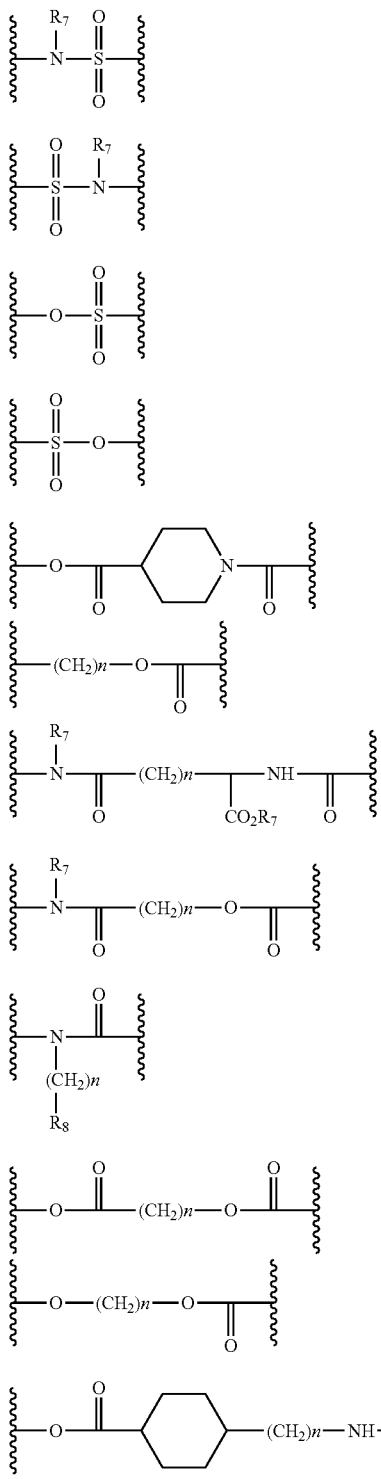

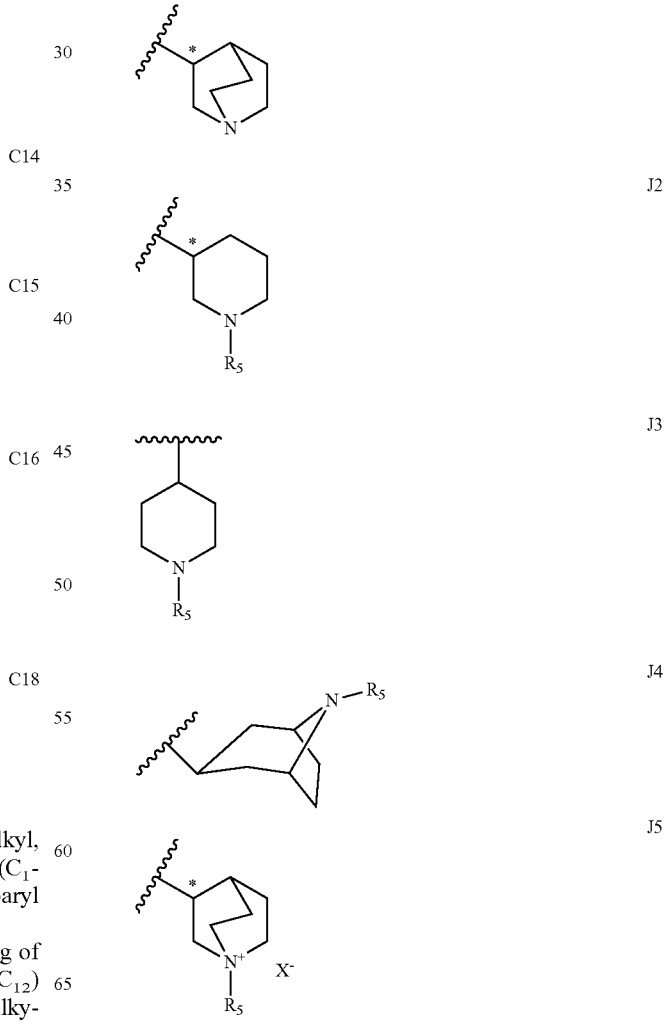

wherein $R_7$ is H or is linear or branched $(C_1-C_8)$alkyl, $(C_3-C_8)$cycloalkyl, $(C_3-C_8)$heterocycloalkyl, aryl, $(C_1-C_6)$arylalkyl, $(C_1-C_6)$alkoxy$(C_1-C_6)$alkyl, or heteroaryl and $R_8$ is $(C_1-C_8)$alkoxycarbonyl;

D is absent or is selected from the group consisting of $(C_1-C_{12})$alkylene, —C(CH$_3$)$_2$—, arylene, $(C_2-C_{12})$alkenylene, heteroarylene, $(C_3-C_8)$heterocycloalkylene, and $(C_2-C_6)$alkynylene;

n is 0 or an integer of 1 to 3;

E is absent or is —O—, —OC(O)— or —S—;

G is arylene or heteroarylene, optionally substituted by one or more substituents selected from the group consisting of a halogen atom, —OH, oxo (=O), —SH, —NO$_2$, —CN, —CON(R$_6$)$_2$, —NH$_2$, —NHCOR$_6$, —CO$_2$R$_6$, $(C_1-C_{10})$alkylsulfanyl, $(C_1-C_{10})$alkylsulfinyl, $(C_1-C_{10})$alkylsulfonyl, $(C_1-C_{10})$alkyl, aryl, haloaryl, heteroaryl and $(C_1-C_{10})$alkoxy;

$R_1$ and $R_2$ are independently H or selected from the group consisting of $(C_1-C_8)$alkyl, $(C_3-C_8)$cycloalkyl, $(C_3-C_8)$heterocycloalkyl, aryl, heteroaryl, aryl$(C_1-C_6)$alkyl, heteroaryl$(C_1-C_6)$alkyl, and $(C_3-C_8)$cycloalkyl$(C_1-C_6)$alkyl, optionally substituted by one or more halogen atoms or $(C_1-C_8)$alkyl groups or, taken together with the carbon atom to which they are bounded, $R_1$ and $R_2$ form a $(C_3-C_8)$cycloalkyl, when $R_1$ and $R_2$ are not simultaneously H;

M is —O— or —N(R$_3$)—;

$R_3$ is H or is selected from the group consisting of $(C_1-C_8)$alkyl, $(C_3-C_8)$cycloalkyl, aryl and heteroaryl;

$R_4$ is a group of formula J1, J2, J3, J4, or J5

$R_5$ is a group of formula K

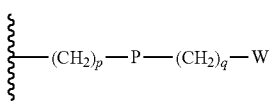

K wherein p is 0 or an integer of 1 to 4; q is 0 or an integer of 1 to 4;

P is absent or is a divalent group selected from the group consisting of O, S, SO, $SO_2$, CO, $NR_6$ CH=CH, $N(R_6)SO_2$, $N(R_6)COO$, $N(R_6)C(O)$, $SO_2N(R_6)$, $CO(O)N(R_6)$, and $C(O)N(R_6)$;

W is selected from the group consisting of H, $(C_1$-$C_6)$ alkyl, $(C_3$-$C_8)$cycloalkyl, aryl, and heteroaryl, optionally substituted by one or more substituents selected from the group consisting of a halogen atom, —OH, oxo (=O), —SH, —$NO_2$, —CN, —$CON(R_6)_2$, —$NH_2$, —$NHCOR_6$, —$CO_2R_6$, $(C_1$-$C_{10})$alkylsulfanyl, $(C_1$-$C_{10})$alkylsulfinyl, $(C_1$-$C_{10})$alkylsulfonyl, $(C_1$-$C_{10})$alkyl and $(C_1$-$C_{10})$alkoxy;

$X^-$ is a physiological acceptable anion;

$R_6$ is H or is selected from the group consisting of $(C_1$-$C_{10})$alkyl, $(C_1$-$C_6)$haloalkyl, $(C_2$-$C_6)$alkynyl, $(C_2$-$C_6)$ alkenyl, $(C_3$-$C_8)$cycloalkyl, $(C_3$-$C_8)$cycloalkyl$(C_1$-$C_6)$alkyl, heteroaryl, and aryl optionally substituted by one or more substituents selected from the group consisting of halogen atoms, —OH, oxo (=O), —SH, —$NO_2$, —CN, —$CONH_2$, —COOH, $(C_1$-$C_{10})$alkoxycarbonyl, $(C_1$-$C_{10})$alkylsulfanyl, $(C_1$-$C_{10})$ alkylsulfinyl, $(C_1$-$C_{10})$alkylsulfonyl, $(C_1$-$C_{10})$alkyl, and $(C_1$-$C_{10})$alkoxy;

or a pharmaceutically acceptable salt.

2. A compound or salt according to claim 1, wherein B is absent or is selected from the group consisting of $(C_3$-$C_8)$ cycloalkylene, $(C_3$-$C_8)$heterocycloalkylene, arylene, and heteroarylene; C is absent or is selected from the group consisting of —O—, —CO—, —OC(O)—, —C(OO)—, —S—, —S(O)—, —$S(O)_2$—, and —$N(R_7)$—, wherein $R_7$ is H or is selected from the group consisting of $(C_1$-$C_8)$alkyl, $(C_3$-$C_8)$ cycloalkyl, $(C_3$-$C_8)$heterocycloalkyl, aryl, and heteroaryl; and G is arylene or heteroarylene, optionally substituted by one or more substituents selected from the group consisting of halogen atoms, —OH, oxo (=O), —SH, —$NO_2$, —CN, —$CON(R_6)_2$, —$NH_2$, —$NHCOR_6$, —$CO_2R_6$, $(C_1$-$C_{10})$ alkylsulfanyl, $(C_1$-$C_{10})$alkylsulfinyl, $(C_1$-$C_{10})$alkylsulfonyl, $(C_1$-$C_{10})$alkyl, and $(C_1$-$C_{10})$alkoxy.

3. A compound or salt according to claim 2, wherein Q is Q1:

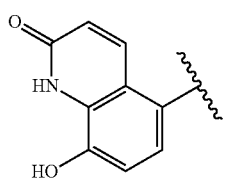

Q1

Z is —OH, A1 is absent or is selected from the group consisting of $(C_3$-$C_8)$heterocycloalkylene and $(C_1$-$C_{12})$ alkylene, A2 is absent or $(C_1$-$C_6)$alkylene, B is absent or arylene, C is absent, D is absent or is selected from the group consisting of $(C_1$-$C_{12})$alkylene, heteroarylene, and arylene, E is absent or is —O—, and G is arylene optionally substituted by one or more halogen atoms.

4. A compound or salt according to claim 3, wherein A1 is absent or is selected from the group consisting of methylene, ethylene, propylene, butylene, pentylene, hexylene, hepthylene, octylene, and nonylene, A2 is absent or is selected from the group consisting of methylene and oxadiazolene, B is selected from the group consisting of phenylene and cyclohexylene or is absent, C is absent, D is absent or is selected from the group consisting of methylene, ethylene, propylene, butylene, pentylene, hexylene, hepthylene, octylene, nonylene, phenylene, and oxadiazolene; and G is selected from the group consisting of fluoro-biphenylene and phenylene.

5. A compound or salt according to claim 4, wherein A1 is selected from the group consisting of ethylene, pentylene, hexylene, heptylene, octylene, and nonylene, D is absent, $R_1$ is H, $R_2$ is selected from the group consisting of phenyl, biphenyl, napthyl, pyridinyl, difluorophenyl, methylphenyl, fluorophenyl, and thiophenyl, M is —N(H)—, $R_4$ is a group of formula J1

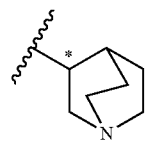

J1 or J3

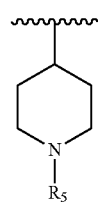

J3 or J4

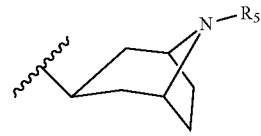

J4 or J5

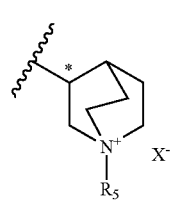

J5 wherein $R_5$ is a group of formula K, wherein p is 0 or 1, P is absent or is CO, q is absent or is 1 and W is H or is selected from the group consisting of $(C_1$-$C_6)$alkyl and aryl.

6. A compound according to claim 2, wherein Q is Q3

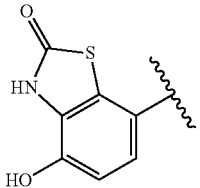

Z is H, A1 is absent or is $(C_1-C_{12})$alkylene, A2 is absent, B is absent, C is absent, D is absent or $(C_1-C_{12})$alkylene, E is —O—, and G is arylene.

7. A compound or salt according to claim 6, wherein A1 is absent or is selected from the group consisting of methylene, ethylene, propylene, butylene, pentylene, hexylene, hepthylene, octylene, and nonylene, A2 is absent, B is absent, C is absent, D is absent or is selected from methylene, ethylene, propylene, butylene, pentylene, hexylene, hepthylene, octylene, and nonylene; and G is phenylene.

8. A compound or salt according to claim 1, wherein $R_1$ and $R_2$ are independently H or selected from the group consisting of $(C_1-C_8)$alkyl, $(C_3-C_8)$cycloalkyl, $(C_3-C_8)$heterocycloalkyl, aryl, heteroaryl, aryl$(C_1-C_6)$alkyl, heteroaryl$(C_1-C_6)$alkyl, and $(C_3-C_8)$cycloalkyl$(C_1-C_6)$alkyl, optionally substituted by one or more halogen atoms or $(C_1-C_8)$alkyl groups or, taken together with the carbon atom they are linked to, $R_1$ and $R_2$ may form a $(C_3-C_8)$cycloalkyl group, wherein $R_1$ and $R_2$ are not simultaneously H; M is —O— or —N($R_3$)—; $R_3$ is H or is selected from the group consisting of $(C_1-C_8)$alkyl, $(C_3-C_8)$cycloalkyl, aryl, and heteroaryl; $R_4$ is a group of formula J1, J2, J3, J4 or J5

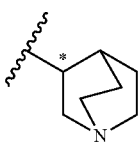

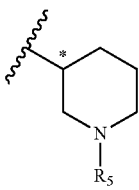

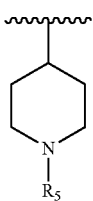

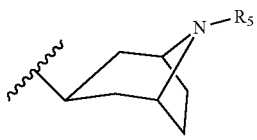

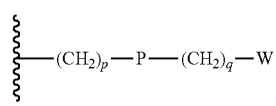

$R_5$ is a group of formula K

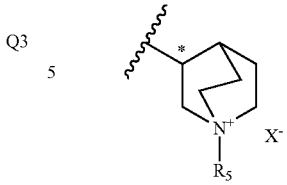

wherein p is 0 or an integer of 1 to 4; q is 0 or an integer of 1 to 4; P is absent or is selected from the group consisting of —O—, —S—, —S(O)—, —S(O$_2$)—, —C(O)—, —N($R_6$)—, —CH═CH—, —N($R_6$)S(O$_2$)—, —N($R_6$)CO(O)—, —N($R_6$)C(O)—, —SO$_2$N($R_6$)—, —CO(O)N($R_6$)— and —C(O)N($R_6$)—; W is selected from the group consisting of $(C_1-C_6)$alkyl, $(C_3-C_8)$cycloalkyl, aryl, and heteroaryl, optionally substituted by one or more substituents selected from the group consisting of halogen atoms, —OH, oxo (═O), —SH, —NO$_2$, —CN, —CON($R_6$)$_2$, —NH$_2$, —NHCOR$_6$, —CO$_2$R$_6$, $(C_1-C_{10})$alkylsulfanyl, $(C_1-C_{10})$alkylsulfinyl, $(C_1-C_{10})$alkylsulfonyl, $(C_1-C_{10})$alkyl, and $(C_1-C_{10})$alkoxy; and $R_6$ is selected from the group consisting of H, $(C_1-C_{10})$alkyl, $(C_1-C_6)$haloalkyl, $(C_3-C_8)$cycloalkyl, heteroaryl, and aryl.

9. A compound or salt according to claim 8, wherein R1 and R2 are independently H or selected from the group consisting of $(C_1-C_8)$alkyl, $(C_3-C_8)$cycloalkyl, aryl, and heteroaryl, optionally substituted by one or more halogen atoms or $(C_1-C_8)$alkyl groups or, taken together with the carbon atom to which they are bounded, $R_1$ and $R_2$ form a $(C_3-C_8)$ cycloalkyl group, when $R_1$ and $R_2$ are not simultaneously H; M is —N($R_3$)—; $R_3$ is H; $R_4$ is a group of formula J1

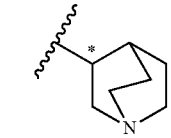

or J3

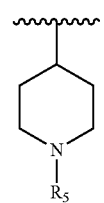

or J4

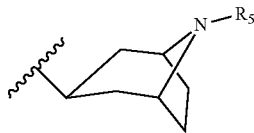

wherein R₅ is a group of formula K, wherein p is 0, P is absent, q is 1 and W is H or is selected from the group consisting of $(C_1-C_6)$alkyl and aryl.

10. A compound or salt according to claim 9, wherein W is H or phenyl; $R_1$ is H, $R_2$ is selected from the group consisting of phenyl, biphenyl, napthyl, thiophenyl, pyridinyl, difluorophenyl, methylphenyl, and fluorophenyl; M is —N(H)—; and $R_4$ is selected from the group consisting of quinuclidinyl, benzylpiperidinyl, methylpiperidinyl, benzyl-8-azabicyclo[3.2.1]octan-3-yl, and azoniabicyclo[2.2.2]octanyl.

11. A compound or salt according to claim 1, wherein Z is H or OH; Y1 is a group of formula

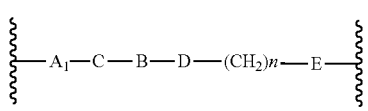

wherein A1 is $(C_1-C_{12})$alkylene; C is absent or is selected from the group consisting of —O—, —CO—, —OC(O)— or is a group of formula C1-C18 wherein $R_7$ is H or is linear or branched $(C_1-C_8)$alkyl, $(C_3-C_8)$cycloalkyl, $(C_3-C_8)$heterocycloalkyl, aryl, $(C_1-C_6)$arylalkyl, $(C_1-C_6)$alkoxy$(C_1-C_6)$alkyl, or heteroaryl and $R_8$ is $(C_1-C_8)$alkoxycarbonyl; B is absent or is selected from the group consisting of $(C_3-C_8)$cycloalkylene and arylene; D is absent or is selected from the group consisting of $(C_1-C_{12})$alkylene, —C(CH₃)₂—, heteroarylene, and arylene; n is 0 or an integer of 1 to 2; E is —O—; and G is arylene or heteroarylene, optionally substituted by one or more substituents selected from the group consisting of halogen atoms, —OH, oxo (=O), —SH, —NO₂, —CN, —CON(R₆)₂, —NH₂, —NHCOR₆, —CO₂R₆, $(C_1-C_{10})$alkylsulfanyl, $(C_1-C_{10})$alkylsulfinyl, $(C_1-C_{10})$alkylsulfonyl, $(C_1-C_{10})$alkyl, aryl, haloaryl, heteroaryl, and $(C_1-C_{10})$alkoxy.

12. A compound or salt according to claim 11, wherein A1 is selected from the group consisting of methylene, ethylene, propylene, butylene, pentylene, and hexylene; C is absent or is selected from the group consisting of —O—, —CO—, —OC(O)—, C11, C13, C14, C16, C17, and C18 wherein $R_7$ is H or is selected from the group consisting of methyl, ethyl, and isopropyl and C15 wherein n is 0 or 1 and $R_8$ is ethoxycarbonyl; B is absent or is selected from phenylene, piperidinylene, cyclopropylene, cyclohexylene, piridinediyl, furanediyl, and oxazolediyl, optionally substituted by one or more halogen atoms; D is absent or is selected from methylene, —C(CH₃)₂—, phenylene, and oxadiazolylene; n is 0 or an integer of 1 to 2; E is —O—; and G is selected from phenylene and biphenylene, optionally substituted by one or more substituents selected from the group consisting of fluorine, phenyl, and 2-thiophenyl.

13. A compound, which is selected from the group consisting of
(R)-quinuclidin-3-yl (3-(9-((R)-2-hydroxy-2-(8-hydroxy-2-oxo-1,2-dihydroquinolin-5-yl)ethylamino)nonyloxy)phenyl)(phenyl)methylcarbamate;
(R)-quinuclidin-3-yl (3-(8-((R)-2-hydroxy-2-(8-hydroxy-2-oxo-1,2-dihydroquinolin-5-yl)ethylamino)octyloxy)phenyl)(phenyl)methylcarbamate;
(R)-quinuclidin-3-yl(3-(7-((R)-2-hydroxy-2-(8-hydroxy-2-oxo-1,2-dihydroquinolin-5-yl)ethylamino)heptyloxy)phenyl)(phenyl)methylcarbamate;
(R)-quinuclidin-3-yl (3-(6-((R)-2-hydroxy-2-(8-hydroxy-2-oxo-1,2-dihydroquinolin-5-yl)ethylamino)hexyloxy)phenyl)(phenyl)methylcarbamate;
(R)-quinuclidin-3-yl (3-(5-((R)-2-hydroxy-2-(8-hydroxy-2-oxo-1,2-dihydroquinolin-5-yl)ethylamino)pentyloxy)phenyl)(phenyl)methylcarbamate;
1-benzylpiperidin-4-yl (3-(9-((R)-2-hydroxy-2-(8-hydroxy-2-oxo-1,2-dihydroquinolin-5-yl)ethylamino)nonyloxy)phenyl)(phenyl)methylcarbamate;
1-methylpiperidin-4-yl (3-(9-((R)-2-hydroxy-2-(8-hydroxy-2-oxo-1,2-dihydroquinolin-5-yl)ethylamino)nonyloxy)phenyl)(phenyl)methylcarbamate;
8-benzyl-8-azabicyclo[3.2.1]octan-3-yl (3-(9-((R)-2-hydroxy-2-(8-hydroxy-2-oxo-1,2-dihydroquinolin-5-yl)ethylamino)nonyloxy)phenyl)(phenyl)methylcarbamate;
(R)-quinuclidin-3-yl (4-(9-((R)-2-hydroxy-2-(8-hydroxy-2-oxo-1,2-dihydroquinolin-5-yl)ethylamino)nonyloxy)phenyl)(phenyl)methylcarbamate;
(R)-quinuclidin-3-yl (3-(9-((R)-2-hydroxy-2-(8-hydroxy-2-oxo-1,2-dihydroquinolin-5-yl)ethylamino)nonyloxy)phenyl)(thiophen-2-yl)methylcarbamate;
(R)-quinuclidin-3-yl biphenyl-4-yl(3-(9-((R)-2-hydroxy-2-(8-hydroxy-2-oxo-1,2-dihydroquinolin-5-yl)ethylamino)nonyloxy)phenyl)methylcarbamate;
(R)-quinuclidin-3-yl (3-(9-((R)-2-hydroxy-2-(8-hydroxy-2-oxo-1,2-dihydroquinolin-5-yl)ethylamino)nonyloxy)phenyl)(naphthalen-1-yl)methylcarbamate;
(R)-quinuclidin-3-yl biphenyl-3-yl(3-(9-((R)-2-hydroxy-2-(8-hydroxy-2-oxo-1,2-dihydroquinolin-5-yl)ethylamino)nonyloxy)phenyl)methylcarbamate;
(R)-quinuclidin-3-yl (3-(9-((R)-2-hydroxy-2-(8-hydroxy-2-oxo-1,2-dihydroquinolin-5-yl)ethylamino)nonyloxy)phenyl)(pyridin-2-yl)methylcarbamate;
(R)-quinuclidin-3-yl (3,5-difluorophenyl)(3-(9-((R)-2-hydroxy-2-(8-hydroxy-2-oxo-1,2-dihydroquinolin-5-yl)ethylamino)nonyloxy)phenyl)methylcarbamate;
(R)-quinuclidin-3-yl (3,4,5-difluorophenyl)(3-(9-((R)-2-hydroxy-2-(8-hydroxy-2-oxo-1,2-dihydroquinolin-5-yl)ethylamino)nonyloxy)phenyl)methylcarbamate;
(R)-quinuclidin-3-yl (3-(9-((R)-2-hydroxy-2-(8-hydroxy-2-oxo-1,2-dihydroquinolin-5-yl)ethylamino)nonyloxy)phenyl)(o-tolyl)methylcarbamate;
(R)-quinuclidin-3-yl (3-(9-((R)-2-hydroxy-2-(8-hydroxy-2-oxo-1,2-dihydroquinolin-5-yl)ethylamino)nonyloxy)phenyl)(m-tolyl)methylcarbamate;
(R)-quinuclidin-3-yl (3-(9-((R)-2-hydroxy-2-(8-hydroxy-2-oxo-1,2-dihydroquinolin-5-yl)ethylamino)nonyloxy)phenyl)(p-tolyl)methylcarbamate;
(R)-quinuclidin-3-yl (4-difluorophenyl)(3-(9-((R)-2-hydroxy-2-(8-hydroxy-2-oxo-1,2-dihydroquinolin-5-yl)ethylamino)nonyloxy)phenyl)methylcarbamate;
(R)-quinuclidin-3-yl (3-fluorophenyl)(3-(9-((R)-2-hydroxy-2-(8-hydroxy-2-oxo-1,2-dihydroquinolin-5-yl)ethylamino)nonyloxy)phenyl)methylcarbamate;

(R)-quinuclidin-3-yl (3-chlorophenyl)(3-(9-((R)-2-hydroxy-2-(8-hydroxy-2-oxo-1,2-dihydroquinolin-5-yl)ethylamino)nonyloxy)phenyl)methylcarbamate;

(R)-quinuclidin-3-yl (cyclohexyl(3-((9-(((R)-2-hydroxy-2-(8-hydroxy-2-oxo-1,2-dihydroquinolin-5-yl)ethyl)amino)nonyl)oxy)phenyl)methyl)carbamate;

(R)-quinuclidin-3-yl ((3-((6-((R)-2-hydroxy-2-(8-hydroxy-2-oxo-1,2-dihydroquinolin-5-yl)ethyl)amino)hexyl)oxy)phenyl)(thiophen-2-yl)methyl)carbamate;

(R)-quinuclidin-3-yl ((3-((6-(((R)-2-hydroxy-2-(8-hydroxy-2-oxo-1,2-dihydroquinolin-5-yl)ethyl)amino)hexyl)oxy)phenyl)(thiophen-3-yl)methyl)carbamate;

(R)-quinuclidin-3-yl (3-(9-(2-(4-hydroxy-2-oxo-2,3-dihydrobenzo[d]thiazol-7-yl)ethylamino)nonyloxy)phenyl)(phenyl)methylcarbamate;

(R)-quinuclidin-3-yl (3-(4-(2-((R)-2-hydroxy-2-(8-hydroxy-2-oxo-1,2-dihydroquinolin-5-yl)ethylamino)ethyl)benzyloxy)phenyl)(phenyl)methylcarbamate;

(R)-quinuclidin-3-yl (3-(2-((R)-2-hydroxy-2-(8-hydroxy-2-oxo-1,2-dihydroquinolin-5-yl)ethylamino)ethyl)phenyl)(phenyl)methylcarbamate;

(3R)-3-((3-(6-((R)-2-hydroxy-2-(8-hydroxy-2-oxo-1,2-dihydroquinolin-5-yl)ethylamino)hexyloxy)phenyl)(phenyl)methylcarbamoyloxy)-1-(2-oxo-2-phenylethyl)-1-azoniabicyclo[2.2.2]octane;

(R)-quinuclidin-3-yl (3-(3-(2-((R)-2-hydroxy-2-(8-hydroxy-2-oxo-1,2-dihydroquinolin-5-yl)ethylamino)ethyl)benzyloxy)phenyl)(phenyl)methylcarbamate formate;

(3R)-3-((((3-((4-(2-(((R)-2-hydroxy-2-(8-hydroxy-2-oxo-1,2-dihydroquinolin-5-yl)ethyl)amino)ethyl)benzyl)oxy)phenyl)(phenyl)methyl)carbamoyl)oxy)-1-(2-oxo-2-phenylethyl)quinuclidin-1-ium;

(3R)-3-((((3-chlorophenyl)(3-((9-(((R)-2-hydroxy-2-(8-hydroxy-2-oxo-1,2-dihydroquinolin-5-yl)ethyl)amino)nonyl)oxy)phenyl)methyl)carbamoyl)oxy)-1-(2-oxo-2-phenylethyl)quinuclidin-1-ium;

(3R)-3-((((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium;

(R)-quinuclidin-3-yl (2-chloro-3-(9-((R)-2-hydroxy-2-(8-hydroxy-2-oxo-1,2-dihydroquinolin-5-yl)ethylamino)nonyloxy)phenyl)(phenyl)methylcarbamate;

(R)-quinuclidin-3-yl ((2,6-difluoro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamate;

(R)-Quinuclidin-3-yl ((2-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate;

(3R)-3-((((2-chloro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium;

(3R)-3-(((((2,6-difluoro-3-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium;

(3R)-3-((((2-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamoyl)oxy)-1-(2-oxo-2-phenylethyl)quinuclidin-1-ium;

(3R)-3-((((3-((9-(((R)-2-hydroxy-2-(8-hydroxy-2-oxo-1,2-dihydroquinolin-5-yl)ethyl)amino)nonyl)oxy)-4-methylphenyl)(phenyl)methyl)carbamoyl)oxy)-1-(2-oxo-2-phenylethyl)quinuclidin-1-ium;

(R)-quinuclidin-3-yl ((3-((9-(((R)-2-hydroxy-2-(8-hydroxy-2-oxo-1,2-dihydroquinolin-5-yl)ethyl)amino)nonyl)oxy)-4-methoxyphenyl)(phenyl)methyl)carbamate;

(R)-quinuclidin-3-yl ((3-((9-(((R)-2-hydroxy-2-(8-hydroxy-2-oxo-1,2-dihydroquinolin-5-yl)ethyl)amino)nonyl)oxy)-5-methoxyphenyl)(phenyl)methyl)carbamate;

(3R)-3-((((3-((9-(((R)-2-hydroxy-2-(8-hydroxy-2-oxo-1,2-dihydroquinolin-5-yl)ethyl)amino)nonyl)oxy)-4-methoxyphenyl)(phenyl)methyl)carbamoyl)oxy)-1-(2-oxo-2-phenylethyl)quinuclidin-1-ium;

(3R)-3-((((3-((9-(((R)-2-hydroxy-2-(8-hydroxy-2-oxo-1,2-dihydroquinolin-5-yl)ethyl)amino)nonyl)oxy)-5-methoxyphenyl)(phenyl)methyl)carbamoyl)oxy)-1-(2-oxo-2-phenylethyl)quinuclidin-1-ium;

(3R)-3-((((5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)methyl)carbamoyl)oxy)-1-(2-oxo-2-phenylethyl)quinuclidin-1-ium;

(R)-quinuclidin-3-yl (3-(9-((R)-2-hydroxy-2-(8-hydroxy-2-oxo-1,2-dihydroquinolin-5-yl)ethylamino)nonyloxy)-5-(thiophen-2-yl)phenyl)(phenyl)methylcarbamate;

(3R)-3-(((((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamoyl)oxy)-1-(2-oxo-2-phenylethyl)quinuclidin-1-ium;

(3R)-3-(((((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamoyl)oxy)-1-(2-phenoxyethyl)quinuclidin-1-ium;

(3R)-3-(((((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)carbamoyl)oxy)-1-(2-oxo-2-phenylethyl)quinuclidin-1-ium;

(3R)-3-(((((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)carbamoyl)oxy)-1-(2-phenoxyethyl)quinuclidin-1-ium;

(R)-quinuclidin-3-yl (3-fluorophenyl)(3-(6-((R)-2-hydroxy-2-(8-hydroxy-2-oxo-1,2-dihydroquinolin-5-yl)ethylamino)hexyloxy)phenyl)methylcarbamate;

(3R)-3-(((((3-((5-(((R)-2-hydroxy-2-(8-hydroxy-2-oxo-1,2-dihydroquinolin-5-yl)ethyl)amino)pentyl)oxy)phenyl)(phenyl)methyl)carbamoyl)oxy)-1-(4-phenylbutyl)quinuclidin-1-ium;

(R)-Quinuclidin-3-yl (3-fluorophenyl)(3-(3-(2-((R)-2-hydroxy-2-(8-hydroxy-2-oxo-1,2-dihydroquinolin-5-yl)ethylamino)ethyl)benzyloxy)phenyl)methylcarbamate;

(3R)-3-((((3-fluorophenyl)(3-((3-(2-(((R)-2-hydroxy-2-(8-hydroxy-2-oxo-1,2-dihydroquinolin-5-yl)ethyl)amino)ethyl)benzyl)oxy)phenyl)methyl)carbamoyl)oxy)-1-(2-oxo-2-phenylethyl)quinuclidin-1-ium;

(3R)-3-((((3-((4-(((R)-2-hydroxy-2-(8-hydroxy-2-oxo-1,2-dihydroquinolin-5-yl)ethyl)amino)methyl)benzyl)oxy)phenyl)(phenyl)methyl)carbamoyl)oxy)-1-(2-oxo-2-phenylethyl)quinuclidin-1-ium;

(R)-Quinuclidin-3-yl (3-((4'-(2-((R)-2-hydroxy-2-(8-hydroxy-2-oxo-1,2-dihydroquinolin-5-yl)ethylamino)ethyl)biphenyl-3-yl)methoxy)phenyl)(phenyl)methylcarbamate;

(R)-quinuclidin-3-yl ((3-((4-((4-(((R)-2-hydroxy-2-(8-hydroxy-2-oxo-1,2-dihydroquinolin-5-yl)ethyl)amino)butyl)carbamoyl)benzyl)oxy)phenyl)-(phenyl)methyl)carbamate;

(R)-quinuclidin-3-yl (3-(4-(3-((R)-2-hydroxy-2-(8-hydroxy-2-oxo-1,2-dihydroquinolin-5-yl)ethylamino)propylcarbamoyl)benzyloxy)phenyl)(phenyl)methylcarbamate;

(3R)-3-((((3-((4-((3-(((R)-2-hydroxy-2-(8-hydroxy-2-oxo-1,2-dihydroquinolin-5-yl)ethyl)amino)propyl)carbamoyl)benzyl)oxy)phenyl)(phenyl)methyl)carbamoyl)oxy)-1-(2-oxo-2-phenylethyl)quinuclidin-1-ium;

4-(((R)-2-Hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)phenoxy)methyl)benzoate;

5-(((R)-2-hydroxy-2-(8-hydroxy-2-oxo-1,2-dihydroquinolin-5-yl)ethylamino)pentyl 4-((3-(phenyl((((R)-quinuclidin-3-yloxy)carbonylamino)methyl)phenoxy)methyl)benzoate;

6-(((R)-2-hydroxy-2-(8-hydroxy-2-oxo-1,2-dihydroquinolin-5-yl)ethylamino)hexyl 4-((3-(phenyl((((R)-quinuclidin-3-yloxy)carbonylamino)methyl)phenoxy)methyl)benzoate;

7-(((R)-2-hydroxy-2-(8-hydroxy-2-oxo-1,2-dihydroquinolin-5-yl)ethyl)amino)heptyl 4-((3-(phenyl((((R)-quinuclidin-3-yloxy)carbonyl)amino)methyl)phenoxy)methyl)benzoate;

4-((((R)-2-hydroxy-2-(8-hydroxy-2-oxo-1,2-dihydroquinolin-5-yl)ethyl)amino)methyl)-benzyl 4-((3-(phenyl((((R)-quinuclidin-3-yloxy)carbonyl)amino)methyl)phenoxy)-methyl)benzoate;

4-(2-(((R)-2-hydroxy-2-(8-hydroxy-2-oxo-1,2-dihydroquinolin-5-yl)ethyl)amino)ethyl)-phenyl 4-((3-(phenyl((((R)-quinuclidin-3-yloxy)carbonyl)amino)methyl)phenoxy)-methyl)benzoate;

4-((((R)-2-hydroxy-2-(8-hydroxy-2-oxo-1,2-dihydroquinolin-5-yl)ethyl)amino)methyl)-phenyl 4-((3-(phenyl((((R)-quinuclidin-3-yloxy)carbonyl)amino)methyl)phenoxy)-methyl)benzoate 4-(2-(((R)-2-hydroxy-2-(8-hydroxy-2-oxo-1,2-dihydroquinolin-5-yl)ethyl)amino)ethyl)-benzyl 4-((3-(phenyl((((R)-quinuclidin-3-yloxy)carbonyl)amino)methyl)phenoxy)-methyl)benzoate;

(3R)-3-((((3-((4-(1-((4-(((R)-2-hydroxy-2-oxo-1,2-dihydroquinolin-5-yl)ethyl)amino)butoxy)carbonyl)cyclopropyl)benzyl)oxy)phenyl)(phenyl)methyl)carbamoyl)oxy)-1-(2-oxo-2-phenylethyl)quinuclidin-1-ium;

(R)-quinuclidin-3-yl (3-(2-(3'-(((R)-2-hydroxy-2-(8-hydroxy-2-oxo-1,2-dihydroquinolin-5-yl)ethylamino)methyl)biphenyl-4-yl)ethoxy)phenyl)(phenyl)methylcarbamate;

(R)-quinuclidin-3-yl (3-(2-(3'-(((R)-2-hydroxy-2-(8-hydroxy-2-oxo-1,2-dihydroquinolin-5-yl)ethylamino)methyl)biphenyl-4-yl)ethoxy)phenyl)(phenyl)methylcarbamate;

6-((R)-2-hydroxy-2-(8-hydroxy-2-oxo-1,2-dihydroquinolin-5-yl)ethylamino)hexyl 2-(3-(phenyl(((R)-quinuclidin-3-yloxy)carbonylamino)methyl)phenoxy)acetate;

(R)-quinuclidin-3-yl ((3-((6-(((R)-2-hydroxy-2-(8-hydroxy-2-oxo-1,2-dihydroquinolin-5-yl)ethyl)amino)hexyl)oxy)phenyl)(phenyl)methyl)carbamate;

(R)-quinuclidin-3-yl((3-((6-(((R)-2-hydroxy-2-(8-hydroxy-2-oxo-1,2-dihydroquinolin-5-yl)ethyl)amino)hexyl)oxy)phenyl)(phenyl)methyl)carbamate;

(3R)-3-((((3-((6-(((R)-2-hydroxy-2-oxo-1,2-dihydroquinolin-5-yl)ethyl)amino)hexyl)oxy)phenyl)(phenyl)methyl)carbamoyl)oxy)-1-(2-oxo-2-phenylethyl)quinuclidin-1-ium;

(3R)-3-((((3-((6-(((R)-2-hydroxy-2-(8-hydroxy-2-dihydroquinolin-5-yl)ethyl)amino)hexyl)oxy)phenyl)(phenyl)methyl)carbamoyl)oxy)-1-(2-oxo-2-phenylethyl)quinuclidin-1-ium;

4-(((R)-2-hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)phenoxy)methyl)benzoate;

4-(((R)-2-hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)phenoxy)methyl)benzoate;

5-(((R)-2-hydroxy-2-(8-hydroxy-2-oxo-1,2-dihydroquinolin-5-yl)ethyl)amino)pentyl 2-(3-(phenyl((((R)-quinuclidin-3-yloxy)carbonyl)amino)methyl)phenoxy)acetate;

4-(((R)-2-hydroxy-2-(8-hydroxy-2-oxo-1,2-dihydroquinolin-5-yl)ethyl)amino)butyl 2-(3-(phenyl((((R)-quinuclidin-3-yloxy)carbonyl)amino)methyl)phenoxy)acetate;

5-(((R)-2-hydroxy-2-(8-hydroxy-2-oxo-1,2-dihydroquinolin-5-yl)ethyl)amino)pentyl 2-methyl-2-(3-(phenyl((((R)-quinuclidin-3-yloxy)carbonyl)amino)methyl)phenoxy)propanoate;

4-(((R)-2-hydroxy-2-(8-hydroxy-2-oxo-1,2-dihydroquinolin-5-yl)ethyl)amino)butyl 2-methyl-2-(3-(phenyl((((R)-quinuclidin-3-yloxy)carbonyl)amino)methyl)phenoxy)propanoate;

5-(((R)-2-hydroxy-2-(8-hydroxy-2-oxo-1,2-dihydroquinolin-5-yl)ethyl)amino)pentyl 2,2-dimethyl-3-(3-(phenyl((((R)-quinuclidin-3-yloxy)carbonyl)amino)methyl)phenoxy)propanoate;

4-(((R)-2-hydroxy-2-(8-hydroxy-2-oxo-1,2-dihydroquinolin-5-yl)ethyl)amino)butyl 1-(2-(3-(phenyl((((R)-quinuclidin-3-yloxy)carbonyl)amino)methyl)phenoxy)acetyl)piperidine-4-carboxylate;

4-(2-(((R)-2-hydroxy-2-(8-hydroxy-2-oxo-1,2-dihydroquinolin-5-yl)ethyl)amino)ethyl)-benzyl 2-(3-(phenyl((((R)-quinuclidin-3-yloxy)carbonyl)amino)methyl)phenoxy)acetate;

(R)-quinuclidin-3-yl ((3-((9-(((R)-2-hydroxy-2-(8-hydroxy-2-oxo-1,2-dihydroquinolin-5-yl)ethyl)amino)nonyl)oxy)-4-methylphenyl)(phenyl)methyl)carbamate;

(R)-Quinuclidin-3-yl ((3-bromo-5-((9-(((R)-2-hydroxy-2-(8-hydroxy-2-oxo-1,2-dihydroquinolin-5-yl)ethyl)amino)nonyl)oxy)phenyl)(phenyl)methyl)carbamate;

(R)-quinuclidin-3-yl ((5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)methyl)carbamate;

(R)-quinuclidin-3-yl ((2-bromo-3-((9-(((R)-2-hydroxy-2-(8-hydroxy-2-oxo-1,2-dihydroquinolin-5-yl)ethyl)amino)nonyl)oxy)phenyl)(phenyl)methyl)carbamate;

(R)-quinuclidin-3-yl ((3'-fluoro-5-((9-(((R)-2-hydroxy-2-(8-hydroxy-2-oxo-1,2-dihydroquinolin-5-yl)ethyl)amino)nonyl)oxy)-[1,1'-biphenyl]-3-yl)(phenyl)methyl)carbamate;

(R)-quinuclidin-3-yl ((3-((3-(4-(((R)-2-hydroxy-2-(8-hydroxy-2-oxo-1,2-dihydroquinolin-5-yl)ethyl)amino)butoxy)benzyl)oxy)phenyl)(phenyl)methyl)carbamate;

(R)-quinuclidin-3-yl ((3-((3-((5-(((R)-2-hydroxy-2-(8-hydroxy-2-oxo-1,2-dihydroquinolin-5-yl)ethyl)amino)pentyl)oxy)benzyl)oxy)phenyl)(phenyl)methyl)carbamate;

(3R)-3-(((cyclohexyl(3-((9-(((R)-2-hydroxy-2-(8-hydroxy-2-oxo-1,2-dihydroquinolin-5-yl)ethyl)amino)

nonyl)oxy)phenyl)methyl)carbamoyl)oxy)-1-(2-oxo-2-phenylethyl)quinuclidin-1-ium;

(3R)-3-((((3-((6-(((R)-2-hydroxy-2-(8-hydroxy-2-oxo-1,2-dihydroquinolin-5-yl)ethyl)amino)hexyl)oxy)phenyl)(thiophen-2-yl)methyl)carbamoyl)oxy)-1-(2-oxo-2-phenylethyl)quinuclidin-1-ium;

(3R)-3-((((3-fluorophenyl)(3-((6-(((R)-2-hydroxy-2-(8-hydroxy-2-oxo-1,2-dihydroquinolin-5-yl)ethyl)amino)hexyl)oxy)phenyl)methyl)carbamoyl)oxy)-1-(2-oxo-2-phenylethyl)quinuclidin-1-ium;

(3R)-3-((((3-((6-(((R)-2-hydroxy-2-(8-hydroxy-2-oxo-1,2-dihydroquinolin-5-yl)ethyl)amino)hexyl)oxy)phenyl)(thiophen-3-yl)methyl)carbamoyl)oxy)-1-(2-oxo-2-phenylethyl)quinuclidin-1-ium;

(3R)-3-((((3-((4-((4-(((R)-2-hydroxy-2-(8-hydroxy-2-oxo-1,2-dihydroquinolin-5-yl)ethyl)amino)butyl)carbamoyl)benzyl)oxy)phenyl)(phenyl)methyl)carbamoyl)oxy)-1-(2-oxo-2-phenylethyl)quinuclidin-1-ium;

(3R)-3-((((3-((7-(((R)-2-hydroxy-2-(8-hydroxy-2-oxo-1,2-dihydroquinolin-5-yl)ethyl)amino)heptyl)oxy)phenyl)(phenyl)methyl)carbamoyl)oxy)-1-(2-oxo-2-phenylethyl)quinuclidin-1-ium;

(3R)-3-((((3-((7-(((R)-2-hydroxy-2-(8-hydroxy-2-oxo-1,2-dihydroquinolin-5-yl)ethyl)amino)heptyl)oxy)phenyl)(phenyl)methyl)carbamoyl)oxy)-1-(3-phenylpropyl)quinuclidin-1-ium;

(3R)-3-((((3-((5-(((R)-2-hydroxy-2-(8-hydroxy-2-oxo-1,2-dihydroquinolin-5-yl)ethyl)amino)pentyl)oxy)phenyl)(phenyl)methyl)carbamoyl)oxy)-1-(2-oxo-2-phenylethyl)quinuclidin-1-ium;

4-(((R)-2-hydroxy-2-(8-hydroxy-2-oxo-1,2-dihydroquinolin-5-yl)ethyl)amino)butyl 1-(4-((3-(phenyl((((R)-quinuclidin-3-yloxy)carbonyl)amino)methyl)phenoxy)methyl)phenyl)-cyclopentanecarboxylate;

4-(((R)-2-hydroxy-2-(8-hydroxy-2-oxo-1,2-dihydroquinolin-5-yl)ethyl)amino)butyl 1-(4-((3-(phenyl((((R)-quinuclidin-3-yloxy)carbonyl)amino)methyl)phenoxy)methyl)phenyl)-cyclohexanecarboxylate;

4-(((R)-2-hydroxy-2-(8-hydroxy-2-oxo-1,2-dihydroquinolin-5-yl)ethyl)amino)butyl 2-methyl-2-(4-((3-(phenyl((((R)-quinuclidin-3-yloxy)carbonyl)amino)methyl)phenoxy)methyl)-phenyl)propanoate;

8-(((R)-2-hydroxy-2-(8-hydroxy-2-oxo-1,2-dihydroquinolin-5-yl)ethyl)amino)octyl 3-(phenyl((((R)-quinuclidin-3-yloxy)carbonyl)amino)methyl)benzoate;

9-(((R)-2-hydroxy-2-(8-hydroxy-2-oxo-1,2-dihydroquinolin-5-yl)ethyl)amino)nonyl 3-(phenyl((((R)-quinuclidin-3-yloxy)carbonyl)amino)methyl)benzoate;

7-(((R)-2-hydroxy-2-(8-hydroxy-2-oxo-1,2-dihydroquinolin-5-yl)ethyl)amino)heptyl 3-(phenyl((((R)-quinuclidin-3-yloxy)carbonyl)amino)methyl)benzoate;

6-(((R)-2-hydroxy-2-(8-hydroxy-2-oxo-1,2-dihydroquinolin-5-yl)ethyl)amino)hexyl 3-(phenyl((((R)-quinuclidin-3-yloxy)carbonyl)amino)methyl)benzoate;

5-(((R)-2-hydroxy-2-(8-hydroxy-2-oxo-1,2-dihydroquinolin-5-yl)ethyl)amino)pentyl 3-(phenyl((((R)-quinuclidin-3-yloxy)carbonyl)amino)methyl)benzoate;

4-((4-(((R)-2-hydroxy-2-(8-hydroxy-2-oxo-1,2-dihydroquinolin-5-yl)ethyl)amino)butyl)-carbamoyl)benzyl 3-(phenyl((((R)-quinuclidin-3-yloxy)carbonyl)amino)methyl)benzoate;

4-(N-(4-(((R)-2-hydroxy-2-(8-hydroxy-2-oxo-1,2-dihydroquinolin-5-yl)ethyl)amino)-butyl)sulfamoyl)benzyl 3-(phenyl((((R)-quinuclidin-3-yloxy)carbonyl)amino)methyl)benzoate;

4-(2-(((R)-2-hydroxy-2-(8-hydroxy-2-oxo-1,2-dihydroquinolin-5-yl)ethyl)amino)ethyl)-benzyl 3-(phenyl((((R)-quinuclidin-3-yloxy)carbonyl)amino)methyl)benzoate;

4-(((R)-2-hydroxy-2-(8-hydroxy-2-oxo-1,2-dihydroquinolin-5-yl)ethyl)amino)butyl 4-((3-(phenyl((((R)-quinuclidin-3-yloxy)carbonyl)amino)methyl)benzamido)methyl)benzoate;

(2S)-4-(((R)-2-hydroxy-2-(8-hydroxy-2-oxo-1,2-dihydroquinolin-5-yl)ethyl)amino)butyl 3-phenyl-2-(4-((3-(phenyl((((R)-quinuclidin-3-yloxy)carbonyl)amino)methyl)phenoxy)-methyl)benzamido)propanoate;

(R)-quinuclidin-3-yl ((3-((3-(4-(2-(((R)-2-hydroxy-2-(8-hydroxy-2-oxo-1,2-dihydroquinolin-5-yl)ethyl)amino)ethyl)phenyl)-1,2,4-oxadiazol-5-yl)methoxy)phenyl)(phenyl)-methyl)carbamate;

(R)-quinuclidin-3-yl ((5-((9-(((R)-2-hydroxy-2-(8-hydroxy-2-oxo-1,2-dihydroquinolin-5-yl)ethyl)amino)nonyl)oxy)pyridin-3-yl)(phenyl)methyl)carbamate;

(R)-quinuclidin-3-yl ((3-fluorophenyl)(5-((9-(((R)-2-hydroxy-2-(8-hydroxy-2-oxo-1,2-dihydroquinolin-5-yl)ethyl)amino)nonyl)oxy)pyridin-3-yl)methyl)carbamate;

4-(((R)-2-hydroxy-2-(8-hydroxy-2-oxo-1,2-dihydroquinolin-5-yl)ethyl)amino)butyl 2-chloro-4-((3-(phenyl((((R)-quinuclidin-3-yloxy)carbonyl)amino)methyl)phenoxy)-methyl)benzoate;

4-(((R)-2-hydroxy-2-(8-hydroxy-2-oxo-1,2-dihydroquinolin-5-yl)ethyl)amino)butyl 2-fluoro-4-((3-(phenyl((((R)-quinuclidin-3-yloxy)carbonyl)amino)methyl)phenoxy)methyl)-benzoate;

4-(((R)-2-hydroxy-2-(8-hydroxy-2-oxo-1,2-dihydroquinolin-5-yl)ethyl)amino)butyl 6-((3-(phenyl((((R)-quinuclidin-3-yloxy)carbonyl)amino)methyl)phenoxy)methyl)nicotinate;

4-(((R)-2-hydroxy-2-(8-hydroxy-2-oxo-1,2-dihydroquinolin-5-yl)ethyl)amino)butyl 5-((3-(phenyl((((R)-quinuclidin-3-yloxy)carbonyl)amino)methyl)phenoxy)methyl)furan-2-carboxylate;

4-(((R)-2-hydroxy-2-(8-hydroxy-2-oxo-1,2-dihydroquinolin-5-yl)ethyl)amino)butyl 2-((3-(phenyl((((R)-quinuclidin-3-yloxy)carbonyl)amino)methyl)phenoxy)methyl)oxazole-4-carboxylate;

4-(((R)-2-hydroxy-2-(8-hydroxy-2-oxo-1,2-dihydroquinolin-5-yl)ethyl)amino)butyl 3-((3-(phenyl((((R)-quinuclidin-3-yloxy)carbonyl)amino)methyl)phenoxy)methyl)benzoate;

5-(((R)-2-hydroxy-2-(8-hydroxy-2-oxo-1,2-dihydroquinolin-5-yl)ethyl)amino)pentyl 2-(3-(phenyl((((R)-quinuclidin-3-yloxy)carbonyl)amino)methyl)phenoxy)acetate;

5-(((R)-2-hydroxy-2-(8-hydroxy-2-oxo-1,2-dihydroquinolin-5-yl)ethyl)amino)pentyl 2-(3-(phenyl((((R)-quinuclidin-3-yloxy)carbonyl)amino)methyl)phenoxy)acetate;

5-(((R)-2-hydroxy-2-(8-hydroxy-2-oxo-1,2-dihydroquinolin-5-yl)ethyl)amino)hexyl 2-(3-(phenyl((((R)-quinuclidin-3-yloxy)carbonyl)amino)methyl)phenoxy)acetate;

5-(((R)-2-hydroxy-2-(8-hydroxy-2-oxo-1,2-dihydroquinolin-5-yl)ethyl)amino)hexyl 2-(3-(phenyl((((R)-quinuclidin-3-yloxy)carbonyl)amino)methyl)phenoxy)acetate;

(R)-quinuclidin-3-yl ((3-((4-((3-(((R)-2-hydroxy-2-(8-hydroxy-2-oxo-1,2-dihydroquinolin-5-yl)ethyl)amino)propyl)carbamoyl)benzyl)oxy)phenyl)(phenyl)methyl)-carbamate;

(R)-quinuclidin-3-yl ((3-((4-((3-(((R)-2-hydroxy-2-(8-hydroxy-2-oxo-1,2-dihydroquinolin-5-yl)ethyl)amino)ethyl)carbamoyl)benzyl)oxy)phenyl)(phenyl)methyl)-carbamate;

(R)-quinuclidin-3-yl ((3-((4-(ethyl(3-(((R)-2-hydroxy-2-(8-hydroxy-2-oxo-1,2-dihydroquinolin-5-yl)ethyl)amino)propyl)carbamoyl)benzyl)oxy)phenyl)(phenyl)methyl)-carbamate;

(R)-quinuclidin-3-yl ((3-((4-((3-(((R)-2-hydroxy-2-(8-hydroxy-2-oxo-1,2-dihydroquinolin-5-yl)ethyl)amino)propyl)(methyl)carbamoyl)benzyl)oxy)phenyl)(phenyl)-methyl)carbamate;

(R)-quinuclidin-3-yl ((3-((4-((3-(((R)-2-hydroxy-2-(8-hydroxy-2-oxo-1,2-dihydroquinolin-5-yl)ethyl)amino)propyl)(isopropyl)carbamoyl)benzyl)oxy)phenyl)(phenyl)-methyl)carbamate;

(1R,4R)-4-(((R)-2-hydroxy-2-(8-hydroxy-2-oxo-1,2-dihydroquinolin-5-yl)ethyl)-amino)butyl 4-((4-((3-(phenyl((((R)-quinuclidin-3-yloxy)carbonyl)amino)methyl)-phenoxy)methyl)benzamido)methyl)cyclohexanecarboxylate;

(2S)-methyl 4-((2-(((R)-2-hydroxy-2-(8-hydroxy-2-oxo-1,2-dihydroquinolin-5-yl)ethyl)-amino)ethyl)(methyl)amino)-4-oxo-2-(4-((3-(phenyl((((R)-quinuclidin-3-yloxy)carbonyl)amino)-methyl)phenoxy)methyl)benzamido)butanoate;

((1R,4R)-4-((((R)-2-hydroxy-2-(8-hydroxy-2-oxo-1,2-dihydroquinolin-5-yl)ethyl)-amino)methyl)cyclohexyl)methyl 4-((3-(phenyl(((quinuclidin-4-yloxy)carbonyl)amino)-methyl)phenoxy)methyl)benzoate;

2-((4-(((R)-2-hydroxy-2-(8-hydroxy-2-oxo-1,2-dihydroquinolin-5-yl)ethyl)-amino)butyl)amino)-2-oxoethyl 4-((3-(phenyl((((R)-quinuclidin-3-yloxy)carbonyl)amino)-methyl)phenoxy)methyl)benzoate;

2-((3-(((R)-2-hydroxy-2-(8-hydroxy-2-oxo-1,2-dihydroquinolin-5-yl)ethyl)-amino)propyl)amino)-2-oxoethyl 4-((3-(phenyl((((R)-quinuclidin-3-yloxy)carbonyl)amino)-methyl)phenoxy)methyl)benzoate;

2-(4-(((R)-2-hydroxy-2-(8-hydroxy-2-oxo-1,2-dihydroquinolin-5-yl)ethyl)amino)butoxy)-2-oxoethyl 4-((3-(phenyl((((R)-quinuclidin-3-yloxy)carbonyl)amino)methyl)phenoxy)methyl)-benzoate;

2-((5-(((R)-2-hydroxy-2-(8-hydroxy-2-oxo-1,2-dihydroquinolin-5-yl)ethyl)amino)-pentyl)oxy)-2-oxoethyl 4-((3-(phenyl((((R)-quinuclidin-3-yloxy)carbonyl)amino)methyl)-phenoxy)methyl)benzoate;

2-(2-(((R)-2-hydroxy-2-(8-hydroxy-2-oxo-1,2-dihydroquinolin-5-yl)ethyl)amino)-ethoxy)ethyl 4-((3-(phenyl((((R)-quinuclidin-3-yloxy)carbonyl)amino)methyl)phenoxy)-methyl)benzoate;

2-(4-(((R)-2-hydroxy-2-(8-hydroxy-2-oxo-1,2-dihydroquinolin-5-yl)ethyl)amino)butoxy)ethyl 4-((3-(phenyl((((R)-quinuclidin-3-yloxy)carbonyl)amino)-methyl)phenoxy)methyl)benzoate;

2-((5-(((R)-2-hydroxy-2-(8-hydroxy-2-oxo-1,2-dihydroquinolin-5-yl)ethyl)-amino)pentyl)oxy)-2-oxoethyl 4-((3-(phenyl((((R)-quinuclidin-3-yloxy)carbonyl)amino)-methyl)phenoxy)methyl)benzoate;

2-(2-(((R)-2-hydroxy-2-(8-hydroxy-2-oxo-1,2-dihydroquinolin-5-yl)ethyl)amino)-ethoxy)ethyl 4-((3-(phenyl((((R)-quinuclidin-3-yloxy)carbonyl)amino)methyl)phenoxy)-methyl)benzoate;

2-(4-(((R)-2-hydroxy-2-(8-hydroxy-2-oxo-1,2-dihydroquinolin-5-yl)ethyl)amino)-butoxy)ethyl 4-((3-(phenyl((((R)-quinuclidin-3-yloxy)carbonyl)amino)methyl)phenoxy)-methyl)benzoate;

3-(2-(((R)-2-hydroxy-2-(8-hydroxy-2-oxo-1,2-dihydroquinolin-5-yl)ethyl)amino)-ethyl)benzyl 4-((3-(phenyl((((R)-quinuclidin-3-yloxy)carbonyl)amino)methyl)phenoxy)-methyl)benzoate;

3-(3-(phenyl((((R)-quinuclidin-3-yloxy)carbonyl)amino)methyl)phenoxy)propyl 4-(2-(((R)-2-hydroxy-2-(8-hydroxy-2-oxo-1,2-dihydroquinolin-5-yl)ethyl)amino)ethyl)benzoate;

4-(((R)-2-hydroxy-2-(8-hydroxy-2-oxo-1,2-dihydroquinolin-5-yl)ethyl)amino)butyl 4-(2-(3-(phenyl((((R)-quinuclidin-3-yloxy)carbonyl)amino)methyl)phenoxy)ethyl)benzoate;

4-(((R)-2-hydroxy-2-(8-hydroxy-2-oxo-1,2-dihydroquinolin-5-yl)ethyl)amino)butyl 4-(5-((3-(phenyl((((R)-quinuclidin-3-yloxy)carbonyl)amino)methyl)phenoxy)methyl)-)-1,2,4-oxadiazol-3-yl)benzoate;

4-(((R)-2-hydroxy-2-(8-hydroxy-2-oxo-1,2-dihydroquinolin-5-yl)ethyl)amino)butyl 4-((4-((3-(phenyl((((R)-quinuclidin-3-yloxy)carbonyl)amino)methyl)phenoxy)methyl)piperidin-1-yl)methyl)benzoate;

2-(4-(((R)-2-hydroxy-2-(8-hydroxy-2-oxo-1,2-dihydroquinolin-5-yl)ethyl)amino)-butoxy)ethyl 4-((3-(phenyl((((R)-quinuclidin-3-yloxy)carbonyl)amino)methyl)phenoxy)-methyl)benzoate;

4-(2-(((R)-2-hydroxy-2-(8-hydroxy-2-oxo-1,2-dihydroquinolin-5-yl)ethyl)amino)-ethyl)benzyl 4-((3-(phenyl((((R)-quinuclidin-3-yloxy)carbonyl)amino)methyl)phenoxy)-methyl)benzoate;

2-(2-(((R)-2-hydroxy-2-(8-hydroxy-2-oxo-1,2-dihydroquinolin-5-yl)ethyl)amino)-ethoxy)ethyl 4-((3-(phenyl((((R)-quinuclidin-3-yloxy)carbonyl)amino)methyl)phenoxy)-methyl)benzoate;

4-(((R)-2-hydroxy-2-(8-hydroxy-2-oxo-1,2-dihydroquinolin-5-yl)ethyl)amino)butyl 2-chloro-4-((3-(phenyl((((R)-quinuclidin-3-yloxy)carbonyl)amino)methyl)phenoxy)-methyl)benzoate; and 4-(((R)-2-hydroxy-2-(8-hydroxy-2-oxo-1,2-dihydroquinolin-5-yl)ethyl)amino)butyl 2-fluoro-4-((3-(phenyl((((R)-quinuclidin-3-yloxy)carbonyl)amino)methyl)phenoxy)-methyl)benzoate, or a pharmaceutically acceptable salt of said compound.

14. A pharmaceutical composition, comprising a compound or salt according to claim 1 and one or more pharmaceutically acceptable carriers and/or excipients.

15. A method for the treatment of asthma, chronic bronchitis, or chronic obstructive pulmonary disease, comprising administering an effective amount of a compound or salt according to claim 1 to a subject in need thereof.

16. A combination, comprising a compound or salt according to claim 1 and one or more active ingredients selected from the group consisting of a corticosteroid, a P38 MAP kinase inhibitor, a IKK2 inhibitor, a HNE inhibitor, a PDE4 inhibitor, a leukotriene modulator, a NSAID, and a mucus regulator.

17. A pharmaceutical composition according to claim 14, which is in a form suitable to be administered by inhalation.

18. A pharmaceutical composition according to claim 14, which is an inhalable powder, a propellant-containing metering aerosol, or a propellant-free inhalable formulation.

19. A device, comprising a pharmaceutical composition according to claim 18, and which is a single- or multi-dose dry powder inhaler, a metered dose inhaler, or a soft mist nebulizer.

20. A pharmaceutical composition, comprising a compound or salt according to claim 13 and one or more pharmaceutically acceptable carriers and/or excipients.

21. A method for the treatment of asthma, chronic bronchitis, or chronic obstructive pulmonary disease, comprising administering an effective amount of a compound or salt according to claim 13 to a subject in need thereof.

* * * * *

UNITED STATES PATENT AND TRADEMARK OFFICE
CERTIFICATE OF CORRECTION

PATENT NO. : 8,877,774 B2
APPLICATION NO. : 13/492458
DATED : November 4, 2014
INVENTOR(S) : Fabio Rancati et al.

Page 1 of 3

It is certified that error appears in the above-identified patent and that said Letters Patent is hereby corrected as shown below:

In the Specification

Column 49, line 33, "9-bromononanol" should read --9-bromononanal--.

Column 69, the formula at the bottom center of the page

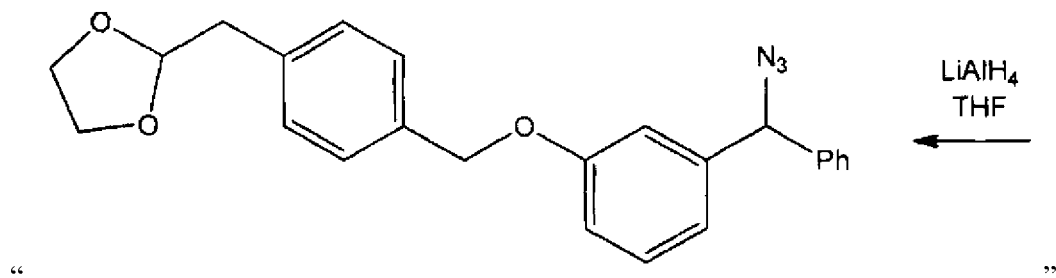

"

should read:

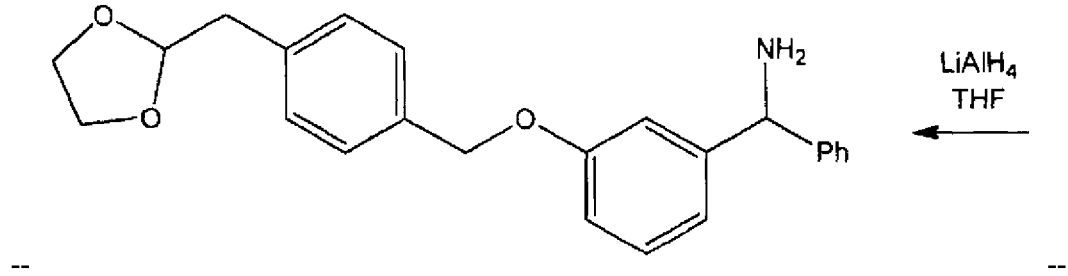

--

--.

Column 105, line 35, "3-bromophenetole" should read --β-bromophenetole--.

Column 177, line 6, "$CH_{30}OH-d_4$" should read --$CH_3OH-d_4$--.

Column 204, line 2, after "propyl" add --benzoate--.

Signed and Sealed this
Eighteenth Day of August, 2015

Michelle K. Lee
*Director of the United States Patent and Trademark Office*

In the Claims
Claim 1, Column 247, line 25,
"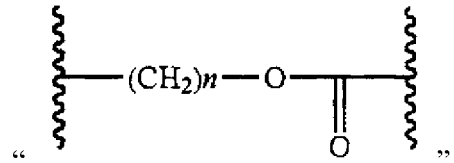"
should read:
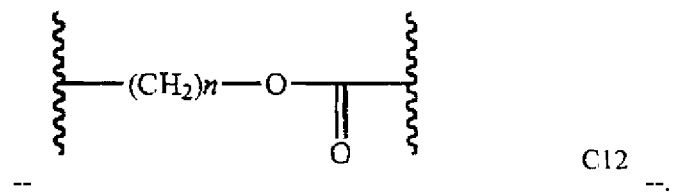
--.
Claim 1, Column 247, line 30,
"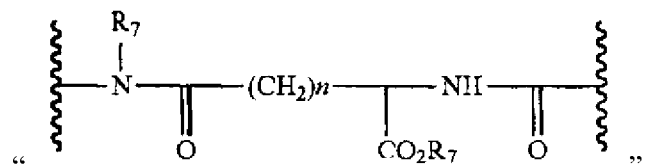"
should read:
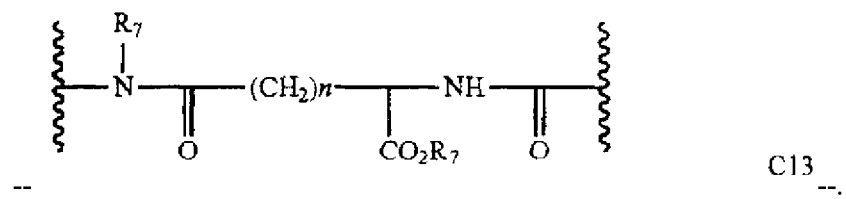
--.
Claim 1, Column 247, line 50,
"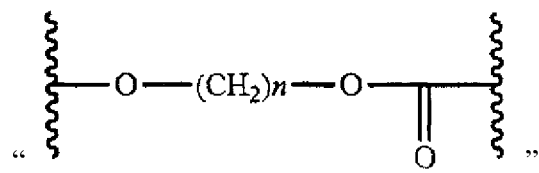"
should read:

CERTIFICATE OF CORRECTION (continued)
U.S. Pat. No. 8,877,774 B2

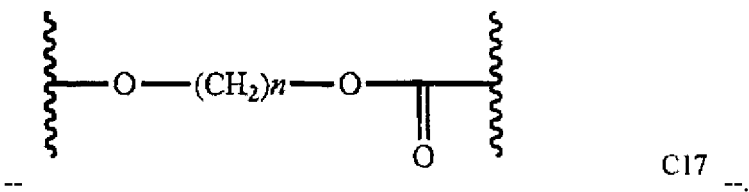

-- C17 --.

Claim 1, Column 248, line 2,

"-O-, -OC(O)- or -S-;" should read -- -O-, $NR_7$-, -OC(O)- or -S-;--.